(12) United States Patent
Brown

(10) Patent No.: US 11,434,249 B1
(45) Date of Patent: Sep. 6, 2022

(54) ASK1 INHIBITOR COMPOUNDS AND USES THEREOF

(71) Applicant: Seal Rock Therapeutics, Inc., Seattle, WA (US)

(72) Inventor: Samuel David Brown, San Carlos, CA (US)

(73) Assignee: SEAL ROCK THERAPEUTICS, INC., Seattle, WA (US)

(*) Notice: Subject to any disclaimer, the term of this patent is extended or adjusted under 35 U.S.C. 154(b) by 56 days.

(21) Appl. No.: 16/958,053

(22) PCT Filed: Dec. 31, 2018

(86) PCT No.: PCT/US2018/068187
§ 371 (c)(1),
(2) Date: Jun. 25, 2020

(87) PCT Pub. No.: WO2019/136025
PCT Pub. Date: Jul. 11, 2019

Related U.S. Application Data

(60) Provisional application No. 62/783,746, filed on Dec. 21, 2018, provisional application No. 62/612,990, filed on Jan. 2, 2018.

(51) Int. Cl.
| | | |
|---|---|---|
| *C07D 401/00* | (2006.01) |
| *A61K 31/44* | (2006.01) |
| *C07D 495/04* | (2006.01) |
| *A61P 1/16* | (2006.01) |
| *A61K 31/4439* | (2006.01) |

(52) U.S. Cl.
CPC ........ *C07D 495/04* (2013.01); *A61K 31/4439* (2013.01); *A61P 1/16* (2018.01)

(58) Field of Classification Search
CPC ...... A61P 1/16; A61K 31/4439; C07D 409/14
USPC ...... 546/272.4, 180, 224, 242, 336; 514/339
See application file for complete search history.

(56) References Cited

U.S. PATENT DOCUMENTS

| | | |
|---|---|---|
| 4,229,447 A | 10/1980 | Porter |
| 4,596,795 A | 6/1986 | Pitha |
| 4,755,386 A | 7/1988 | Hsiao et al. |
| 5,739,136 A | 4/1998 | Ellinwood, Jr. et al. |
| 8,344,160 B2 | 1/2013 | Zhao et al. |
| 8,975,260 B2 | 3/2015 | Currie et al. |
| 9,067,933 B2 | 6/2015 | Corkey et al. |
| 10,150,755 B2 | 12/2018 | Brown |
| 2011/0009410 A1 | 1/2011 | Corkey et al. |
| 2013/0143863 A1 | 6/2013 | Aebi et al. |
| 2013/0150408 A1 | 6/2013 | Liu et al. |
| 2013/0197037 A1 | 8/2013 | Notte |
| 2014/0038957 A1 | 2/2014 | Witty et al. |
| 2014/0329850 A1 | 11/2014 | Chang et al. |
| 2015/0336949 A1 | 11/2015 | Gummadi et al. |
| 2016/0067251 A1 | 3/2016 | Witty et al. |
| 2016/0130251 A1 | 5/2016 | Graupe et al. |
| 2018/0362503 A1 | 12/2018 | Granger et al. |
| 2021/0087167 A1 | 3/2021 | Brown |

FOREIGN PATENT DOCUMENTS

| | | |
|---|---|---|
| CL | 2010001637 A1 | 7/2011 |
| CL | 2014001988 A1 | 11/2014 |
| CL | 2016001538 A1 | 10/2016 |
| WO | WO-2005060963 A1 | 7/2005 |
| WO | WO-2009019656 A1 | 2/2009 |
| WO | WO-2010018458 A2 | 2/2010 |
| WO | WO-2012030990 A1 | 3/2012 |
| WO | WO-2015163472 A1 | 10/2015 |
| WO | WO-2016049069 A1 | 3/2016 |
| WO | WO-2017214359 A1 | 12/2017 |
| WO | WO-2018133865 A1 | 7/2018 |
| WO | WO-2018133866 A1 | 7/2018 |
| WO | WO-2018148204 A1 | 8/2018 |
| WO | WO-2018149284 A1 | 8/2018 |
| WO | WO-2018151830 A1 | 8/2018 |
| WO | WO-2018157277 A1 | 9/2018 |
| WO | WO-2018157856 | 9/2018 |
| WO | WO-2018157857 | 9/2018 |
| WO | WO-2018160406 A1 | 9/2018 |
| WO | WO-2018183122 A1 | 10/2018 |
| WO | WO-2018187506 A1 | 10/2018 |
| WO | WO-2019055540 A1 | 3/2019 |
| WO | WO-2019136025 A1 | 7/2019 |

OTHER PUBLICATIONS

Ogier et al. "ASK1 inhibition: a therapeutic strategy with multi-system benefits," J. Molecular Medicine, 2020, vol. 98, pp. 335-348. (Year: 2020).*
Crawford et al. Discovery of GDC-0853: A Potent, Selective, and Noncovalent Bruton's Tyrosine Kinase Inhibitor in Early Clinical Development. J Med Chem 61(6):2227-2245 (2018).
Banini et al. Current and future pharmacologic treatment of nonalcoholic steatohepatitis. Curr Opin Gastroenterol 33(3):134-141 (2017).
Berge et al. Pharmaceutical Salts. Journal of Pharmaceutical Sciences 66(1):1-19 (Jan. 1977).
Ciapetti et al. Chapter 15: Molecular Variations Based on Isosteric Replacements. Editor Camille Georges Wermuth. The Practice of Medicinal Chemistry (Third Edition), Elsevier, NL (pp. 290-342) (Jan. 1, 2008).
Dou et al. Efficient and Convenient Synthesis of Indazol-3(2 H)-ones and 2-Aminobenzonitriles. J Comb Chem 11(6):1073-1077 (2009).
Gibson et al. Structure-based drug design of novel ASK1 inhibitors using an integrated lead optimization strategy. Bioorg Med Chem Lett 27(8):1709-1713 (2017).

(Continued)

*Primary Examiner* — Shengjun Wang
(74) *Attorney, Agent, or Firm* — Wilson Sonsini Goodrich & Rosati

(57) ABSTRACT

Described herein are compounds, including pharmaceutically acceptable salts and solvates thereof, methods of making such compounds, pharmaceutical compositions comprising such compounds, and methods of using such compounds to treat non-alcoholic steatohepatitis and other diseases characterized by dysfunctional tissue healing and fibrosis.

12 Claims, No Drawings

(56) References Cited

OTHER PUBLICATIONS

Gilead Presents Data on Multiple Investigational Regimens for the Treatment of Patients With Nonalcoholic Steatohepatitis (NASH) and Advanced Fibrosis at the International Liver Congress™ 2018 Press Release (4 pgs).
Lanier et al. Structure-Based Design of ASK1 Inhibitors as Potential Agents for Heart Failure. ACS Med Chem Lett 8(3):316-320 (2017).
Loomba et al. The ASK1 inhibitor selonsertib in patients with nonalcoholic steatohepatitis: A randomized, phase 2 trial. Hepatology 67(2):549-559. (2018).
PCT/US2018/068187 International Search Report and Written Opinion dated May 8, 2019.
PCT/US2018/068187 Invitation to Pay Additional Fees dated Mar. 12, 2019.
Ratziu et al. Current efforts and trends in the treatment of NASH. Journal of Hepatology 62:S65-S75 (2015).
Rotman et al. Current and upcoming pharmacotherapy for non-alcoholic fatty liver disease. Gut 66(1):180-190 (2017).
Singh et al. Encyclopedia of Pharmaceutical Technology 2nd Ed., pp. 754-757 (2002).
Yamamoto et al. Copper-Catalyzed Intramolecular Benzylic C—H Amination for the Synthesis of Isoindolinones. J Org Chem 81(17):7675-7684 (2016).

* cited by examiner

ASK1 INHIBITOR COMPOUNDS AND USES THEREOF

CROSS-REFERENCE

This application claims benefit of U.S. Provisional Application No. 62/612,990, filed on Jan. 2, 2018, and U.S. Provisional Application No. 62/783,746, filed on Dec. 21, 2018, which are herein incorporated by reference in their entireties.

BACKGROUND OF THE INVENTION

Non-alcoholic steatohepatitis (NASH) is an extreme form of non-alcoholic fatty liver disease (NAFLD), a condition resembling alcohol-induced liver injury associated with obesity and metabolic syndrome rather than alcohol abuse. In NAFLD, triglycerides accumulate within hepatocytes due to alterations in lipid synthesis, storage, movement, or clearance processes causing steatosis. While steatosis typically has no large risk implications on its own, in a subset of NAFLD patients the steatosis progresses to include inflammation, necrosis, and fibrosis (hepatitis), a condition known as NASH. These NASH patients have highly elevated risks of both hepatocellular carcinoma (HCC, as high as 7.6% total risk in one study) and cirrhosis (as high as 25% total risk), ultimately leading to liver failure or death.

Current population-based studies indicate that at least 25% of the US population has NAFLD and about 25% of NAFLD patients will go on to develop NASH, making these conditions a significant epidemiologic contributor to organ failure and cancer. As these conditions are associated with obesity and metabolic disease, their prevalence is likely to increase in the future.

SUMMARY OF THE INVENTION

In one aspect, described herein are compounds of Formula (I), (Ia), (Ib), or (Ic), or a pharmaceutically acceptable salt or solvate thereof, that inhibit apoptosis signal-regulating kinase 1 (ASK1).

In another aspect, presented herein are compounds of Formula (I), or a pharmaceutically acceptable salt or solvate thereof:

Formula (I)

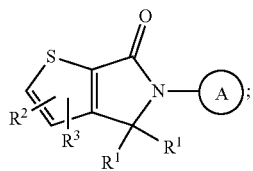

wherein

A is

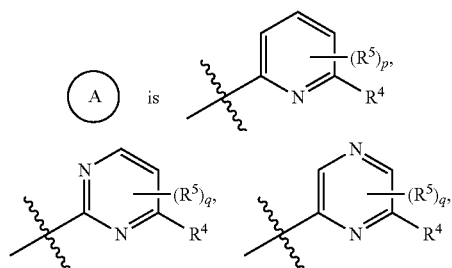

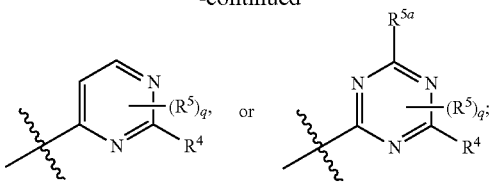

each $R^1$ is independently selected from a group consisting of hydrogen, halogen, and $C_{1-6}$alkyl;

$R^2$ is selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;

$R^3$ is selected from a group consisting of hydrogen, halogen, —CN, and $C_{1-6}$alkyl; or $R^2$ and $R^3$ are combined to form a phenyl ring optionally substituted with one, two, or three $R^8$ substituents;

$R^4$ is selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;

each $R^5$ is independently selected from a group consisting of halogen, —CN, and $C_{1-6}$alkyl;

$R^{5a}$ is selected from the group consisting of hydrogen and $C_{1-6}$alkyl;

each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl;

each $R^7$ is independently selected from the group consisting of $C_{1-6}$alkyl, $C_{3-8}$cycloalkyl, and $C_{2-9}$heterocycle;

each $R^8$ is independently selected from the group consisting of halogen, —CN, $C_{1-6}$alkyl, —$C_{1-6}$ alkyl-OH, $C_{1-6}$haloalkyl, $C_{3-8}$cycloalkyl, $C_{2-9}$heterocycle, $C_{6-10}$aryl, $C_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$;

each R$^{13}$ is independently selected from the group consisting of hydrogen, $C_{1-6}$alkyl, and $C_{3-8}$cycloalkyl; or two R$^{13}$ on the same heteroatom are taken together with that heteroatom to which they are attached to form a $C_{2-9}$heterocycle;

each R$^{14}$ is independently selected from the group consisting of $C_{1-6}$alkyl and $C_{3-8}$cycloalkyl;

p is 0, 1, 2, or 3; and q is 0, 1, or 2.

In some embodiments is a compound of Formula (I) having the structure of Formula (Ia), or a pharmaceutically acceptable salt or solvate thereof:

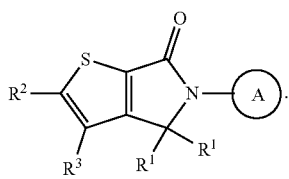

Formula (Ia)

In some embodiments is a compound of Formula (I) having the structure of Formula (Ib), or a pharmaceutically acceptable salt or solvate thereof:

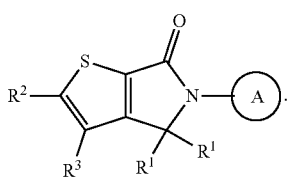

Formula (Ib)

In some embodiments is a compound of Formula (I), (Ia), or (Ib), or a pharmaceutically acceptable salt or solvate thereof, wherein R$^2$ is selected from a group consisting of hydrogen, halogen, or $C_{1-6}$alkyl. In some embodiments is a compound of Formula (I), (Ia), or (Ib), or a pharmaceutically acceptable salt or solvate thereof, wherein R$^2$ is hydrogen. In some embodiments is a compound of Formula (I), (Ia), or (Ib), or a pharmaceutically acceptable salt or solvate thereof, wherein R$^2$ is halogen. In some embodiments is a compound of Formula (I), (Ia), or (Ib), or a pharmaceutically acceptable salt or solvate thereof, wherein R$^2$ is $C_{1-6}$alkyl. In some embodiments is a compound of Formula (I), (Ia), or (Ib), or a pharmaceutically acceptable salt or solvate thereof, wherein R$^2$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments is a compound of Formula (I), (Ia), or (Ib), or a pharmaceutically acceptable salt or solvate thereof, wherein R$^2$ is selected from a group consisting of $C_{2-9}$heterocycle and $C_{1-9}$heteroaryl; wherein $C_{2-9}$heterocycle and $C_{1-9}$heteroaryl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments is a compound of Formula (I), (Ia), or (Ib), or a pharmaceutically acceptable salt or solvate thereof, wherein R$^2$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments is a compound of Formula (I), (Ia), or (Ib), or a pharmaceutically acceptable salt or solvate thereof, wherein R$^2$ is selected from a group consisting of pyrazole, imidazole, thiazole, and pyridine; wherein pyrazole, imidazole, thiazole, and pyridine are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(═O)R$^{14}$, —C(═O)OR$^{13}$, —C(═O)N(R$^{13}$)$_2$, —S(═O)R$^{14}$, —S(═O)$_2$R$^{13}$, —S(═O)$_2$—N(R$^{13}$)$_2$, —N(R$^{13}$)$_2$, —N(R$^{13}$)C(═O)R$^{14}$, and —N(R$^{13}$)S(═O)$_2$R$^{13}$.

In some embodiments is a compound of Formula (I), (Ia), or (Ib), or a pharmaceutically acceptable salt or solvate thereof, wherein R$^2$ is selected from a group consisting of pyrazole, imidazole, thiazole, and pyridine; wherein pyrazole, imidazole, thiazole, and pyridine are optionally substituted with one or two substituents selected from the group consisting of halogen, $C_{1-6}$alkyl, and $C_{3-8}$cycloalkyl. In some embodiments is a compound of Formula (I), (Ia), or (Ib), or a pharmaceutically acceptable salt or solvate thereof, wherein R$^2$ is

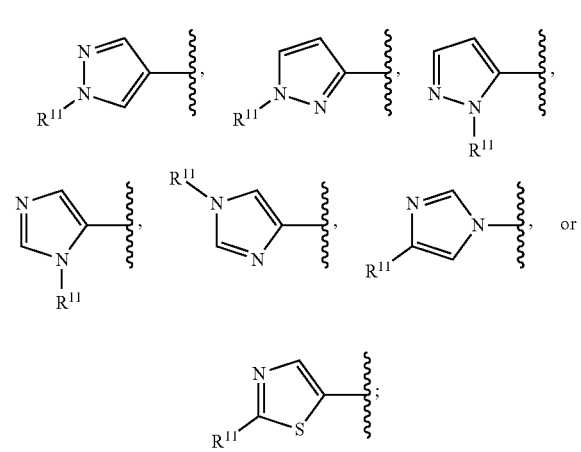

wherein R$^{11}$ is $C_{1-6}$alkyl or $C_{3-6}$cycloalkyl. In some embodiments is a compound of Formula (I), (Ia), or (Ib), or a pharmaceutically acceptable salt or solvate thereof, wherein R$^2$ is

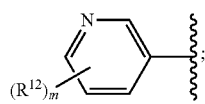

wherein each $R^{12}$ is independently hydrogen, halogen, CN, $C_{1-6}$alkyl, or $C_{3-6}$cycloalkyl; and m is 1 or 2. In some embodiments is a compound of Formula (I), (Ia), or (Ib), or a pharmaceutically acceptable salt or solvate thereof, wherein $R^2$ is selected from a group consisting of unsubstituted pyrazole, unsubstituted imidazole, unsubstituted thiazole, and unsubstituted pyridine. In some embodiments, $R^2$ is $C_{6-10}$aryl optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^3$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^3$)S(=O)$_2R^{13}$. In some embodiments is a compound of Formula (I), (Ia), or (Ib), or a pharmaceutically acceptable salt or solvate thereof, wherein $R^2$ is phenyl optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), (Ia), or (Ib), or a pharmaceutically acceptable salt or solvate thereof, wherein $R^2$ is —C(=O)N($R^6$)$_2$ and each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl. In some embodiments is a compound of Formula (I), (Ia), or (Ib), or a pharmaceutically acceptable salt or solvate thereof, wherein $R^2$ is

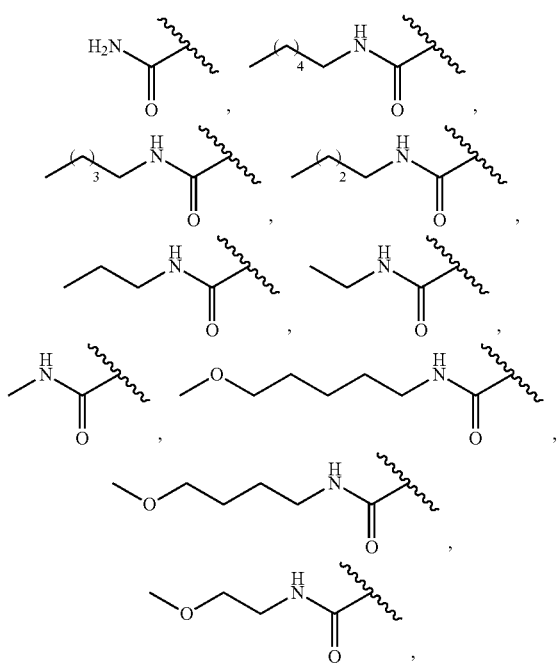

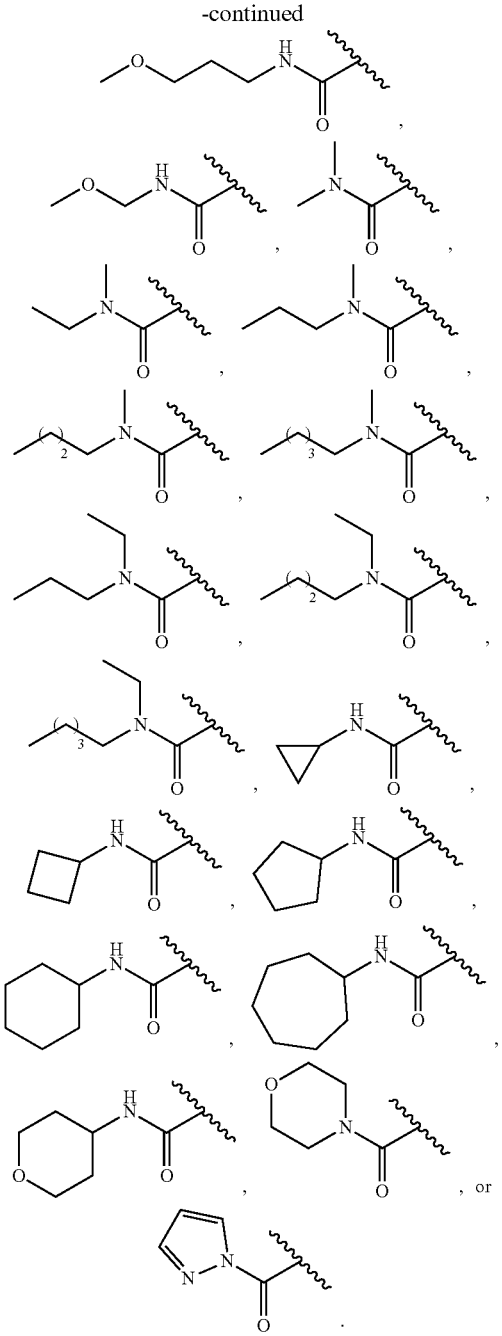

In some embodiments is a compound of Formula (I), (Ia), or (Ib), or a pharmaceutically acceptable salt or solvate thereof, wherein $R^2$ is

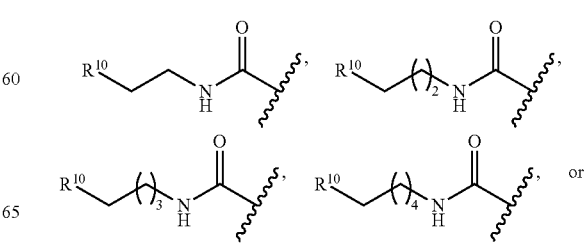

-continued

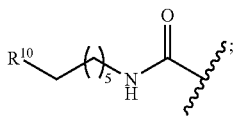

wherein $R^{10}$ is $C_{1-9}$heteroaryl. In some embodiments is a compound of Formula (I), (Ia), or (Ib), or a pharmaceutically acceptable salt or solvate thereof, wherein $R^2$ is —NHC(=O)$R^7$. In some embodiments is a compound of Formula (I), (Ia), or (Ib), or a pharmaceutically acceptable salt or solvate thereof, wherein $R^2$ is

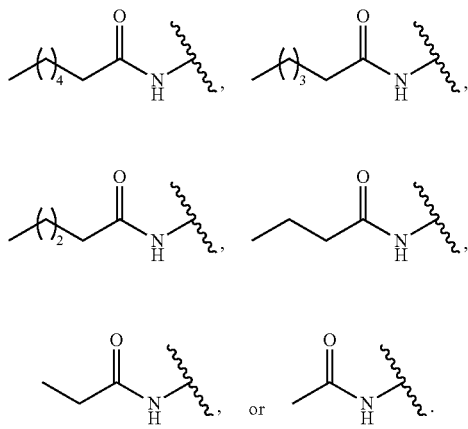

In some embodiments is a compound of Formula (I), (Ia), or (Ib), or a pharmaceutically acceptable salt or solvate thereof, wherein $R^2$ is —C(=O)$R^7$. In some embodiments is a compound of Formula (I), (Ia), or (Ib), or a pharmaceutically acceptable salt or solvate thereof, wherein $R^2$ is

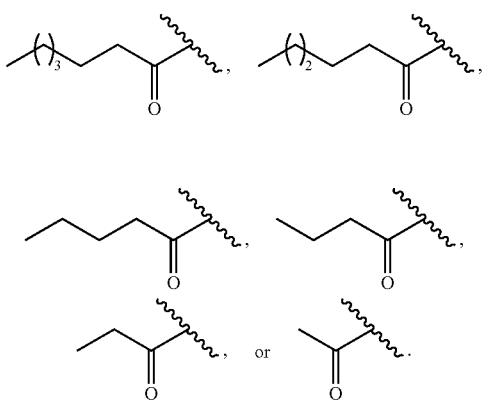

In some embodiments is a compound of Formula (I), (Ia), or (Ib), or a pharmaceutically acceptable salt or solvate thereof, wherein $R^3$ is hydrogen. In some embodiments is a compound of Formula (I), (Ia), or (Ib), or a pharmaceutically acceptable salt or solvate thereof, wherein $R^2$ and $R^3$ are combined to form a phenyl ring optionally substituted with one, two, or three $R^8$ substituents.

In some embodiments is a compound of Formula (I) having the structure of Formula (Ic), or a pharmaceutically acceptable salt or solvate thereof:

Formula (Ic)

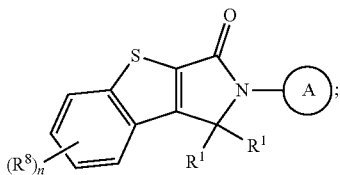

wherein n is 0, 1, 2, or 3.

In some embodiments is a compound of Formula (Ic), or a pharmaceutically acceptable salt or solvate thereof, wherein n is 0. In some embodiments is a compound of Formula (Ic), or a pharmaceutically acceptable salt or solvate thereof, wherein n is 1. In some embodiments is a compound of Formula (Ic), or a pharmaceutically acceptable salt or solvate thereof, wherein n is 2. In some embodiments is a compound of Formula (I), (Ia), (Ib), or (Ic), or a pharmaceutically acceptable salt or solvate thereof, wherein $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), (Ia), (Ib), or (Ic), or a pharmaceutically acceptable salt or solvate thereof, wherein $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), (Ia), (Ib), or (Ic), or a pharmaceutically acceptable salt or solvate thereof, wherein $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), (Ia), (Ib), or (Ic), or a pharmaceutically acceptable salt or solvate thereof, wherein $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments is a compound of Formula (I), (Ia), (Ib), or (Ic), or a pharmaceutically acceptable salt or solvate thereof, wherein $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (I), (Ia), (Ib), or (Ic), or a pharmaceutically acceptable salt or solvate thereof, wherein $R^4$ is

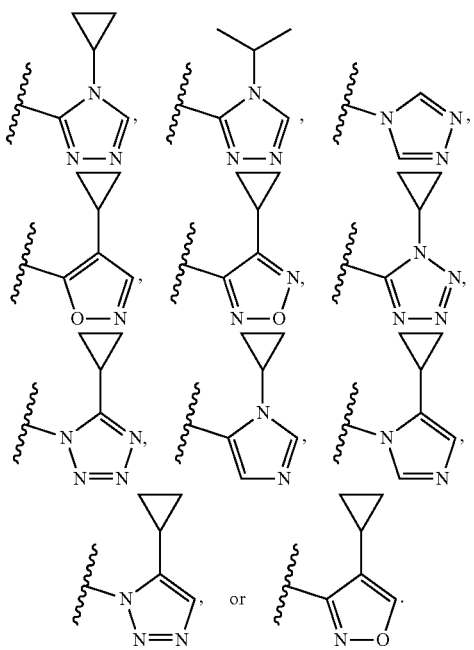

In some embodiments is a compound of Formula (I), (Ia), (Ib), or (Ic), or a pharmaceutically acceptable salt or solvate thereof, wherein $R^4$ is

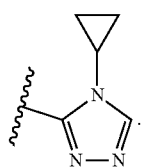

In some embodiments is a compound of Formula (I), (Ia), (Ib), or (Ic), or a pharmaceutically acceptable salt or solvate thereof, wherein $R^4$ is

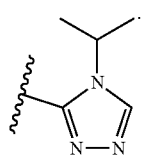

In some embodiments is a compound of Formula (I), (Ia), (Ib), or (Ic), or a pharmaceutically acceptable salt or solvate thereof, wherein $R^4$ is

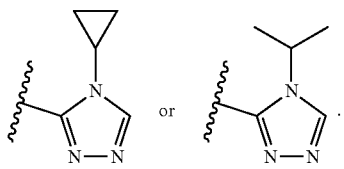

In some embodiments is a compound of Formula (I), (Ia), (Ib), or (Ic), or a pharmaceutically acceptable salt or solvate thereof, wherein $R^4$ is

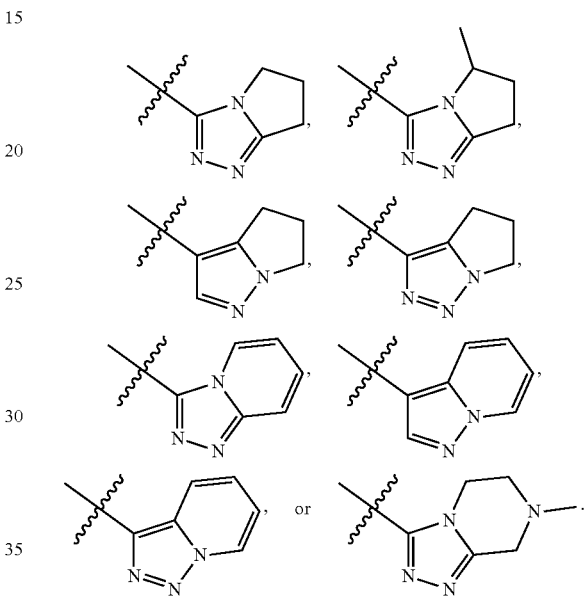

In some embodiments is a compound of Formula (I), (Ia), (Ib), or (Ic), or a pharmaceutically acceptable salt or solvate thereof, wherein

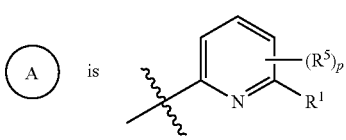

In some embodiments is a compound of Formula (I), (Ia), (Ib), or (Ic), or a pharmaceutically acceptable salt or solvate thereof, wherein p is 0. In some embodiments is a compound of Formula (I), (Ia), (Ib), or (Ic), or a pharmaceutically acceptable salt or solvate thereof, wherein

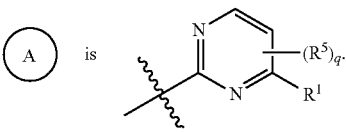

In some embodiments is a compound of Formula (I), (Ia), (Ib), or (Ic), or a pharmaceutically acceptable salt or solvate thereof, wherein

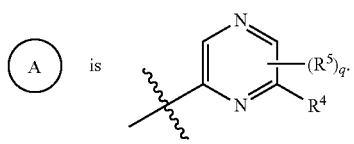

In some embodiments is a compound of Formula (I), (Ia), (Ib), or (Ic), or a pharmaceutically acceptable salt or solvate thereof, wherein

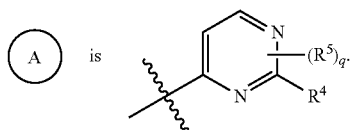

In some embodiments is a compound of Formula (I), (Ia), (Ib), or (Ic), or a pharmaceutically acceptable salt or solvate thereof, wherein q is 0. In some embodiments is a compound of Formula (I), (Ia), (Ib), or (Ic), or a pharmaceutically acceptable salt or solvate thereof, wherein

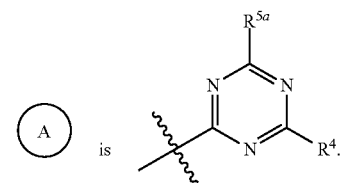

In some embodiments is a compound of Formula (I), (Ia), (Ib), or (Ic), or a pharmaceutically acceptable salt or solvate thereof, wherein $R^{5a}$ is hydrogen. In some embodiments is a compound of Formula (I), (Ia), (Ib), or (Ic), or a pharmaceutically acceptable salt or solvate thereof, wherein each $R^1$ is hydrogen.

In another aspect, described herein is a pharmaceutical composition comprising a compound of Formula (I), (Ia), (Ib), or (Ic), or a pharmaceutically acceptable salt or solvate thereof, and at least one pharmaceutically acceptable excipient.

In another aspect, described herein is a method of treating non-alcoholic steatohepatitis in a subject in need thereof, comprising administering to the subject a therapeutically effective amount of a compound of Formula (I), (Ia), (Ib), or (Ic), or a therapeutically effective amount of a pharmaceutically acceptable salt or solvate thereof.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Apoptosis signal-regulating kinase 1 (ASK1), a ubiquitously expressed 1375 amino acid serine/threonine-selective kinase, is a member of the mitogen-activated protein kinases (MAPKs) family.

The MAPK pathway is one of the intracellular signaling systems that regulate essential cellular functions, such as proliferation, motility, differentiation, stress response and apoptosis. Each MAPK pathway consists of three classes of protein kinases: MAPK kinase kinase (MAP3K), MAPK kinase (MAP2K), and MAPK. MAP3K phosphorylates and thereby activates MAP2K, and activated MAP2K, in turn, phosphorylates and activates MAPK. Activated MAPK then translocate to the cell nucleus and regulates the activities of transcription factors to control gene expression.

ASK1 is a membrane-proximal MAP3K (MAP-kinase-kinase-kinase) upstream of pathways which play important roles in the cellular response to environmental stresses (e.g. the c-Jun and p38 pathways, which are known to be responsive to UV and oxidative damage), is a promising therapeutic target for NASH. A positive regulator of mitochondrial apoptosis, ASK1 is tightly regulated and activated by cellular damage signals as diverse as receptor-acting inflammatory cytokines (e.g. TNFa and LPS), calcium and intracellular sensors (e.g. the redox sensor thioredoxin, and the ER-stress-responsive IRE1).

Consistent with this role as an effector of stress signals, ASK1 has been shown as an important mediator of pathological stress-induced hepatic tissue remodeling. In a mouse model of non-alcoholic liver injury, ASK1 null mice show resistance to diet-induced steatohepatitis and subsequent fibrosis. Human data is consistent with this role in directing responses to diet-induced liver damage; ASK1 inhibitors (e.g. the small molecule selonsertib/GS-4997 in clinical trial NCT02466516) have recently shown utility in phase II trials against non-alcoholic steatohepatitis (NASH) in affected patients, and NASH patients show upregulation of ASK1 activity in separate molecular analyses.

Certain Terminology

Unless otherwise stated, the terms used in this application, including the specification and claims, have the definitions given below. The singular forms "a," "an" and "the" include plural referents unless the context clearly dictates otherwise. The use of "or" or "and" means "and/or" unless stated otherwise. Use of the term "including" as well as other forms, such as "include", "includes," and "included," and equivalent forms such as "comprising," "comprise," "comprises," "comprised," and "having" is not limiting; it is not intended to exclude that which would be excluded by the term "consisting of" or "consisting essentially of." The section headings used herein are for organizational purposes only and are not to be construed as limiting the disclosure herein.

$C_{1-x}$ includes $C_{1-2}$, $C_{1-3}$ ... $C_{1-x}$, where x is an integer. $C_{1-x}$ refers to the number of carbon atoms in the designated group (excluding optional substituents).

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to fifteen carbon atoms (e.g., $C_{1-15}$ alkyl). In certain embodiments, an alkyl comprises one to thirteen carbon atoms (e.g., $C_{1-13}$ alkyl). In certain embodiments, an alkyl comprises one to eight carbon atoms (e.g., $C_{1-8}$ alkyl). In other embodiments, an alkyl comprises one to six carbon atoms (e.g., $C_{1-6}$ alkyl). In other embodiments, an alkyl comprises one to five carbon atoms (e.g., $C_{1-5}$ alkyl). In other embodiments, an alkyl comprises one to four carbon atoms (e.g., $C_{1-4}$ alkyl). In other embodiments, an alkyl comprises one to three carbon atoms (e.g., $C_{1-3}$ alkyl). In other embodiments, an alkyl comprises one to two carbon atoms (e.g., $C_{1-2}$ alkyl). In other embodiments, an alkyl comprises one carbon atom (e.g., $C_1$ alkyl). In other embodiments, an alkyl comprises five to fifteen carbon atoms (e.g., $C_{5-15}$ alkyl). In other embodiments, an alkyl comprises five to eight carbon atoms (e.g., $C_{5-8}$ alkyl). In other embodiments, an alkyl comprises two to five carbon atoms (e.g., $C_{2-5}$ alkyl). In other embodiments, an alkyl comprises three to five carbon atoms (e.g., $C_{3-5}$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halogen, cyano, nitro, oxo, thioxo, imino, oximo, trimethylsilanyl, cycloalkyl, aryl, heterocycloalkyl, heteroaryl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" or "alkenylene" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halogen, cyano, nitro, oxo, thioxo, imino, oximo, trimethylsilanyl, cycloalkyl, aryl, heterocycloalkyl, heteroaryl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkynyl" or "alkynylene" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halogen, cyano, nitro, oxo, thioxo, imino, oximo, trimethylsilanyl, cycloalkyl, aryl, heterocycloalkyl, heteroaryl, —$OR^a$, —$SR^a$, —OC(O)—$R^f$, —$N(R^a)_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$R$^f$ (where t is 1 or 2), —S(O)$_t$OR$^a$ (where t is 1 or 2), —S(O)$_t$R$^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond.

Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_{3-8}$ cycloalkyl). In other embodiments, a cycloalkyl comprises three to seven carbon atoms (e.g., $C_{3-7}$ cycloalkyl). In other embodiments, a cycloalkyl comprises three to six carbon atoms (e.g., $C_{3-6}$ cycloalkyl). In other embodiments, a cycloalkyl comprises three to five carbon atoms (e.g., $C_{3-5}$ cycloalkyl). In other embodiments, a cycloalkyl comprises three to four carbon atoms (e.g., $C_{3-4}$ cycloalkyl). A partially unsaturated cycloalkyl is also referred to as "cycloalkenyl" if it includes one or more double bonds. Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halogen, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$R$^a$ (where t is 1 or 2), —$R^b$—S(O)$_t$OR$^a$ (where t is 1 or 2), —$R^b$—S(O)$_t$R$^a$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halogen, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which includes fused, spiro, or bridged ring systems. The heteroatoms in the heterocycloalkyl radical are optionally oxidized. In some embodiments, if present, sulfur is present as —S—, —S(=O)—, or —S(=O)$_2$—. One or more nitrogen atoms, if present, are optionally quaternized. The heterocycloalkyl radical is fully saturated, or partially unsaturated. In some embodiments, the heterocycloalkyl is attached to the rest of the molecule through any atom of the ring(s). Examples of such heterocycloalkyl radicals include, but are not limited to, 1,1-dioxo-thiomorpholinyl, 1,2,3,6-tetrahydropyridinyl, 1,3-dioxolanyl, 1-oxo-thiomorpholinyl, 2H-pyranyl, 4H-pyranyl, 2-oxopiperazinyl, 2-oxopiperidinyl, 2-oxopyrrolidinyl, 3-azabicyclo[3.1.0]hexanyl, 3-azabicyclo[4.1.0]heptanyl, 3H-indolyl, 4-piperidonyl, azetidinyl, aziridinyl, decahydroisoquinolyl, diazepinyl, dihydrofuranyl, dihydropyranyl, dihydrothienyl, dioxanyl, dioxolanyl, dithianyl, dithiolanyl, homopiperidinyl, imidazolidinyl, imidazolinyl, indolinyl, isothiazolidinyl, isoxazolidinyl, morpholinyl, octahydroindolyl, octahydroisoindolyl, oxazepinyl, oxazolidinonyl, oxazolidinyl, oxepanyl, oxetanyl, piperazinyl, piperidinyl, pyrazolidinyl, pyrazolinyl, pyrrolidinyl, pyrrolin-2-yl, pyrrolin-3-yl, quinolizinyl, quinuclidinyl, tetrahydrofuranyl, tetrahydropyranyl, tetrahydrothienyl, tetrahydrothiopyranyl, thiazepinyl, thiazolidinyl, thienyl[1,3]dithianyl, thiepanyl, thietanyl, thiomorpholinyl, thioxanyl, and trithianyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halogen, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a stable 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. In some embodiments, if present, sulfur is present as —S—, —S(=O)—, or —S(=O)$_2$—. One or more nitrogen atoms, if present, are optionally quaternized. The heteroaryl is attached to the rest of the molecule through any atom of the ring(s). Examples of such heteroaryl radicals include, but are not limited to, benzimidazolyl, benzofuranyl, benzofurazanyl, benzothiazolyl, benzothiophenyl, benzoxazolyl, cinnolinyl, furazanyl, furopyridinyl, furyl, imidazolyl, indazolyl, indolizinyl, indolyl, isoindolyl, isoquinolinyl, isothiazolyl, isoxazolyl, naphthyridinyl, oxadiazolyl, oxazolyl, phthalazinyl, pteridinyl, purinyl, pyrazinyl, pyrazolyl, pyridazinyl, pyridinyl, pyrimidinyl, pyrrolyl, quinazolinyl, quinolinyl, quinoxalinyl, tetrazolyl, thiadiazolyl, thiazolyl, thienyl, triazinyl, and triazolyl.

Illustrative examples of structures of heteroaryls include radicals corresponding to the following compounds (by C-, or N-attachment, as described below):

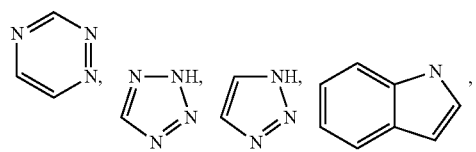

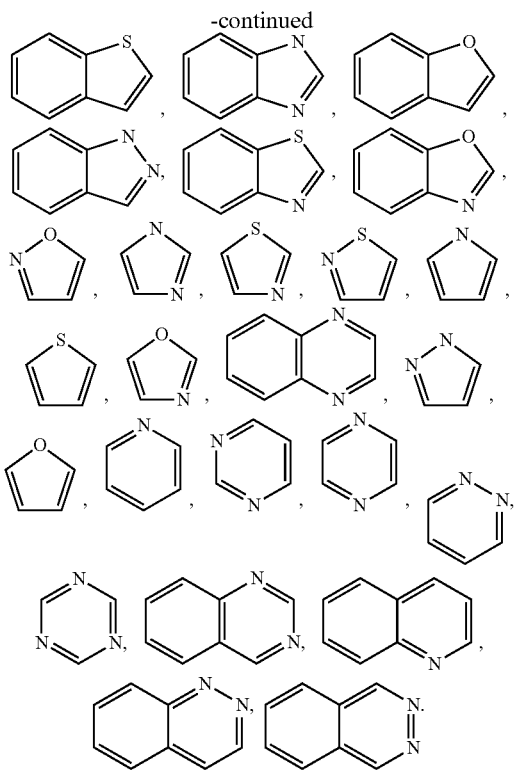

Unless stated otherwise specifically in the specification, the term "heteroaryl" is meant to include heteroaryl radicals as defined above which are optionally substituted by one or more substituents selected from alkyl, alkenyl, alkynyl, halogen, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

In some embodiments, the heterocycloalkyl or heteroaryl is attached through a bond to carbon. In some embodiments, the heterocycloalkyl or heteroaryl is attached through a bond to nitrogen. For example, in some embodiments, pyrrolyl, a heteroaryl, is attached through a bond to nitrogen, a pyrrol-1-yl, and in some embodiments it is attached through a bond to carbon, a pyrrol-2-yl or pyrrol-3-yl.

"N-hetercycloalkyl" and "N-heteroaryl" refer respectively to heterocycloalkyl and heteroaryl radicals, each as defined above, containing at least one nitrogen and where the point of attachment of the heterocycloalkyl or heteroaryl radical to the rest of the molecule is through a nitrogen atom in the heterocycloalkyl or heteroaryl radical. An N-heterocycloalkyl or N-heteroaryl radical is optionally substituted as described above for heterocycloalkyl or heteroaryl radicals.

"C-heterocycloalkyl" and "C-heteroaryl" refer respectively to heterocycloalkyl and heteroaryl radicals, each as defined above, and where the point of attachment of the heterocycloalkyl or heteroaryl radical to the rest of the molecule is through a carbon atom in the heterocycloalkyl or heteroaryl radical. A C-heterocycloalkyl or C-heteroaryl radical is optionally substituted as described above for heterocycloalkyl or heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The term "halogen" or, alternatively, "halo" or "halide" refers to fluoro (F), chloro (Cl), bromo (Br), or iodo (I). In some embodiments, halogen is F or Cl. In some embodiments, halogen is F.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical is optionally substituted as defined above for an alkyl group.

The term "bond" or "single bond" refers to a chemical bond between two atoms, or two moieties when the atoms joined by the bond are considered to be part of a larger substructure. In one aspect, when a group described herein is a bond, the referenced group is absent, thereby allowing a bond to be formed between the remaining identified groups.

The term "moiety" or "group" refers to a specific segment or functional group of a molecule. Chemical moieties are often recognized chemical entities included in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halogen, nitro, haloalkyl, fluoroalkyl, fluoroalkoxy, and amino, including mono- and di-substituted amino groups, and the protected derivatives thereof. In some embodiments, optional substituents are independently selected from halogen, —CN, —$NH_2$, —$NH(CH_3)$, —N(CH$_3$)$_2$, —OH, —CO$_2$H, —CO$_2$alkyl, —C(═O)NH$_2$, —C(═O)NH(alkyl), —C(═O)N(alkyl)$_2$, —S(═O)$_2$NH$_2$, —S(═O)$_2$NH(alkyl), —S(═O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (═O).

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. Stereoisomers, or mixtures enriched in a particular stereoisomer, are obtained, if desired, by methods such as, stereoselective synthesis and/or separation of stereoisomers by known methods, including using chiral chromatographic columns. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

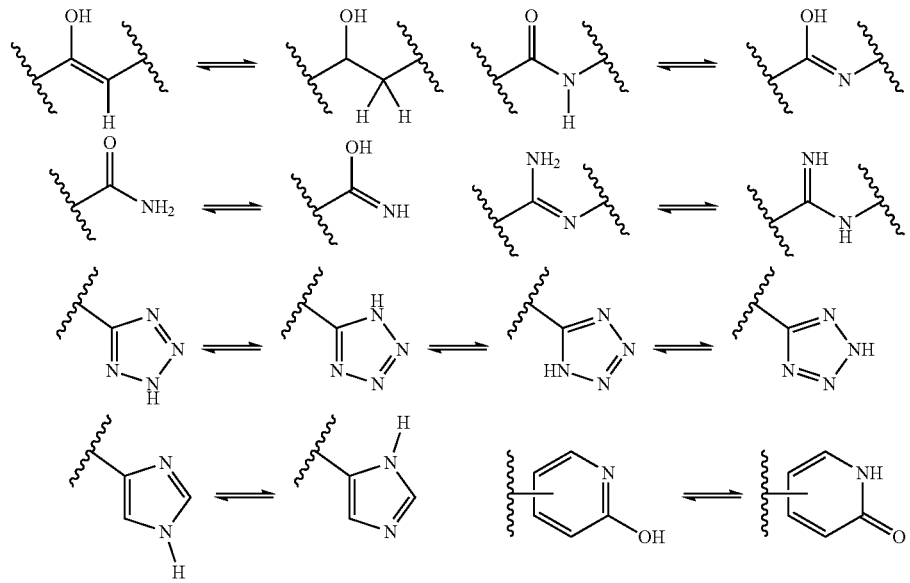

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

The methods and formulations described herein include the use of N-oxides (if appropriate) or pharmaceutically acceptable salts of compounds having the structure of Formula (I), (Ia), (Ib), or (Ic), as well as active metabolites of these compounds having the same type of activity. In some embodiments, the compounds described herein exist in solvated forms with pharmaceutically acceptable solvents such as water, ethanol, and the like. In other embodiments, the compounds described herein exist in unsolvated form.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "acceptable" with respect to a formulation, composition or ingredient, as used herein, means having no persistent detrimental effect on the general health of the subject being treated.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (Ib), or (Ic), or a pharmaceutically acceptable salt thereof, and a co-agent, are both administered to a patient simultaneously in the form of a single entity or dosage. The term "non-fixed combination" means that the active ingredients, e.g. a compound of Formula (I), (Ia), (Ib), or (Ic), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Compounds

In some embodiments, presented herein are compounds of Formula (I), or a pharmaceutically acceptable salt or solvate thereof:

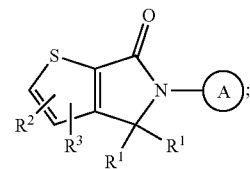

Formula (I)

wherein

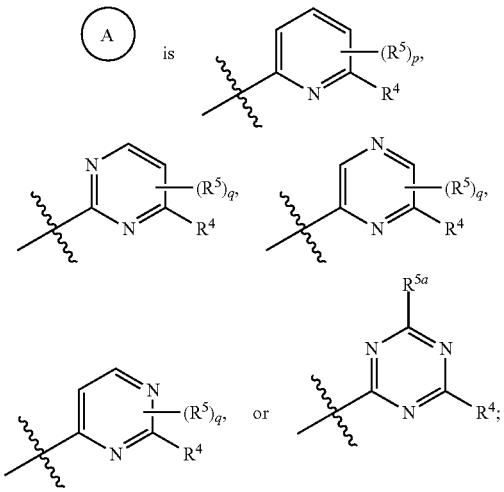

each $R^1$ is independently selected from a group consisting of hydrogen, halogen, and $C_{1-6}$alkyl;

$R^2$ is selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

$R^3$ is selected from a group consisting of hydrogen, halogen, —CN, and $C_{1-6}$alkyl; or $R^2$ and $R^3$ are combined to form a phenyl ring optionally substituted with one, two, or three $R^8$ substituents;

$R^4$ is selected from a group consisting of hydrogen, halogen, —CN, —OH, —O$R^6$, —S$R^6$, —S(=O)$R^7$, —NO$_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —N$R^6$C(=O)N($R^6$)$_2$, —N$R^6$C(=O)$R^7$, —N$R^6$C(=O)O$R^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^5$ is independently selected from a group consisting of halogen, —CN, and $C_{1-6}$alkyl;

$R^{5a}$ is selected from the group consisting of hydrogen and $C_{1-6}$alkyl;

each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl;

each $R^7$ is independently selected from the group consisting of $C_{1-6}$alkyl, $C_{3-8}$cycloalkyl, and $C_{2-9}$ heterocycle;

each $R^8$ is independently selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^{13}$ is independently selected from the group consisting of hydrogen, $C_{1-6}$alkyl, and $C_{3-8}$cycloalkyl; or two $R^3$ on the same heteroatom are taken together with that heteroatom to which they are attached to form a $C_{2-9}$heterocycle;

each $R^{14}$ is independently selected from the group consisting of $C_{1-6}$alkyl and $C_{3-8}$cycloalkyl;

p is 0, 1, 2, or 3; and q is 0, 1, or 2.

In some embodiments is a compound of Formula (I), or a pharmaceutically acceptable salt or solvate thereof, wherein each $R^1$ is hydrogen. In some embodiments is a compound of Formula (I), or a pharmaceutically acceptable salt or solvate thereof, wherein one $R^1$ is hydrogen and one $R^1$ is $C_{1-6}$alkyl. In some embodiments is a compound of Formula (I), or a pharmaceutically acceptable salt or solvate thereof, wherein each $R^1$ is $C_{1-6}$alkyl. In some embodiments is a compound of Formula (I), or a pharmaceutically acceptable salt or solvate thereof, wherein each $R^1$ is halogen.

In some embodiments is a compound of Formula (I), or a pharmaceutically acceptable salt or solvate thereof, wherein $R^2$ is selected from a group consisting of hydrogen, halogen, and $C_{1-6}$alkyl.

In some embodiments is a compound of Formula (I), or a pharmaceutically acceptable salt or solvate thereof, wherein $R^2$ is hydrogen.

In some embodiments is a compound of Formula (I), or a pharmaceutically acceptable salt or solvate thereof, wherein $R^2$ is halogen.

In some embodiments is a compound of Formula (I), or a pharmaceutically acceptable salt or solvate thereof, wherein $R^2$ is $C_{1-6}$alkyl.

In some embodiments is a compound of Formula (I), or a pharmaceutically acceptable salt or solvate thereof, wherein $R^2$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{3-8}$ cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein $R^2$ is selected from a group consisting of $C_{2-9}$heterocycle and $C_{1-9}$heteroaryl; wherein $C_{2-9}$heterocycle and $C_{1-9}$heteroaryl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, $R^2$ is selected from a group consisting of $C_{2-9}$heterocycle and $C_{1-9}$heteroaryl; wherein $C_{2-9}$heterocycle and $C_{1-9}$heteroaryl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein $R^2$ is selected from a group consisting of pyrazole, imidazole, thiazole, and pyridine; wherein pyrazole, imidazole, thiazole, and pyridine are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein $R^2$ is selected from a group consisting of pyrazole, imidazole, thiazole, and pyridine; wherein pyrazole, imidazole, thiazole, and pyridine are optionally substituted with one or two substituents selected from the group consisting of halogen, $C_{1-6}$alkyl, and $C_{3-8}$cycloalkyl. In some embodiments is a compound of Formula (I), or a pharmaceutically acceptable salt or solvate thereof, wherein $R^2$ is

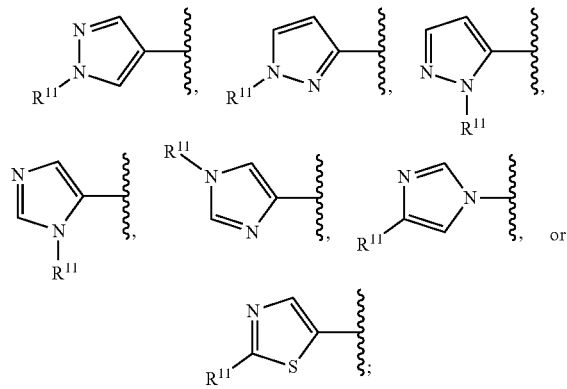

wherein $R^{11}$ is $C_{1-6}$alkyl or $C_{3-6}$cycloalkyl. In some embodiments is a compound of Formula (I), or a pharmaceutically acceptable salt or solvate thereof, wherein $R^2$ is

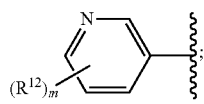

wherein each $R^{12}$ is independently hydrogen, halogen, CN, $C_{1-6}$alkyl, or $C_{3-6}$cycloalkyl; and m is 1 or 2. In some embodiments is a compound of Formula (I), or a pharmaceutically acceptable salt or solvate thereof, wherein $R^2$ is selected from a group consisting of unsubstituted pyrazole, unsubstituted imidazole, unsubstituted thiazole, and unsubstituted pyridine. In some embodiments, $R^2$ is $C_{6-10}$aryl optionally substituted with one, two, or three substituents selected from the group consisting of halogen, —CN, $C_{1-6}$alkyl, —$C_{1-6}$ alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^1$, —C(=O)OR$^{13}$, —C(=O)N(R$^{13}$)$_2$, —S(=O)R$^{14}$, —S(=O)$_2$R$^{13}$, —S(=O)$_2$—N(R$^3$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (I), or a pharmaceutically acceptable salt or solvate thereof, wherein $R^2$ is phenyl optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (I), or a pharmaceutically acceptable salt or solvate thereof, wherein $R^2$ is —C(=O)N(R$^6$)$_2$ and each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl. In some embodiments is a compound of Formula (I), or a pharmaceutically acceptable salt or solvate thereof, wherein $R^2$ is

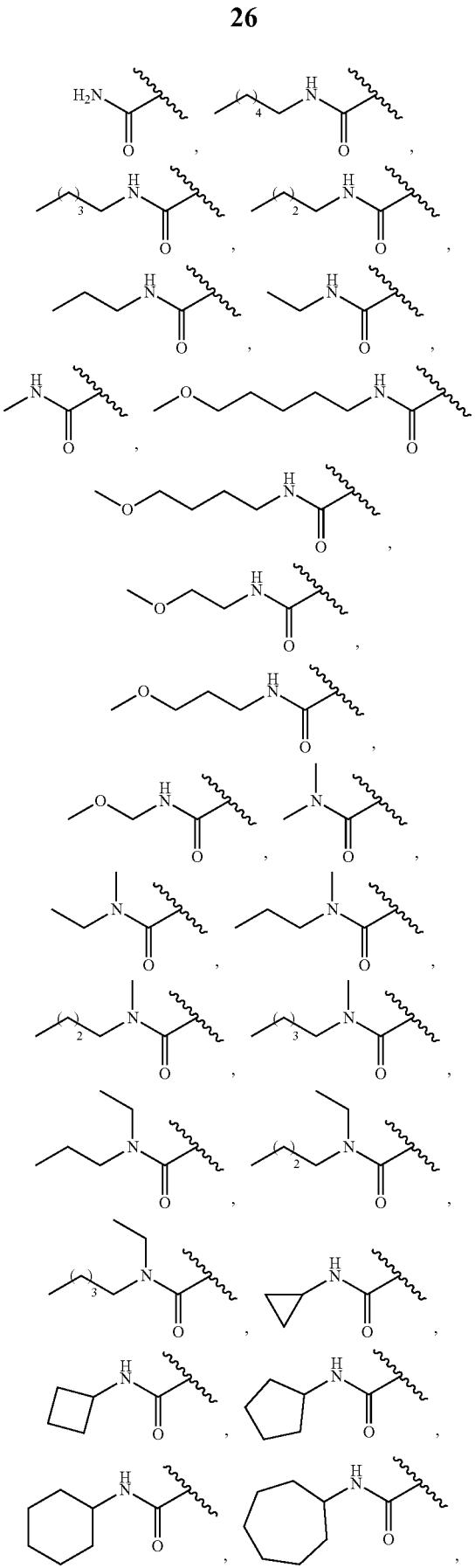

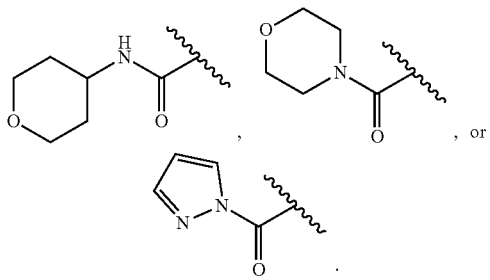

In some embodiments is a compound of Formula (I), or a pharmaceutically acceptable salt or solvate thereof, wherein $R^2$ is

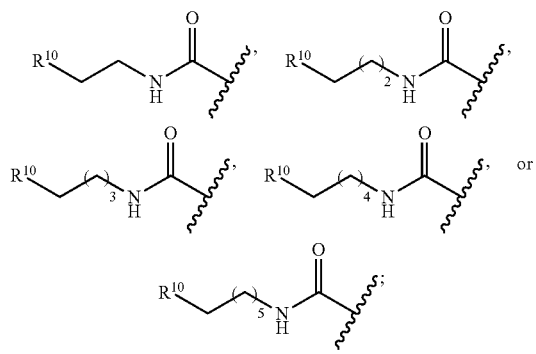

wherein $R^{10}$ is $C_{1-9}$heteroaryl. In some embodiments is a compound of Formula (I), or a pharmaceutically acceptable salt or solvate thereof, wherein $R^2$ is —NHC(=O)$R^7$. In some embodiments is a compound of Formula (I), or a pharmaceutically acceptable salt or solvate thereof, wherein $R^2$ is

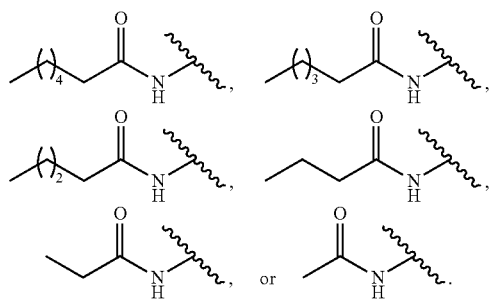

In some embodiments is a compound of Formula (I), or a pharmaceutically acceptable salt or solvate thereof, wherein $R^2$ is —C(=O)$R^7$. In some embodiments is a compound of Formula (I), or a pharmaceutically acceptable salt or solvate thereof, wherein $R^2$ is

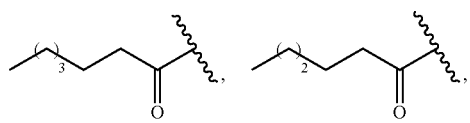

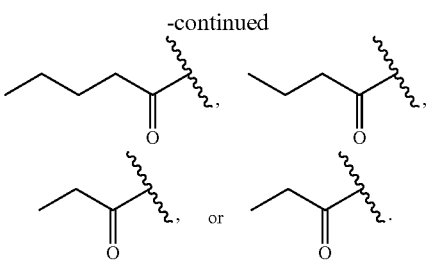

In some embodiments is a compound of Formula (I), or a pharmaceutically acceptable salt or solvate thereof, wherein $R^3$ is hydrogen. In some embodiments is a compound of Formula (I), or a pharmaceutically acceptable salt or solvate thereof, wherein $R^3$ is $C_{1-6}$alkyl. In some embodiments is a compound of Formula (I), or a pharmaceutically acceptable salt or solvate thereof, wherein $R^3$ is halogen.

In some embodiments is a compound of Formula (I), or a pharmaceutically acceptable salt or solvate thereof, wherein

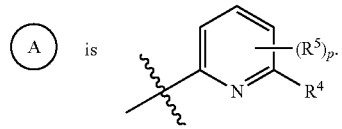

In some embodiments is a compound of Formula (I), or a pharmaceutically acceptable salt or solvate thereof, wherein

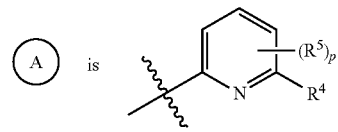

and p is 2. In some embodiments is a compound of Formula (I), or a pharmaceutically acceptable salt or solvate thereof, wherein

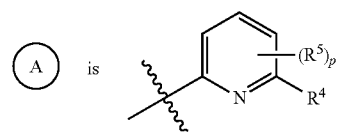

and p is 1. In some embodiments is a compound of Formula (I), or a pharmaceutically acceptable salt or solvate thereof, wherein

and p is 0. In some embodiments is a compound of Formula (I), or a pharmaceutically acceptable salt or solvate thereof, wherein

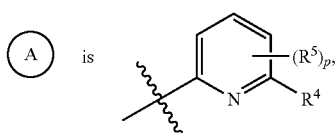

p is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R³)S(=O)₂R. In some embodiments is a compound of Formula (I), or a pharmaceutically acceptable salt or solvate thereof, wherein

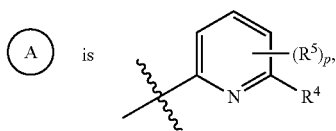

p is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein is

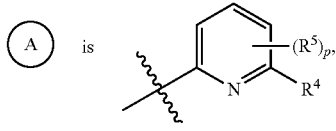

p is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein

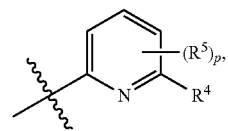

p is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³.
In some embodiments is a compound of Formula (I), or a pharmaceutically acceptable salt or solvate thereof, wherein

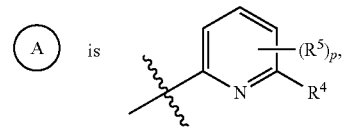

p is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (I), or a pharmaceutically acceptable salt or solvate thereof, wherein

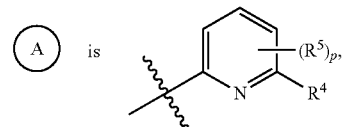

p is 0, and R⁴ is

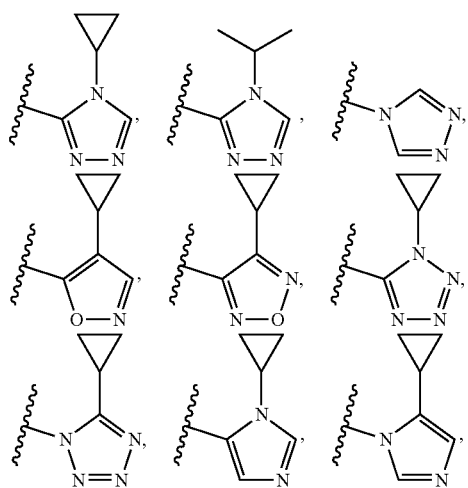

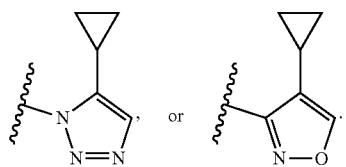, or 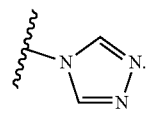

In some embodiments is a compound of Formula (I), or a pharmaceutically acceptable salt or solvate thereof, wherein

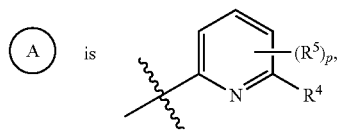

p is 0, and R⁴ is

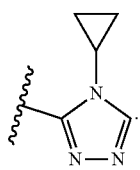

In some embodiments is a compound of Formula (I), or a pharmaceutically acceptable salt or solvate thereof, wherein

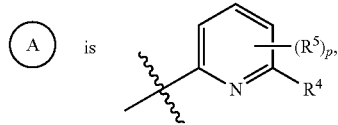

p is 0, and R⁴ is

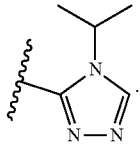 [SMILES: *c1nncn1C(C)C]

In some embodiments is a compound of Formula (I), or a pharmaceutically acceptable salt or solvate thereof, wherein

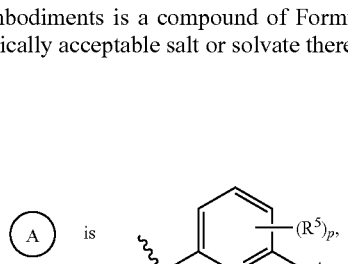

In some embodiments is a compound of Formula (I), or a pharmaceutically acceptable salt or solvate thereof, wherein

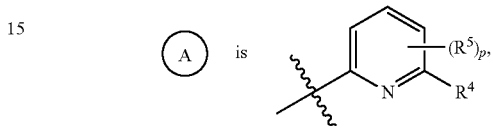

p is 0, and R⁴ is

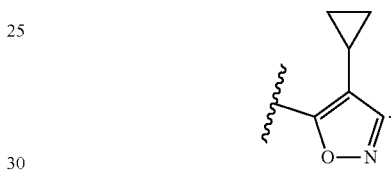

In some embodiments is a compound of Formula (I), or a pharmaceutically acceptable salt or solvate thereof, wherein

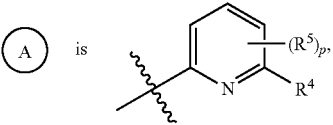

p is 0, and R⁴ is

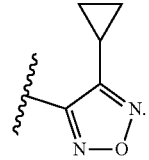 [SMILES: *c1nonc1C1CC1]

In some embodiments is a compound of Formula (I), or a pharmaceutically acceptable salt or solvate thereof, wherein

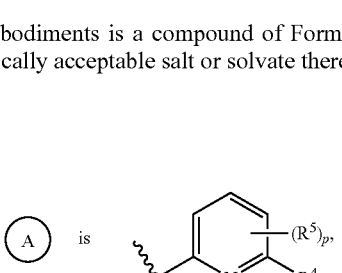

p is 0, and R⁴ is

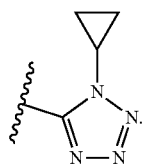 [SMILES: *c1nnnn1C1CC1]

In some embodiments is a compound of Formula (I), or a pharmaceutically acceptable salt or solvate thereof, wherein

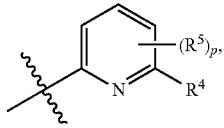

p is 0, and R⁴ is

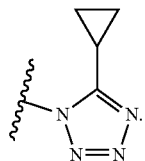 [SMILES: *n1nnnc1C1CC1]

In some embodiments is a compound of Formula (I), or a pharmaceutically acceptable salt or solvate thereof, wherein

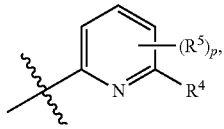

p is 0, and R⁴ is

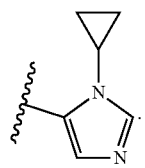

In some embodiments is a compound of Formula (I), or a pharmaceutically acceptable salt or solvate thereof, wherein

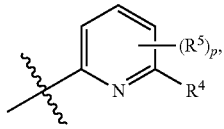

p is 0, and R⁴ is

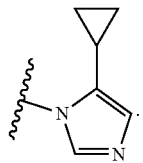

In some embodiments is a compound of Formula (I), or a pharmaceutically acceptable salt or solvate thereof, wherein

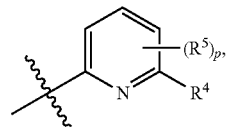

p is 0, and R⁴ is

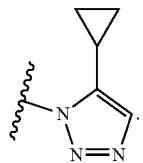

In some embodiments is a compound of Formula (I), or a pharmaceutically acceptable salt or solvate thereof, wherein

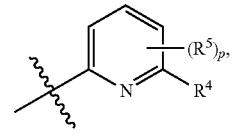

p is 0, and R⁴ is

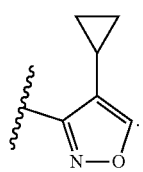

In some embodiments is a compound of Formula (I), or a pharmaceutically acceptable salt or solvate thereof, wherein

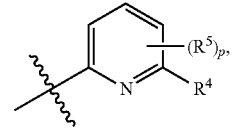

p is 0, and R⁴ is

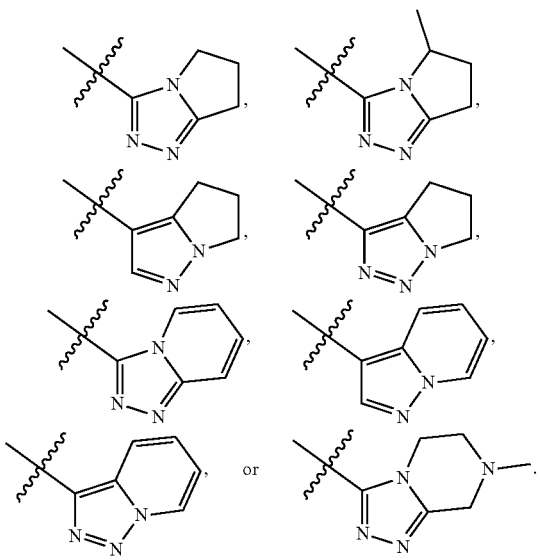

In some embodiments is a compound of Formula (I), or a pharmaceutically acceptable salt or solvate thereof, wherein

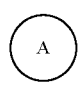 is 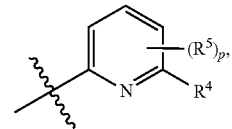

p is 0, and R⁴ is

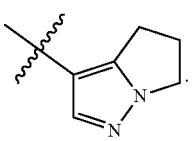

In some embodiments is a compound of Formula (I), or a pharmaceutically acceptable salt or solvate thereof, wherein

 is 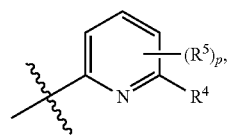

p is 0, and R⁴ is

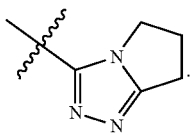 [SMILES: *c1nnc2n1CCC2]

In some embodiments is a compound of Formula (I), or a pharmaceutically acceptable salt or solvate thereof, wherein

 is 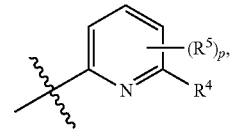

p is 0, and R⁴ is

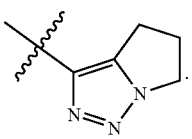

In some embodiments is a compound of Formula (I), or a pharmaceutically acceptable salt or solvate thereof, wherein

 is 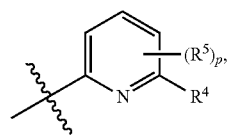

p is 0, and R⁴ is

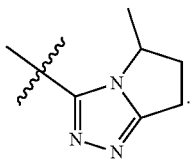 [SMILES: *c1nnc2n1C(C)CC2]

In some embodiments is a compound of Formula (I), or a pharmaceutically acceptable salt or solvate thereof, wherein

 is 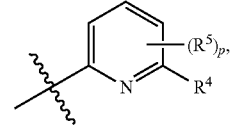

p is 0, and R⁴ is

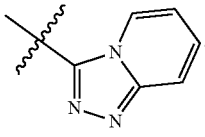

In some embodiments is a compound of Formula (I), or a pharmaceutically acceptable salt or solvate thereof, wherein

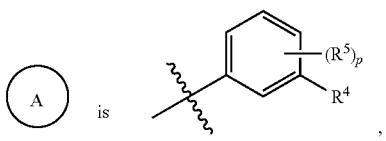

p is 0, and R⁴ is

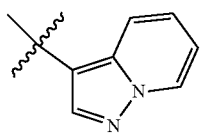

In some embodiments is a compound of Formula (I), or a pharmaceutically acceptable salt or solvate thereof, wherein

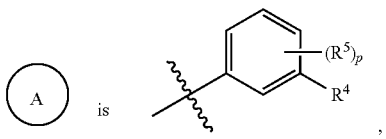

p is 0, and R⁴ is

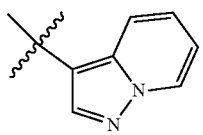

In some embodiments is a compound of Formula (I), or a pharmaceutically acceptable salt or solvate thereof, wherein

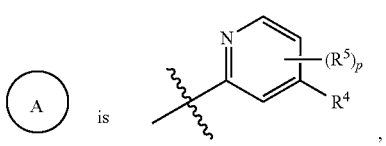

p is 0, and R⁴ is

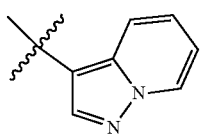

In some embodiments is a compound of Formula (I), or a pharmaceutically acceptable salt or solvate thereof, wherein

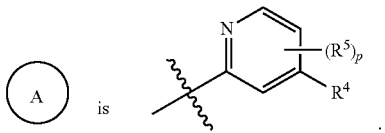

In some embodiments is a compound of Formula (I), or a pharmaceutically acceptable salt or solvate thereof, wherein

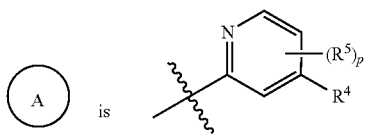

and q is 2. In some embodiments is a compound of Formula (I), or a pharmaceutically acceptable salt or solvate thereof, wherein

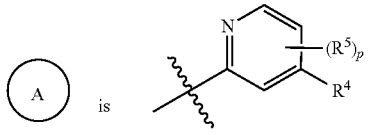

and q is 1. In some embodiments is a compound of Formula (I), or a pharmaceutically acceptable salt or solvate thereof, wherein

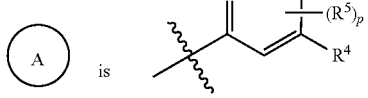

and q is 0. In some embodiments is a compound of Formula (I), or a pharmaceutically acceptable salt or solvate thereof, wherein

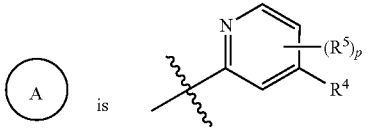

q is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein

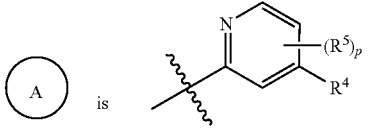

q is 0, and R⁴ is selected from a group consisting of a C₁₋₉heteroaryl and a fused C₅₋₉heteroaryl-cycloalkyl; wherein the C₁₋₉heteroaryl and fused C₅₋₉heteroaryl-cycloalkyl are optionally substituted with one, two, or three substituents selected from the group consisting of halogen, —CN, C₁₋₆alkyl, —C₁₋₆alkyl-OH, C₁₋₆ haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein

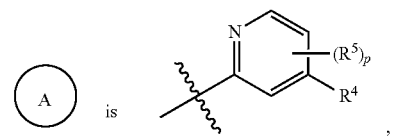

, q is 0, and R⁴ is selected from a group consisting of a C₁₋₉heteroaryl and a fused C₅₋₉heteroaryl-cycloalkyl; wherein the C₁₋₉heteroaryl and fused C₅₋₉heteroaryl-cycloalkyl are optionally substituted with one or two substituents selected from the group consisting of halogen, —CN, C₁₋₆alkyl, —C₁₋₆alkyl-OH, C₁₋₆ haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein

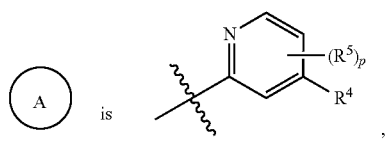

, q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, C₁₋₆ alkyl, —C₁₋₆alkyl-OH, C₁₋₆haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (I), or a pharmaceutically acceptable salt or solvate thereof, wherein

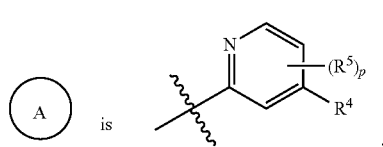

, q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, C₁₋₆alkyl, and C₃₋₈cycloalkyl. In some embodiments is a compound of Formula (I), or a pharmaceutically acceptable salt or solvate thereof, wherein

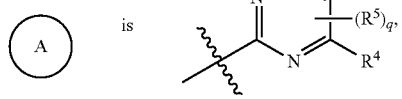

q is 0, and

R⁴ is 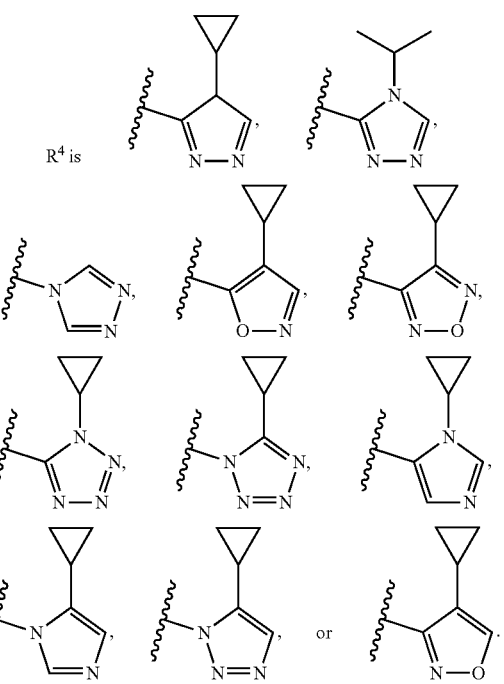

In some embodiments is a compound of Formula (I), or a pharmaceutically acceptable salt or solvate thereof, wherein

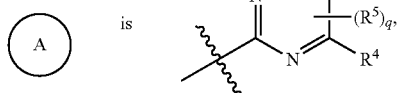

q is 0, and R⁴ is

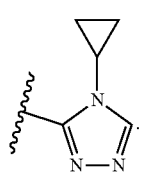

In some embodiments is a compound of Formula (I), or a pharmaceutically acceptable salt or solvate thereof, wherein

 is 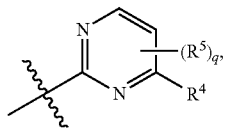

q is 0, and R⁴ is

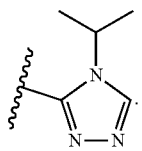 [SMILES: *c1nncn1C(C)C]

In some embodiments is a compound of Formula (I), or a pharmaceutically acceptable salt or solvate thereof, wherein

 is 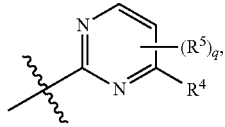

q is 0, and R is

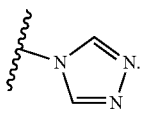

In some embodiments is a compound of Formula (I), or a pharmaceutically acceptable salt or solvate thereof, wherein

 is 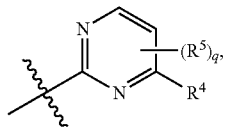

q is 0, and R⁴ is

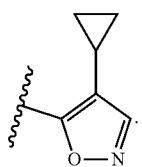

In some embodiments is a compound of Formula (I), or a pharmaceutically acceptable salt or solvate thereof, wherein

 is 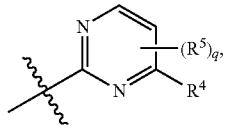

q is 0, and R⁴ is

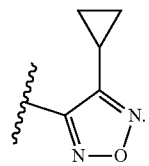

In some embodiments is a compound of Formula (I), or a pharmaceutically acceptable salt or solvate thereof, wherein

 is 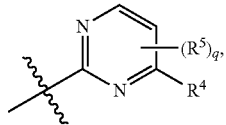

q is 0, and R⁴ is

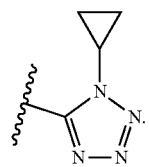

In some embodiments is a compound of Formula (I), or a pharmaceutically acceptable salt or solvate thereof, wherein

 is 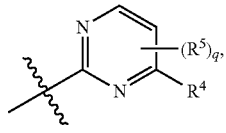

q is 0, and R⁴ is

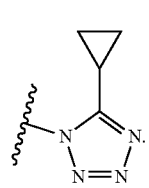

In some embodiments is a compound of Formula (I), or a pharmaceutically acceptable salt or solvate thereof, wherein q is 0, and R⁴ is

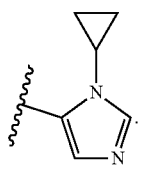

In some embodiments is a compound of Formula (I), or a pharmaceutically acceptable salt or solvate thereof, wherein

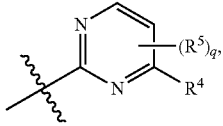

q is 0, and R⁴ is

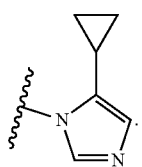

In some embodiments is a compound of Formula (I), or a pharmaceutically acceptable salt or solvate thereof, wherein

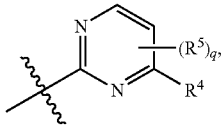

q is 0, and R⁴ is

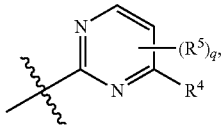

In some embodiments is a compound of Formula (I), or a pharmaceutically acceptable salt or solvate thereof, wherein q is 0, and R⁴ is

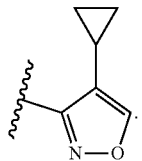 [SMILES: *c1nocc1C1CC1]

In some embodiments is a compound of Formula (I), or a pharmaceutically acceptable salt or solvate thereof, wherein

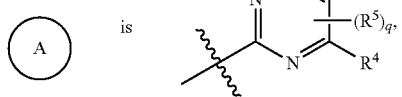

q is 0, and R⁴ is

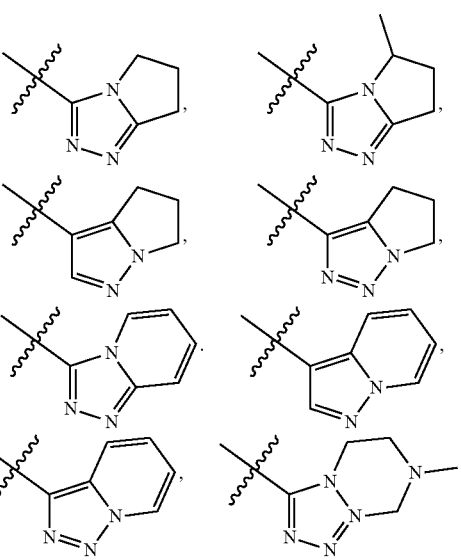

In some embodiments is a compound of Formula (I), or a pharmaceutically acceptable salt or solvate thereof, wherein q is 0, and R⁴ is

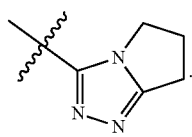 [SMILES: *c1nnc2n1CCC2]

In some embodiments is a compound of Formula (I), or a pharmaceutically acceptable salt or solvate thereof, wherein

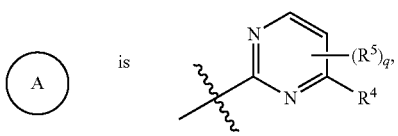 is q is 0, and R⁴ is

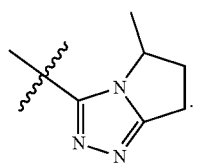

In some embodiments is a compound of Formula (I), or a pharmaceutically acceptable salt or solvate thereof, wherein

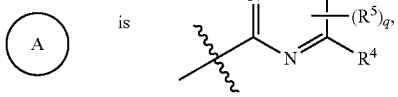 is q is 0, and R⁴ is

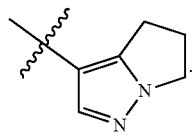

In some embodiments is a compound of Formula (I), or a pharmaceutically acceptable salt or solvate thereof, wherein

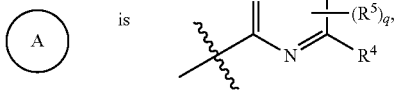 is q is 0, and R⁴ is

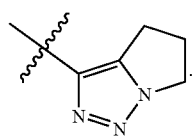

In some embodiments is a compound of Formula (I), or a pharmaceutically acceptable salt or solvate thereof, wherein

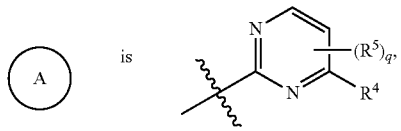 is q is 0, and R⁴ is

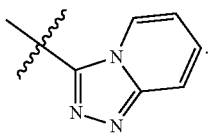 [SMILES: *c1nnc2ccccn12]

In some embodiments is a compound of Formula (I), or a pharmaceutically acceptable salt or solvate thereof, wherein

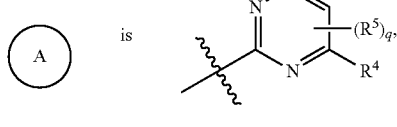 is q is 0, and R⁴ is

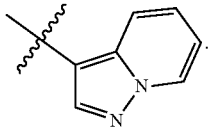 [SMILES: *c1cnn2ccccc12]

In some embodiments is a compound of Formula (I), or a pharmaceutically acceptable salt or solvate thereof, wherein

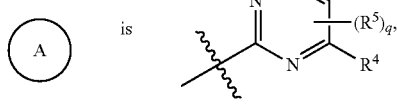 is q is 0, and R⁴ is

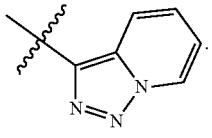

In some embodiments is a compound of Formula (I), or a pharmaceutically acceptable salt or solvate thereof, wherein

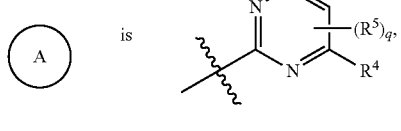

q is 0, and $R^4$ is

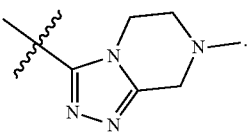 [SMILES: *c1nnc2n1CCN(C)C2]

In some embodiments is a compound of Formula (I), or a pharmaceutically acceptable salt or solvate thereof, wherein

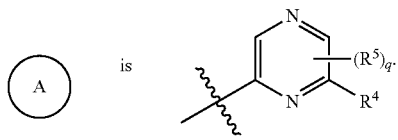

In some embodiments is a compound of Formula (I), or a pharmaceutically acceptable salt or solvate thereof, wherein

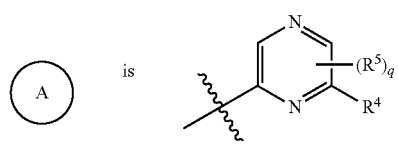

and q is 2. In some embodiments is a compound of Formula (I), or a pharmaceutically acceptable salt or solvate thereof, wherein

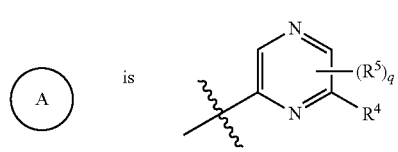

and q is 1. In some embodiments is a compound of Formula (I), or a pharmaceutically acceptable salt or solvate thereof, wherein

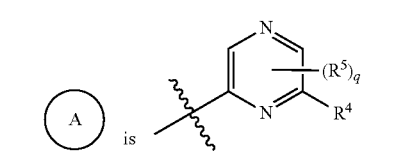

and q is 0. In some embodiments is a compound of Formula (I), or a pharmaceutically acceptable salt or solvate thereof, wherein

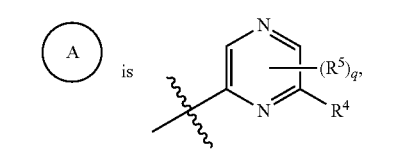

q is 0, and $R^4$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$ aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$ cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein

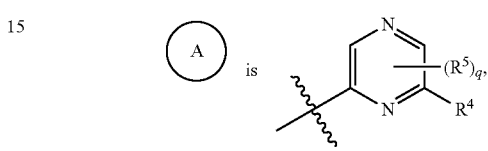

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein

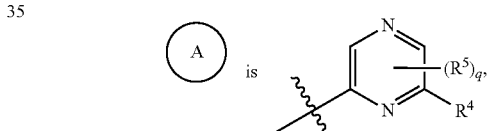

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein

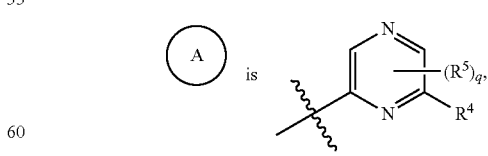

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.
In some embodiments is a compound of Formula (I), or a pharmaceutically acceptable salt or solvate thereof, wherein

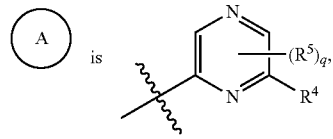

q is 0, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (I), or a pharmaceutically acceptable salt or solvate thereof, wherein

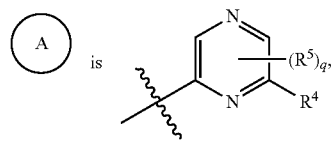

q is 0, and R$^4$ is

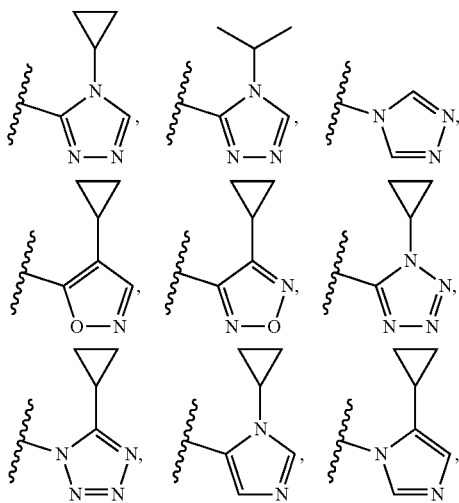

In some embodiments is a compound of Formula (I), or a pharmaceutically acceptable salt or solvate thereof, wherein

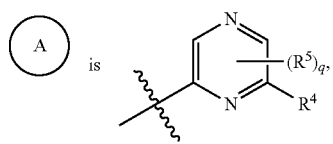

q is 0, and R$^4$ is

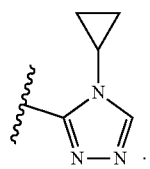

In some embodiments is a compound of Formula (I), or a pharmaceutically acceptable salt or solvate thereof, wherein

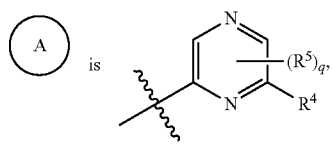

q is 0, and R$^4$ is

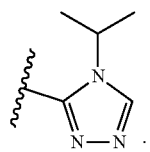 [SMILES: *c1nncn1C(C)C]

In some embodiments is a compound of Formula (I), or a pharmaceutically acceptable salt or solvate thereof, wherein

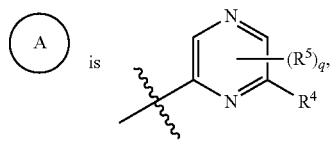

q is 0, and R$^4$ is

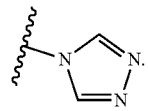

In some embodiments is a compound of Formula (I), or a pharmaceutically acceptable salt or solvate thereof, wherein

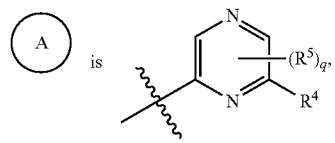

q is 0, and R⁴ is

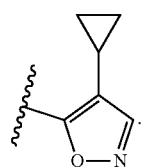

In some embodiments is a compound of Formula (I), or a pharmaceutically acceptable salt or solvate thereof, wherein

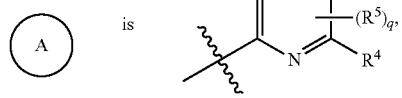

q is 0, and R⁴ is

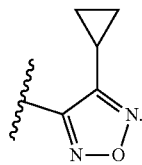 [SMILES: *c1nonc1C1CC1]

In some embodiments is a compound of Formula (I), or a pharmaceutically acceptable salt or solvate thereof, wherein

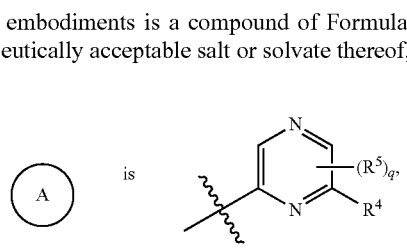

q is 0, and R is

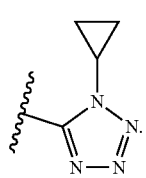 [SMILES: *c1nnnn1C1CC1]

In some embodiments is a compound of Formula (I), or a pharmaceutically acceptable salt or solvate thereof, wherein

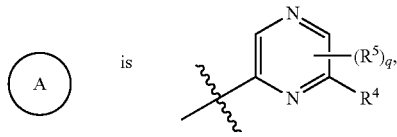

q is 0, and R⁴ is

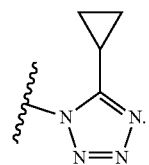 [SMILES: *n1nnnc1C1CC1]

In some embodiments is a compound of Formula (I), or a pharmaceutically acceptable salt or solvate thereof, wherein

q is 0, and

R⁴ is 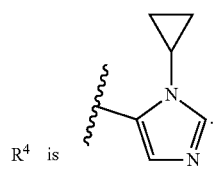

In some embodiments is a compound of Formula (I), or a pharmaceutically acceptable salt or solvate thereof, wherein

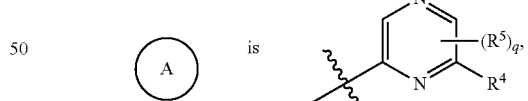

q is 0, and R⁴ is

In some embodiments is a compound of Formula (I), or a pharmaceutically acceptable salt or solvate thereof, wherein

 is 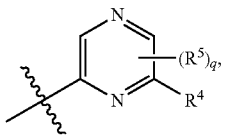

q is 0, and R⁴ is

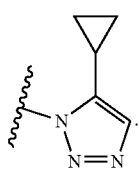

In some embodiments is a compound of Formula (I), or a pharmaceutically acceptable salt or solvate thereof, wherein

 is 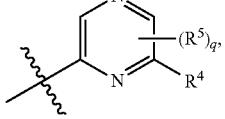

q is 0, and R⁴ is

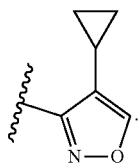

In some embodiments is a compound of Formula (I), or a pharmaceutically acceptable salt or solvate thereof, wherein

 is 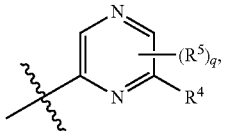

q is 0, and R⁴ is

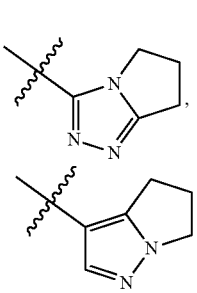, 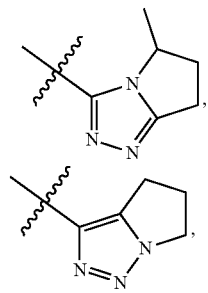,

-continued

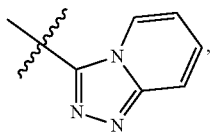, 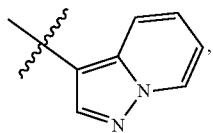

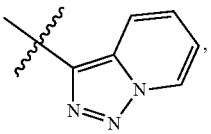, or 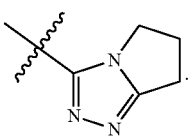.

In some embodiments is a compound of Formula (I), or a pharmaceutically acceptable salt or solvate thereof,

 is 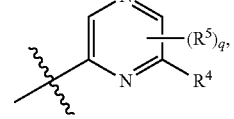

q is 0, an R⁴ is

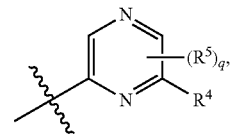

In some embodiments is a compound of Formula (I), or a pharmaceutically acceptable salt or solvate thereof,

 is 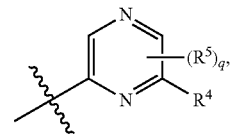

q is 0, and R⁴ is

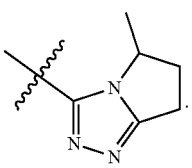 [SMILES: *c1nnc2n1C(C)CC2].

In some embodiments is a compound of Formula (I), or a pharmaceutically acceptable salt or solvate thereof, wherein

 is 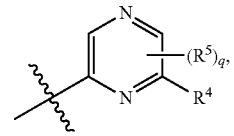

q is 0, and R⁴ is

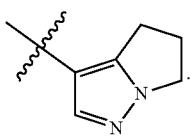

In some embodiments is a compound of Formula (I), or a pharmaceutically acceptable salt or solvate thereof, wherein

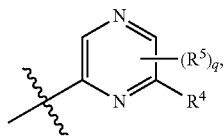

q is 0, and R⁴ is

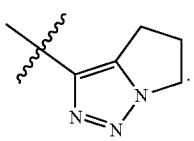

In some embodiments is a compound of Formula (I), or a pharmaceutically acceptable salt or solvate thereof, wherein

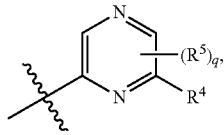

q is 0, and R⁴ is

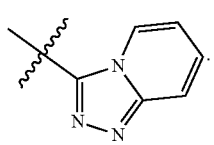 [SMILES: *c1nnc2ccccn12]

In some embodiments is a compound of Formula (I), or a pharmaceutically acceptable salt or solvate thereof, wherein

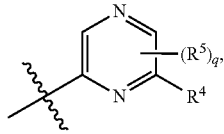

q is 0, and R⁴ is

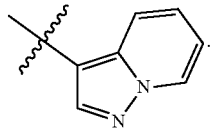 [SMILES: *c1cnn2ccccc12]

In some embodiments is a compound of Formula (I), or a pharmaceutically acceptable salt or solvate thereof, wherein

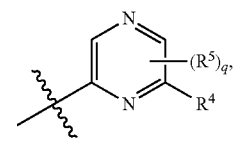

q is 0, and R⁴ is

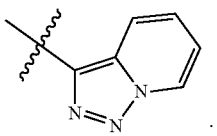 [SMILES: *c1nnn2ccccc12]

In some embodiments is a compound of Formula (I), or a pharmaceutically acceptable salt or solvate thereof, wherein

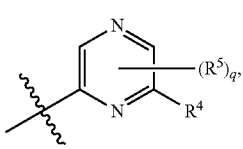

q is 0, and R⁴ is

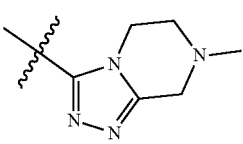

In some embodiments is a compound of Formula (I), or a pharmaceutically acceptable salt or solvate thereof, wherein

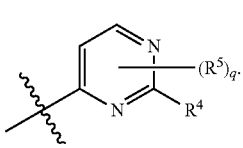

In some embodiments is a compound of Formula (I), or a pharmaceutically acceptable salt or solvate thereof, wherein

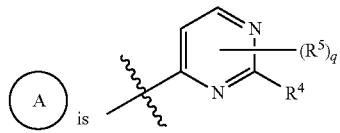

and q is 2. In some embodiments is a compound of Formula (I), or a pharmaceutically acceptable salt or solvate thereof, wherein

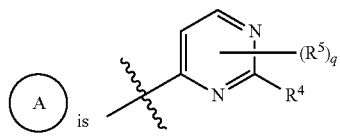

and q is 1. In some embodiments is a compound of Formula (I), or a pharmaceutically acceptable salt or solvate thereof, wherein

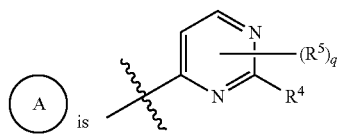

and q is 0. In some embodiments is a compound of Formula (I), or a pharmaceutically acceptable salt or solvate thereof, wherein

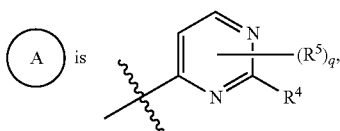

q is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.
In some embodiments is a compound of Formula (I), or a pharmaceutically acceptable salt or solvate thereof, wherein

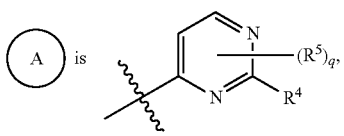

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.
In some embodiments is a compound of Formula (I), or a pharmaceutically acceptable salt or solvate thereof, wherein

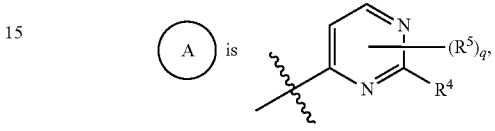

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (I), or a pharmaceutically acceptable salt or solvate thereof, wherein

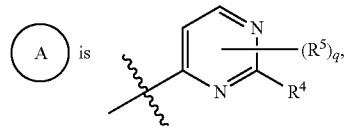

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.
In some embodiments is a compound of Formula (I), or a pharmaceutically acceptable salt or solvate thereof, wherein

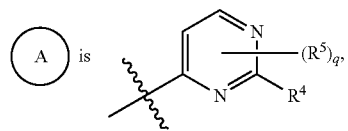

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (I), or a pharmaceutically acceptable salt or solvate thereof, wherein,

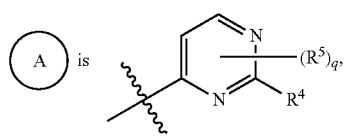 is 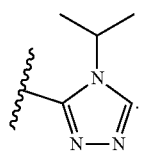

q is 0, and R⁴ is

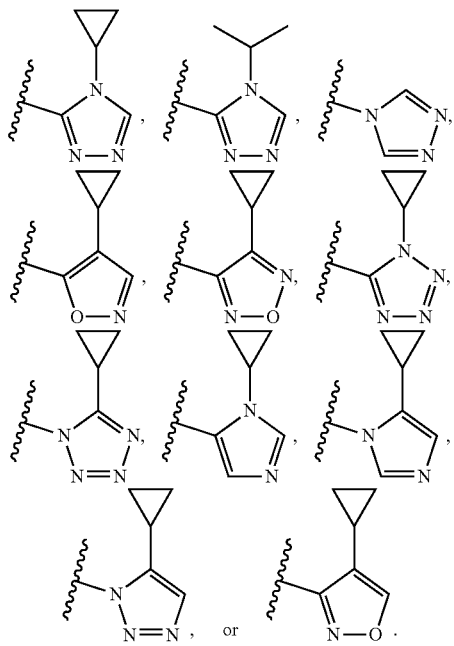

In some embodiments is a compound of Formula (I), or a pharmaceutically acceptable salt or solvate thereof, wherein

 is 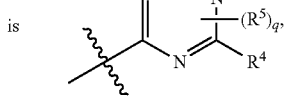

q is 0, and R⁴ is

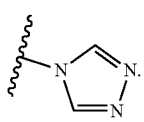

In some embodiments is a compound of Formula (I), or a pharmaceutically acceptable salt or solvate thereof, wherein

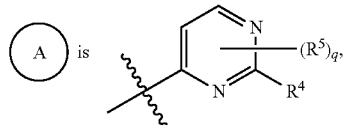 is 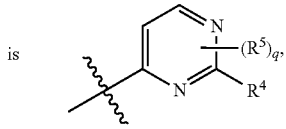

q is 0, and R⁴ is

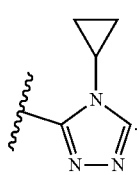

In some embodiments is a compound of Formula (I), or a pharmaceutically acceptable salt or solvate thereof, wherein

 is 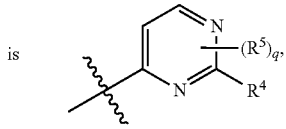

q is 0, and R⁴ is

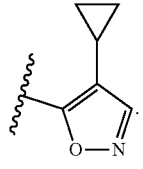

In some embodiments is a compound of Formula (I), or a pharmaceutically acceptable salt or solvate thereof, wherein

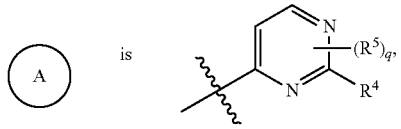 is

 is 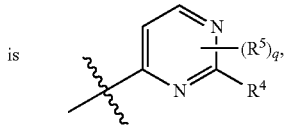

q is 0, and R⁴ is

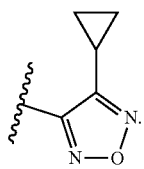 [SMILES: *c1nonc1C1CC1]

In some embodiments is a compound of Formula (I), or a pharmaceutically acceptable salt or solvate thereof, wherein is

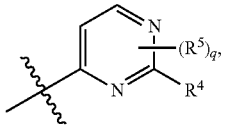

q is 0, and R⁴ is

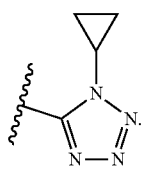

In some embodiments is a compound of Formula (I), or a pharmaceutically acceptable salt or solvate thereof, wherein

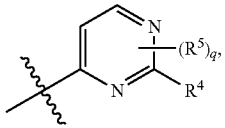

q is 0, and R⁴ is

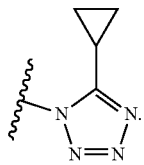 [SMILES: *n1nnnc1C1CC1]

In some embodiments is a compound of Formula (I), or a pharmaceutically acceptable salt or solvate thereof, wherein

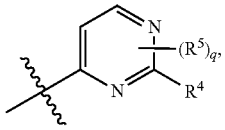

q is 0, and R⁴ is

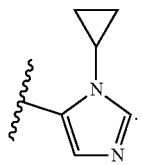 [SMILES: *c1cncn1C1CC1]

In some embodiments is a compound of Formula (I), or a pharmaceutically acceptable salt or solvate thereof, wherein

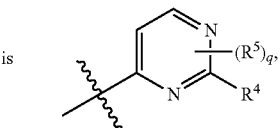

q is 0, and R⁴ is

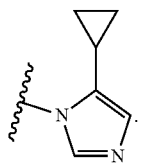 [SMILES: *n1cncc1C1CC1]

In some embodiments is a compound of Formula (I), or a pharmaceutically acceptable salt or solvate thereof, wherein

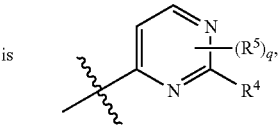

q is 0, and R⁴ is

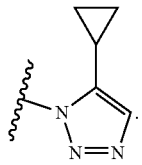

In some embodiments is a compound of Formula (I), or a pharmaceutically acceptable salt or solvate thereof, wherein

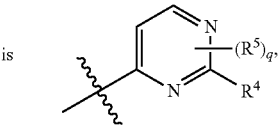

q is 0, and R⁴ is

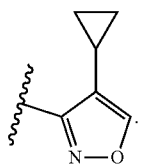

In some embodiments is a compound of Formula (I), or a pharmaceutically acceptable salt or solvate thereof, wherein

q is 0, and R⁴ is

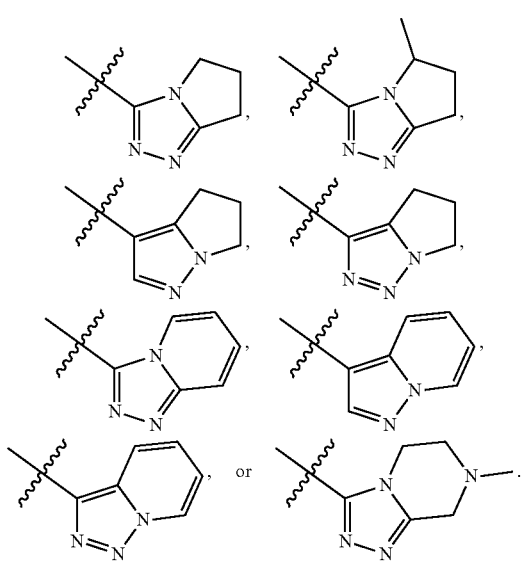

In some embodiments is a compound of Formula (I), or a pharmaceutically acceptable salt or solvate thereof, wherein

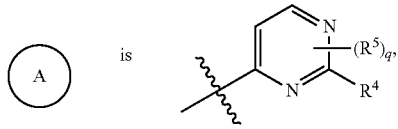

q is 0, and R⁴ is

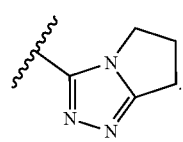 [SMILES: *c1nnc2n1CCC2]

In some embodiments is a compound of Formula (I), or a pharmaceutically acceptable salt or solvate thereof, wherein

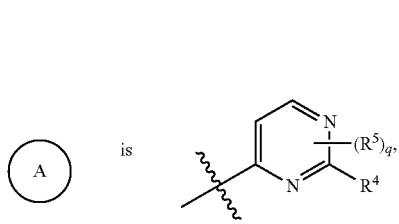

q is 0, and R⁴ is

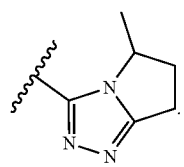 [SMILES: *c1nnc2n1C(C)CC2]

In some embodiments is a compound of Formula (I), or a pharmaceutically acceptable salt or solvate thereof, wherein

q is 0, and R⁴ is

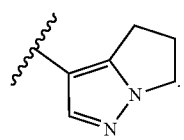 [SMILES: *c1cnn2c1CCC2]

In some embodiments is a compound of Formula (I), or a pharmaceutically acceptable salt or solvate thereof, wherein

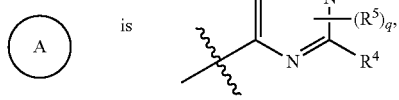

q is 0, and R⁴ is

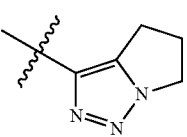

In some embodiments is a compound of Formula (I), or a pharmaceutically acceptable salt or solvate thereof, wherein

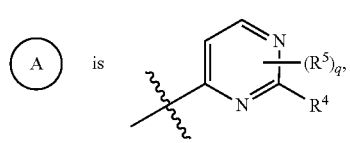

q is 0, and R⁴ is

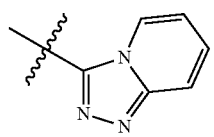

In some embodiments is a compound of Formula (I), or a pharmaceutically acceptable salt or solvate thereof, wherein

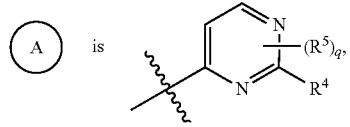

q is 0, and R⁴ is

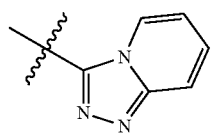

In some embodiments is a compound of Formula (I), or a pharmaceutically acceptable salt or solvate thereof, wherein

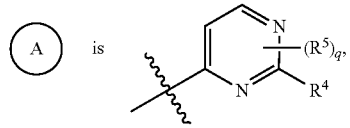

q is 0, and R⁴ is

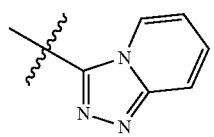

In some embodiments is a compound of Formula (I), or a pharmaceutically acceptable salt or solvate thereof, wherein

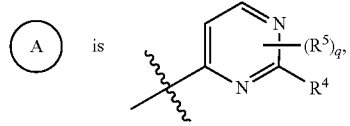

q is 0, and R⁴ is

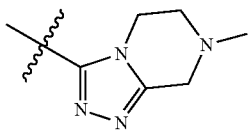

In some embodiments is a compound of Formula (I), or a pharmaceutically acceptable salt or solvate thereof, wherein

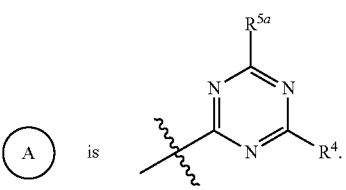

In some embodiments is a compound of Formula (I), or a pharmaceutically acceptable salt or solvate thereof, wherein

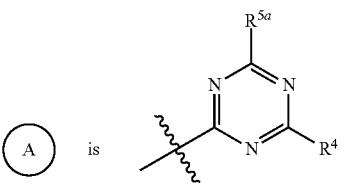

and q is 2. In some embodiments is a compound of Formula (I), or a pharmaceutically acceptable salt or solvate thereof, wherein

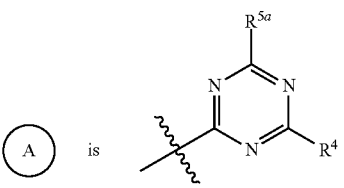

and q is 1. In some embodiments is a compound of Formula (I), or a pharmaceutically acceptable salt or solvate thereof, wherein

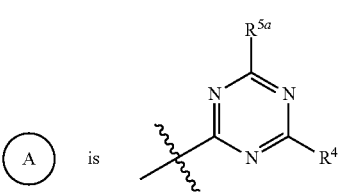

and q is 0. In some embodiments is a compound of Formula (I), or a pharmaceutically acceptable salt or solvate thereof, wherein

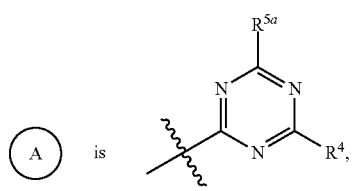

R$^{5a}$ is hydrogen, and R$^4$ is selected from a group consisting of C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$ heteroaryl-cycloalkyl are optionally substituted with one, two, or three substituents selected from the group consisting of halogen, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (I), or a pharmaceutically acceptable salt or solvate thereof, wherein

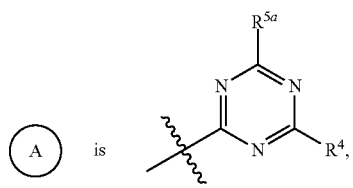

R$^{5a}$ is hydrogen, and R$^4$ is selected from a group consisting of a C$_{1-9}$heteroaryl and a fused C$_{5-9}$heteroaryl-cycloalkyl; wherein the C$_{1-9}$heteroaryl and fused C$_{5-9}$heteroaryl-cycloalkyl are optionally substituted with one, two, or three substituents selected from the group consisting of halogen, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (I), or a pharmaceutically acceptable salt or solvate thereof, wherein

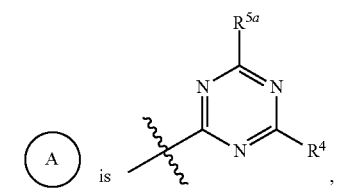

R$^{5a}$ is hydrogen, and R$^4$ is selected from a group consisting of a C$_{1-9}$heteroaryl and a fused C$_{5-9}$heteroaryl-cycloalkyl; wherein the C$_{1-9}$heteroaryl and fused C$_{5-9}$heteroaryl-cycloalkyl are optionally substituted with one or two substituents selected from the group consisting of halogen, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$) C(=O)R$^{14}$, and —N(R$^{13}$)S(=O)$_2$R$^{13}$. In some embodiments is a compound of Formula (I), or a pharmaceutically acceptable salt or solvate thereof, wherein

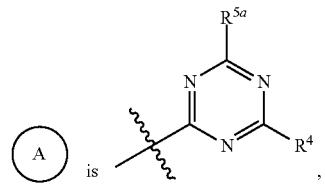

R$^{5a}$ is hydrogen, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (I), or a pharmaceutically acceptable salt or solvate thereof, wherein

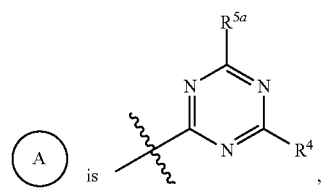

R$^{5a}$ is hydrogen, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, C$_{1-6}$alkyl, and C$_{3-8}$cycloalkyl. In some embodiments is a compound of Formula (I), or a pharmaceutically acceptable salt or solvate thereof, wherein R$^a$ is hydrogen, and R$^4$ is

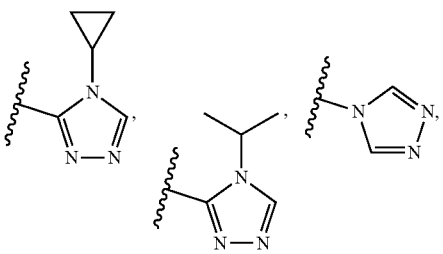

-continued

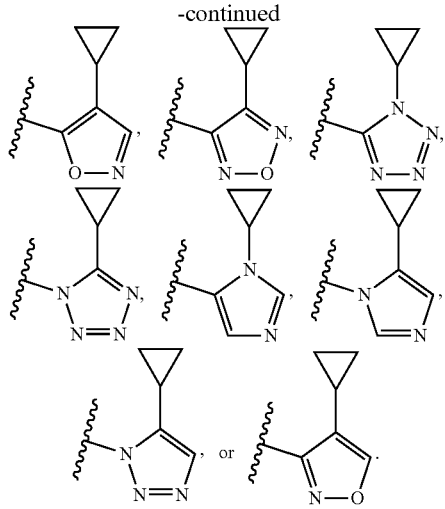

In some embodiments is a compound of Formula (I), or a pharmaceutically acceptable salt or solvate thereof, wherein

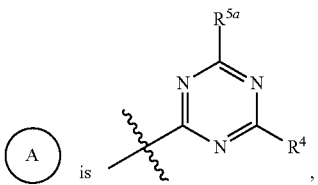

$R^{5a}$ is hydrogen, and $R^4$ is

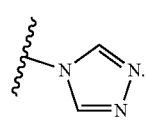

In some embodiments is a compound of Formula (I), or a pharmaceutically acceptable salt or solvate thereof, wherein

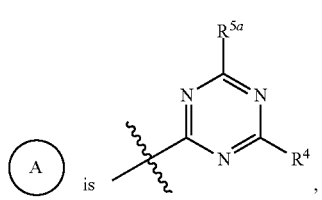

$R^{5a}$ is hydrogen, and $R^4$ is

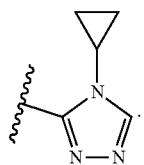

In some embodiments is a compound of Formula (I), or a pharmaceutically acceptable salt or solvate thereof, wherein

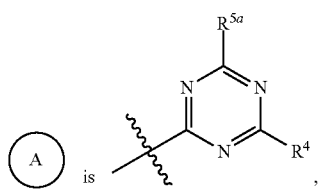

$R^{5a}$ is hydrogen, and $R^4$ is

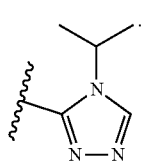 [SMILES: *c1nncn1C(C)C]

In some embodiments is a compound of Formula (I), or a pharmaceutically acceptable salt or solvate thereof, wherein

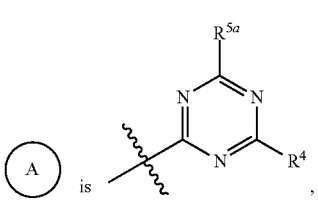

$R^{5a}$ is hydrogen, and $R^4$ is

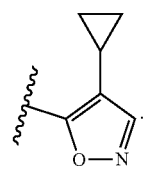

In some embodiments is a compound of Formula (I), or a pharmaceutically acceptable salt or solvate thereof, wherein

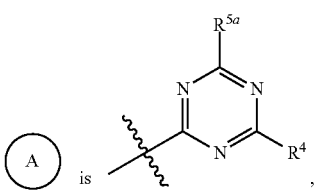

$R^{5a}$ is hydrogen, and $R^4$ is

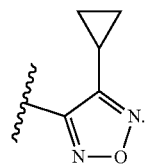 [SMILES: *c1nonc1C1CC1]

In some embodiments is a compound of Formula (I), or a pharmaceutically acceptable salt or solvate thereof, wherein

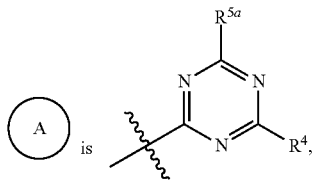

$R^{5a}$ is hydrogen, and $R^4$ is

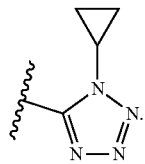 [SMILES: *c1nnnn1C1CC1]

In some embodiments is a compound of Formula (I), or a pharmaceutically acceptable salt or solvate thereof, wherein

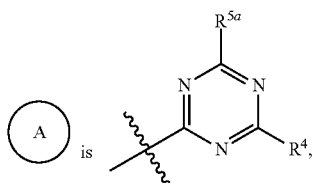

$R^{5a}$ is hydrogen, and $R^4$ is

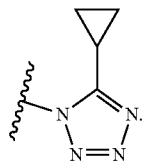 [SMILES: *n1nnnc1C1CC1]

In some embodiments is a compound of Formula (I), or a pharmaceutically acceptable salt or solvate thereof, wherein

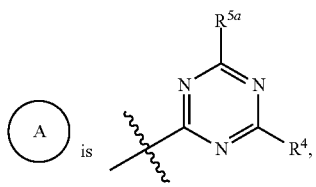

$R^{5a}$ is hydrogen, and $R^4$ is

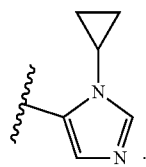

In some embodiments is a compound of Formula (I), or a pharmaceutically acceptable salt or solvate thereof, wherein

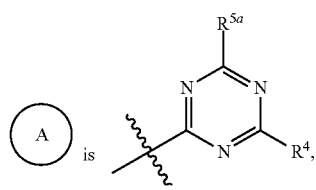

$R^{5a}$ is hydrogen, and $R^4$ is

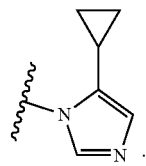

In some embodiments is a compound of Formula (I), or a pharmaceutically acceptable salt or solvate thereof, wherein

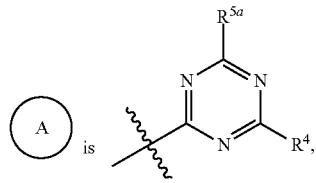

$R^{5a}$ is hydrogen, and $R^4$ is

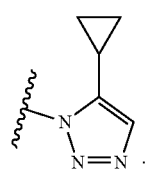

In some embodiments is a compound of Formula (I), or a pharmaceutically acceptable salt or solvate thereof, wherein

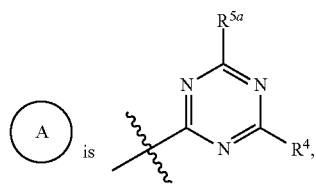

$R^{5a}$ is hydrogen, and $R^4$ is

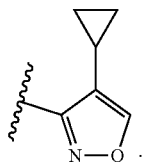 [SMILES: *c1nocc1C1CC1]

In some embodiments is a compound of Formula (I), or a pharmaceutically acceptable salt or solvate thereof, wherein

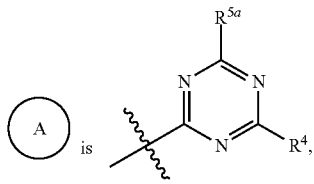

$R^{5a}$ is hydrogen, and $R^4$ is

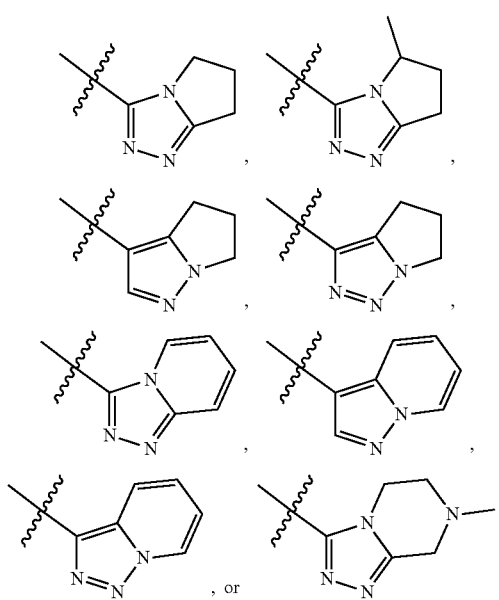

In some embodiments is a compound of Formula (I), or a pharmaceutically acceptable salt or solvate thereof, wherein

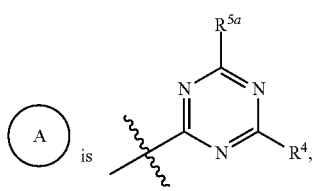

$R^{5a}$ is hydrogen, and $R^4$ is

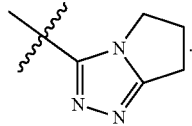

In some embodiments is a compound of Formula (I), or a pharmaceutically acceptable salt or solvate thereof, wherein

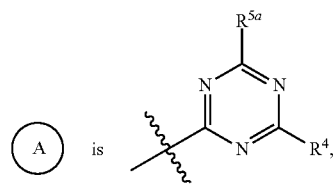

$R^{5a}$ is hydrogen, and $R^4$ is

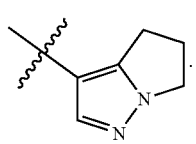

In some embodiments is a compound of Formula (I), or a pharmaceutically acceptable salt or solvate thereof, wherein

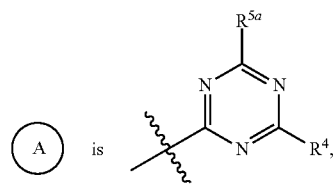

$R^{5a}$ is hydrogen, and $R^4$ is

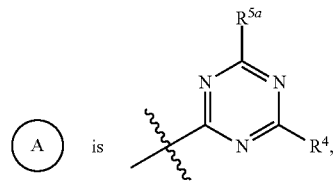

In some embodiments is a compound of Formula (I), or a pharmaceutically acceptable salt or solvate thereof, wherein

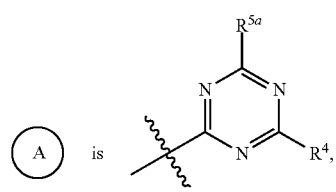

$R^{5a}$ is hydrogen, and $R^4$ is

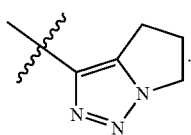

In some embodiments is a compound of Formula (I), or a pharmaceutically acceptable salt or solvate thereof, wherein

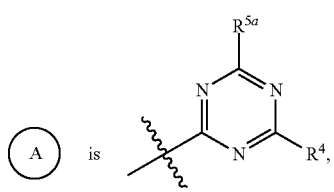

$R^{5a}$ is hydrogen, and $R^4$ is

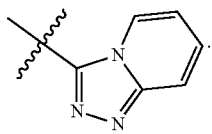

In some embodiments is a compound of Formula (I), or a pharmaceutically acceptable salt or solvate thereof, wherein

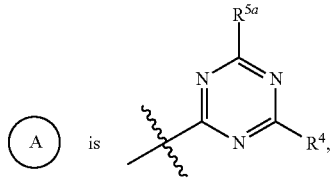

$R^{5a}$ is hydrogen, and $R^4$ is

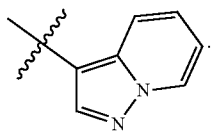

In some embodiments is a compound of Formula (I), or a pharmaceutically acceptable salt or solvate thereof, wherein

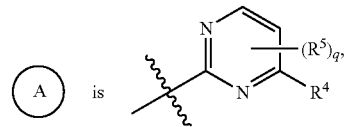

$R^{5a}$ is hydrogen, and $R^4$ is

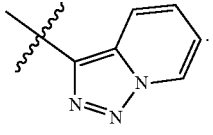 [SMILES: *c1nnn2ccccc12]

In some embodiments is a compound of Formula (I), or a pharmaceutically acceptable salt or solvate thereof, wherein

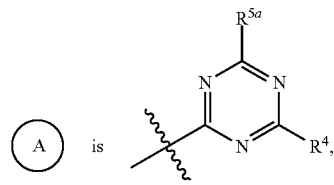

$R^{5a}$ is hydrogen, and $R^4$ is

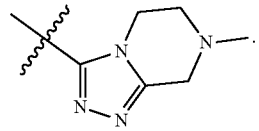

In some embodiments, presented herein are compounds of Formula (Ia), or a pharmaceutically acceptable salt or solvate thereof:

Formula (Ia)

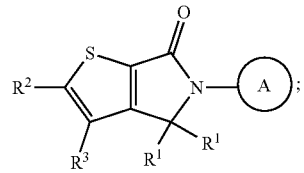

wherein

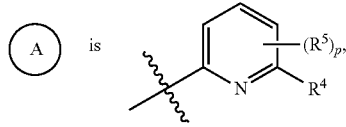

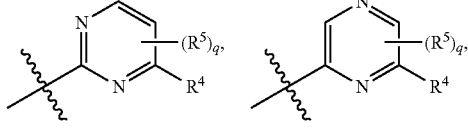

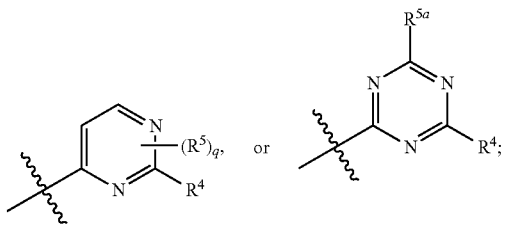

each $R^1$ is independently selected from a group consisting of hydrogen, halogen, and $C_{1-6}$alkyl;

$R^2$ is selected from a group consisting of hydrogen, halogen, —CN, —OH, —$OR^6$, —$SR^6$, —S(=O)$R^7$, —$NO_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —$NR^6$C(=O)N($R^6$)$_2$, —$NR^6$C(=O)$R^7$, —$NR^6$C(=O)O$R^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

$R^3$ is selected from a group consisting of hydrogen, halogen, —CN, and $C_{1-6}$alkyl; or $R^2$ and $R^3$ are combined to form a phenyl ring optionally substituted with one, two, or three $R^8$ substituents;

$R^4$ is selected from a group consisting of hydrogen, halogen, —CN, —OH, —$OR^6$, —$SR^6$, —S(=O)$R^7$, —$NO_2$, —N($R^6$)$_2$, —S(=O)$_2R^7$, —NHS(=O)$_2R^7$, —S(=O)$_2$N($R^6$)$_2$, —C(=O)$R^7$, —C(=O)O$R^6$, —OC(=O)$R^7$, —C(=O)N($R^6$)$_2$, —OC(=O)N($R^6$)$_2$, —$NR^6$C(=O)N($R^6$)$_2$, —$NR^6$C(=O)$R^7$, —$NR^6$C(=O)O$R^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^5$ is independently selected from a group consisting of halogen, —CN, and $C_{1-6}$alkyl;

$R^{5a}$ is selected from the group consisting of hydrogen and $C_{1-6}$alkyl;

each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl;

each $R^7$ is independently selected from the group consisting of $C_{1-6}$alkyl, $C_{3-8}$cycloalkyl, and $C_{2-9}$ heterocycle;

each $R^8$ is independently selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^{13}$ is independently selected from the group consisting of hydrogen, $C_{1-6}$alkyl, and $C_{3-8}$cycloalkyl; or two $R^{13}$ on the same heteroatom are taken together with that heteroatom to which they are attached to form a $C_{2-9}$heterocycle;

each $R^{14}$ is independently selected from the group consisting of $C_{1-6}$alkyl and $C_{3-8}$cycloalkyl;

p is 0, 1, 2, or 3; and q is 0, 1, or 2.

In some embodiments is a compound of Formula (Ia), or a pharmaceutically acceptable salt or solvate thereof, wherein each $R^1$ is hydrogen. In some embodiments is a compound of Formula (Ia), or a pharmaceutically acceptable salt or solvate thereof, wherein one $R^1$ is hydrogen and one $R^1$ is $C_{1-6}$alkyl. In some embodiments is a compound of Formula (Ia), or a pharmaceutically acceptable salt or solvate thereof, wherein each $R^1$ is $C_{1-6}$alkyl. In some embodiments is a compound of Formula (Ia), or a pharmaceutically acceptable salt or solvate thereof, wherein each $R^1$ is halogen.

In some embodiments is a compound of Formula (Ia), or a pharmaceutically acceptable salt or solvate thereof, wherein $R^2$ is selected from a group consisting of hydrogen, halogen, and $C_{1-6}$alkyl.

In some embodiments is a compound of Formula (Ia), or a pharmaceutically acceptable salt or solvate thereof, wherein $R^2$ is hydrogen.

In some embodiments is a compound of Formula (Ia), or a pharmaceutically acceptable salt or solvate thereof, wherein $R^2$ is halogen.

In some embodiments is a compound of Formula (Ia), or a pharmaceutically acceptable salt or solvate thereof, wherein $R^2$ is $C_{1-6}$alkyl.

In some embodiments is a compound of Formula (Ia), or a pharmaceutically acceptable salt or solvate thereof, wherein $R^2$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^3$)$_2$, —N($R^{13}$)$_2$, —N($R^{13}$)C(=O)$R^{14}$, and —N($R^{13}$)S(=O)$_2R^{13}$.

In some embodiments is a compound of Formula (Ia), or a pharmaceutically acceptable salt or solvate thereof, wherein $R^2$ is selected from a group consisting of $C_{2-9}$heterocycle and $C_{1-9}$heteroaryl; wherein $C_{2-9}$heterocycle and $C_{1-9}$heteroaryl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments is a compound of Formula (Ia), or a pharmaceutically acceptable salt or solvate thereof, wherein $R^2$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein $R^2$ is selected from a group consisting of pyrazole, imidazole, thiazole, and pyridine; wherein pyrazole, imidazole, thiazole, and pyridine are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein $R^2$ is selected from a group consisting of pyrazole, imidazole, thiazole, and pyridine; wherein pyrazole, imidazole, thiazole, and pyridine are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein $R^2$ is

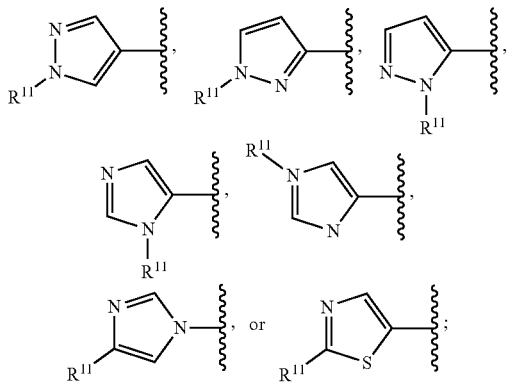

wherein $R^{11}$ is $C_{1-6}$alkyl or $C_{3-6}$cycloalkyl. In some embodiments is a compound of Formula (Ia), or a pharmaceutically acceptable salt or solvate thereof, wherein $R^2$ is

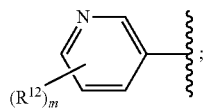

wherein each $R^{12}$ is independently hydrogen, halogen, CN, $C_{1-6}$alkyl, or $C_{3-6}$cycloalkyl; and m is 1 or 2. In some embodiments is a compound of Formula (Ia), or a pharmaceutically acceptable salt or solvate thereof, wherein $R^2$ is selected from a group consisting of unsubstituted pyrazole, unsubstituted imidazole, unsubstituted thiazole, and unsubstituted pyridine. In some embodiments, $R^2$ is $C_{6-10}$aryl optionally substituted with one, two, or three substituents selected from the group consisting of halogen, —CN, $C_{1-6}$alkyl, —$C_{1-6}$ alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein $R^2$ is phenyl optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^3$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein $R^2$ is —C(=O)N($R^6$)$_2$ and each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl. In some embodiments is a compound of Formula (Ia), or a pharmaceutically acceptable salt or solvate thereof, wherein $R^2$ is

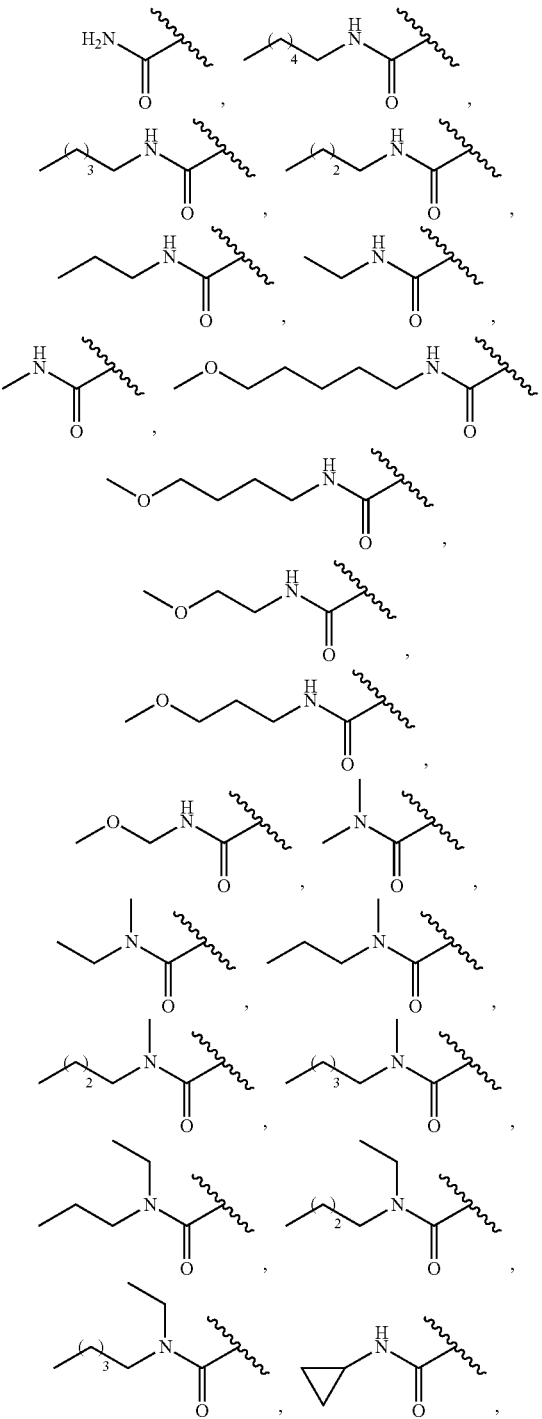

-continued

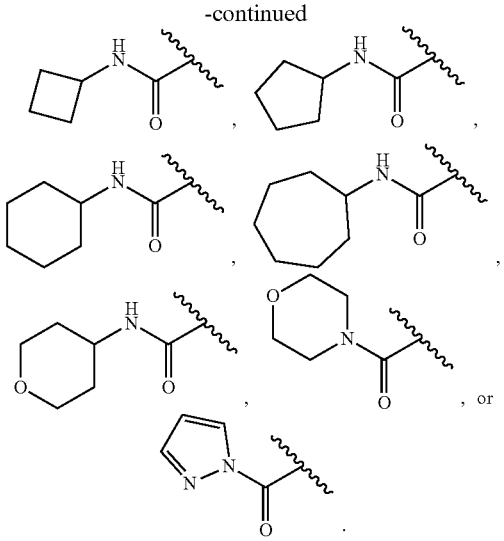

In some embodiments is a compound of Formula (Ia), or a pharmaceutically acceptable salt or solvate thereof, wherein $R^2$ is

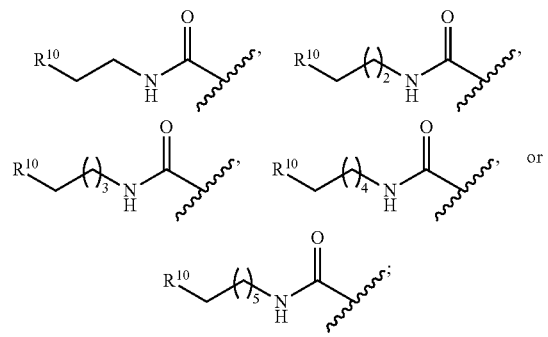

wherein $R^{10}$ is $C_{1-9}$heteroaryl. In some embodiments is a compound of Formula (Ia), or a pharmaceutically acceptable salt or solvate thereof, wherein $R^2$ is —NHC(=O)$R^7$. In some embodiments is a compound of Formula (Ia), or a pharmaceutically acceptable salt or solvate thereof, wherein $R^2$ is

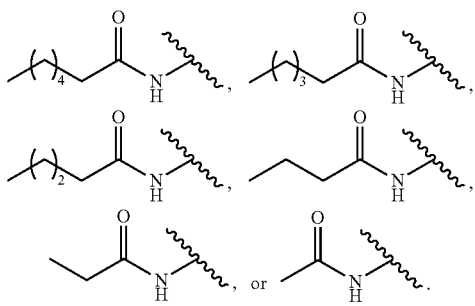

In some embodiments is a compound of Formula (Ia), or a pharmaceutically acceptable salt or solvate thereof, wherein $R^2$ is —C(=O)$R^7$. In some embodiments is a compound of Formula (Ia), or a pharmaceutically acceptable salt or solvate thereof, wherein $R^2$ is

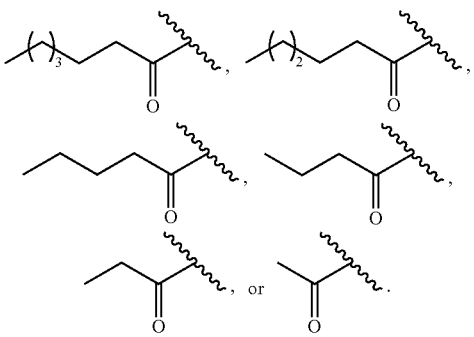

In some embodiments is a compound of Formula (Ia), or a pharmaceutically acceptable salt or solvate thereof, wherein $R^3$ is hydrogen. In some embodiments is a compound of Formula (Ia), or a pharmaceutically acceptable salt or solvate thereof, wherein $R^3$ is $C_{1-6}$alkyl. In some embodiments is a compound of Formula (Ia), or a pharmaceutically acceptable salt or solvate thereof, wherein $R^3$ is halogen.

In some embodiments is a compound of Formula (Ia), or a pharmaceutically acceptable salt or solvate thereof, wherein

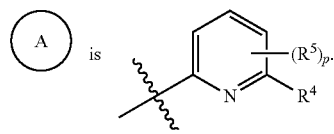

In some embodiments is a compound of Formula (Ia), or a pharmaceutically acceptable salt or solvate thereof, wherein

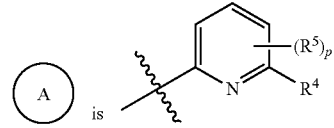

and p is 2. In some embodiments is a compound of Formula (Ia), or a pharmaceutically acceptable salt or solvate thereof, wherein

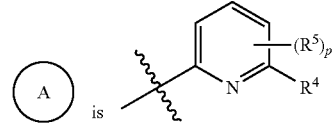

and p is 1. In some embodiments is a compound of Formula (Ia), or a pharmaceutically acceptable salt or solvate thereof, wherein

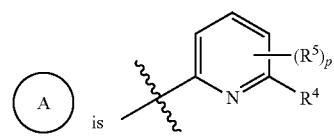

and p is 0. In some embodiments is a compound of Formula (Ia), or a pharmaceutically acceptable salt or solvate thereof, wherein

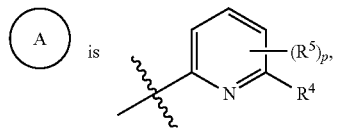

p is 0, and $R^4$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

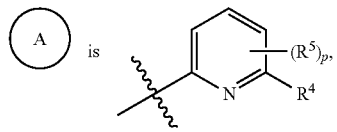

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

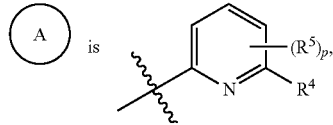

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

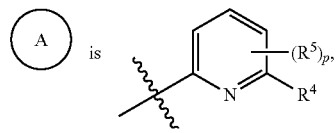

p is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

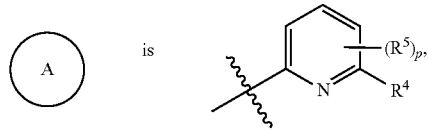

p is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein

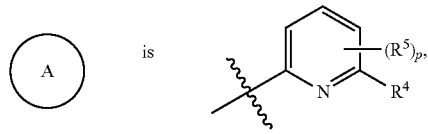

p is 0, and $R^4$ is

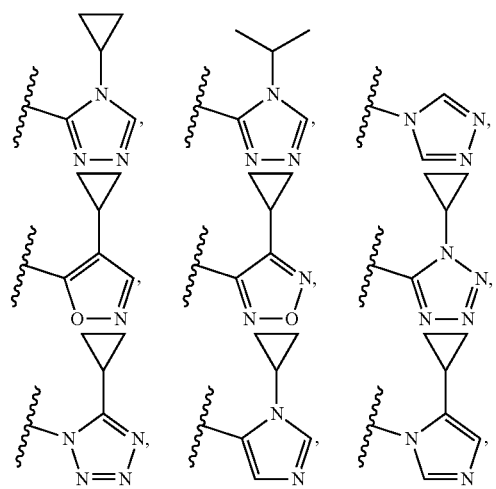

-continued

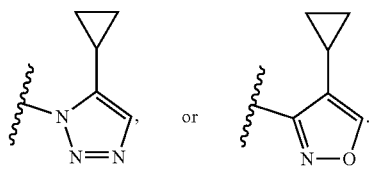 or 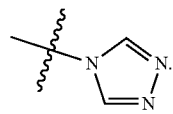

In some embodiments is a compound of Formula (Ia), or a pharmaceutically acceptable salt or solvate thereof, wherein

 is 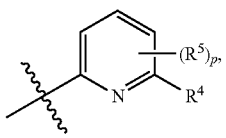

p is 0, and $R^4$ is

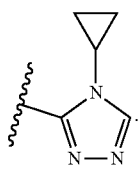

In some embodiments is a compound of Formula (Ia), or a pharmaceutically acceptable salt or solvate thereof, wherein

 is 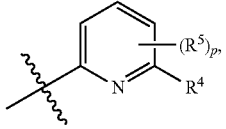

p is 0, and $R^4$ is

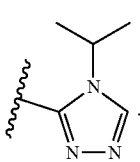

In some embodiments is a compound of Formula (Ia), or a pharmaceutically acceptable salt or solvate thereof, wherein

 is 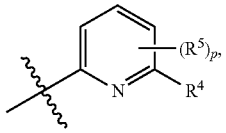

p is 0, and $R^4$ is

 is 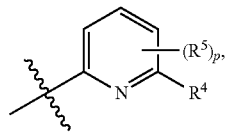

p is 0, and $R^4$ is

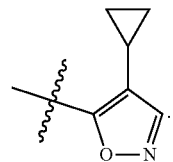 [SMILES: *c1oncc1C1CC1]

In some embodiments is a compound of Formula (Ia), or a pharmaceutically acceptable salt or solvate thereof, wherein

 is 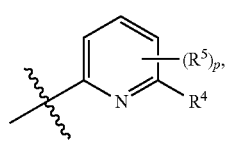

p is 0, and $R^4$ is

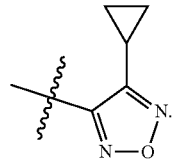 [SMILES: *c1nonc1C1CC1]

In some embodiments is a compound of Formula (Ia), or a pharmaceutically acceptable salt or solvate thereof, wherein

 is 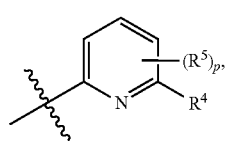

p is 0, and R⁴ is

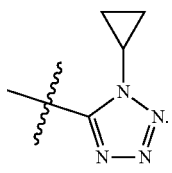 [SMILES: *c1nnnn1C1CC1]

In some embodiments is a compound of Formula (Ia), or a pharmaceutically acceptable salt or solvate thereof, wherein

 is 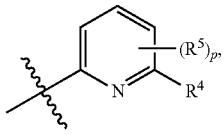

p is 0, and R⁴ is

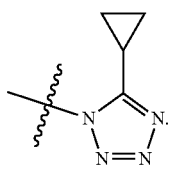 [SMILES: *n1nnnc1C1CC1]

In some embodiments is a compound of Formula (Ia), or a pharmaceutically acceptable salt or solvate thereof, wherein

 is 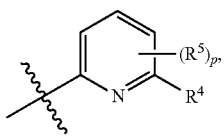

p is 0, and R⁴ is

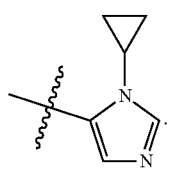 [SMILES: *c1cncn1C1CC1]

In some embodiments is a compound of Formula (Ia), or a pharmaceutically acceptable salt or solvate thereof, wherein

 is 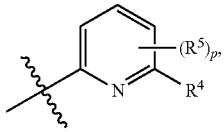

p is 0, and R⁴ is

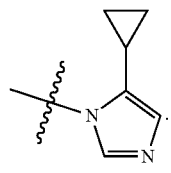 [SMILES: *n1cncc1C1CC1]

In some embodiments is a compound of Formula (Ia), or a pharmaceutically acceptable salt or solvate thereof, wherein

 is 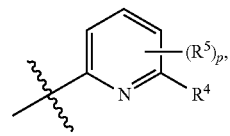

p is 0, and R⁴ is

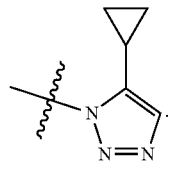 [SMILES: *n1nncc1C1CC1]

In some embodiments is a compound of Formula (Ia), or a pharmaceutically acceptable salt or solvate thereof, wherein

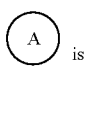 is 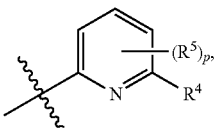

p is 0, and R⁴ is

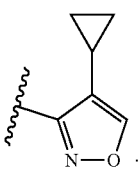

In some embodiments is a compound of Formula (Ia), or a pharmaceutically acceptable salt or solvate thereof, wherein

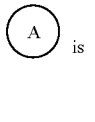 is 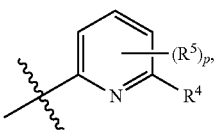

p is 0, and R⁴ is

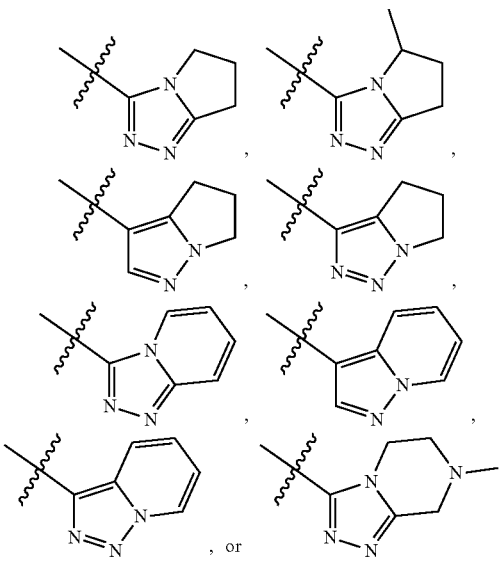

, or

In some embodiments is a compound of Formula (Ia), or a pharmaceutically acceptable salt or solvate thereof, wherein

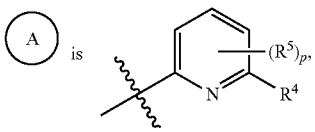

p is 0, and R⁴ is

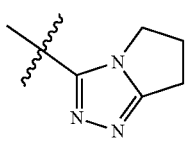

In some embodiments is a compound of Formula (Ia), or a pharmaceutically acceptable salt or solvate thereof, wherein

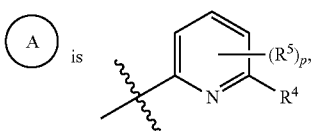

p is 0, and R⁴ is

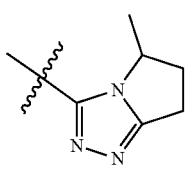

In some embodiments is a compound of Formula (Ia), or a pharmaceutically acceptable salt or solvate thereof, wherein

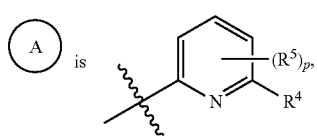

p is 0, and R⁴ is

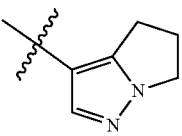

In some embodiments is a compound of Formula Ia), or a pharmaceutically acceptable salt or solvate thereof, wherein

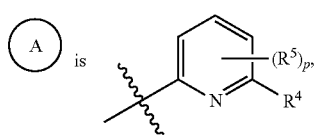

p is 0, and R⁴ is

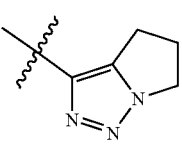

In some embodiments is a compound of Formula (Ia), or a pharmaceutically acceptable salt or solvate thereof, wherein

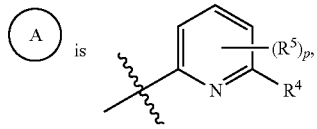

p is 0, and R⁴ is

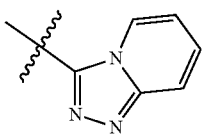

In some embodiments is a compound of Formula (Ia), or a pharmaceutically acceptable salt or solvate thereof, wherein

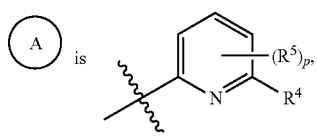

p is 0, and R⁴ is

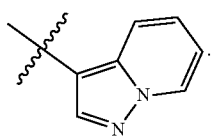 [SMILES: *c1cnn2ccccc12]

In some embodiments is a compound of Formula (Ia), or a pharmaceutically acceptable salt or solvate thereof, wherein

 is 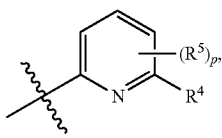

p is 0, and R⁴ is

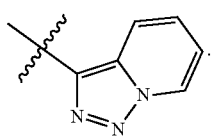 [SMILES: *c1nnn2ccccc12]

In some embodiments is a compound of Formula (Ia), or a pharmaceutically acceptable salt or solvate thereof, wherein

 is 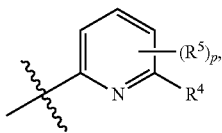

p is 0, and R⁴ is

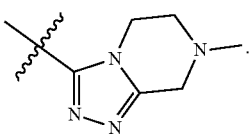 [SMILES: *c1nnc2n1CCN(C)C2]

In some embodiments is a compound of Formula (Ia), or a pharmaceutically acceptable salt or solvate thereof, wherein

 is 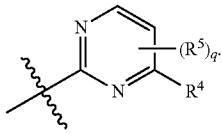

In some embodiments is a compound of Formula (Ia), or a pharmaceutically acceptable salt or solvate thereof, wherein

 is 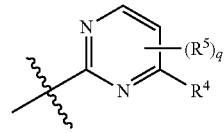

and q is 2. In some embodiments is a compound of Formula (Ia), or a pharmaceutically acceptable salt or solvate thereof, wherein

 is 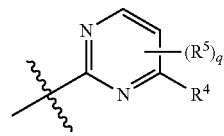

and q is 1. In some embodiments is a compound of Formula (Ia), or a pharmaceutically acceptable salt or solvate thereof, wherein

 is 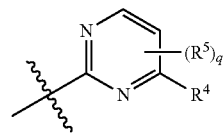

and q is 0. In some embodiments is a compound of Formula (Ia), or a pharmaceutically acceptable salt or solvate thereof, wherein

 is 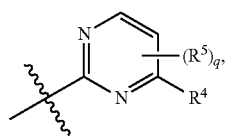

q is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R In some embodiments is a compound of Formula (Ia), or a pharmaceutically acceptable salt or solvate thereof, wherein

 is 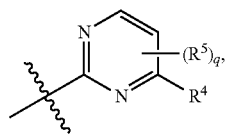

q is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.
In some embodiments is a compound of Formula (Ia), or a pharmaceutically acceptable salt or solvate thereof, wherein

 is 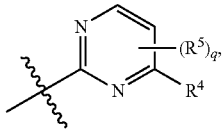

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

 is 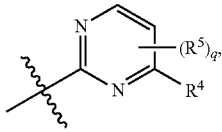

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.
In some embodiments is a compound of Formula (Ia), or a pharmaceutically acceptable salt or solvate thereof, wherein

 is 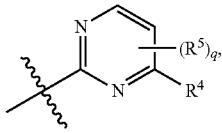

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein

 is 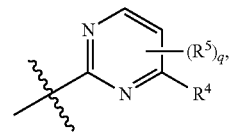

q is 0, and $R^4$ is

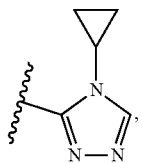 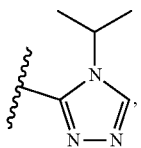 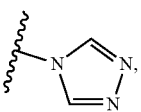

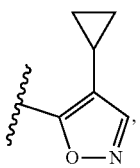 [SMILES: *c1oncc1C1CC1] 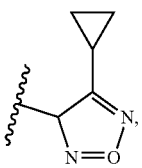 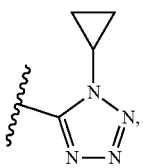

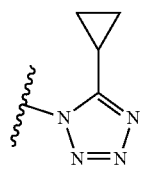 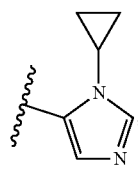 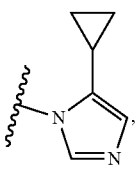

or

In some embodiments is a compound of Formula (Ia), or a pharmaceutically acceptable salt or solvate thereof, wherein

 is 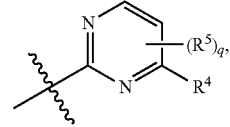

q is 0, and $R^4$ is

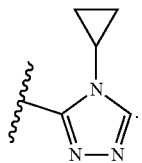

In some embodiments is a compound of Formula (Ia), or a pharmaceutically acceptable salt or solvate thereof, wherein

 is 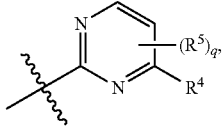

q is 0, and $R^4$ is

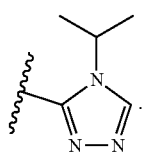

In some embodiments is a compound of Formula (Ia), or a pharmaceutically acceptable salt or solvate thereof, wherein

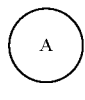 is 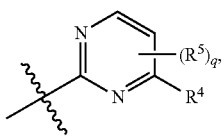

q is 0, and $R^4$ is

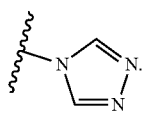

In some embodiments is a compound of Formula (Ia), or a pharmaceutically acceptable salt or solvate thereof, wherein

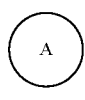 is 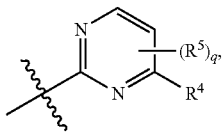

q is 0, and $R^4$ is

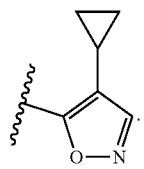

In some embodiments is a compound of Formula (Ia), or a pharmaceutically acceptable salt or solvate thereof, wherein

 is 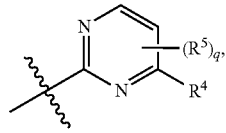

q is 0, and $R^4$ is

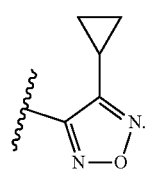

In some embodiments is a compound of Formula (Ia), or a pharmaceutically acceptable salt or solvate thereof, wherein

 is 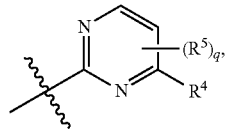

q is 0, and $R^4$ is

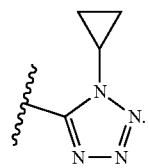

In some embodiments is a compound of Formula (Ia), or a pharmaceutically acceptable salt or solvate thereof, wherein

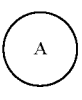 is 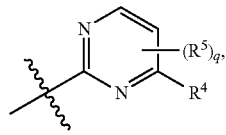

is 0, and $R^4$ is

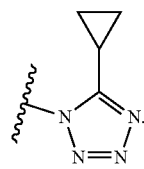 [SMILES: *n1nnnc1C1CC1]

In some embodiments is a compound of Formula (Ia), or a pharmaceutically acceptable salt or solvate thereof, wherein

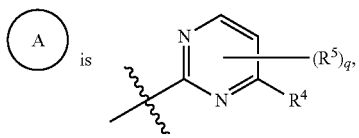

q is 0, and R⁴ is

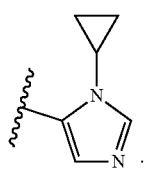

In some embodiments is a compound of Formula (Ia), or a pharmaceutically acceptable salt or solvate thereof, wherein

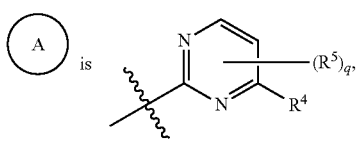

q is 0, and R⁴ is

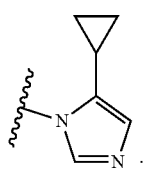

In some embodiments is a compound of Formula (Ia), or a pharmaceutically acceptable salt or solvate thereof, wherein

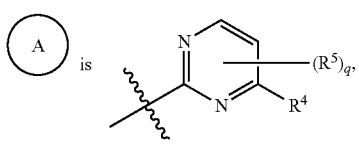

q is 0, and R⁴ is

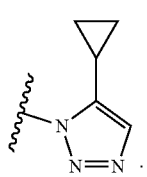

In some embodiments is a compound of Formula (Ia), or a pharmaceutically acceptable salt or solvate thereof, wherein

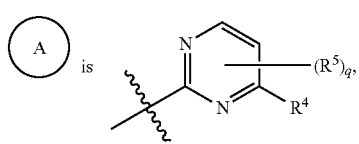

q is 0, and R⁴ is

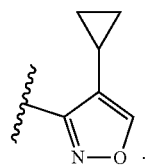

In some embodiments is a compound of Formula (Ia), or a pharmaceutically acceptable salt or solvate thereof, wherein

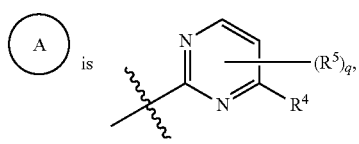

q is 0, and R⁴ is

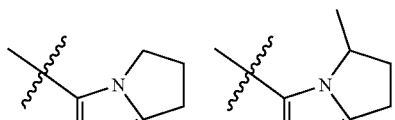

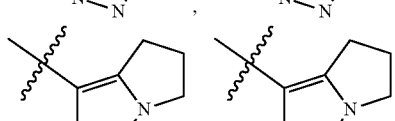

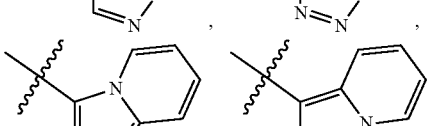

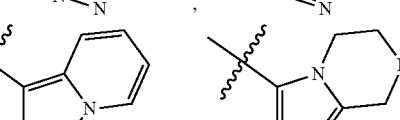

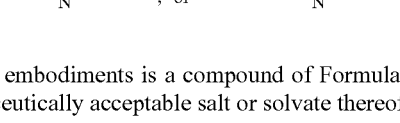

, or

In some embodiments is a compound of Formula (Ia), or a pharmaceutically acceptable salt or solvate thereof, wherein

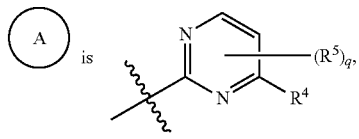

q is 0, and R⁴ is

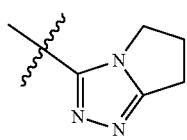

In some embodiments is a compound of Formula (Ia), or a pharmaceutically acceptable salt or solvate thereof, wherein

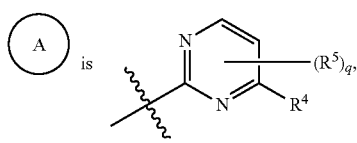

q is 0, and R⁴ is

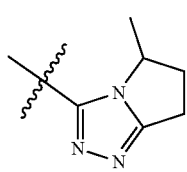

In some embodiments is a compound of Formula (Ia), or a pharmaceutically acceptable salt or solvate thereof, wherein

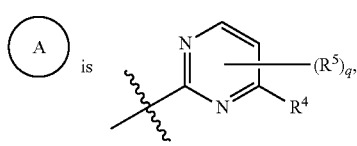

q is 0, and R⁴ is

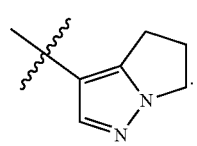

In some embodiments is a compound of Formula (Ia), or a pharmaceutically acceptable salt or solvate thereof, wherein

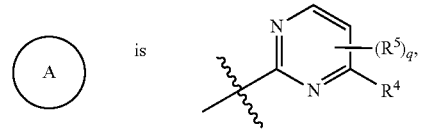

q is 0, and R⁴ is

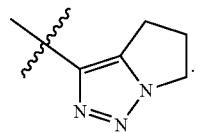

In some embodiments is a compound of Formula (Ia), or a pharmaceutically acceptable salt or solvate thereof, wherein

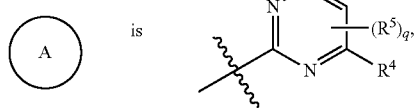

q is 0, and R⁴ is

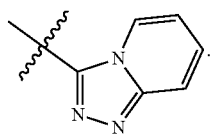 [SMILES: *c1nnc2ccccn12]

In some embodiments is a compound of Formula (Ia), or a pharmaceutically acceptable salt or solvate thereof, wherein

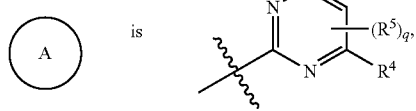

q is 0, and R⁴ is

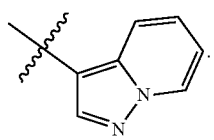

In some embodiments is a compound of Formula (Ia), or a pharmaceutically acceptable salt or solvate thereof, wherein

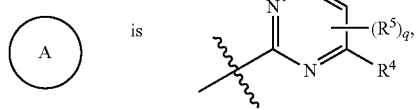

q is 0, and R⁴ is

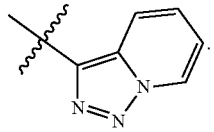

In some embodiments is a compound of Formula (Ia), or a pharmaceutically acceptable salt or solvate thereof, wherein

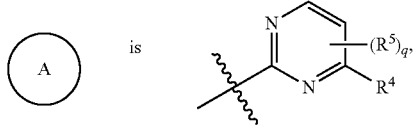

q is 0, and $R^4$ is

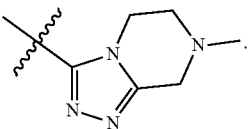 [SMILES: *c1nnc2n1CCN(C)C2]

In some embodiments is a compound of Formula (Ia), or a pharmaceutically acceptable salt or solvate thereof, wherein

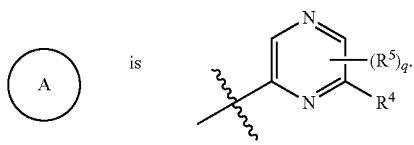

In some embodiments is a compound of Formula (Ia), or a pharmaceutically acceptable salt or solvate thereof, wherein

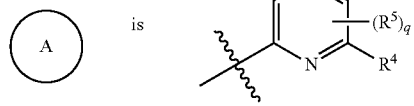

and q is 2. In some embodiments is a compound of Formula (Ia), or a pharmaceutically acceptable salt or solvate thereof, wherein

and q is 1. In some embodiments is a compound of Formula (Ia), or a pharmaceutically acceptable salt or solvate thereof, wherein

and q is 0. In some embodiments is a compound of Formula (Ia), or a pharmaceutically acceptable salt or solvate thereof, wherein

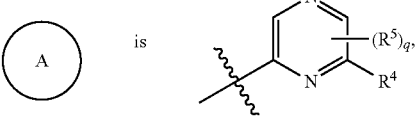

q is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^3$)S(=O)$_2$$R^{13}$.
In some embodiments is a compound of Formula (Ia), or a pharmaceutically acceptable salt or solvate thereof, wherein

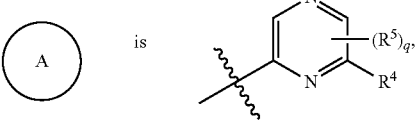

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$.
In some embodiments is a compound of Formula (Ia), or a pharmaceutically acceptable salt or solvate thereof, wherein

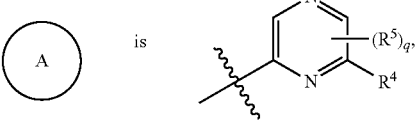

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ia), or a pharmaceutically acceptable salt or solvate thereof, wherein

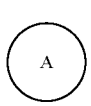 is 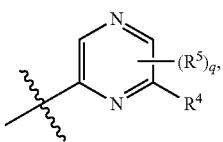

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ia), or a pharmaceutically acceptable salt or solvate thereof, wherein

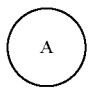 is 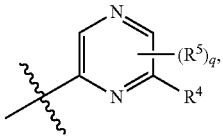

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein

 is 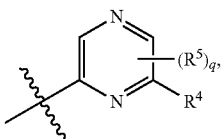

q is 0, and R⁴ is

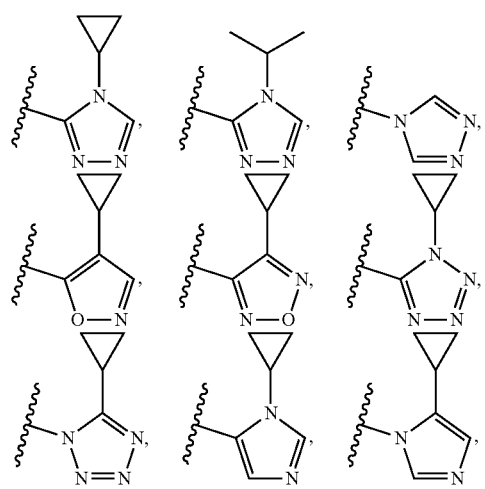

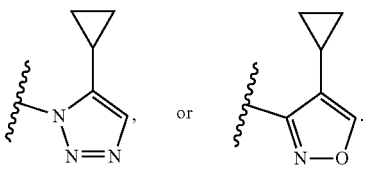

In some embodiments is a compound of Formula (Ia), or a pharmaceutically acceptable salt or solvate thereof, wherein

 is 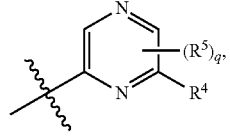

q is 0, and R⁴ is

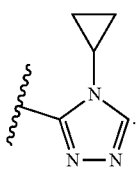 [SMILES: *c1nncn1C1CC1]

In some embodiments is a compound of Formula (Ia), or a pharmaceutically acceptable salt or solvate thereof, wherein

 is 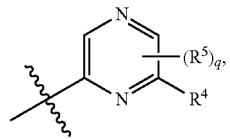

q is 0, and R⁴ is

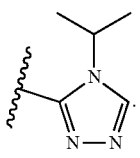 [SMILES: *c1nncn1C(C)C]

In some embodiments is a compound of Formula (Ia), or a pharmaceutically acceptable salt or solvate thereof, wherein

 is 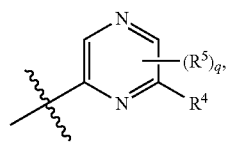

q is 0, and R⁴ is

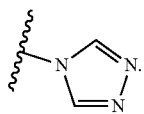

In some embodiments is a compound of Formula (Ia), or a pharmaceutically acceptable salt or solvate thereof, wherein

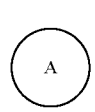 is 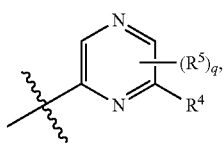

q is 0, and R⁴ is

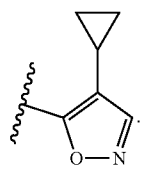

In some embodiments is a compound of Formula (Ia), or a pharmaceutically acceptable salt or solvate thereof, wherein

 is 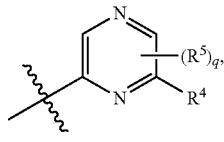

q is 0, and R⁴ is

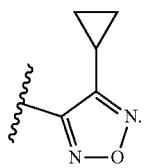 [SMILES: *c1nonc1C1CC1]

In some embodiments is a compound of Formula (Ia), or a pharmaceutically acceptable salt or solvate thereof, wherein

 is 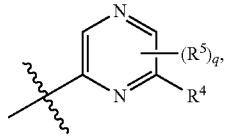

q is 0, and R⁴ is

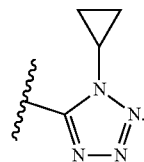 [SMILES: *c1nnnn1C1CC1]

In some embodiments is a compound of Formula (Ia), or a pharmaceutically acceptable salt or solvate thereof, wherein

 is 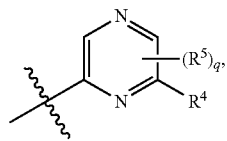

q is 0, and R⁴ is

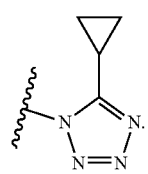

In some embodiments is a compound of Formula (Ia), or a pharmaceutically acceptable salt or solvate thereof, wherein

 is 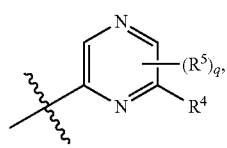

q is 0, and R⁴ is

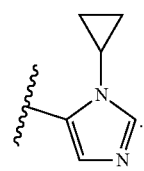 [SMILES: *c1cncn1C1CC1]

In some embodiments is a compound of Formula (Ia), or a pharmaceutically acceptable salt or solvate thereof, wherein

 is 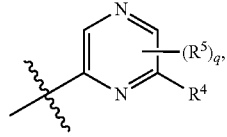

q is 0, and R⁴ is

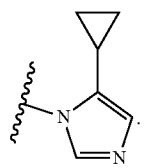

In some embodiments is a compound of Formula (Ia), or a pharmaceutically acceptable salt or solvate thereof, wherein

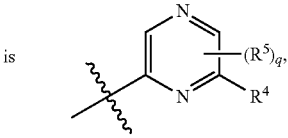

q is 0, and R⁴ is

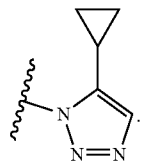

In some embodiments is a compound of Formula (Ia), or a pharmaceutically acceptable salt or solvate thereof wherein

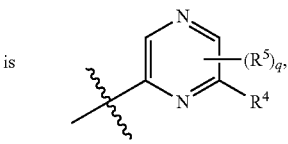

q is 0 and R⁴ is

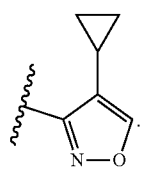

In some embodiments is a compound of Formula (Ia), or a pharmaceutically acceptable salt or solvate thereof, wherein

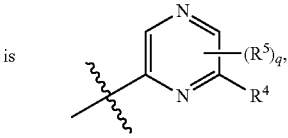

q is 0, and R⁴ is

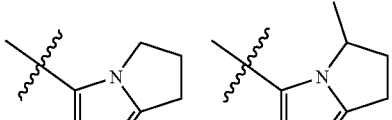

In some embodiments is a compound of Formula (Ia), or a pharmaceutically acceptable salt or solvate thereof, wherein

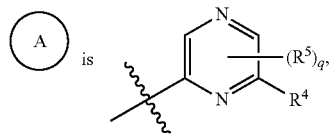

q is 0, and R⁴ is

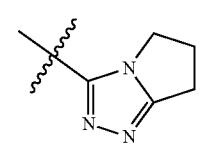

In some embodiments is a compound of Formula (Ia), or a pharmaceutically acceptable salt or solvate thereof, wherein

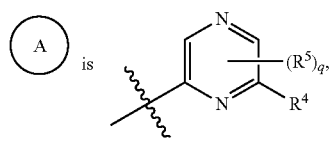

q is 0, and R⁴ is

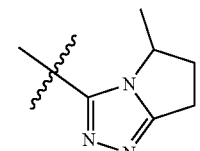

In some embodiments is a compound of Formula (Ia), or a pharmaceutically acceptable salt or solvate thereof, wherein

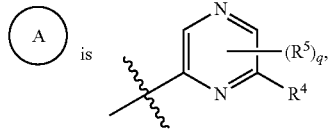

q is 0, and R⁴ is

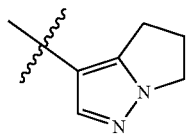

In some embodiments is a compound of Formula (Ia), or a pharmaceutically acceptable salt or solvate thereof, wherein

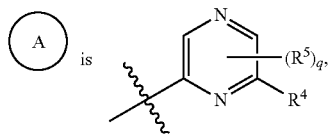

q is 0, and R is

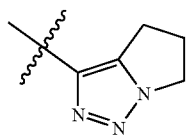

In some embodiments is a compound of Formula (Ia), or a pharmaceutically acceptable salt or solvate thereof, wherein

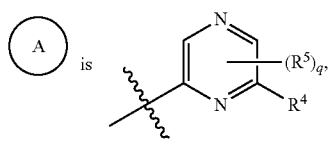

q is 0, and R⁴ is

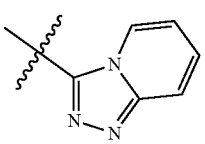

In some embodiments is a compound of Formula (Ia), or a pharmaceutically acceptable salt or solvate thereof, wherein

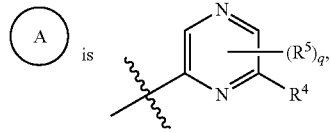

q is 0 and R⁴ is

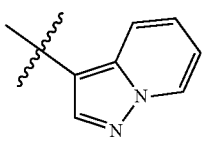

In some embodiments is a compound of Formula (Ia), or a pharmaceutically acceptable salt or solvate thereof, wherein

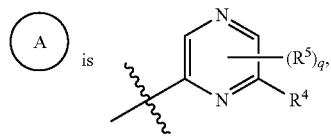

q is 0, and R⁴ is

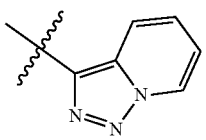

In some embodiments is a compound of Formula (Ia), or a pharmaceutically acceptable salt or solvate thereof, wherein

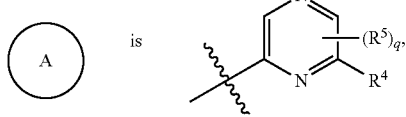

q is 0, and R⁴ is

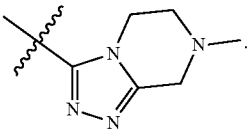 [SMILES: *c1nnc2n1CCN(C)C2]

In some embodiments is a compound of Formula (Ia), or a pharmaceutically acceptable salt or solvate thereof, wherein

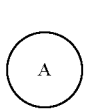 is 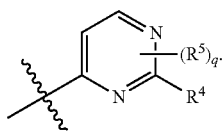

In some embodiments is a compound of Formula (Ia), or a pharmaceutically acceptable salt or solvate thereof, wherein

 is 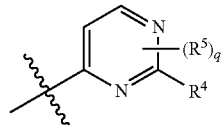

and q is 2. In some embodiments is a compound of Formula (Ia), or a pharmaceutically acceptable salt or solvate thereof, wherein

 is 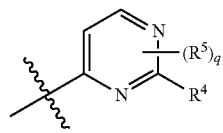

and q is 1. In some embodiments is a compound of Formula (Ia), or a pharmaceutically acceptable salt or solvate thereof, wherein

 is 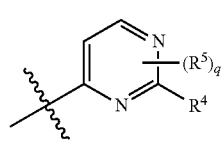

and q is 0. In some embodiments is a compound of Formula (Ia), or a pharmaceutically acceptable salt or solvate thereof, wherein

 is 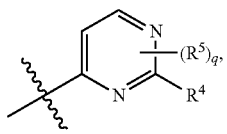

q is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$R In some embodiments is a compound of Formula (Ia), or a pharmaceutically acceptable salt or solvate thereof, wherein

 is 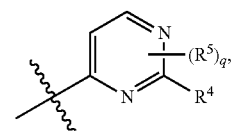

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

 is 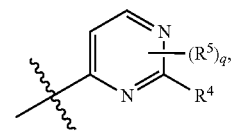

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

 is 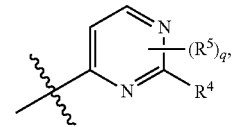

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein

 is 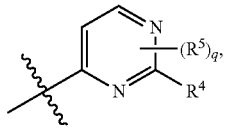

q is 0, and R⁴ is

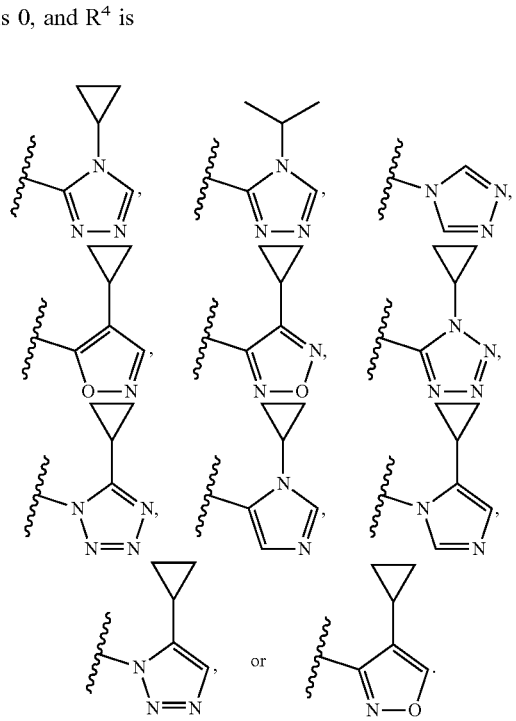

In some embodiments is a compound of Formula (Ia), or a pharmaceutically acceptable salt or solvate thereof,

 is 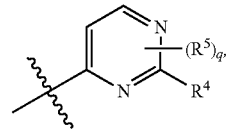

q is 0, and R⁴ is

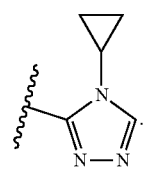

In some embodiments is a compound of Formula (Ia), or a pharmaceutically acceptable salt or solvate thereof, wherein

 is 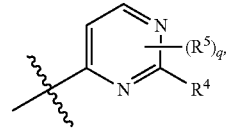

q is 0, and R⁴ is

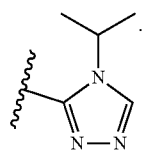

In some embodiments is a compound of Formula (Ia), or a pharmaceutically acceptable salt or solvate thereof, is

 is 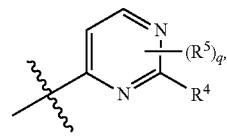

q is 0, and R⁴ is

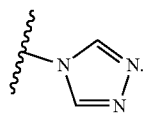

In some embodiments is a compound of Formula (Ia), or a pharmaceutically acceptable salt or solvate thereof, wherein

 is 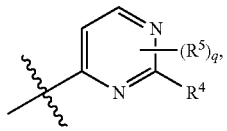

q is 0, and R⁴ is

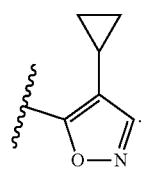

In some embodiments is a compound of Formula (Ia), or a pharmaceutically acceptable salt or solvate thereof, wherein

 is 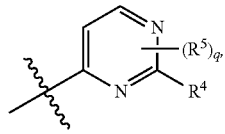

q is 0, and $R^4$ is

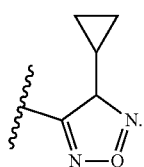

In some embodiments is a compound of Formula (Ia), or a pharmaceutically acceptable salt or solvate thereof, wherein

 is 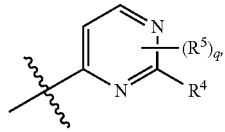

q is 0, and $R^4$ is

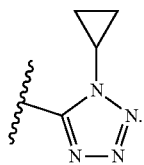

In some embodiments is a compound of Formula (Ia), or a pharmaceutically acceptable salt or solvate thereof, wherein

 is 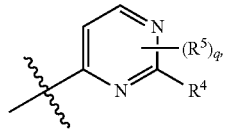

is 0, and $R^4$ is

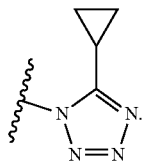

In some embodiments is a compound of Formula (Ia), or a pharmaceutically acceptable salt or solvate thereof, wherein

 is 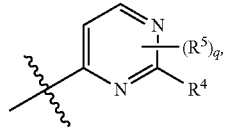

q is 0, and $R^4$ is

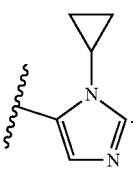

In some embodiments is a compound of Formula (Ia), or a pharmaceutically acceptable salt or solvate thereof, wherein

 is 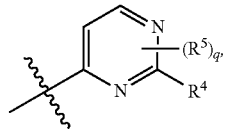

q is 0, and $R^4$ is

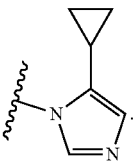

In some embodiments is a compound of Formula (Ia), or a pharmaceutically acceptable salt or solvate thereof, wherein

 is 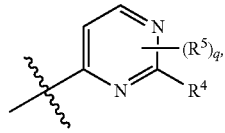

q is 0, and $R^4$ is

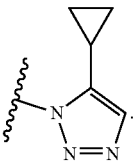

In some embodiments is a compound of Formula (Ia), or a pharmaceutically acceptable salt or solvate thereof, wherein

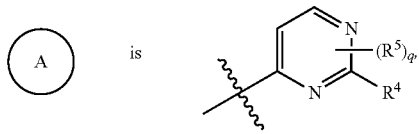

q is 0, and $R^4$ is

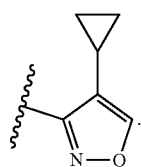

In some embodiments is a compound of Formula (Ia), or a pharmaceutically acceptable salt or solvate thereof, wherein

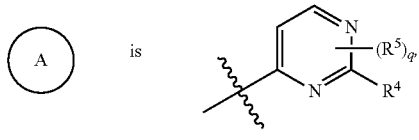

q is 0, and $R^4$ is

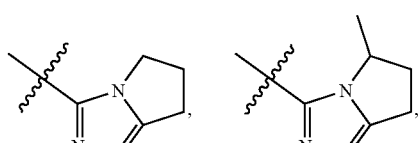
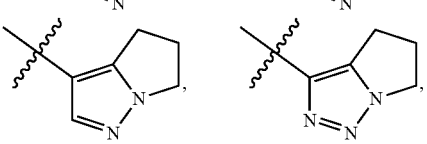
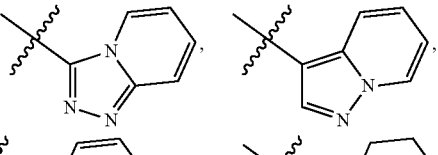
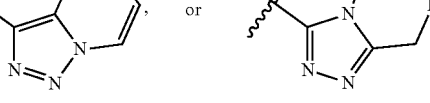
or
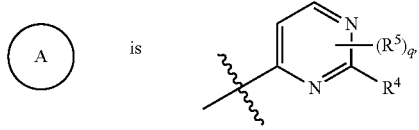

In some embodiments is a compound of Formula (Ia), or a pharmaceutically acceptable salt or solvate thereof, wherein q is 0, and $R^4$ is

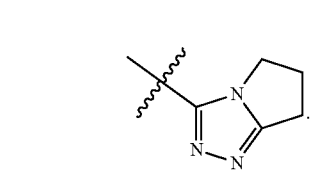

In some embodiments is a compound of Formula (Ia), or a pharmaceutically acceptable salt or solvate thereof, wherein

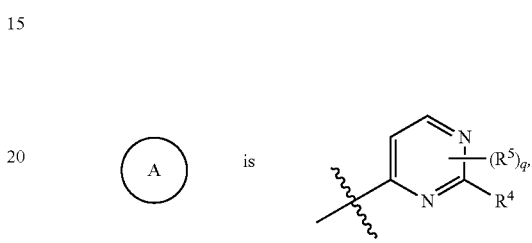

q is 0, and $R^4$ is

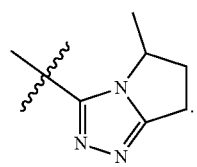 [SMILES: *c1nnc2n1C(C)CC2]

In some embodiments is a compound of Formula (Ia), or a pharmaceutically acceptable salt or solvate thereof, wherein

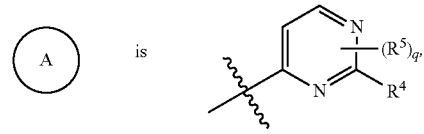

q is 0, and $R^4$ is

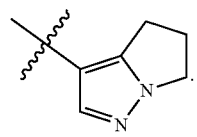

In some embodiments is a compound of Formula (Ia), or a pharmaceutically acceptable salt or solvate thereof, wherein

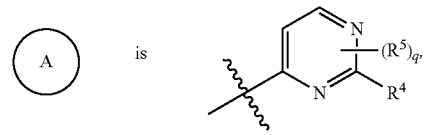

q is 0, and R⁴ is

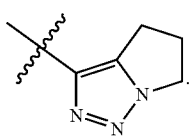

In some embodiments is a compound of Formula (Ia), or a pharmaceutically acceptable salt or solvate thereof, wherein

 is 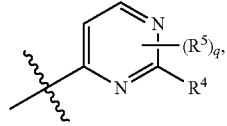

q is 0, and R⁴ is

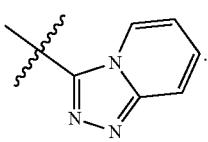

In some embodiments is a compound of Formula (Ia), or a pharmaceutically acceptable salt or solvate thereof, wherein

 is 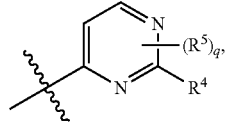

q is 0, and R⁴ is

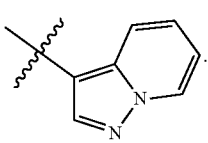 [SMILES: *c1cnn2ccccc12]

In some embodiments is a compound of Formula (Ia), or a pharmaceutically acceptable salt or solvate thereof, wherein

 is 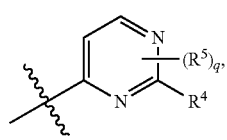

q is 0, and R⁴ is

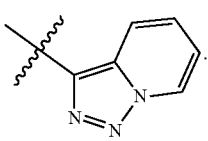

In some embodiments is a compound of Formula (Ia), or a pharmaceutically acceptable salt or solvate thereof, wherein

 is 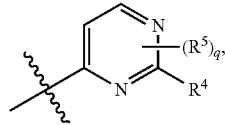

q is 0, and R⁴ is

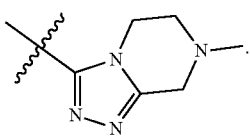 [SMILES: *c1nnc2n1CCN(C)C2]

In some embodiments is a compound of Formula (Ia), or a pharmaceutically acceptable salt or solvate thereof, wherein

 is 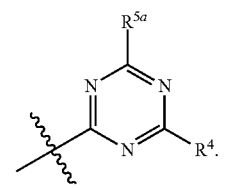

In some embodiments is a compound of Formula (Ia), or a pharmaceutically acceptable salt or solvate thereof, wherein

 is 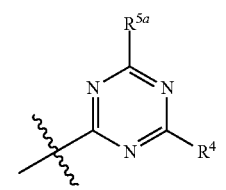

and q is 2. In some embodiments is a compound of Formula (Ia), or a pharmaceutically acceptable salt or solvate thereof, wherein

 is 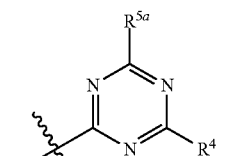

and q is 1. In some embodiments is a compound of Formula (Ia), or a pharmaceutically acceptable salt or solvate thereof, wherein

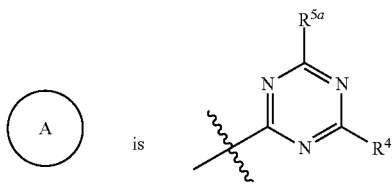

and q is 0. In some embodiments is a compound of Formula (Ia), or a pharmaceutically acceptable salt or solvate thereof, wherein

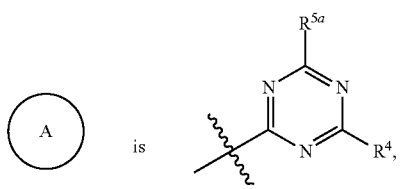

$R^{5a}$ is hydrogen, and $R^4$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

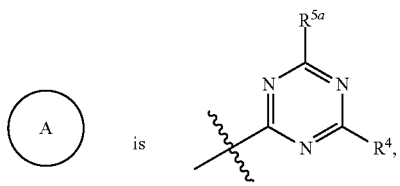

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

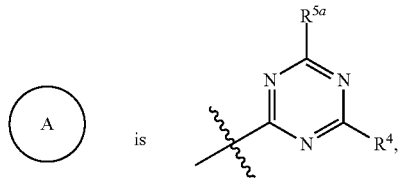

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^4$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

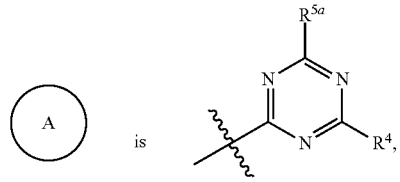

$R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ia), or a pharmaceutically acceptable salt or solvate thereof, wherein

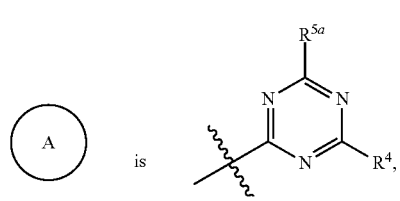

$R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ia), or a pharmaceutically acceptable salt or solvate thereof, wherein

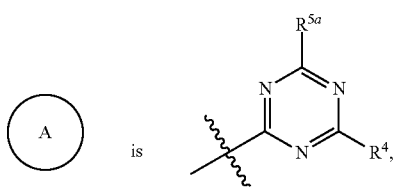 is 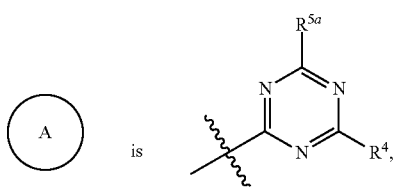, $R^{5a}$ is hydrogen, and $R^4$ is

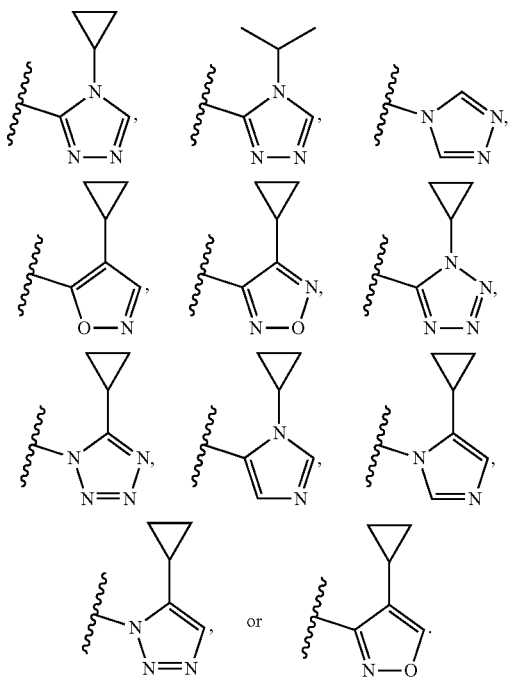

or

In some embodiments is a compound of Formula (Ia), or a pharmaceutically acceptable salt or solvate thereof, wherein

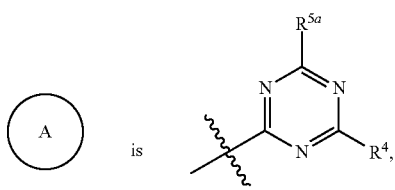 is 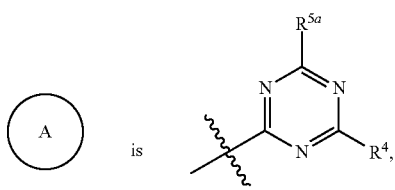, $R^{5a}$ is hydrogen, and $R^4$ is

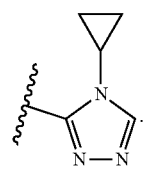

In some embodiments is a compound of Formula (Ia), or a pharmaceutically acceptable salt or solvate thereof, wherein

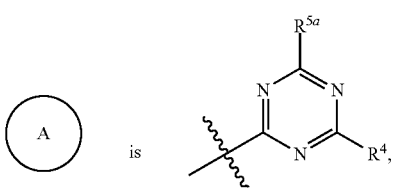 is 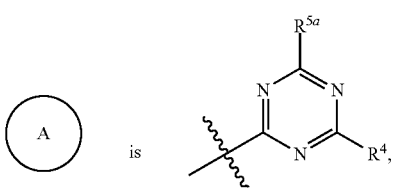, $R^{5a}$ is hydrogen, and $R^4$ is

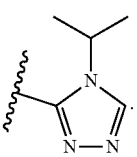 [SMILES: *c1nncn1C(C)C]

In some embodiments is a compound of Formula (Ia), or a pharmaceutically acceptable salt or solvate thereof, wherein

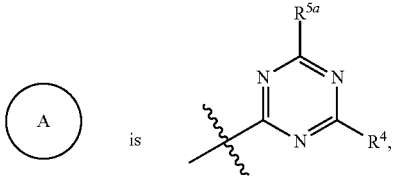 is 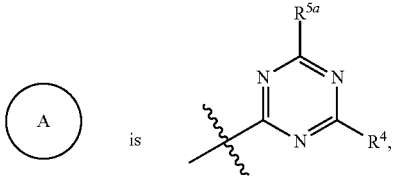, $R^{5a}$ is hydrogen, and $R^4$ is

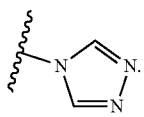

In some embodiments is a compound of Formula (Ia), or a pharmaceutically acceptable salt or solvate thereof, wherein

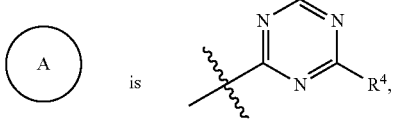 is 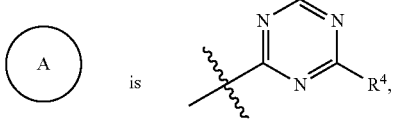, $R^{5a}$ is hydrogen, and $R^4$ is

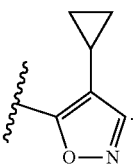 [SMILES: *c1oncc1C1CC1]

In some embodiments is a compound of Formula (Ia), or a pharmaceutically acceptable salt or solvate thereof, wherein

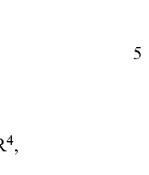 is 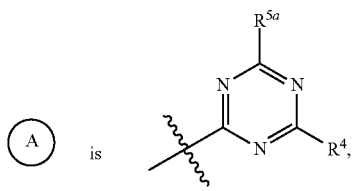, $R^{5a}$ is hydrogen, and $R^4$ is

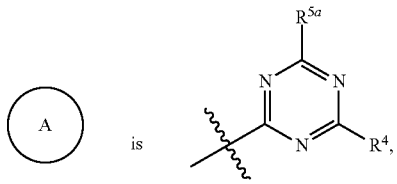

In some embodiments is a compound of Formula (Ia), or a pharmaceutically acceptable salt or solvate thereof, wherein

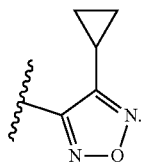 [SMILES: *c1nonc1C1CC1] is 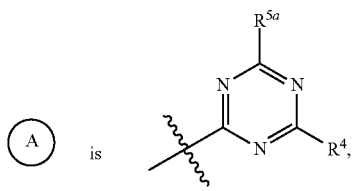, $R^{5a}$ is hydrogen, and $R^4$ is

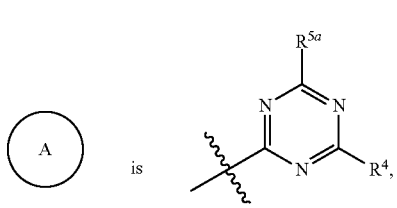

In some embodiments is a compound of Formula (Ia), or a pharmaceutically acceptable salt or solvate thereof, wherein

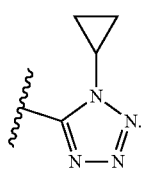 [SMILES: *c1nnnn1C1CC1] is 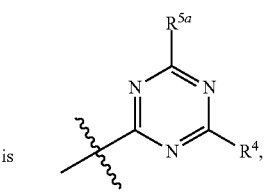, $R^{5a}$ is hydrogen, and $R^4$ is

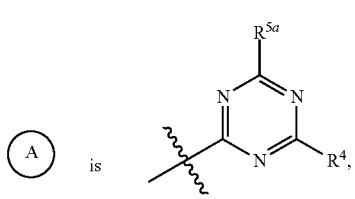

In some embodiments is a compound of Formula (Ia), or a pharmaceutically acceptable salt or solvate thereof, wherein

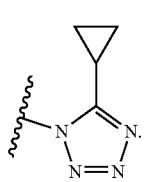 [SMILES: *n1nnnc1C1CC1] is 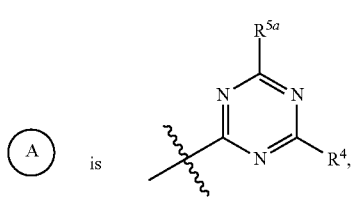, $R^{5a}$ is hydrogen, and $R^4$ is

In some embodiments is a compound of Formula (Ia), or a pharmaceutically acceptable salt or solvate thereof, wherein $R^{5a}$ is hydrogen, and $R^4$ is

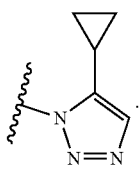 [SMILES: *n1nncc1C1CC1]

In some embodiments is a compound of Formula (Ia), or a pharmaceutically acceptable salt or solvate thereof, wherein

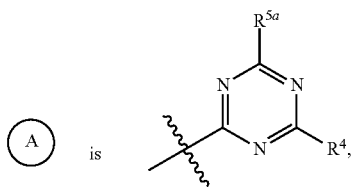

$R^{5a}$ is hydrogen, and $R^4$ is

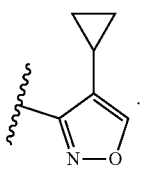

In some embodiments is a compound of Formula (Ia), or a pharmaceutically acceptable salt or solvate thereof, wherein

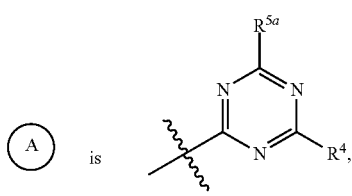

$R^{5a}$ is hydrogen, and $R^4$ is

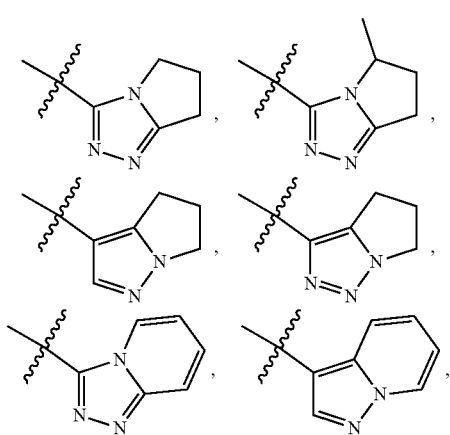

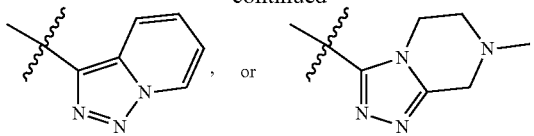

In some embodiments is a compound of Formula (Ia), or a pharmaceutically acceptable salt or solvate thereof, wherein

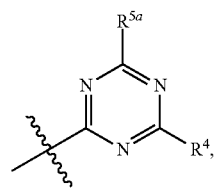

$R^{5a}$ is hydrogen, and $R^4$ is

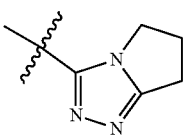

In some embodiments is a compound of Formula (Ia), or a pharmaceutically acceptable salt or solvate thereof, wherein

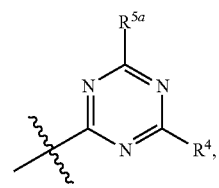

$R^{5a}$ is hydrogen, and $R^4$ is

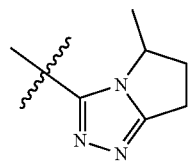

In some embodiments is a compound of Formula (Ia), or a pharmaceutically acceptable salt or solvate thereof, wherein

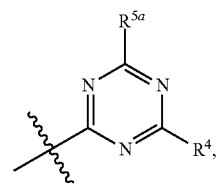

$R^{5a}$ is hydrogen, and $R^4$ is

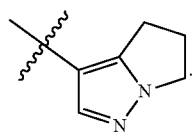

In some embodiments is a compound of Formula (Ia), or a pharmaceutically acceptable salt or solvate thereof, wherein

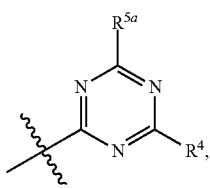

$R^{5a}$ is hydrogen, and $R^4$ is

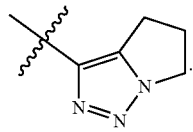 [SMILES: *c1nnn2c1CCC2]

In some embodiments is a compound of Formula (Ia), or a pharmaceutically acceptable salt or solvate thereof, wherein

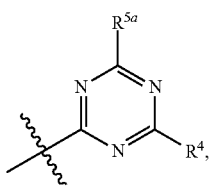

$R^{5a}$ is hydrogen, and $R^4$ is

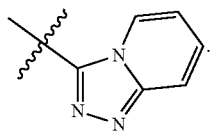

In some embodiments is a compound of Formula (Ia), or a pharmaceutically acceptable salt or solvate thereof, wherein

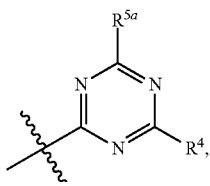

$R^{5a}$ is hydrogen, and $R^4$ is

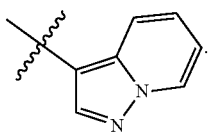 [SMILES: *c1cnn2ccccc12]

In some embodiments is a compound of Formula (Ia), or a pharmaceutically acceptable salt or solvate thereof, wherein

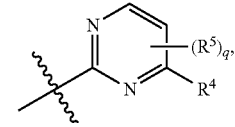

$R^{5a}$ is hydrogen, and $R^4$ is

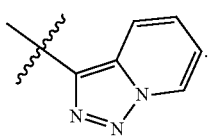 [SMILES: *c1nnn2ccccc12]

In some embodiments is a compound of Formula (Ia), or a pharmaceutically acceptable salt or solvate thereof, wherein

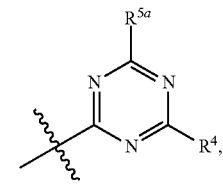

$R^{5a}$ is hydrogen, and $R^4$ is

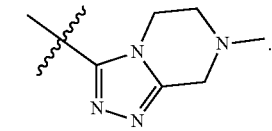 [SMILES: *c1nnc2n1CCN(C)C2]

In some embodiments, presented herein are compounds of Formula (Ib), or a pharmaceutically acceptable salt or solvate thereof:

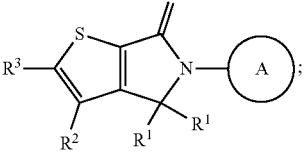

Formula (Ib)

wherein

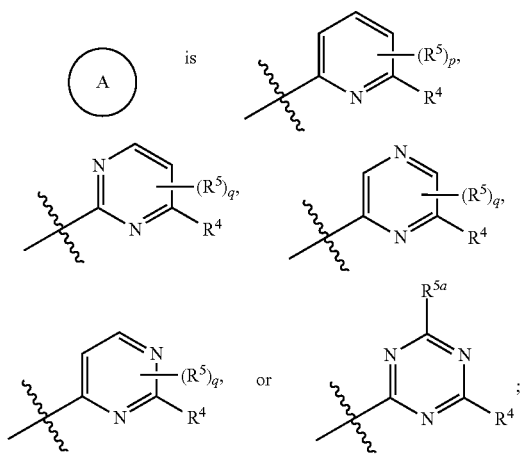

each R$^1$ is independently selected from a group consisting of hydrogen, halogen, and C$_{1-6}$alkyl;
R$^2$ is selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$ alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halogen, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;
R$^3$ is selected from a group consisting of hydrogen, halogen, —CN, and C$_{1-6}$alkyl; or R$^2$ and R$^3$ are combined to form a phenyl ring optionally substituted with one, two, or three R$^8$ substituents;
R$^4$ is selected from a group consisting of hydrogen, halogen, —CN, —OH, —OR$^6$, —SR$^6$, —S(=O)R$^7$, —NO$_2$, —N(R$^6$)$_2$, —S(=O)$_2$R$^7$, —NHS(=O)$_2$R$^7$, —S(=O)$_2$N(R$^6$)$_2$, —C(=O)R$^7$, —C(=O)OR$^6$, —OC(=O)R$^7$, —C(=O)N(R$^6$)$_2$, —OC(=O)N(R$^6$)$_2$, —NR$^6$C(=O)N(R$^6$)$_2$, —NR$^6$C(=O)R$^7$, —NR$^6$C(=O)OR$^6$, C$_{1-6}$alkyl, C$_{2-6}$alkenyl, C$_{2-6}$alkynyl, C$_{3-8}$cycloalkyl, C$_{2-9}$heterocycle, C$_{6-10}$aryl, C$_{1-9}$heteroaryl, and a fused C$_{5-9}$heteroaryl-cycloalkyl; wherein C$_{1-6}$alkyl, C$_{2-6}$ alkenyl, C$_{2-6}$alkynyl, C$_{3-8}$cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halogen, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;
each R$^5$ is independently selected from a group consisting of halogen, —CN, and C$_{1-6}$alkyl;
R$^{5a}$ is selected from the group consisting of hydrogen and C$_{1-6}$alkyl;
each R$^6$ is independently selected from the group consisting of hydrogen, C$_{1-6}$alkyl, —C$_{1-6}$alkyl-O—C$_{1-6}$alkyl, —C$_{1-6}$alkyl-C$_{2-9}$heterocycle, —C$_{1-6}$alkyl-C$_{2-9}$heteroaryl, C$_{3-8}$cycloalkyl, and C$_{2-9}$heterocycle; or two R$^6$ on the same heteroatom are taken together with that heteroatom to which they are attached to form a C$_{2-9}$heterocycle or a C$_{2-9}$heteroaryl;
each R$^7$ is independently selected from the group consisting of C$_{1-6}$alkyl, C$_{3-8}$cycloalkyl, and C$_{2-9}$heterocycle;
each R$^8$ is independently selected from the group consisting of halogen, —CN, C$_{1-6}$alkyl, —C$_{1-6}$ alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$;
each R$^{13}$ is independently selected from the group consisting of hydrogen, C$_{1-6}$alkyl, and C$_{3-8}$cycloalkyl; or two R$^{13}$ on the same heteroatom are taken together with that heteroatom to which they are attached to form a C$_{2-9}$heterocycle;
each R$^{14}$ is independently selected from the group consisting of C$_L$-6alkyl and C$_{3-8}$cycloalkyl;
p is 0, 1, 2, or 3; and
q is 0, 1, or 2.
In some embodiments is a compound of Formula (Ib), or a pharmaceutically acceptable salt or solvate thereof, wherein each R$^1$ is hydrogen. In some embodiments is a compound of Formula (Ib), or a pharmaceutically acceptable salt or solvate thereof, wherein one R$^1$ is hydrogen and one R$^1$ is C$_{1-6}$alkyl. In some embodiments is a compound of Formula (Ib), or a pharmaceutically acceptable salt or solvate thereof, wherein each R$^1$ is C$_{1-6}$alkyl. In some embodiments is a compound of Formula (Ib), or a pharmaceutically acceptable salt or solvate thereof, wherein each R$^1$ is halogen.

In some embodiments is a compound of Formula (Ib), or a pharmaceutically acceptable salt or solvate thereof, wherein R$^2$ is selected from a group consisting of hydrogen, halogen, and C$_{1-6}$alkyl.

In some embodiments is a compound of Formula (Ib), or a pharmaceutically acceptable salt or solvate thereof, wherein R$^2$ is hydrogen.

In some embodiments is a compound of Formula (Ib), or a pharmaceutically acceptable salt or solvate thereof, wherein R$^2$ is halogen.

In some embodiments is a compound of Formula (Ib), or a pharmaceutically acceptable salt or solvate thereof, wherein R$^2$ is C$_{1-6}$alkyl.

In some embodiments is a compound of Formula (Ib), or a pharmaceutically acceptable salt or solvate thereof, wherein R$^2$ is selected from a group consisting of C$_{3-8}$cycloalkyl, C$_{2-9}$ heterocycle, C$_{6-10}$aryl, C$_{1-9}$heteroaryl, and a fused C$_{5-9}$heteroaryl-cycloalkyl; wherein C$_3$ 8cycloalkyl, C$_{2-9}$heterocycle, C$_{6-10}$aryl, C$_{1-9}$heteroaryl, and fused C$_{5-9}$heteroaryl-cycloalkyl are optionally substituted with one, two, or three substituents selected from the group consisting of halogen, —CN, C$_{1-6}$alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$.
In some embodiments is a compound of Formula (Ib), or a pharmaceutically acceptable salt or solvate thereof, wherein R$^2$ is selected from a group consisting of C$_{2-9}$heterocycle and C$_{1-9}$heteroaryl; wherein C$_{2-9}$heterocycle and C$_{1-9}$heteroaryl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein R$^2$ is selected from a group consisting of $C_{2-9}$heterocycle and $C_{1-9}$ heteroaryl; wherein $C_{2-9}$heterocycle and $C_{1-9}$heteroaryl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^4$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein R$^2$ is selected from a group consisting of pyrazole, imidazole, thiazole, and pyridine; wherein pyrazole, imidazole, thiazole, and pyridine are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein R$^2$ is selected from a group consisting of pyrazole, imidazole, thiazole, and pyridine; wherein pyrazole, imidazole, thiazole, and pyridine are optionally substituted with one or two substituents selected from the group consisting of halogen, $C_{1-6}$alkyl, and $C_{3-8}$cycloalkyl. In some embodiments is a compound of Formula (Ib), or a pharmaceutically acceptable salt or solvate thereof, wherein R$^2$ is

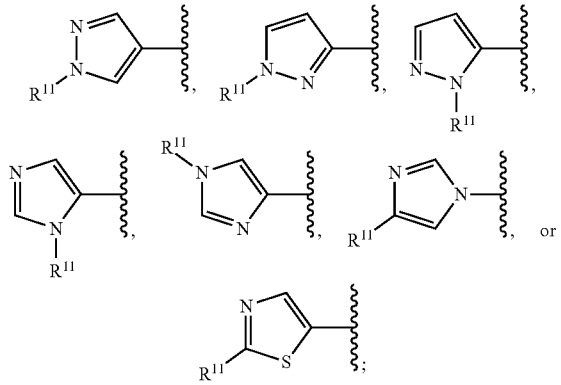

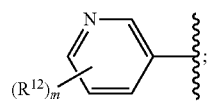

wherein R$^{11}$ is $C_{1-6}$alkyl or $C_{3-6}$cycloalkyl. In some embodiments is a compound of Formula (Ib), or a pharmaceutically acceptable salt or solvate thereof, wherein R$^2$ is wherein each R$^{12}$ is independently hydrogen, halogen, CN, $C_{1-6}$alkyl, or $C_{3-6}$cycloalkyl; and m is 1 or 2. In some embodiments is a compound of Formula (Ib), or a pharmaceutically acceptable salt or solvate thereof, wherein R$^2$ is selected from a group consisting of unsubstituted pyrazole, unsubstituted imidazole, unsubstituted thiazole, and unsubstituted pyridine. In some embodiments, R$^2$ is $C_{6-10}$aryl optionally substituted with one, two, or three substituents selected from the group consisting of halogen, —CN, $C_{1-6}$alkyl, —$C_{1-6}$ alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^3$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein R$^2$ is phenyl optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein R$^2$ is —C(=O)N(R$^6$)$_2$ and each R$^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two R$^6$ on the same heteroatom are taken together with that heteroatom to which they are attached to form a $C_{2-9}$heterocycle or a $C_{2-9}$heteroaryl. In some embodiments is a compound of Formula (Ib), or a pharmaceutically acceptable salt or solvate thereof, wherein R$^2$ is

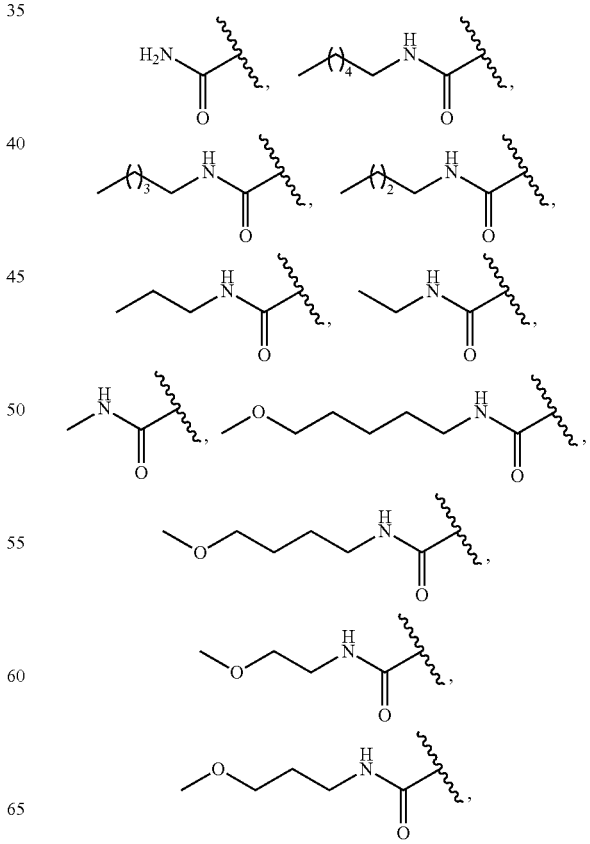

-continued

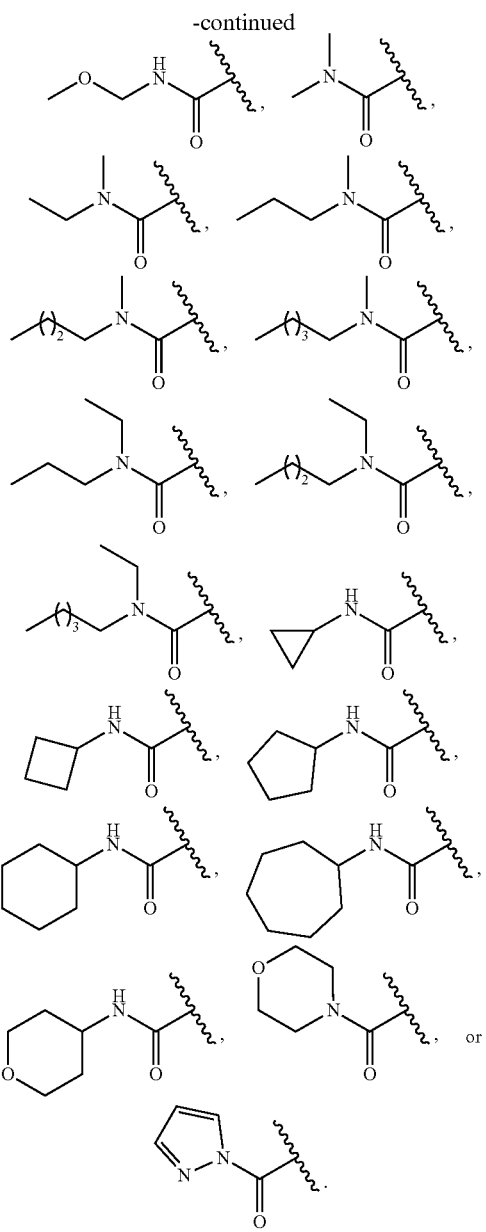

In some embodiments is a compound of Formula (Ib), or a pharmaceutically acceptable salt or solvate thereof, wherein $R^2$ is

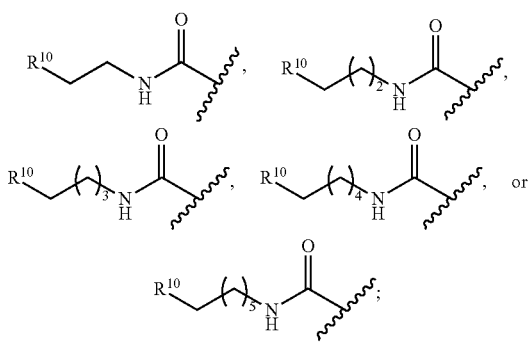

wherein $R^{10}$ is $C_{1-9}$heteroaryl. In some embodiments is a compound of Formula (Ib), or a pharmaceutically acceptable salt or solvate thereof, wherein $R^2$ is —NHC(=O)$R^7$. In some embodiments is a compound of Formula (Ib), or a pharmaceutically acceptable salt or solvate thereof, wherein $R^2$ is

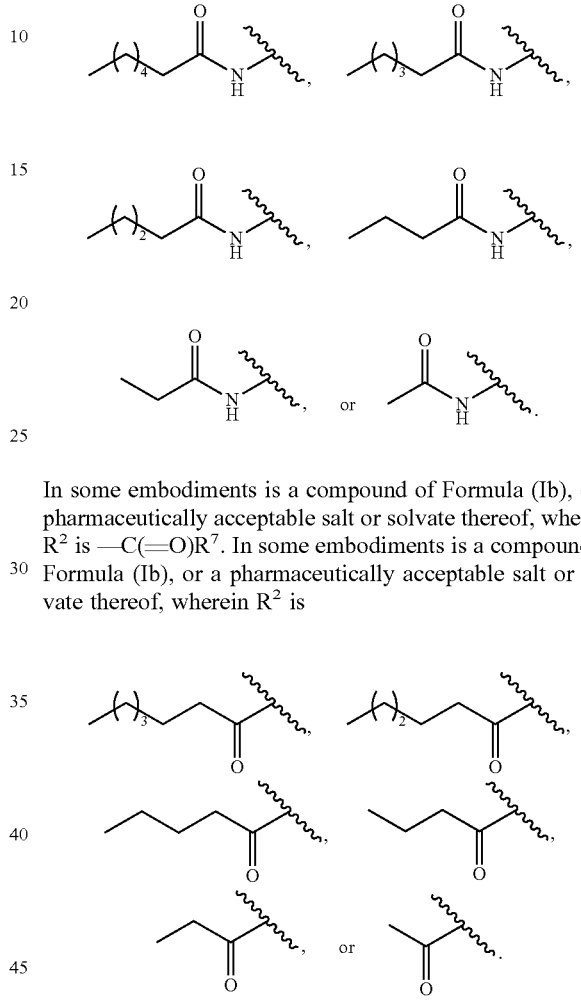

In some embodiments is a compound of Formula (Ib), or a pharmaceutically acceptable salt or solvate thereof, wherein $R^2$ is —C(=O)$R^7$. In some embodiments is a compound of Formula (Ib), or a pharmaceutically acceptable salt or solvate thereof, wherein $R^2$ is In some embodiments is a compound of Formula (Ib), or a pharmaceutically acceptable salt or solvate thereof, wherein $R^3$ is hydrogen. In some embodiments is a compound of Formula (Ib), or a pharmaceutically acceptable salt or solvate thereof, wherein $R^3$ is $C_{1-6}$alkyl. In some embodiments is a compound of Formula (Ib), or a pharmaceutically acceptable salt or solvate thereof, wherein $R^3$ is halogen.

In some embodiments is a compound of Formula (Ib), or a pharmaceutically acceptable salt or solvate thereof, wherein

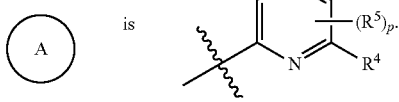

In some embodiments is a compound of Formula (Ib), or a pharmaceutically acceptable salt or solvate thereof, wherein

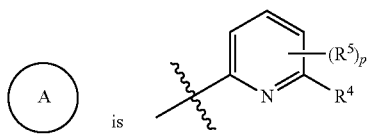

and p is 2. In some embodiments is a compound of Formula (Ib), or a pharmaceutically acceptable salt or solvate thereof, wherein

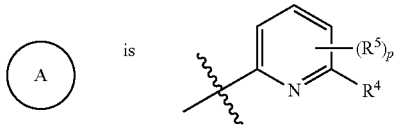

and p is 1. In some embodiments is a compound of Formula (Ib), or a pharmaceutically acceptable salt or solvate thereof, wherein

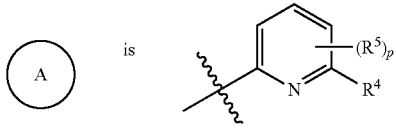

and p is 0. In some embodiments is a compound of Formula (Ib), or a pharmaceutically acceptable salt or solvate thereof, wherein

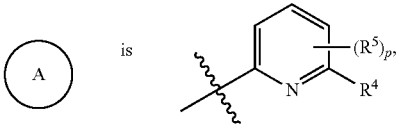

p is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein

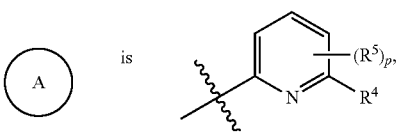

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.
In some embodiments is a compound of Formula (Ib), or a pharmaceutically acceptable salt or solvate thereof, wherein

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein

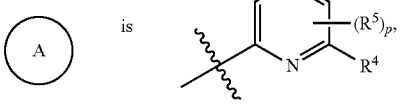

p is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein

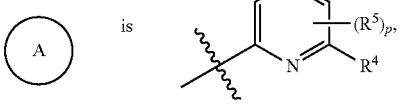

p is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ib), or a pharmaceutically acceptable salt or solvate thereof, wherein

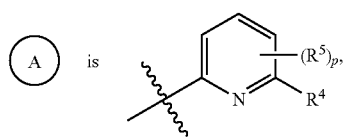

p is 0, and R⁴ is

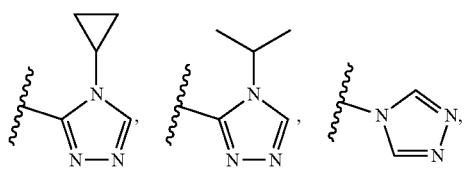

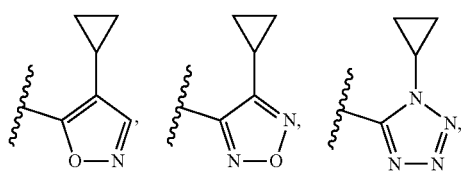

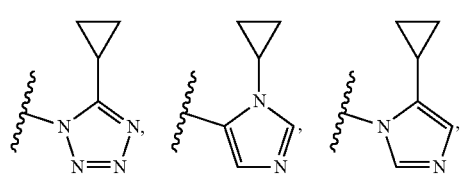

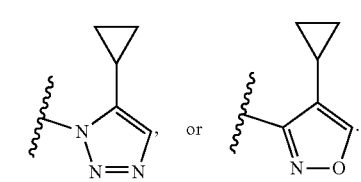

In some embodiments is a compound of Formula (Ib), or a pharmaceutically acceptable salt or solvate thereof, wherein

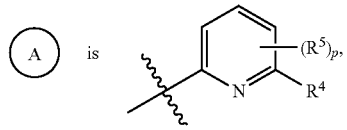

p is 0, and R⁴ is

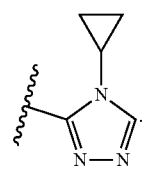

In some embodiments is a compound of Formula (Ib), or a pharmaceutically acceptable salt or solvate thereof, wherein

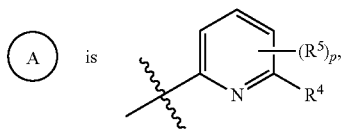

p is 0, and R⁴ is

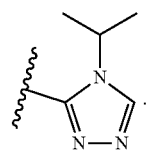

In some embodiments is a compound of Formula (Ib), or a pharmaceutically acceptable salt or solvate thereof, wherein

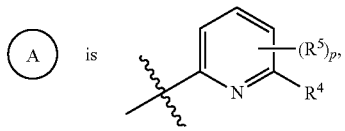

p is 0, and R⁴ is

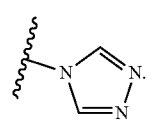

In some embodiments is a compound of Formula (Ib), or a pharmaceutically acceptable salt or solvate thereof, wherein

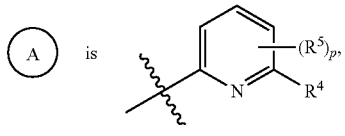

p is 0, and R⁴ is

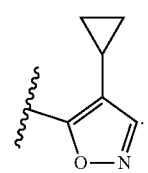 [SMILES: *c1oncc1C1CC1]

In some embodiments is a compound of Formula (Ib), or a pharmaceutically acceptable salt or solvate thereof, wherein

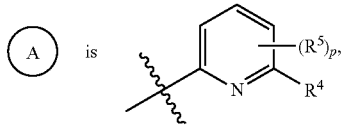

141 p is 0, and R⁴ is

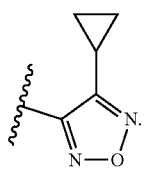 [SMILES: *c1nonc1C1CC1]

In some embodiments is a compound of Formula (Ib), or a pharmaceutically acceptable salt or solvate thereof, wherein

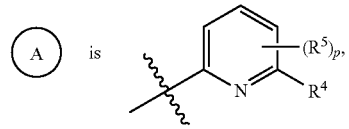

p is 0, and R⁴ is

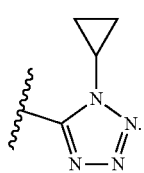 [SMILES: *c1nnnn1C1CC1]

In some embodiments is a compound of Formula (Ib), or a pharmaceutically acceptable salt or solvate thereof, wherein

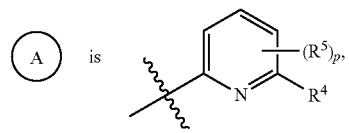

p is 0, and R⁴ is

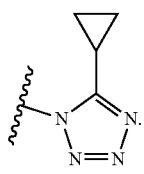 [SMILES: *n1nnnc1C1CC1]

In some embodiments is a compound of Formula (Ib), or a pharmaceutically acceptable salt or solvate thereof, wherein

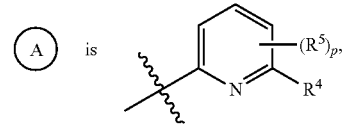

142 p is 0, and R⁴ is

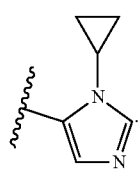 [SMILES: *c1cncn1C1CC1]

In some embodiments is a compound of Formula (Ib), or a pharmaceutically acceptable salt or solvate thereof, wherein

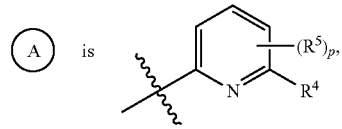

p is 0, and R⁴ is

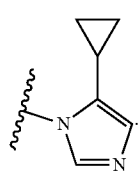 [SMILES: *n1cncc1C1CC1]

In some embodiments is a compound of Formula (Ib), or a pharmaceutically acceptable salt or solvate thereof, wherein

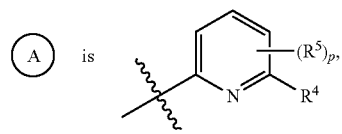

p is 0, and R⁴ is

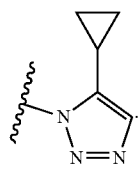 [SMILES: *n1nncc1C1CC1]

In some embodiments is a compound of Formula (Ib), or a pharmaceutically acceptable salt or solvate thereof, wherein

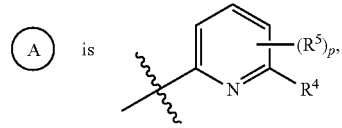

p is 0, and R⁴ is

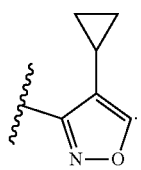

In some embodiments is a compound of Formula (Ib), or a pharmaceutically acceptable salt or solvate thereof, wherein

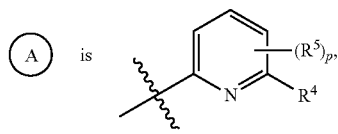

p is 0, and R⁴ is

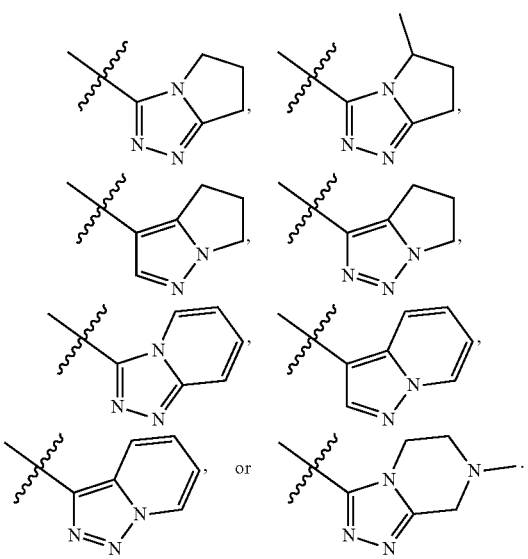

In some embodiments is a compound of Formula (Ib), or a pharmaceutically acceptable salt or solvate thereof, wherein

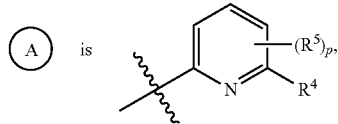

p is 0, and R⁴ is

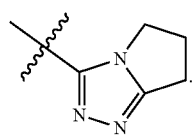 [SMILES: *c1nnc2n1CCC2]

In some embodiments is a compound of Formula (Ib), or a pharmaceutically acceptable salt or solvate thereof, wherein

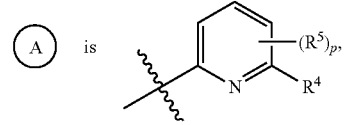

q is 0, and R⁴ is

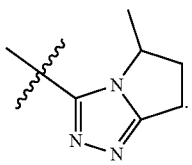 [SMILES: *c1nnc2n1C(C)CC2]

In some embodiments is a compound of Formula (Ib), or a pharmaceutically acceptable salt or solvate thereof, wherein

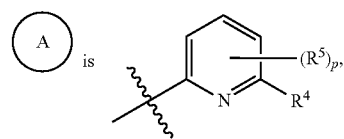

p is 0, and R⁴ is

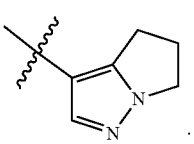 [SMILES: *c1cnn2c1CCC2]

In some embodiments is a compound of Formula (Ib), or a pharmaceutically acceptable salt or solvate thereof, wherein

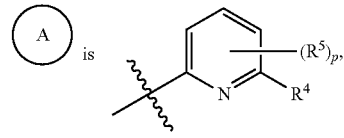

p is 0, and R⁴ is

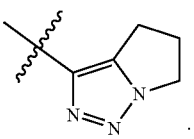

In some embodiments is a compound of Formula (Ib), or a pharmaceutically acceptable salt or solvate thereof, wherein

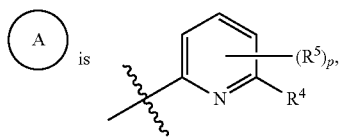

p is 0, and R⁴ is

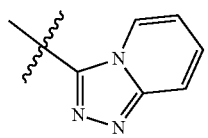

In some embodiments is a compound of Formula (Ib), or a pharmaceutically acceptable salt or solvate thereof, wherein

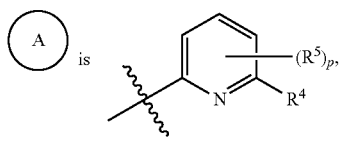

p is 0, and R⁴ is

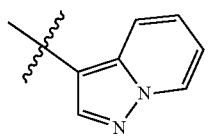

In some embodiments is a compound of Formula (Ib), or a pharmaceutically acceptable salt or solvate thereof, wherein

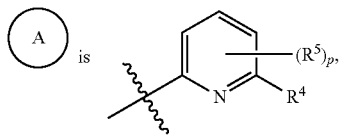

p is 0, and R⁴ is

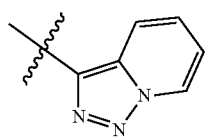

In some embodiments is a compound of Formula (Ib), or a pharmaceutically acceptable salt or solvate thereof, wherein

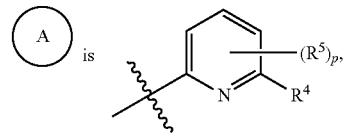

p is 0, and R⁴ is

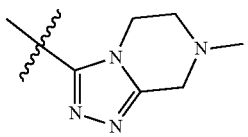

In some embodiments is a compound of Formula (Ib), or a pharmaceutically acceptable salt or solvate thereof, wherein

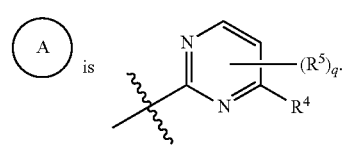

In some embodiments is a compound of Formula (Ib), or a pharmaceutically acceptable salt or solvate thereof, wherein

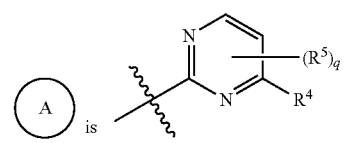

and q is 2. In some embodiments is a compound of Formula (Ib), or a pharmaceutically acceptable salt or solvate thereof, wherein

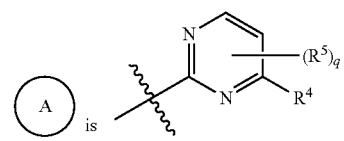

and q is 1. In some embodiments is a compound of Formula (Ib), or a pharmaceutically acceptable salt or solvate thereof, wherein

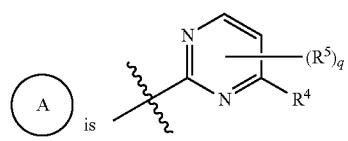

and q is 0. In some embodiments is a compound of Formula (Ib), or a pharmaceutically acceptable salt or solvate thereof, wherein

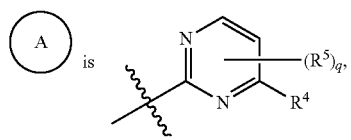

q is 0, and $R^4$ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ib), or a pharmaceutically acceptable salt or solvate thereof, wherein

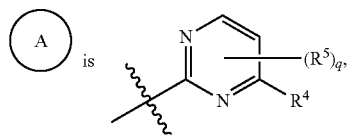

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ib), or a pharmaceutically acceptable salt or solvate thereof, wherein

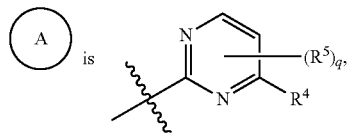

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ib), or a pharmaceutically acceptable salt or solvate thereof, wherein

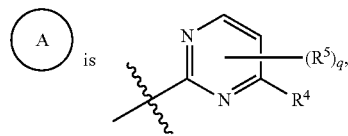

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ib), or a pharmaceutically acceptable salt or solvate thereof, wherein

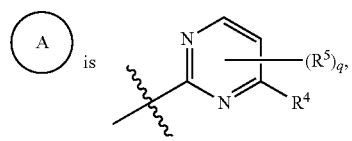

q is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ib), or a pharmaceutically acceptable salt or solvate thereof, wherein

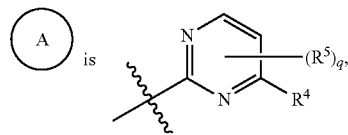

q is 0, and $R^4$ is

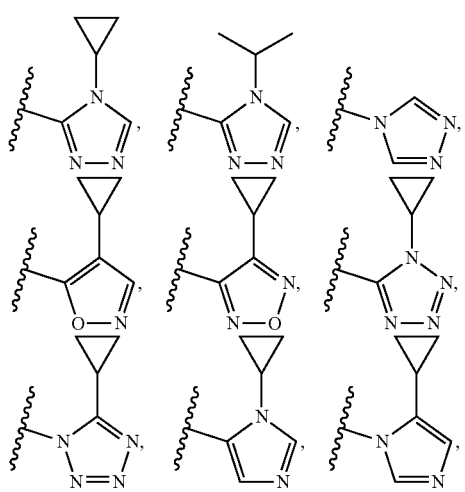

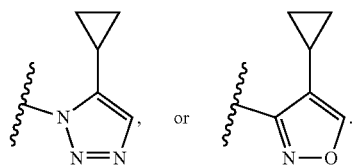, or 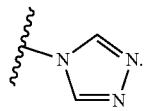

In some embodiments is a compound of Formula (Ib), or a pharmaceutically acceptable salt or solvate thereof, wherein

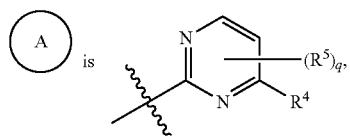

q is 0, and R⁴ is

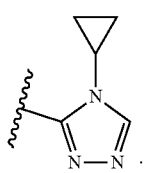

In some embodiments is a compound of Formula (Ib), or a pharmaceutically acceptable salt or solvate thereof, wherein

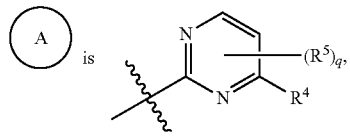

q is 0, and R⁴ is

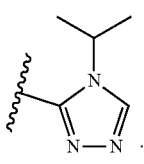

In some embodiments is a compound of Formula (Ib), or a pharmaceutically acceptable salt or solvate thereof, wherein

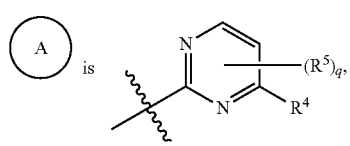

In some embodiments is a compound of Formula (Ib), or a pharmaceutically acceptable salt or solvate thereof, wherein

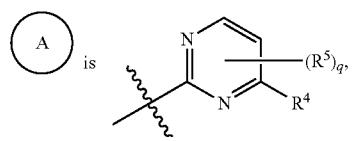

q is 0, and R⁴ is

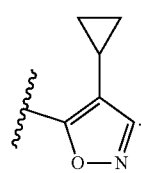

In some embodiments is a compound of Formula (Ib), or a pharmaceutically acceptable salt or solvate thereof, wherein

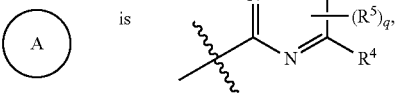

q is 0, and R⁴ is

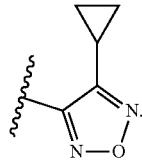 [SMILES: *c1nonc1C1CC1]

In some embodiments is a compound of Formula (Ib), or a pharmaceutically acceptable salt or solvate thereof, wherein

q is 0, and R⁴ is

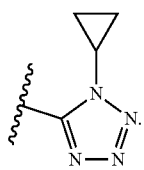 [SMILES: *c1nnnn1C1CC1]

In some embodiments is a compound of Formula (Ib), or a pharmaceutically acceptable salt or solvate thereof, wherein

 is 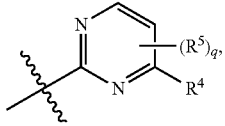

is 0, and R⁴ is

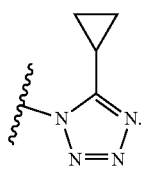 [SMILES: *n1nnnc1C1CC1]

In some embodiments is a compound of Formula (Ib), or a pharmaceutically acceptable salt or solvate thereof, wherein

 is 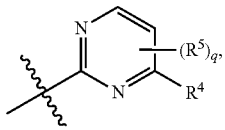

q is 0, and R⁴ is

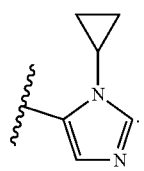

In some embodiments is a compound of Formula (Ib), or a pharmaceutically acceptable salt or solvate thereof, wherein

 is 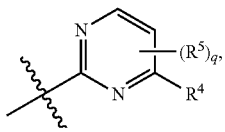

q is 0, and R⁴ is

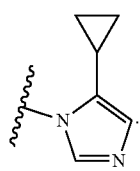

In some embodiments is a compound of Formula (Ib), or a pharmaceutically acceptable salt or solvate thereof, wherein

 is 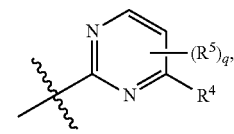

q is 0, and R⁴ is

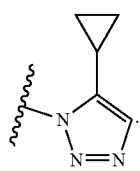

In some embodiments is a compound of Formula (Ib), or a pharmaceutically acceptable salt or solvate thereof, wherein

 is 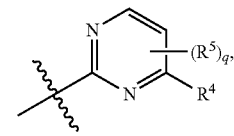

q is 0, and R⁴ is

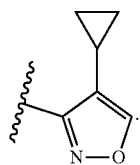 [SMILES: *c1nocc1C1CC1]

In some embodiments is a compound of Formula (Ib), or a pharmaceutically acceptable salt or solvate thereof, wherein

 is 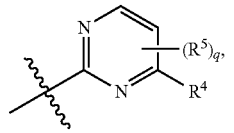

q is 0, and R⁴ is

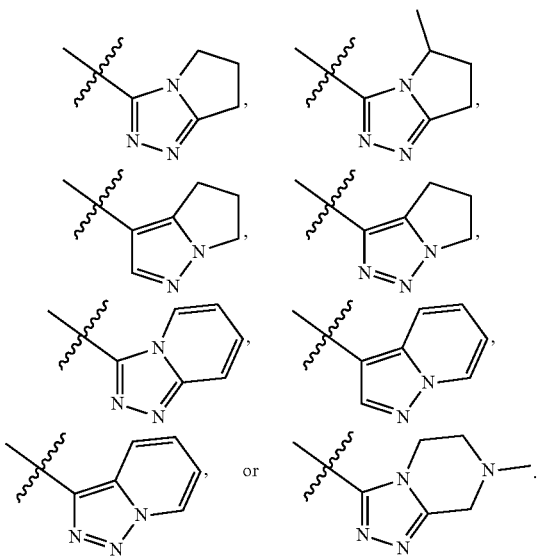

In some embodiments is a compound of Formula (Ib), or a pharmaceutically acceptable salt or solvate thereof, wherein

 is 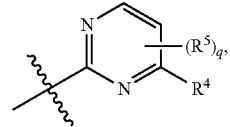

q is 0, and R⁴ is

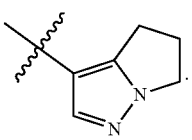

In some embodiments is a compound of Formula (Ib), or a pharmaceutically acceptable salt or solvate thereof, wherein

 is 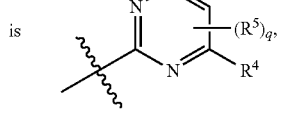

q is 0, and R⁴ is

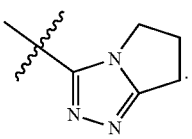 [SMILES: *c1nnc2n1CCC2]

In some embodiments is a compound of Formula (Ib), or a pharmaceutically acceptable salt or solvate thereof, wherein

 is 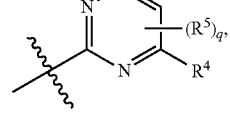

q is 0, and R⁴ is

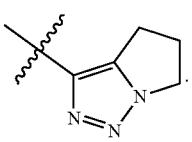 [SMILES: *c1nnn2c1CCC2]

In some embodiments is a compound of Formula (Ib), or a pharmaceutically acceptable salt or solvate thereof, wherein

 is 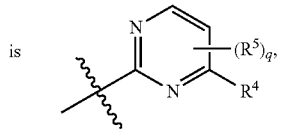

q is 0, and R⁴ is

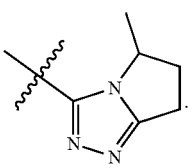

In some embodiments is a compound of Formula (Ib), or a pharmaceutically acceptable salt or solvate thereof, wherein

 is 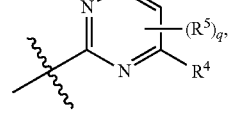

q is 0, and R⁴ is

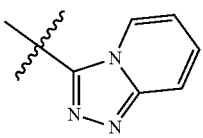

In some embodiments is a compound of Formula (Ib), or a pharmaceutically acceptable salt or solvate thereof, wherein

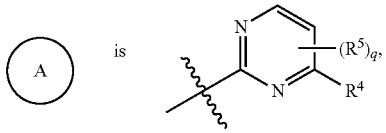

q is 0, and R⁴ is

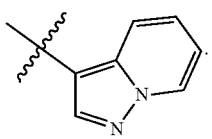

In some embodiments is a compound of Formula (Ib), or a pharmaceutically acceptable salt or solvate thereof, wherein

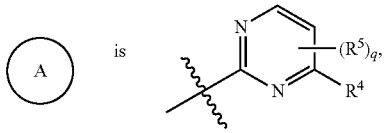

q is 0, and R⁴ is

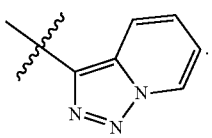 [SMILES: *c1nnn2ccccc12]

In some embodiments is a compound of Formula (Ib), or a pharmaceutically acceptable salt or solvate thereof, wherein

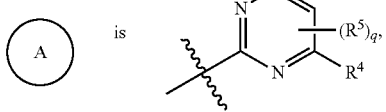

q is 0, and R⁴ is

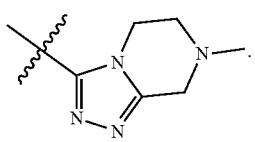 [SMILES: *c1nnc2n1CCN(C)C2]

In some embodiments is a compound of Formula (Ib), or a pharmaceutically acceptable salt or solvate thereof, wherein

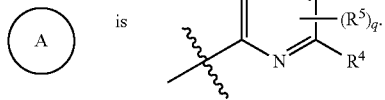

In some embodiments is a compound of Formula (Ib), or a pharmaceutically acceptable salt or solvate thereof, wherein

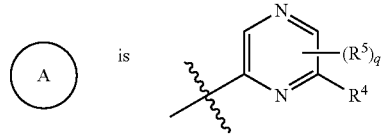

and q is 2. In some embodiments is a compound of Formula (Ib), or a pharmaceutically acceptable salt or solvate thereof, wherein

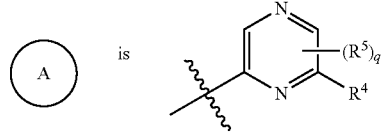

and q is 1. In some embodiments is a compound of Formula (Ib), or a pharmaceutically acceptable salt or solvate thereof, wherein

and q is 0. In some embodiments is a compound of Formula (Ib), or a pharmaceutically acceptable salt or solvate thereof, wherein

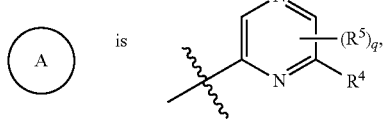

q is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ib), or a pharmaceutically acceptable salt or solvate thereof, wherein

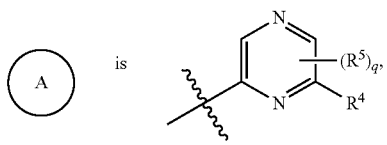

q is 0, and R⁴ is selected from a group consisting of a C$_{1-9}$heteroaryl and a fused C$_{5-9}$heteroaryl-cycloalkyl; wherein the C$_{1-9}$heteroaryl and fused C$_{5-9}$heteroaryl-cycloalkyl are optionally substituted with one, two, or three substituents selected from the group consisting of halogen, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R¹⁴, —C(=O)OR¹³, —C(=O)N(R¹³)$_2$, —S(=O)R¹⁴, —S(=O)$_2$R¹³, —S(=O)$_2$—N(R¹³)$_2$, —N(R¹³)$_2$, —N(R¹³)C(=O)R¹⁴, and —N(R¹³)S(=O)$_2$R¹³. In some embodiments is a compound of Formula (Ib), or a pharmaceutically acceptable salt or solvate thereof, wherein

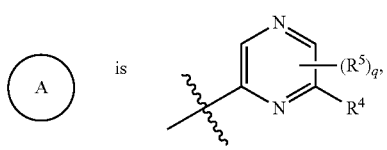

q is 0, and R⁴ is selected from a group consisting of a C$_{1-9}$heteroaryl and a fused C$_{5-9}$heteroaryl-cycloalkyl; wherein the C$_{1-9}$heteroaryl and fused C$_{5-9}$heteroaryl-cycloalkyl are optionally substituted with one or two substituents selected from the group consisting of halogen, —CN, C$_{1-6}$alkyl, —C$_{1-6}$alkyl-OH, C$_{1-6}$ haloalkyl, C$_{3-8}$cycloalkyl, C$_{2-9}$heterocycle, C$_{6-10}$aryl, C$_{1-9}$heteroaryl, —C(=O)R¹⁴, —C(=O)OR¹³, —C(=O)N(R¹³)$_2$, —S(=O)R¹⁴, —S(=O)$_2$R¹³, —S(=O)$_2$—N(R¹³)$_2$, —N(R¹³)$_2$, —N(R¹³)C(=O)R¹⁴, and —N(R¹³)S(=O)$_2$R¹³. In some embodiments is a compound of Formula (Ib), or a pharmaceutically acceptable salt or solvate thereof, wherein

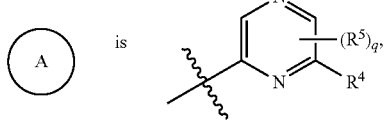

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, C$_{1-6}$ alkyl, —C$_{1-6}$alkyl-OH, C$_{1-6}$haloalkyl, C$_{3-8}$cycloalkyl, C$_{2-9}$heterocycle, C$_{6-10}$aryl, C$_{1-9}$heteroaryl, —C(=O)R¹⁴, —C(=O)OR¹³, —C(=O)N(R¹³)$_2$, —S(=O)R¹⁴, —S(=O)$_2$R¹³, —S(=O)$_2$—N(R¹³)$_2$, —N(R¹³)$_2$, —N(R¹³)C(=O)R¹⁴, and —N(R¹³)S(=O)$_2$R¹³. In some embodiments is a compound of Formula (Ib), or a pharmaceutically acceptable salt or solvate thereof, wherein

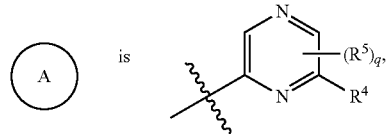

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, C$_{1-6}$alkyl, and C$_{3-8}$cycloalkyl. In some embodiments is a compound of Formula (Ib), or pharmaceutically acceptable salt or solvate thereof, wherein

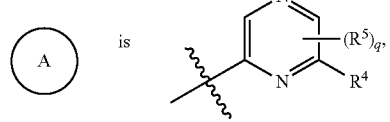

and R⁴ is

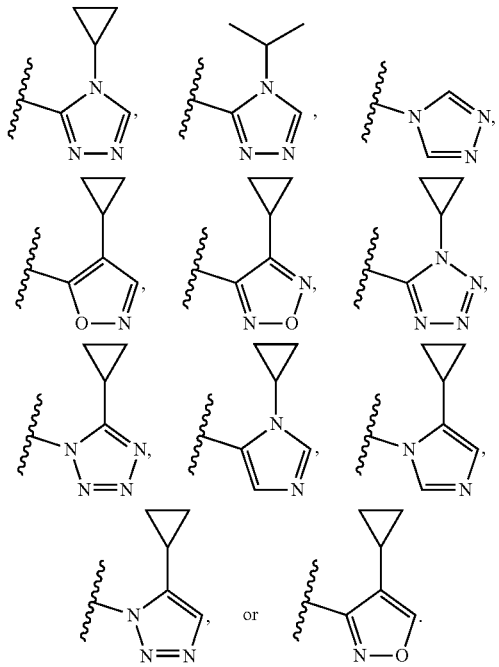

In some embodiments is a compound of Formula (Ib), or a pharmaceutically acceptable salt or solvate thereof, wherein

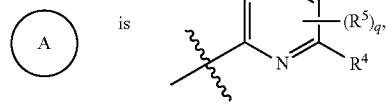

q is 0, and R⁴ is

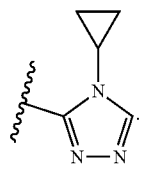

In some embodiments is a compound of Formula (Ib), or a pharmaceutically acceptable salt or solvate thereof, wherein

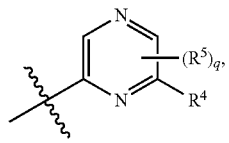

q is 0, and R⁴ is

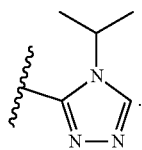

In some embodiments is a compound of Formula (Ib), or a pharmaceutically acceptable salt or solvate thereof, wherein

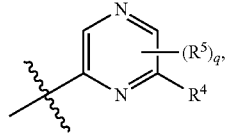

q is 0, and R⁴ is

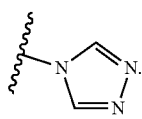

In some embodiments is a compound of Formula (Ib), or a pharmaceutically acceptable salt or solvate thereof, wherein

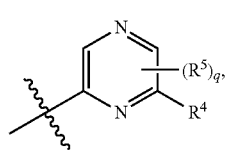

q is 0, and R⁴ is

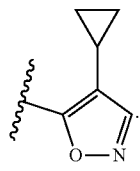 [SMILES: *c1oncc1C1CC1]

In some embodiments is a compound of Formula (Ib), or a pharmaceutically acceptable salt or solvate thereof, wherein

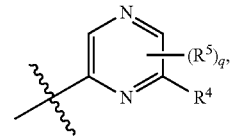

q is 0, and R⁴ is

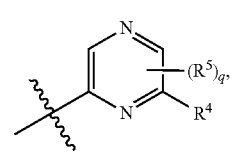

In some embodiments is a compound of Formula (Ib), or a pharmaceutically acceptable salt or solvate thereof, wherein q is 0, and R⁴ is

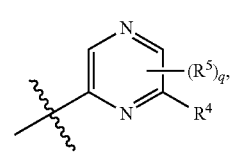

In some embodiments is a compound of Formula (Ib), or a pharmaceutically acceptable salt or solvate thereof, wherein q is 0, and R⁴ is

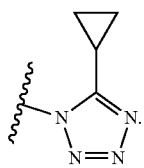 [SMILES: *n1nnnc1C1CC1]

In some embodiments is a compound of Formula (Ib), or a pharmaceutically acceptable salt or solvate thereof, wherein

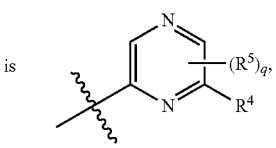

q is 0, and R⁴ is

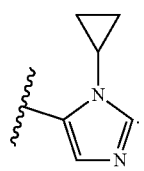 [SMILES: *c1cncn1C1CC1]

In some embodiments is a compound of Formula (Ib), or a pharmaceutically acceptable salt or solvate thereof, wherein

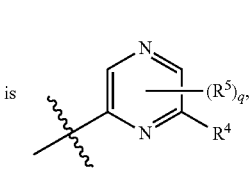

q is 0, and R⁴ is

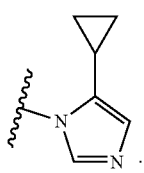

In some embodiments is a compound of Formula (Ib), or a pharmaceutically acceptable salt or solvate thereof, wherein

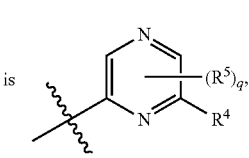

q is 0, and R⁴ is

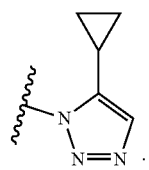

In some embodiments is a compound of Formula (Ib), or a pharmaceutically acceptable salt or solvate thereof, wherein

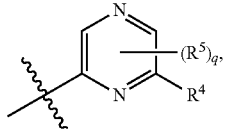

q is 0, and R⁴ is

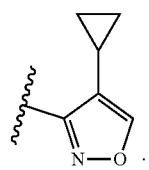

In some embodiments is a compound of Formula (Ib), or a pharmaceutically acceptable salt or solvate thereof, wherein

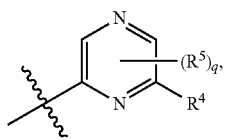

q is 0, and R⁴ is

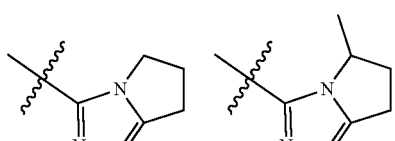

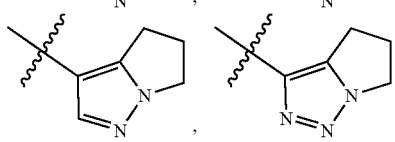

In some embodiments is a compound of Formula (Ib), or a pharmaceutically acceptable salt or solvate thereof, wherein

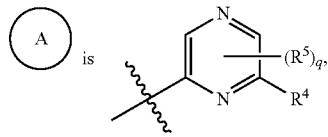

q is 0, and R⁴ is

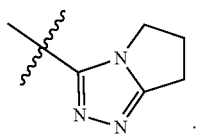 [SMILES: *c1nnc2n1CCC2]

In some embodiments is a compound of Formula (Ib), or a pharmaceutically acceptable salt or solvate thereof, wherein

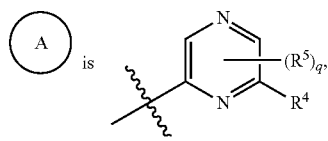

q is 0, and R⁴ is

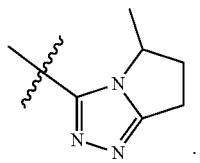 [SMILES: *c1nnc2n1C(C)CC2]

In some embodiments is a compound of Formula (Ib), or a pharmaceutically acceptable salt or solvate thereof, wherein

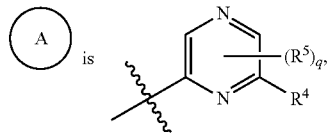

q is 0, and R⁴ is

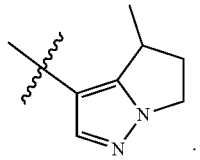 [SMILES: *c1cnn2c1C(C)CC2]

In some embodiments is a compound of Formula (Ib), or a pharmaceutically acceptable salt or solvate thereof, wherein

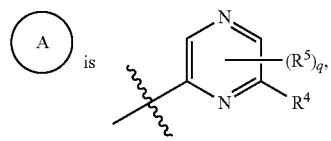

q is 0, and R⁴ is

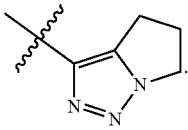 [SMILES: *c1nnn2c1CCC2]

In some embodiments is a compound of Formula (Ib), or a pharmaceutically acceptable salt or solvate thereof, wherein

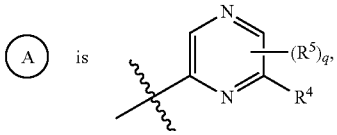

q is 0, and R⁴ is

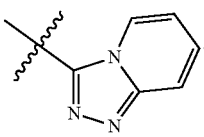

In some embodiments is a compound of Formula (Ib), or a pharmaceutically acceptable salt or solvate thereof, wherein

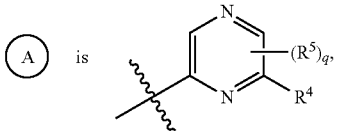

q is 0 and R⁴ is

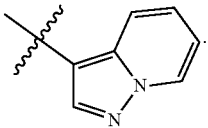

In some embodiments is a compound of Formula (Ib), or a pharmaceutically acceptable salt or solvate thereof, wherein

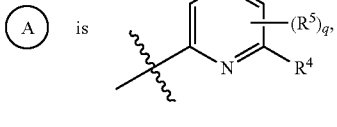

q is 0, and $R^4$ is

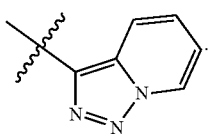

In some embodiments is a compound of Formula Ib, or a pharmaceutically acceptable salt or solvate thereof, wherein

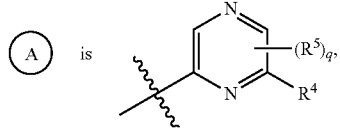

q is 0, and $R^4$ is

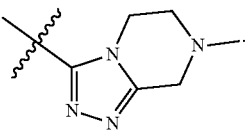 [SMILES: *c1nnc2n1CCN(C)C2]

In some embodiments is a compound of Formula (Ib), or a pharmaceutically acceptable salt or solvate thereof, wherein

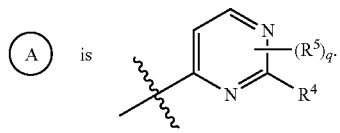

In some embodiments is a compound of Formula (Ib), or a pharmaceutically acceptable salt or solvate thereof, wherein

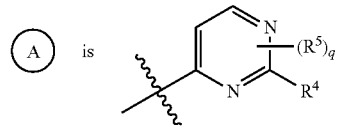

and q is 2. In some embodiments is a compound of Formula (Ib), or a pharmaceutically acceptable salt or solvate thereof, wherein

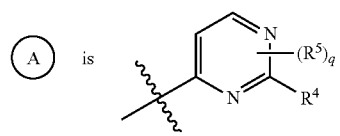

and q is 1. In some embodiments is a compound of Formula (Ib), or a pharmaceutically acceptable salt or solvate thereof, wherein

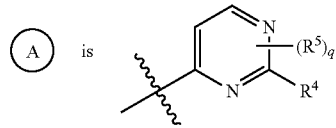

and q is 0. In some embodiments is a compound of Formula (Ib), or a pharmaceutically acceptable salt or solvate thereof, wherein

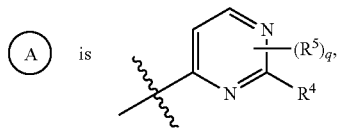

q is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^3$)S(=O)$_2R^{13}$. In some embodiments is a compound of Formula (Ib), or a pharmaceutically acceptable salt or solvate thereof, wherein

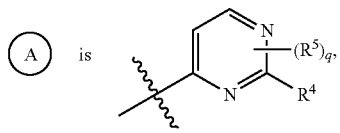

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein

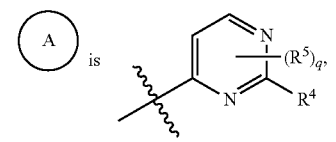

q is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein

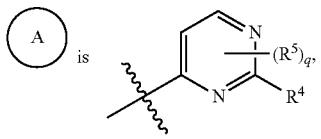

q is 0, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^{13}$, —C(=O)N(R$^{13}$)$_2$, —S(=O)R$^{14}$, —S(=O)$_2$R$^1$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ib), or a pharmaceutically acceptable salt or solvate thereof, wherein

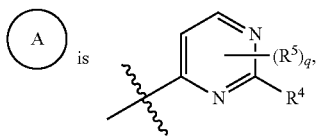

q is 0, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ib), or a pharmaceutically acceptable salt or solvate thereof, wherein

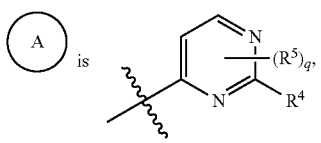

q is 0, and R$^4$ is

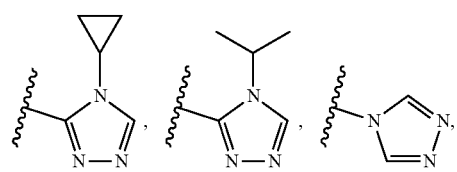

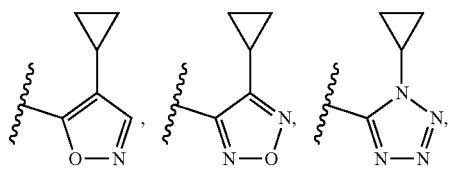

In some embodiments is a compound of Formula (Ib), or a pharmaceutically acceptable salt or solvate thereof, wherein

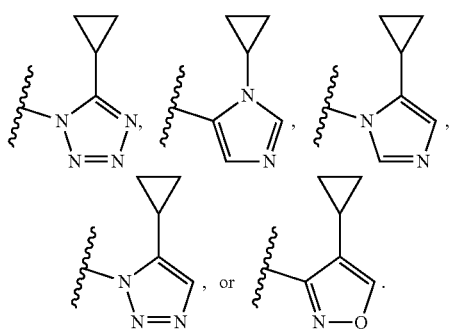

q is 0, and R$^4$ is

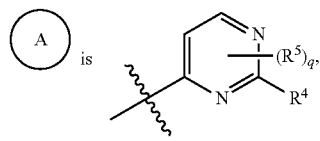

In some embodiments is a compound of Formula (Ib), or a pharmaceutically acceptable salt or solvate thereof, wherein

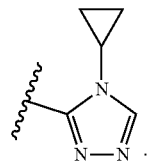

q is 0, and R$^4$ is

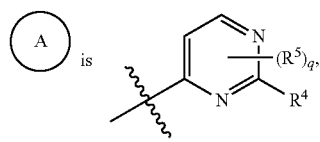

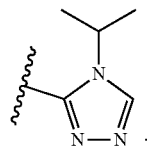 [SMILES: *c1nncn1C(C)C]

In some embodiments is a compound of Formula (Ib), or a pharmaceutically acceptable salt or solvate thereof, wherein

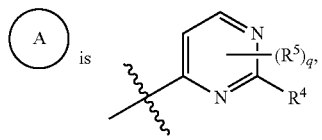

q is 0, and $R^4$ is

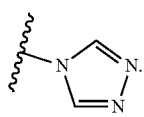

In some embodiments is a compound of Formula (Ib), or a pharmaceutically acceptable salt or solvate thereof, wherein

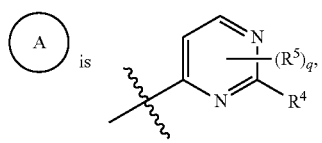

q is 0, and $R^4$ is

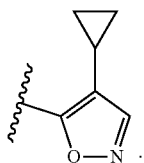

In some embodiments is a compound of Formula (Ib), or a pharmaceutically acceptable salt or solvate thereof, wherein

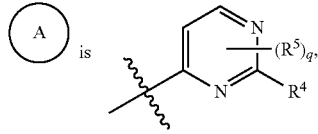

q is 0, and $R^4$ is

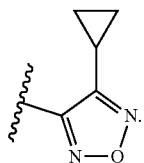

In some embodiments is a compound of Formula (Ib), or a pharmaceutically acceptable salt or solvate thereof, wherein

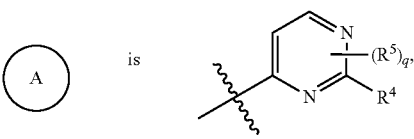

q is 0, and $R^4$ is

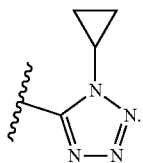 [SMILES: *c1nnnn1C1CC1]

In some embodiments is a compound of Formula (Ib), or a pharmaceutically acceptable salt or solvate thereof, wherein

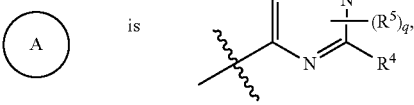

q is 0, and $R^4$ is

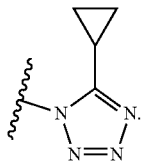 [SMILES: *n1nnnc1C1CC1]

In some embodiments is a compound of Formula (Ib), or a pharmaceutically acceptable salt or solvate thereof, wherein

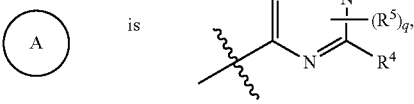

q is 0, and $R^4$ is

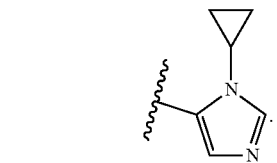 [SMILES: *c1cncn1C1CC1]

In some embodiments is a compound of Formula (Ib), or a pharmaceutically acceptable salt or solvate thereof, wherein

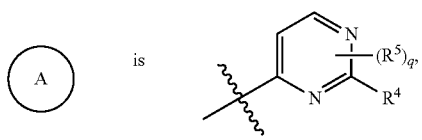

q is 0, and $R^4$ is

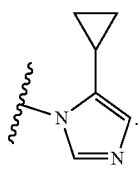

In some embodiments is a compound of Formula (Ib), or a pharmaceutically acceptable salt or solvate thereof, wherein

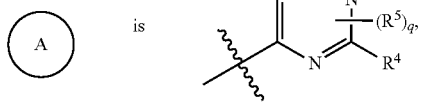

q is 0, and $R^4$ is

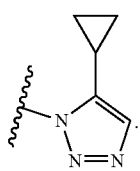

In some embodiments is a compound of Formula (Ib), or a pharmaceutically acceptable salt or solvate thereof, wherein

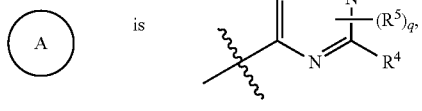

q is 0, and $R^4$ is

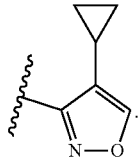

In some embodiments is a compound of Formula (Ib), or a pharmaceutically acceptable salt or solvate thereof, wherein

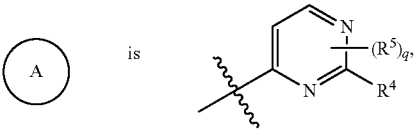

q is 0, and $R^4$ is

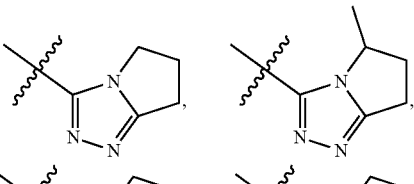
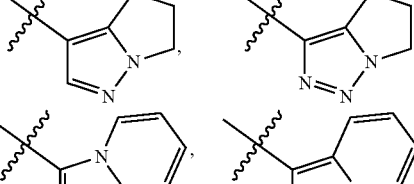
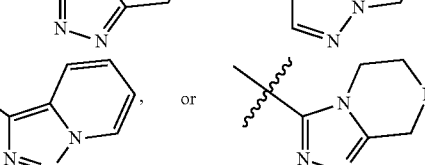
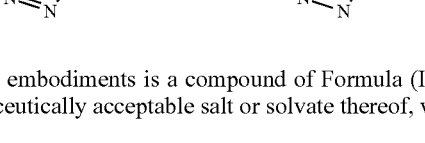
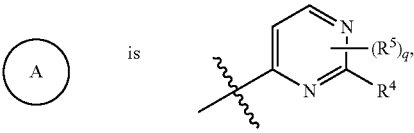

In some embodiments is a compound of Formula (Ib), or a pharmaceutically acceptable salt or solvate thereof, wherein

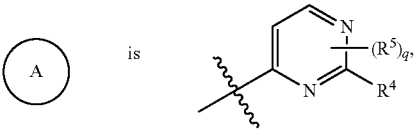

q is 0, and $R^4$ is

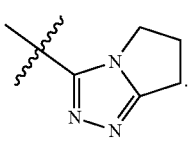 [SMILES: *c1nnc2n1CCC2]

In some embodiments is a compound of Formula (Ib), or a pharmaceutically acceptable salt or solvate thereof, wherein

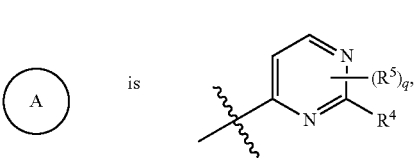

q is 0, and R⁴ is

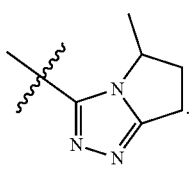 [SMILES: *c1nnc2n1C(C)CC2]

In some embodiments is a compound of Formula (Ib), or a pharmaceutically acceptable salt or solvate thereof, wherein

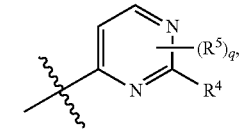

q is 0, and R⁴ is

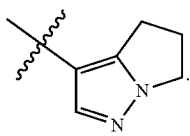

In some embodiments is a compound of Formula (Ib), or a pharmaceutically acceptable salt or solvate thereof, wherein

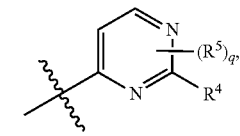

q is 0, and R⁴ is

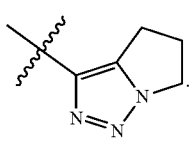

In some embodiments is a compound of Formula (Ib), or a pharmaceutically acceptable salt or solvate thereof, wherein

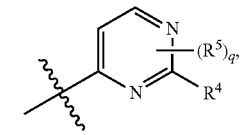

q is 0, and R⁴ is

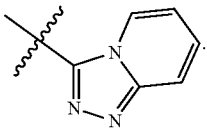 [SMILES: *c1nnc2ccccn12]

In some embodiments is a compound of Formula (Ib), or a pharmaceutically acceptable salt or solvate thereof, wherein

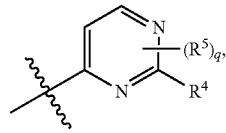

q is 0, and R⁴ is

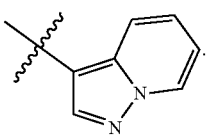

In some embodiments is a compound of Formula (Ib), or a pharmaceutically acceptable salt or solvate thereof, wherein

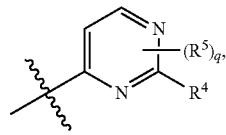

q is 0, and R⁴ is

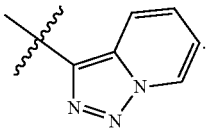 [SMILES: *c1nnn2ccccc12]

In some embodiments is a compound of Formula (Ib), or a pharmaceutically acceptable salt or solvate thereof, wherein

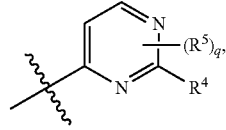

q is 0, and R⁴ is

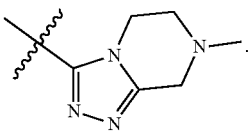

In some embodiments is a compound of Formula (Ib), or a pharmaceutically acceptable salt or solvate thereof, wherein

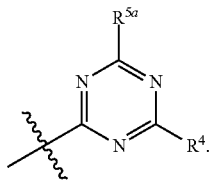

is

In some embodiments is a compound of Formula (Ib), or a pharmaceutically acceptable salt or solvate thereof, wherein

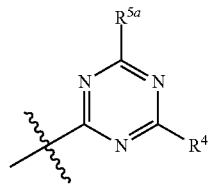

and q is 2. In some embodiments is a compound of Formula (Ib), or a pharmaceutically acceptable salt or solvate thereof, wherein

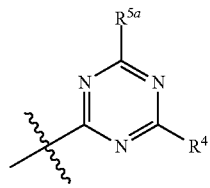

and q is 1. In some embodiments is a compound of Formula (Ib), or a pharmaceutically acceptable salt or solvate thereof, wherein and q is 0. In some embodiments is a compound of Formula (Ib), or a pharmaceutically acceptable salt or solvate thereof, wherein

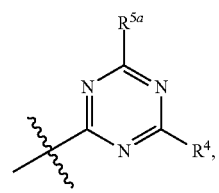

$R^{5a}$ is hydrogen, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments is a compound of Formula (Ib), or a pharmaceutically acceptable salt or solvate thereof, wherein

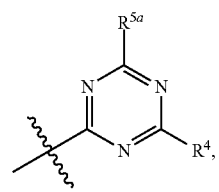

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$.

In some embodiments is a compound of Formula (Ib), or a pharmaceutically acceptable salt or solvate thereof, wherein

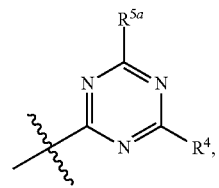

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein $R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^1$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ib), or a pharmaceutically acceptable salt or solvate thereof, wherein

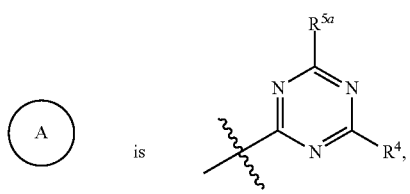

$R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ib), or a pharmaceutically acceptable salt or solvate thereof, wherein

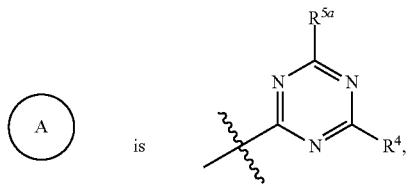

$R^{5a}$ is hydrogen, and $R^4$ is

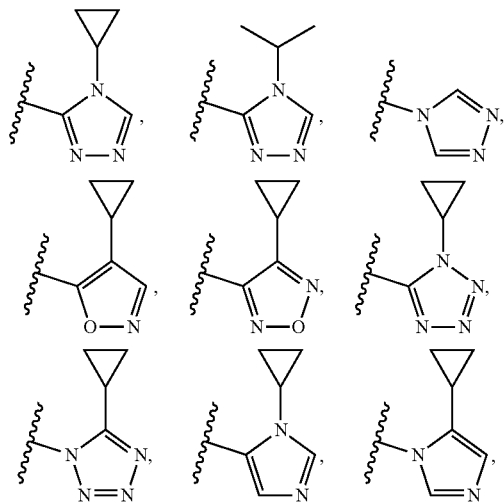

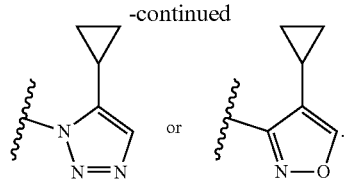

In some embodiments is a compound of Formula (Ib), or a pharmaceutically acceptable salt or solvate thereof, wherein

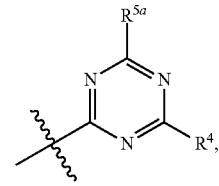

$R^{5a}$ is hydrogen, and $R^4$ is

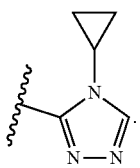

In some embodiments is a compound of Formula (Ib), or a pharmaceutically acceptable salt or solvate thereof, wherein

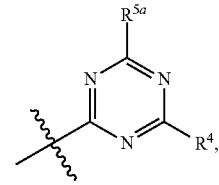

$R^{5a}$ is hydrogen, and $R^4$ is

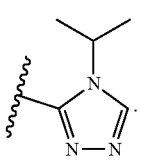

In some embodiments is a compound of Formula (Ib), or a pharmaceutically acceptable salt or solvate thereof, wherein

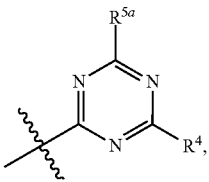

$R^{5a}$ is hydrogen, and $R^4$ is

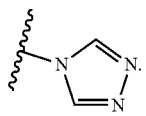 [SMILES: *n1cnnc1]

In some embodiments is a compound of Formula (Ib), or a pharmaceutically acceptable salt or solvate thereof, wherein (A) is 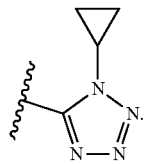 [SMILES: *c1nnnn1C1CC1], $R^{5a}$ is hydrogen, and $R^4$ is In some embodiments is a compound of Formula (Ib), or a pharmaceutically acceptable salt or solvate thereof, wherein (A) is , $R^{5a}$ is hydrogen, and $R^4$ is In some embodiments is a compound of Formula (Ib), or a pharmaceutically acceptable salt or solvate thereof, wherein (A) is , $R^{5a}$ is hydrogen, and $R^4$ is In some embodiments is a compound of Formula (Ib), or a pharmaceutically acceptable salt or solvate thereof, wherein (A) is , $R^{5a}$ is hydrogen, and $R^4$ is In some embodiments is a compound of Formula (Ib), or a pharmaceutically acceptable salt or solvate thereof, wherein (A) is , $R^{5a}$ is hydrogen, and $R^4$ is In some embodiments is a compound of Formula (Ib), or a pharmaceutically acceptable salt or solvate thereof, wherein (A) is , $R^{5a}$ is hydrogen, and $R^4$ is

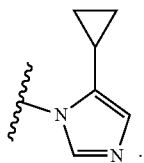

In some embodiments is a compound of Formula (Ib), or a pharmaceutically acceptable salt or solvate thereof, wherein

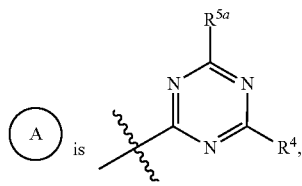 is $R^{5a}$ is hydrogen, and $R^4$ is

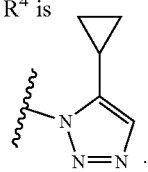

In some embodiments is a compound of Formula (Ib), or a pharmaceutically acceptable salt or solvate thereof, wherein

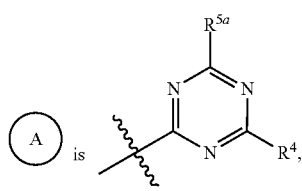 is $R^{5a}$ is hydrogen, and $R^4$ is

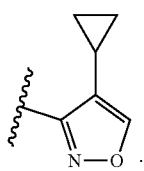 [SMILES: *c1nocc1C1CC1]

In some embodiments is a compound of Formula (Ib), or a pharmaceutically acceptable salt or solvate thereof, wherein

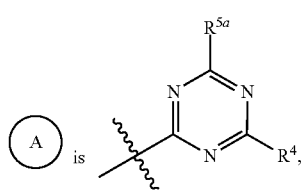 is $R^{5a}$ is hydrogen, and $R^4$ is

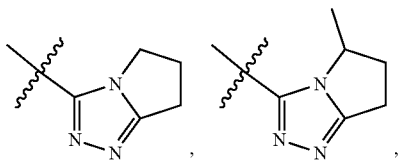

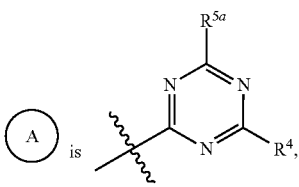

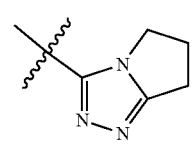, or

In some embodiments is a compound of Formula (Ib), or a pharmaceutically acceptable salt or solvate thereof, wherein

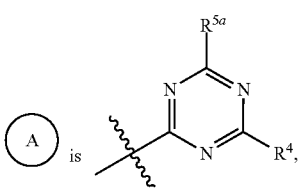 is $R^{5a}$ is hydrogen, and $R^4$ is $R^{5a}$ is hydrogen, and $R^4$ is

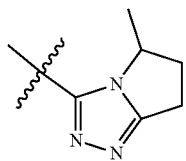

In some embodiments is a compound of Formula (Ib), or a pharmaceutically acceptable salt or solvate thereof, wherein

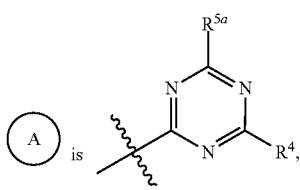

$R^{5a}$ is hydrogen, and $R^4$ is

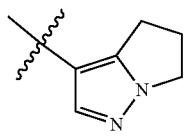

In some embodiments is a compound of Formula (Ib), or a pharmaceutically acceptable salt or solvate thereof, wherein

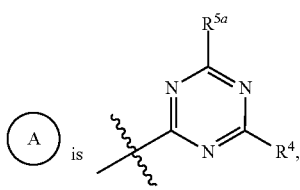

$R^{5a}$ is hydrogen, and $R^4$ is

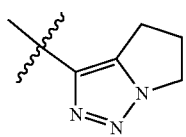

In some embodiments is a compound of Formula (Ib), or a pharmaceutically acceptable salt or solvate thereof, wherein

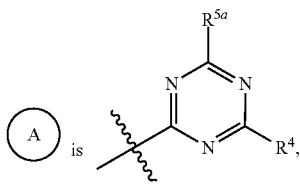

$R^{5a}$ is hydrogen, and $R^4$ is

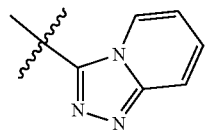

In some embodiments is a compound of Formula (Ib), or a pharmaceutically acceptable salt or solvate thereof, wherein

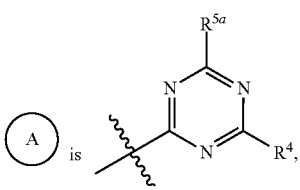

$R^{5a}$ is hydrogen, and $R^4$ is

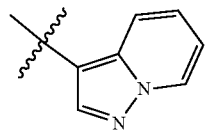

In some embodiments is a compound of Formula (Ib), or a pharmaceutically acceptable salt or solvate thereof, wherein

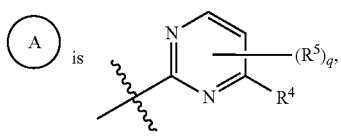

$R^{5a}$ is hydrogen, and $R^4$ is

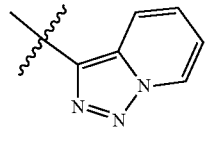

In some embodiments is a compound of Formula (Ib), or a pharmaceutically acceptable salt or solvate thereof, wherein

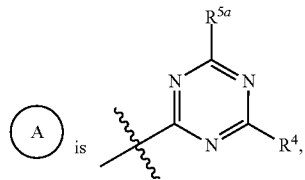

$R^{5a}$ is hydrogen, and $R^4$ is

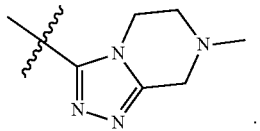 [SMILES: *c1nnc2n1CCN(C)C2]

In some embodiments, presented herein are compounds of Formula (Ic), or a pharmaceutically acceptable salt or solvate thereof:

Formula (Ic)

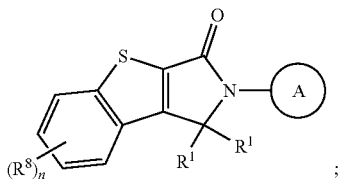

wherein

A is

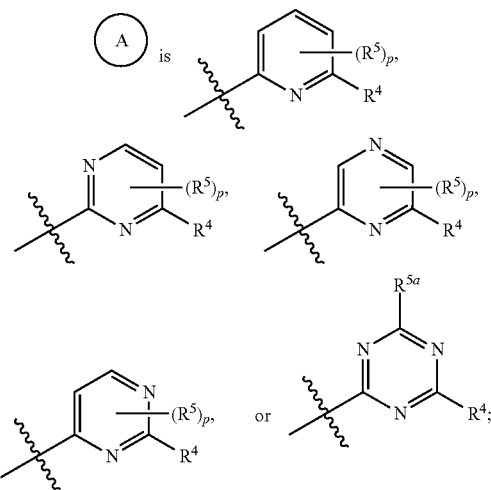

each $R^1$ is independently selected from a group consisting of hydrogen, halogen, and $C_{1-6}$alkyl;
$R^4$ is selected from a group consisting of hydrogen, halogen, —CN, —OH, —$OR^6$, —$SR^6$, —S(=O)$R^7$, —$NO_2$, —N($R^6$)$_2$, —S(=O)$_2R^7$, —NHS(=O)$_2R^7$, —S(=O)$_2$N($R^6$)$_2$, —C(=O)$R^7$, —C(=O)$OR^6$, —OC(=O)$R^7$, —C(=O)N($R^6$)$_2$, —OC(=O)N($R^6$)$_2$, —$NR^6$C(=O)N($R^6$)$_2$, —$NR^6$C(=O)$R^7$, —$NR^6$C(=O)$OR^6$, $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$ alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)$OR^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;

each $R^5$ is independently selected from a group consisting of halogen, —CN, and $C_{1-6}$alkyl;
$R^{5a}$ is selected from the group consisting of hydrogen and $C_{1-6}$alkyl;
each $R^6$ is independently selected from the group consisting of hydrogen, $C_{1-6}$alkyl, —$C_{1-6}$alkyl-O—$C_{1-6}$alkyl, —$C_{1-6}$alkyl-$C_{2-9}$heterocycle, —$C_{1-6}$alkyl-$C_{2-9}$heteroaryl, $C_{3-8}$cycloalkyl, and $C_{2-9}$heterocycle; or two $R^6$ on the same heteroatom are taken together with that heteroatom to which they are attached to form a $C_{2-9}$heterocycle or a $C_{2-9}$heteroaryl;
each $R^7$ is independently selected from the group consisting of $C_{1-6}$alkyl, $C_{3-8}$cycloalkyl, and $C_{2-9}$heterocycle;
each $R^8$ is independently selected from the group consisting of halogen, —CN, $C_{1-6}$alkyl, —$C_{1-6}$ alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)$OR^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$;
each $R^{13}$ is independently selected from the group consisting of hydrogen, $C_{1-6}$alkyl, and $C_{3-8}$cycloalkyl; or two $R^{13}$ on the same heteroatom are taken together with that heteroatom to which they are attached to form a $C_{2-9}$heterocycle;
each $R^{14}$ is independently selected from the group consisting of $C_{1-6}$alkyl and $C_{3-8}$cycloalkyl;
n is 0, 1, 2, or 3;
p is 0, 1, 2, or 3; and
q is 0, 1, or 2.

In some embodiments is a compound of Formula (Ic), or a pharmaceutically acceptable salt or solvate thereof, wherein each $R^1$ is hydrogen. In some embodiments is a compound of Formula (Ic), or a pharmaceutically acceptable salt or solvate thereof, wherein one $R^1$ is hydrogen and one R is $C_{1-6}$alkyl. In some embodiments is a compound of Formula (Ic), or a pharmaceutically acceptable salt or solvate thereof, wherein each $R^1$ is $C_{1-6}$alkyl. In some embodiments is a compound of Formula (Ic), or a pharmaceutically acceptable salt or solvate thereof, wherein each $R^1$ is halogen.

In some embodiments is a compound of Formula (Ic), or a pharmaceutically acceptable salt or solvate thereof, wherein n is 0. In some embodiments is a compound of Formula (Ic), or a pharmaceutically acceptable salt or solvate thereof, wherein n is 1. In some embodiments is a compound of Formula (Ic), or a pharmaceutically acceptable salt or solvate thereof, wherein n is 2. In some embodiments is a compound of Formula (Ic), or a pharmaceutically acceptable salt or solvate thereof, wherein n is 3.

In some embodiments is a compound of Formula (Ic), or a pharmaceutically acceptable salt or solvate thereof, wherein n is 1 or 2 and each $R^8$ is independently selected from the group consisting of halogen, $C_{1-6}$alkyl, and $C_{1-6}$haloalkyl. In some embodiments is a compound of Formula (Ic), or a pharmaceutically acceptable salt or solvate thereof, wherein n is 1 and $R^8$ is halogen. In some embodiments is a compound of Formula (Ic), or a pharmaceutically acceptable salt or solvate thereof, wherein n is 1 and $R^8$ is $C_{1-6}$alkyl. In some embodiments is a compound of Formula (Ic), or a pharmaceutically acceptable salt or solvate thereof, wherein n is 1 and $R^8$ is $C_{1-6}$haloalkyl.

In some embodiments is a compound of Formula (Ic), or a pharmaceutically acceptable salt or solvate thereof, wherein

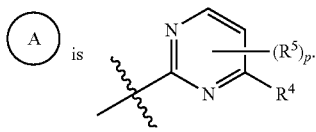

In some embodiments is a compound of Formula (Ic), or a pharmaceutically acceptable salt or solvate thereof, wherein

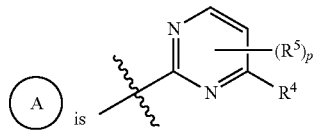

and p is 2. In some embodiments is a compound of Formula (Ic), or a pharmaceutically acceptable salt or solvate thereof, wherein

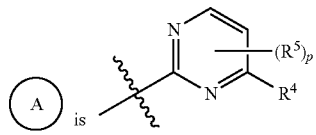

and p is 1. In some embodiments is a compound of Formula (Ic), or a pharmaceutically acceptable salt or solvate thereof, wherein

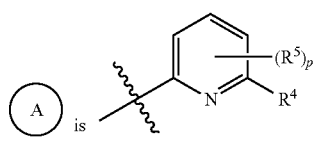

and p is 0. In some embodiments is a compound of Formula (Ic), or a pharmaceutically acceptable salt or solvate thereof, wherein

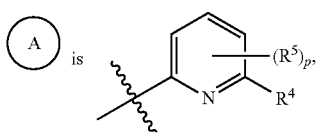

p is 0, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^3$)S(=O)$_2R^{13}$. In some embodiments is a compound of Formula (Ic), or a pharmaceutically acceptable salt or solvate thereof, wherein

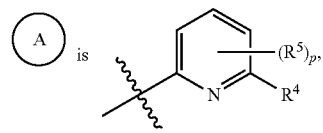

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

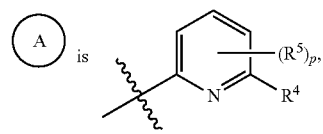

p is 0, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

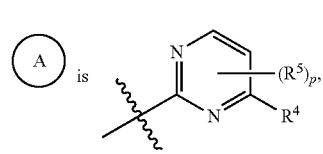

p is 0, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

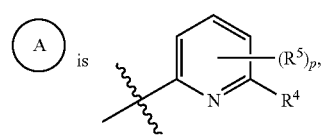

p is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ic), or a pharmaceutically acceptable salt or solvate thereof, wherein

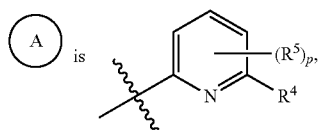

and R⁴ is

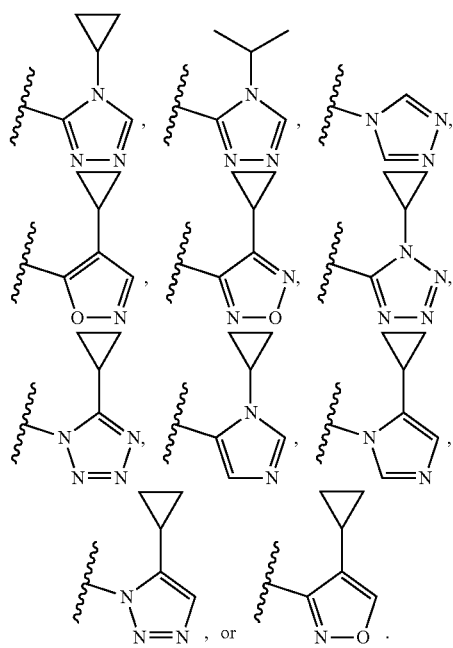

In some embodiments is a compound of Formula (Ic), or a pharmaceutically acceptable salt or solvate thereof, wherein

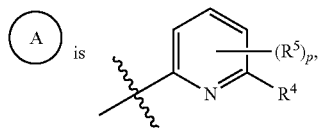

p is 0, and R⁴ is

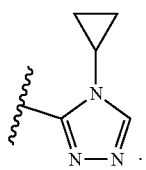

In some embodiments is a compound of Formula (Ic), or a pharmaceutically acceptable salt or solvate thereof, wherein

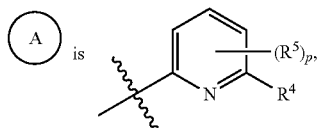

p is 0, and R⁴ is

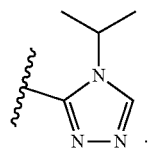 [SMILES: *c1nncn1C(C)C]

In some embodiments is a compound of Formula (Ic), or a pharmaceutically acceptable salt or solvate thereof, wherein

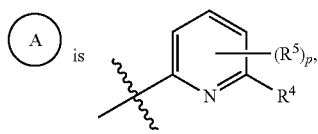

p is 0, and R⁴ is

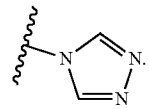

In some embodiments is a compound of Formula (Ic), or a pharmaceutically acceptable salt or solvate thereof, wherein

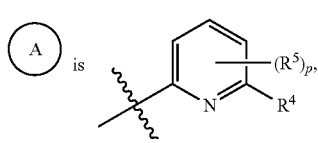

p is 0, and R⁴ is

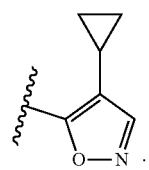 [SMILES: *c1oncc1C1CC1]

In some embodiments is a compound of Formula (Ic), or a pharmaceutically acceptable salt or solvate thereof, wherein

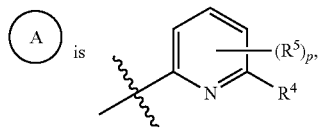

p is 0, and R⁴ is

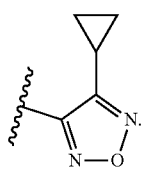 [SMILES: *c1nonc1C1CC1]

In some embodiments is a compound of Formula (Ic), or a pharmaceutically acceptable salt or solvate thereof, wherein

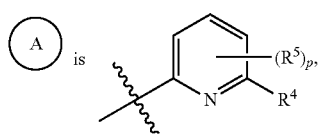

p is 0, and R⁴ is

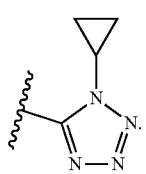 [SMILES: *c1nnnn1C1CC1]

In some embodiments is a compound of Formula (Ic), or a pharmaceutically acceptable salt or solvate thereof, wherein

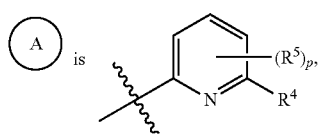

p is 0, and R⁴ is

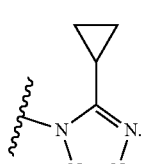

In some embodiments is a compound of Formula (Ic), or a pharmaceutically acceptable salt or solvate thereof, wherein

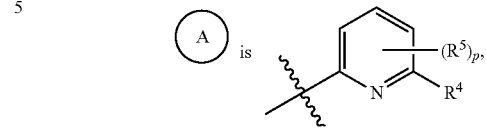

p is 0, and R⁴ is

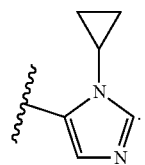 [SMILES: *c1cncn1C1CC1]

In some embodiments is a compound of Formula (Ic), or a pharmaceutically acceptable salt or solvate thereof, wherein

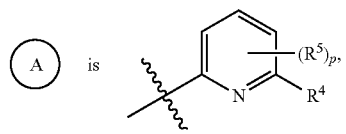

p is 0, and R⁴ is

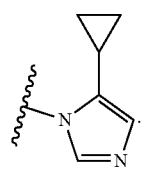 [SMILES: *n1cncc1C1CC1]

In some embodiments is a compound of Formula (Ic), or a pharmaceutically acceptable salt or solvate thereof, wherein

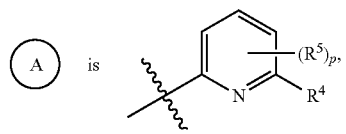

p is 0, and R⁴ is

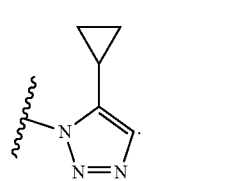 [SMILES: *n1nncc1C1CC1]

In some embodiments is a compound of Formula (Ic), or a pharmaceutically acceptable salt or solvate thereof, wherein

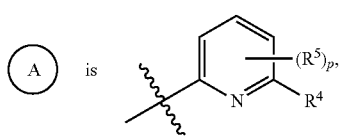

p is 0, and $R^4$ is

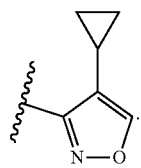 [SMILES: *c1nocc1C1CC1]

In some embodiments is a compound of Formula (Ic), or a pharmaceutically acceptable salt or solvate thereof, wherein

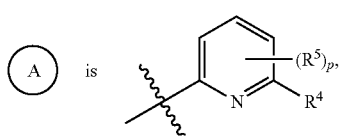

p is 0, and $R^4$ is

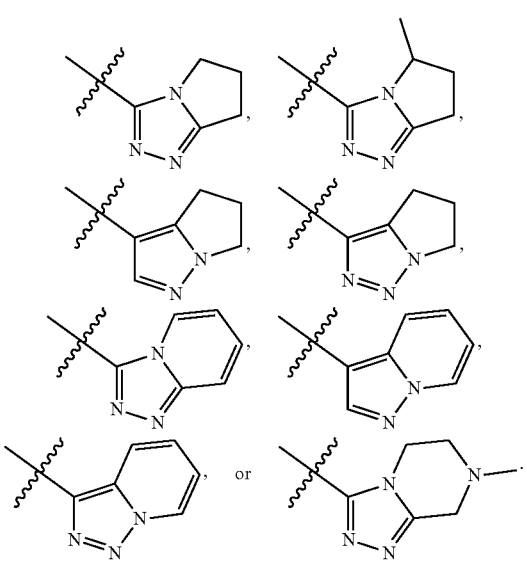

In some embodiments is a compound of Formula (Ic), or a pharmaceutically acceptable salt or solvate thereof, wherein

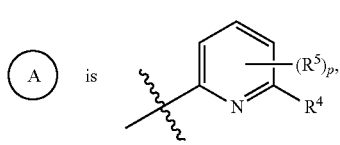

p is 0, and $R^4$ is

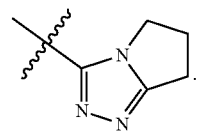 [SMILES: *c1nnc2n1CCC2]

In some embodiments is a compound of Formula (Ic), or a pharmaceutically acceptable salt or solvate thereof, wherein

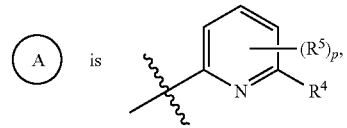

p is 0, and $R^4$ is

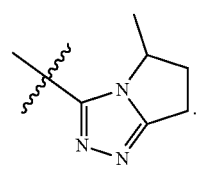 [SMILES: *c1nnc2n1C(C)CC2]

In some embodiments is a compound of Formula (Ic), or a pharmaceutically acceptable salt or solvate thereof, wherein

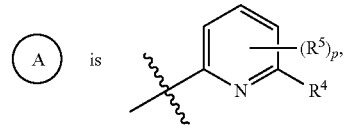

p is 0, and $R^4$ is

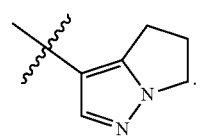

In some embodiments is a compound of Formula (Ic), or a pharmaceutically acceptable salt or solvate thereof, wherein

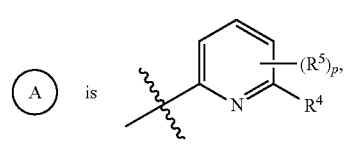

p is 0, and R⁴ is

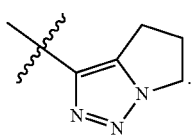

In some embodiments is a compound of Formula (Ic), or a pharmaceutically acceptable salt or solvate thereof, wherein

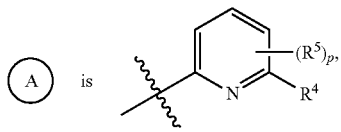

p is 0, and R⁴ is

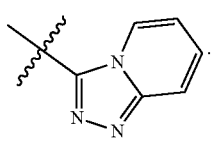

In some embodiments is a compound of Formula (Ic), or a pharmaceutically acceptable salt or solvate thereof, wherein

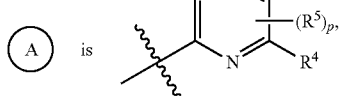

p is 0, and R⁴ is

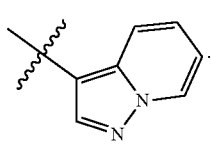

In some embodiments is a compound of Formula (Ic), or a pharmaceutically acceptable salt or solvate thereof, wherein

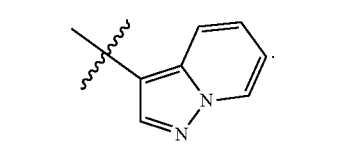

p is 0, and R⁴ is

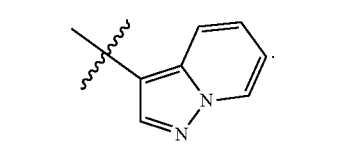

In some embodiments is a compound of Formula (Ic), or a pharmaceutically acceptable salt or solvate thereof, wherein

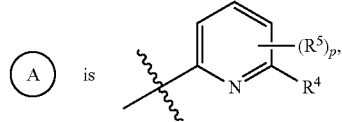

p is 0, and R⁴ is

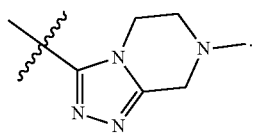 [SMILES: *c1nnc2n1CCN(C)C2]

In some embodiments is a compound of Formula (Ic), or a pharmaceutically acceptable salt or solvate thereof, wherein

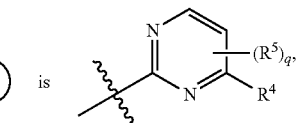

In some embodiments is a compound of Formula (Ic), or a pharmaceutically acceptable salt or solvate thereof, wherein

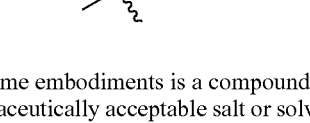

and q is 2. In some embodiments is a compound of Formula (Ic), or a pharmaceutically acceptable salt or solvate thereof, wherein

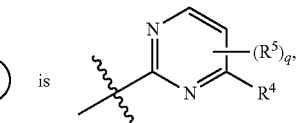

and q is 1. In some embodiments is a compound of Formula (Ic), or a pharmaceutically acceptable salt or solvate thereof, wherein

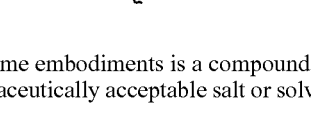

and q is 0. In some embodiments is a compound of Formula (Ic), or a pharmaceutically acceptable salt or solvate thereof, wherein A is 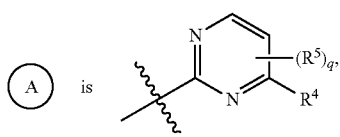

q is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein A is 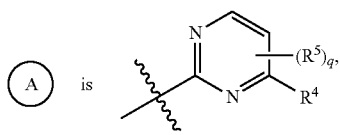

q is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein A is 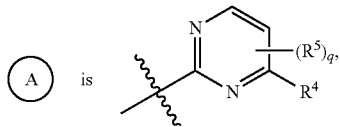

q is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein A is 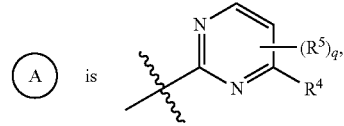

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein A is 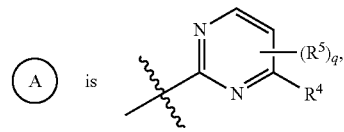

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ic), or a pharmaceutically acceptable salt or solvate thereof, wherein A is 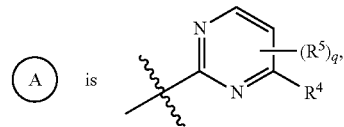

q is 0, and R⁴ is

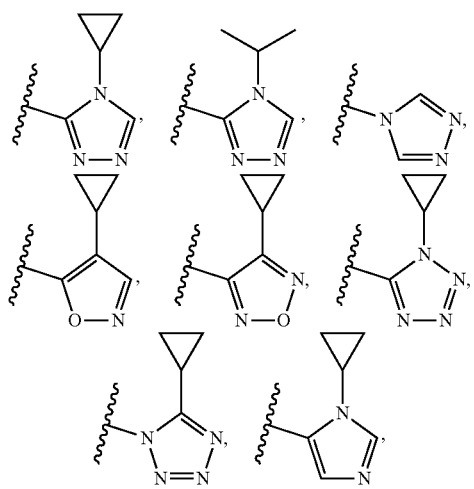

-continued

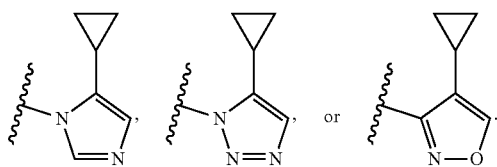

In some embodiments is a compound of Formula (Ic), or a pharmaceutically acceptable salt or solvate thereof, wherein

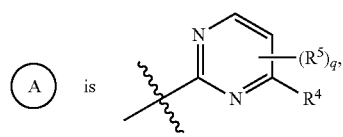

q is 0, and $R^4$ is

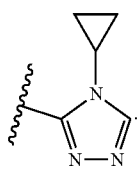 [SMILES: *c1nncn1C1CC1]

In some embodiments is a compound of Formula (Ic), or a pharmaceutically acceptable salt or solvate thereof, wherein

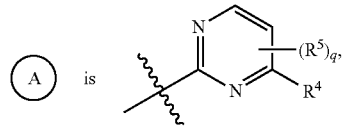

q is 0, and $R^4$ is

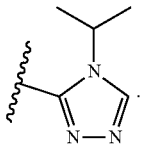

In some embodiments is a compound of Formula (Ic), or a pharmaceutically acceptable salt or solvate thereof, wherein

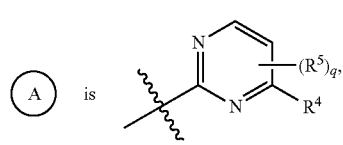

q is 0, and $R^4$ is

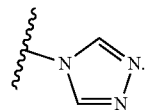 [SMILES: *n1cnnc1]

In some embodiments is a compound of Formula (Ic), or a pharmaceutically acceptable salt or solvate thereof, wherein

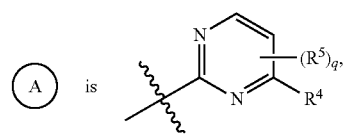

q is 0, and $R^4$ is

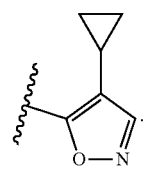 [SMILES: *c1oncc1C1CC1]

In some embodiments is a compound of Formula (Ic), or a pharmaceutically acceptable salt or solvate thereof, wherein

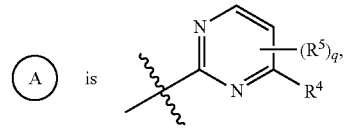

q is 0, and $R^4$ is

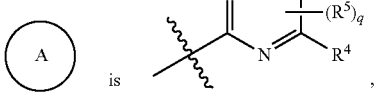

In some embodiments is a compound of Formula (Ic), or a pharmaceutically acceptable salt or solvate thereof, wherein q is 0, and R⁴ is

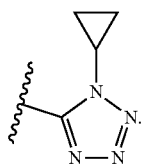 [SMILES: *c1nnnn1C1CC1]

In some embodiments is a compound of Formula (Ic), or a pharmaceutically acceptable salt or solvate thereof, wherein

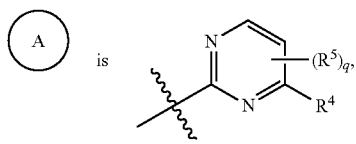

q is 0, and R⁴ is

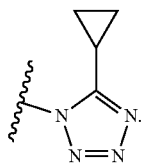 [SMILES: *n1nnnc1C1CC1]

In some embodiments is a compound of Formula (Ic), or a pharmaceutically acceptable salt or solvate thereof, wherein

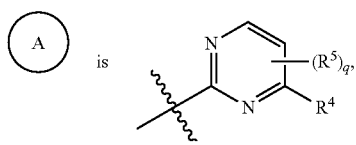

q is 0, and R⁴ is

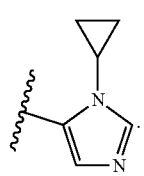

In some embodiments is a compound of Formula (Ic), or a pharmaceutically acceptable salt or solvate thereof, wherein

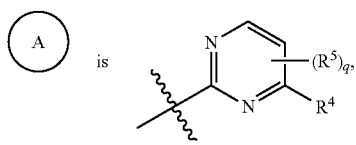

q is 0, and R⁴ is

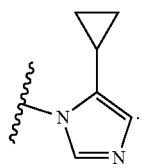

In some embodiments is a compound of Formula (Ic), or a pharmaceutically acceptable salt or solvate thereof, wherein

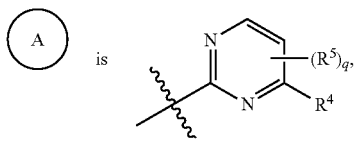

q is 0, and R⁴ is

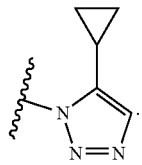

In some embodiments is a compound of Formula (Ic), or a pharmaceutically acceptable salt or solvate thereof, wherein

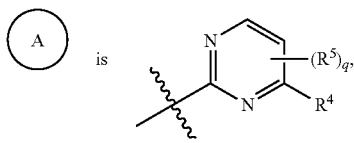

q is 0, and R⁴ is

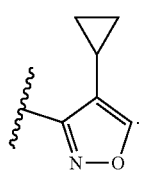

In some embodiments is a compound of Formula (Ic), or a pharmaceutically acceptable salt or solvate thereof, wherein

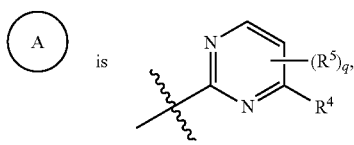

q is 0, and R⁴ is

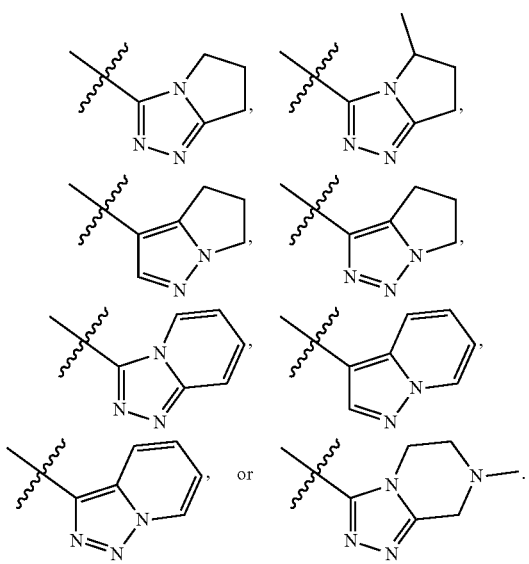

or

In some embodiments is a compound of Formula (Ic), or a pharmaceutically acceptable salt or solvate thereof, wherein

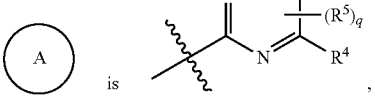

q is 0, and R⁴ is

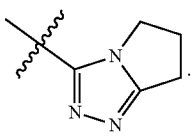 [SMILES: *c1nnc2n1CCC2]

In some embodiments is a compound of Formula (Ic), or a pharmaceutically acceptable salt or solvate thereof, wherein

q is 0, and R⁴ is

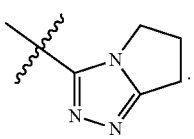

In some embodiments is a compound of Formula (Ic), or a pharmaceutically acceptable salt or solvate thereof, wherein

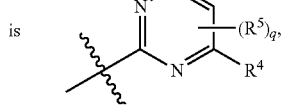

q is 0, and R⁴ is

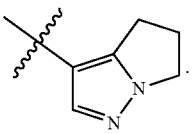 [SMILES: *c1cnn2c1CCC2]

In some embodiments is a compound of Formula (Ic), or a pharmaceutically acceptable salt or solvate thereof, wherein

q is 0, and R⁴ is

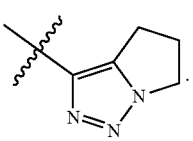

In some embodiments is a compound of Formula (Ic), or a pharmaceutically acceptable salt or solvate thereof, wherein

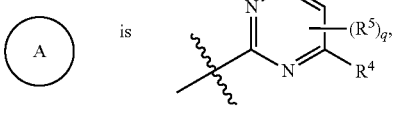

q is 0, and R⁴ is

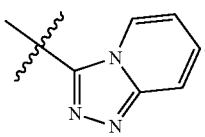

In some embodiments is a compound of Formula (Ic), or a pharmaceutically acceptable salt or solvate thereof, wherein

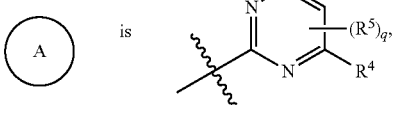

q is 0, and R⁴ is

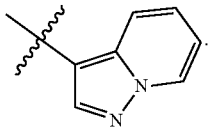

In some embodiments is a compound of Formula (Ic), or a pharmaceutically acceptable salt or solvate thereof, wherein

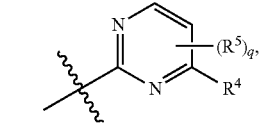

q is 0, and R⁴ is

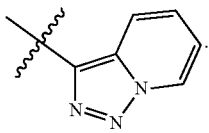

In some embodiments is a compound of Formula (Ic), or a pharmaceutically acceptable salt or solvate thereof, wherein

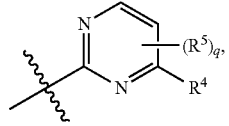

q is 0, and R⁴ is

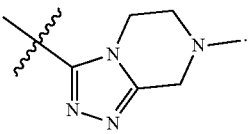

In some embodiments is a compound of Formula (Ic), or a pharmaceutically acceptable salt or solvate thereof, wherein

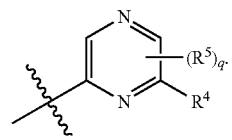

In some embodiments is a compound of Formula (Ic), or a pharmaceutically acceptable salt or solvate thereof, wherein

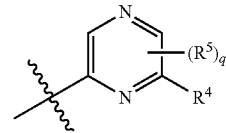

and q is 2. In some embodiments is a compound of Formula (Ic), or a pharmaceutically acceptable salt or solvate thereof, wherein

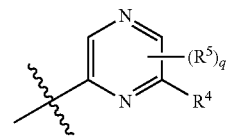

and q is 1. In some embodiments is a compound of Formula (Ic), or a pharmaceutically acceptable salt or solvate thereof, wherein

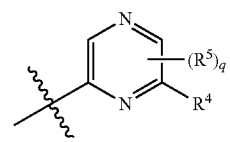

and q is 0. In some embodiments is a compound of Formula (Ic), or a pharmaceutically acceptable salt or solvate thereof, wherein

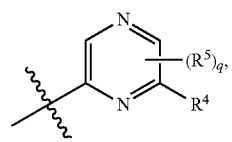

q is 0, and R⁴ is selected from a group consisting of $C_{3-8}$cycloalkyl, $C_{2-9}$ heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein

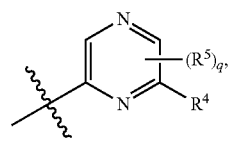

q is 0, and R⁴ is selected from a group consisting of a $C_{1-9}$heteroaryl and a fused $C_{5-9}$heteroaryl-cycloalkyl;

wherein the C₁₋₉heteroaryl and fused C₅₋₉heteroaryl-cycloalkyl are optionally substituted with one, two, or three substituents selected from the group consisting of halogen, —CN, C₁₋₆alkyl, —C₁₋₆alkyl-OH, C₁₋₆haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein

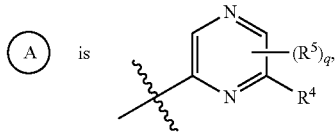

q is 0, and R⁴ is selected from a group consisting of a C₁₋₉heteroaryl and a fused C₅₋₉heteroaryl-cycloalkyl; wherein the C₁₋₉heteroaryl and fused C₅₋₉heteroaryl-cycloalkyl are optionally substituted with one or two substituents selected from the group consisting of halogen, —CN, C₁₋₆alkyl, —C₁₋₆alkyl-OH, C₁₋₆ haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein

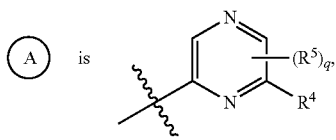

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, C₁₋₆ alkyl, —C₁₋₆alkyl-OH, C₁₋₆haloalkyl, C₃₋₈cycloalkyl, C₂₋₉heterocycle, C₆₋₁₀aryl, C₁₋₉heteroaryl, —C(=O)R¹⁴, —C(=O)OR¹³, —C(=O)N(R¹³)₂, —S(=O)R¹⁴, —S(=O)₂R³, —S(=O)₂—N(R¹³)₂, —N(R¹³)₂, —N(R¹³)C(=O)R¹⁴, and —N(R¹³)S(=O)₂R¹³. In some embodiments is a compound of Formula (Ic), or a pharmaceutically acceptable salt or solvate thereof, wherein

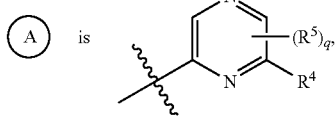

q is 0, and R⁴ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, C₁₋₆alkyl, and C₃₋₈cycloalkyl. In some embodiments is a compound of Formula (Ic), or a pharmaceutically acceptable salt or solvate thereof, wherein

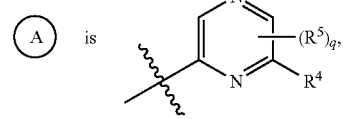

q is 0, and R⁴ is

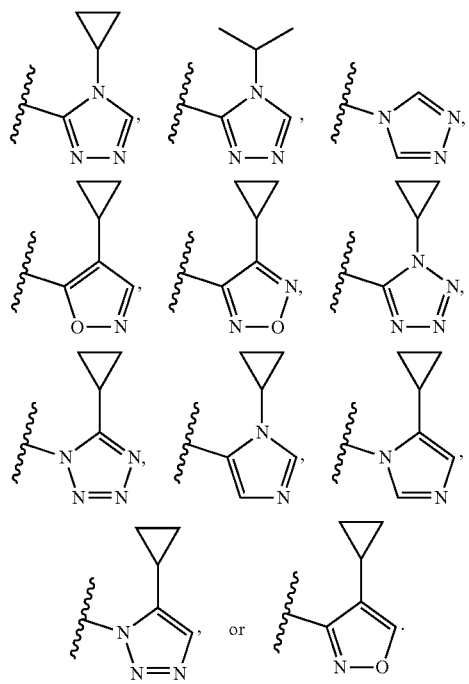

In some embodiments is a compound of Formula (Ic), or a pharmaceutically acceptable salt or solvate thereof, wherein

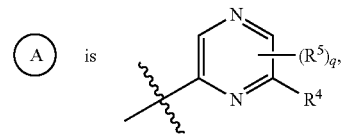

q is 0, and R⁴ is

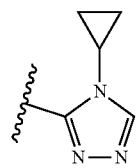

In some embodiments is a compound of Formula (Ic), or a pharmaceutically acceptable salt or solvate thereof, wherein

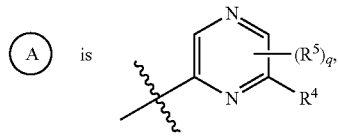

q is 0, and $R^4$ is

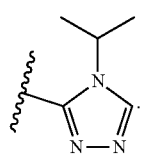 [SMILES: *c1nncn1C(C)C]

In some embodiments is a compound of Formula (Ic), or a pharmaceutically acceptable salt or solvate thereof, wherein

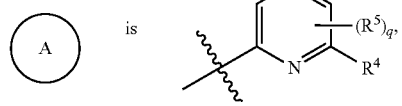

q is 0, and $R^4$ is

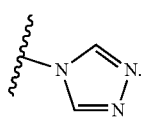

In some embodiments is a compound of Formula (Ic), or a pharmaceutically acceptable salt or solvate thereof, wherein

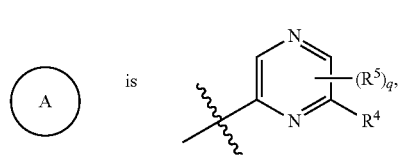

q is 0, and $R^4$ is

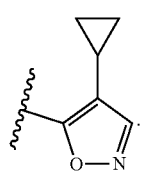

In some embodiments is a compound of Formula (Ic), or a pharmaceutically acceptable salt or solvate thereof, wherein

q is 0, and $R^4$ is

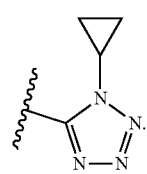 [SMILES: *c1nnnn1C1CC1]

In some embodiments is a compound of Formula (Ic), or a pharmaceutically acceptable salt or solvate thereof, wherein

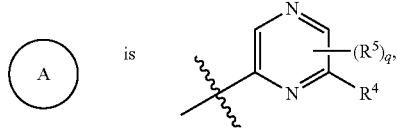

q is 0, and $R^4$ is

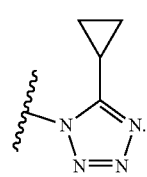

In some embodiments is a compound of Formula (Ic), or a pharmaceutically acceptable salt or solvate thereof, wherein

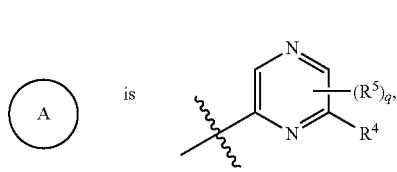

q is 0, and $R^4$ is

In some embodiments is a compound of Formula (Ic), or a pharmaceutically acceptable salt or solvate thereof, wherein

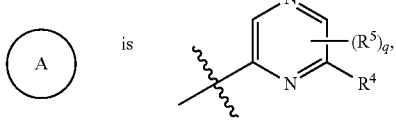

q is 0, and $R^4$ is

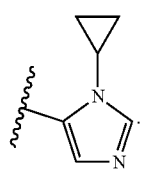

In some embodiments is a compound of Formula (Ic), or a pharmaceutically acceptable salt or solvate thereof, wherein

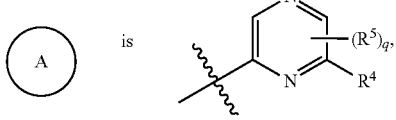

q is 0, and R is

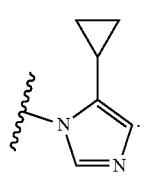

In some embodiments is a compound of Formula (Ic), or a pharmaceutically acceptable salt or solvate thereof, wherein

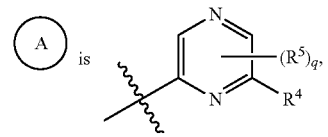

q is 0, and $R^4$ is

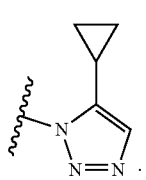 [SMILES: *n1nncc1C1CC1]

In some embodiments is a compound of Formula (Ic), or a pharmaceutically acceptable salt or solvate thereof, wherein

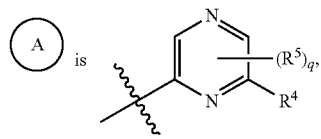

q is 0, and $R^4$ is

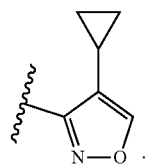

In some embodiments is a compound of Formula (Ic), or a pharmaceutically acceptable salt or solvate thereof, wherein

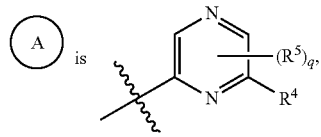

q is 0, and $R^4$ is

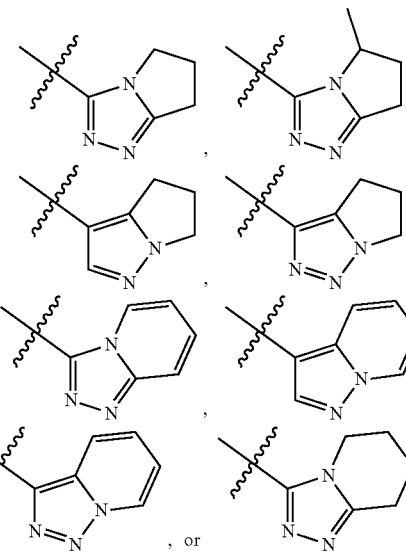

, or

In some embodiments is a compound of Formula (Ic), or a pharmaceutically acceptable salt or solvate thereof, wherein

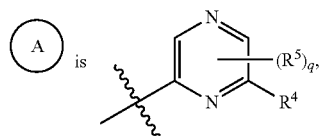

q is 0, and R⁴ is

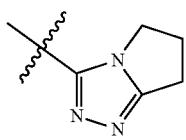

In some embodiments is a compound of Formula (Ic), or a pharmaceutically acceptable salt or solvate thereof, wherein

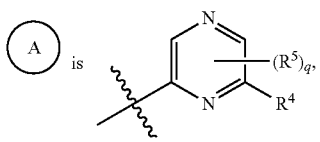

q is 0, and R⁴ is

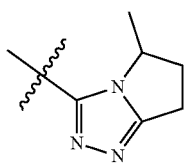

In some embodiments is a compound of Formula (Ic), or a pharmaceutically acceptable salt or solvate thereof, wherein

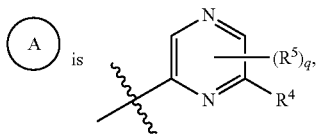

q is 0, and R⁴ is

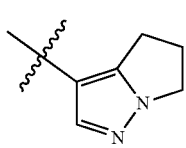

In some embodiments is a compound of Formula (Ic), or a pharmaceutically acceptable salt or solvate thereof, wherein

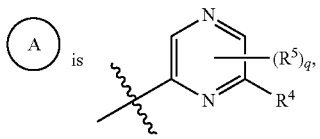

q is 0, and R⁴ is

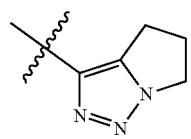

In some embodiments is a compound of Formula (Ic), or a pharmaceutically acceptable salt or solvate thereof, wherein

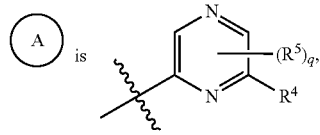

q is 0, and R⁴ is

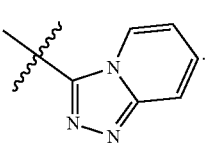 [SMILES: *c1nnc2ccccn12]

In some embodiments is a compound of Formula (Ic), or a pharmaceutically acceptable salt or solvate thereof, wherein

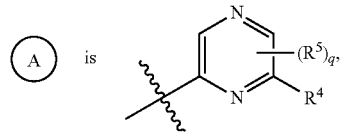

q is 0, and R⁴ is

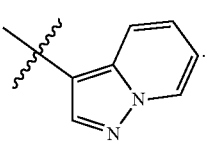

In some embodiments is a compound of Formula (Ic), or a pharmaceutically acceptable salt or solvate thereof, wherein

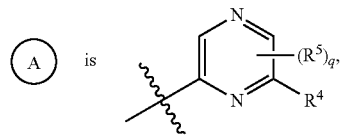

q is 0, and R⁴ is

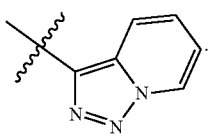

In some embodiments is a compound of Formula (Ic), or a pharmaceutically acceptable salt or solvate thereof, wherein

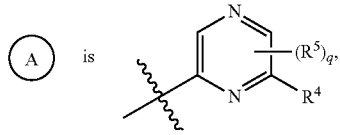

q is 0, and R⁴ is

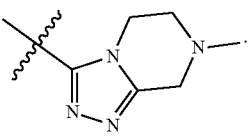 [SMILES: *c1nnc2n1CCN(C)C2]

In some embodiments is a compound of Formula (Ic), or a pharmaceutically acceptable salt or solvate thereof, wherein

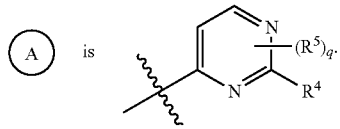

In some embodiments is a compound of Formula (Ic), or a pharmaceutically acceptable salt or solvate thereof, wherein

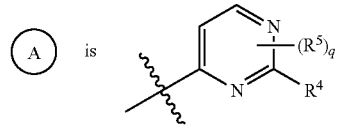

and q is 2. In some embodiments is a compound of Formula (Ic), or a pharmaceutically acceptable salt or solvate thereof, wherein

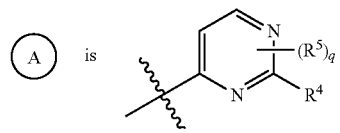

and q is 1. In some embodiments is a compound of Formula (Ic), or a pharmaceutically acceptable salt or solvate thereof, wherein

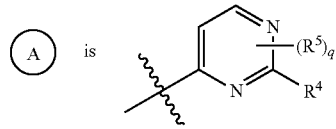

and q is 0. In some embodiments is a compound of Formula (Ic), or a pharmaceutically acceptable salt or solvate thereof, wherein

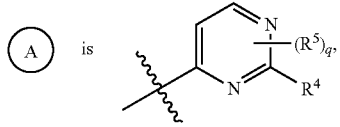

q is 0, and R⁴ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-6}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³.
In some embodiments is a compound of Formula (Ic), or a pharmaceutically acceptable salt or solvate thereof, wherein

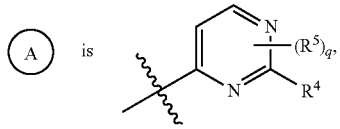

q is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R¹⁴, —C(=O)OR¹³, —C(=O)N(R¹³)₂, —S(=O)R¹⁴, —S(=O)₂R¹³, —S(=O)₂—N(R¹³)₂, —N(R¹³)₂, —N(R¹³)C(=O)R¹⁴, and —N(R¹³)S(=O)₂R¹³.
In some embodiments is a compound of Formula (Ic), or a pharmaceutically acceptable salt or solvate thereof, wherein

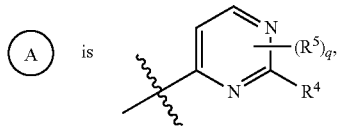

q is 0, and R⁴ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$ haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^1$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ic), or a pharmaceutically acceptable salt or solvate thereof, wherein

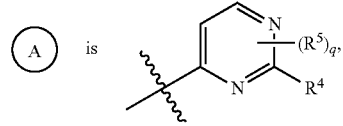

q is 0, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$ alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)R$^{14}$, —C(=O)OR$^1$, —C(=O)N(R$^{13}$)$_2$, —S(=O)R$^{14}$, —S(=O)$_2$R$^{13}$, —S(=O)$_2$—N(R$^{13}$)$_2$, —N(R$^{13}$)$_2$, —N(R$^{13}$)C(=O)R$^{14}$, and —N(R$^{13}$)S(=O)$_2$R$^{13}$. In some embodiments is a compound of Formula (Ic), or a pharmaceutically acceptable salt or solvate thereof, wherein

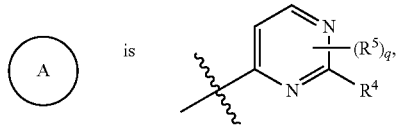

q is 0, and R$^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ic), or a pharmaceutically acceptable salt or solvate thereof, wherein

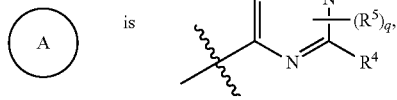

q is 0, and R$^4$ is

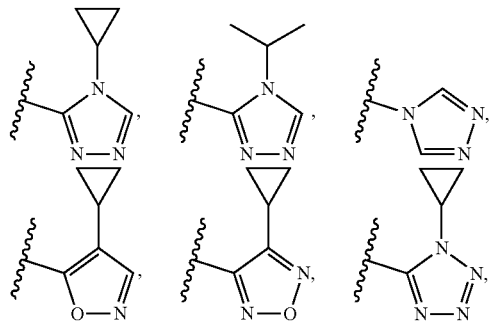

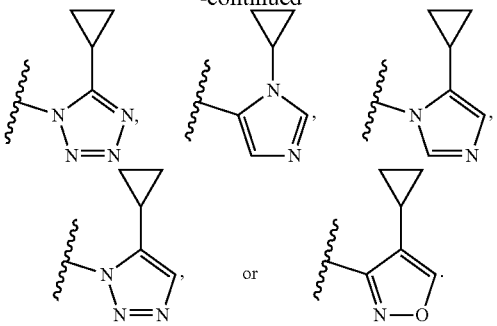

In some embodiments is a compound of Formula (Ic), or a pharmaceutically acceptable salt or solvate thereof, wherein

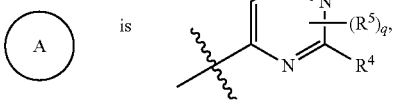

q is 0, and R$^4$ is

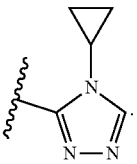

In some embodiments is a compound of Formula (Ic), or a pharmaceutically acceptable salt or solvate thereof, wherein

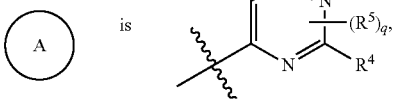

q is 0, and R$^4$ is

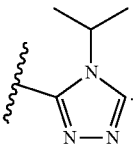

In some embodiments is a compound of Formula (Ic), or a pharmaceutically acceptable salt or solvate thereof, wherein

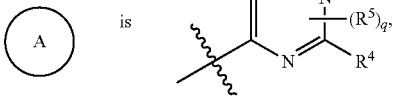

q is 0, and $R^4$ is

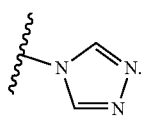

In some embodiments is a compound of Formula (Ic), or a pharmaceutically acceptable salt or solvate thereof, wherein

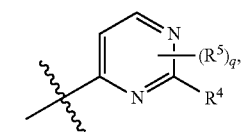

q is 0, and $R^4$ is

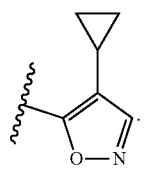

In some embodiments is a compound of Formula (Ic), or a pharmaceutically acceptable salt or solvate thereof, wherein

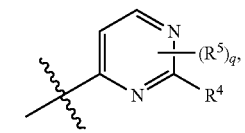

q is 0, and $R^4$ is

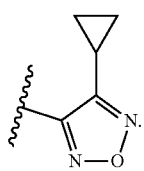 [SMILES: *c1nonc1C1CC1]

In some embodiments is a compound of Formula (Ic), or a pharmaceutically acceptable salt or solvate thereof, wherein

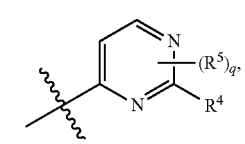

q is 0, and $R^4$ is

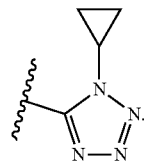 [SMILES: *c1nnnn1C1CC1]

In some embodiments is a compound of Formula (Ic), or a pharmaceutically acceptable salt or solvate thereof, wherein

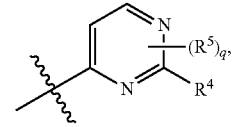

q is 0, and $R^4$ is

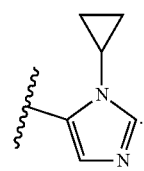 [SMILES: *c1cncn1C1CC1]

In some embodiments is a compound of Formula (Ic), or a pharmaceutically acceptable salt or solvate thereof, wherein

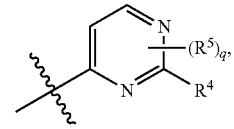

q is 0, and $R^4$ is

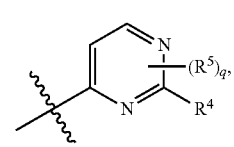

In some embodiments is a compound of Formula (Ic), or a pharmaceutically acceptable salt or solvate thereof, wherein

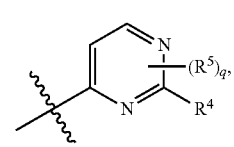

q is 0, and R⁴ is

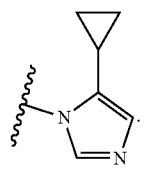

In some embodiments is a compound of Formula (Ic), or a pharmaceutically acceptable salt or solvate thereof, wherein

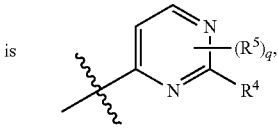

q is 0, and R⁴ is

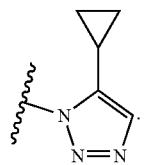

In some embodiments is a compound of Formula (Ic), or a pharmaceutically acceptable salt or solvate thereof, wherein

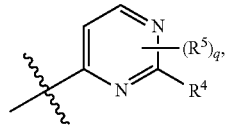

q is 0, and R⁴ is

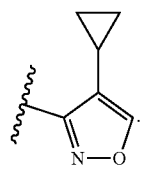

In some embodiments is a compound of Formula (Ic), or a pharmaceutically acceptable salt or solvate thereof, wherein

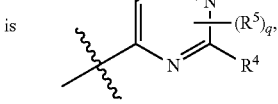

q is 0, and R⁴ is

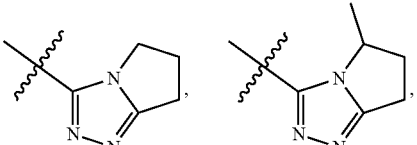

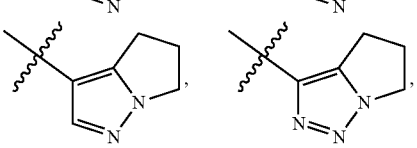

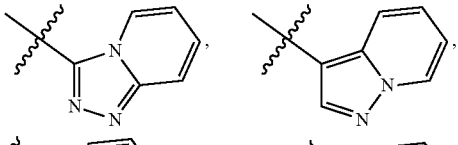

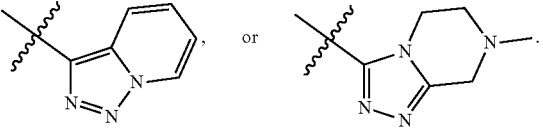

In some embodiments is a compound of Formula (Ic), or a pharmaceutically acceptable salt or solvate thereof, wherein

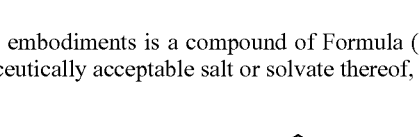

q is 0, and R⁴ is

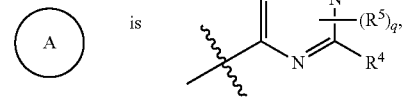

In some embodiments is a compound of Formula (Ic), or a pharmaceutically acceptable salt or solvate thereof, wherein

q is 0, and R⁴ is

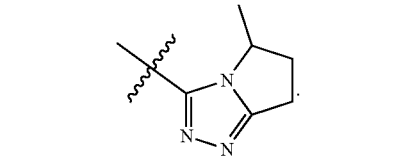 [SMILES: *c1nnc2n1C(C)CC2]

In some embodiments is a compound of Formula (Ic), or a pharmaceutically acceptable salt or solvate thereof, wherein

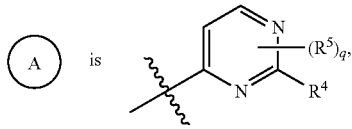

q is 0, and $R^4$ is

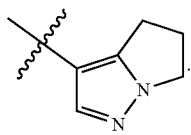 [SMILES: *c1cnn2c1CCC2]

In some embodiments is a compound of Formula (Ic), or a pharmaceutically acceptable salt or solvate thereof, wherein

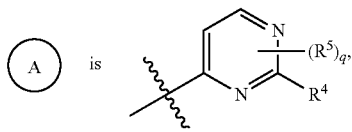

q is 0, and $R^4$ is

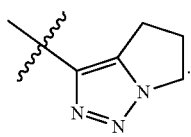 [SMILES: *c1nnn2c1CCC2]

In some embodiments is a compound of Formula (Ic), or a pharmaceutically acceptable salt or solvate thereof, wherein

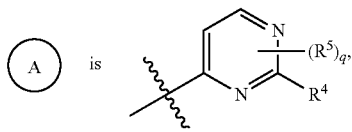

q is 0, and $R^4$ is

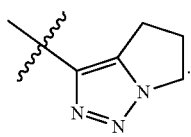 [SMILES: *c1nnn2c1CCC2]

In some embodiments is a compound of Formula (Ic), or a pharmaceutically acceptable salt or solvate thereof, wherein

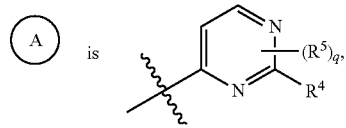

q is 0, and $R^4$

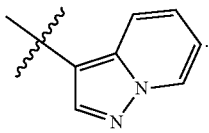

In some embodiments is a compound of Formula (Ic), or a pharmaceutically acceptable salt or solvate thereof, wherein

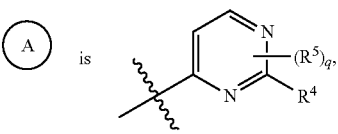

q is 0, and $R^4$ is

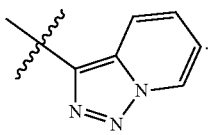 [SMILES: *c1nnn2ccccc12]

In some embodiments is a compound of Formula (Ic), or a pharmaceutically acceptable salt or solvate thereof, wherein

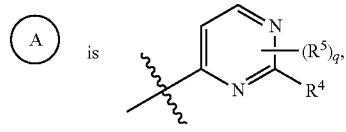

q is 0, and $R^4$ is

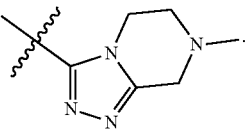 [SMILES: *c1nnc2n1CCN(C)C2]

In some embodiments is a compound of Formula (Ic), or a pharmaceutically acceptable salt or solvate thereof, wherein

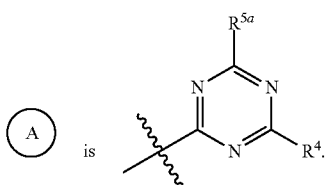

In some embodiments is a compound of Formula (Ic), or a pharmaceutically acceptable salt or solvate thereof, wherein

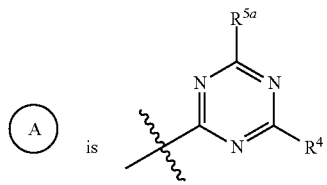

and q is 2. In some embodiments is a compound of Formula (Ic), or a pharmaceutically acceptable salt or solvate thereof, wherein

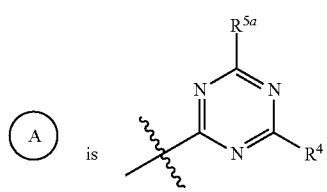

and q is 1. In some embodiments is a compound of Formula (Ic), or a pharmaceutically acceptable salt or solvate thereof, wherein

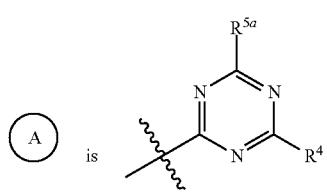

and q is 0. In some embodiments is a compound of Formula (Ic), or a pharmaceutically acceptable salt or solvate thereof, wherein

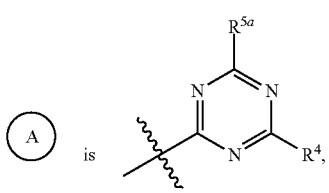

$R^{5a}$ is hydrogen, and $R^4$ is selected from a group consisting of $C_{3-8}$cycloalkyl, $C_{2-9}$heterocycle, $C_{6-10}$aryl, $C_{1-9}$heteroaryl, and a fused $C_{5-9}$heteroaryl-cycloalkyl; wherein $C_{1-6}$alkyl, $C_{2-6}$alkenyl, $C_{2-6}$alkynyl, $C_{3-8}$cycloalkyl, $C_{2-9}$heterocycle, $C_{6-10}$aryl, $C_{1-9}$heteroaryl, and fused $C_{5-9}$ heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

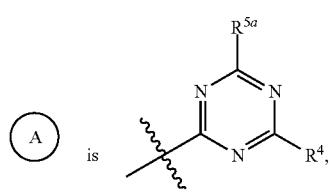

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one, two, or three substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2R^3$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

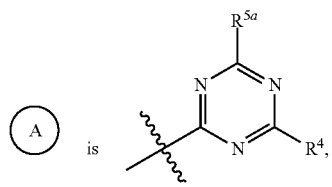

$R^{5a}$ is hydrogen, and $R^4$ is selected from a group consisting of a $C_{1-9}$heteroaryl and a fused $C_{5-9}$heteroaryl-cycloalkyl; wherein the $C_{1-9}$heteroaryl and fused $C_{5-9}$heteroaryl-cycloalkyl are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^4$, —C(=O)O$R^{13}$, —C(=O)N($R^{13}$)$_2$, —S(=O)$R^{14}$, —S(=O)$_2R^{13}$, —S(=O)$_2$—N($R^{13}$)$_2$, —N($R^{13}$)$_2$, —N($R^{13}$)C(=O)$R^{14}$, and —N($R^{13}$)S(=O)$_2R^{13}$. In some embodiments is a compound of Formula (Ic), or a pharmaceutically acceptable salt or solvate thereof, wherein

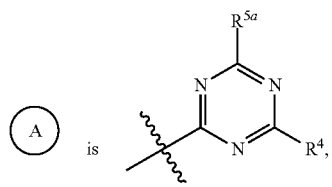

$R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, —CN, $C_{1-6}$alkyl, —$C_{1-6}$alkyl-OH, $C_{1-6}$haloalkyl, $C_{3-8}$cycloalkyl, $C_{2-9}$heterocycle, $C_{6-10}$aryl, $C_{1-9}$heteroaryl, —C(=O)$R^{14}$, —C(=O)O$R^{13}$, —C(=O)N($R^{13}$)$_2$, —S(=O)$R^{14}$, —S(=O)$_2$$R^{13}$, —S(=O)$_2$—N($R^{13}$)$_2$, —N($R^{13}$)$_2$, —N($R^{13}$)C(=O)$R^{14}$, and —N($R^{13}$)S(=O)$_2$$R^{13}$. In some embodiments is a compound of Formula (Ic), or a pharmaceutically acceptable salt or solvate thereof, wherein

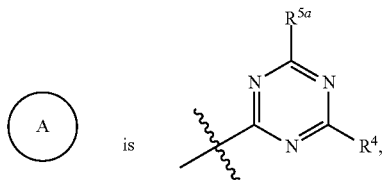

$R^{5a}$ is hydrogen, and $R^4$ is selected from a group consisting of triazole, imidazole, oxazole, isoxazole, oxadiazole, and tetrazole; wherein triazole, imidazole, oxazole, isoxazole, oxadiazole, and tetrazole are optionally substituted with one or two substituents selected from the group consisting of halogen, $C_{1-6}$alkyl, and $C_{3-8}$cycloalkyl. In some embodiments is a compound of Formula (Ic), or a pharmaceutically acceptable salt or solvate thereof, wherein

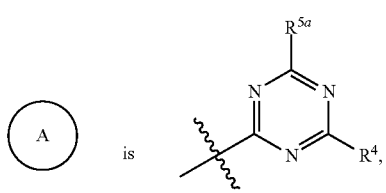

$R^{5a}$ is hydrogen, and $R^4$ is

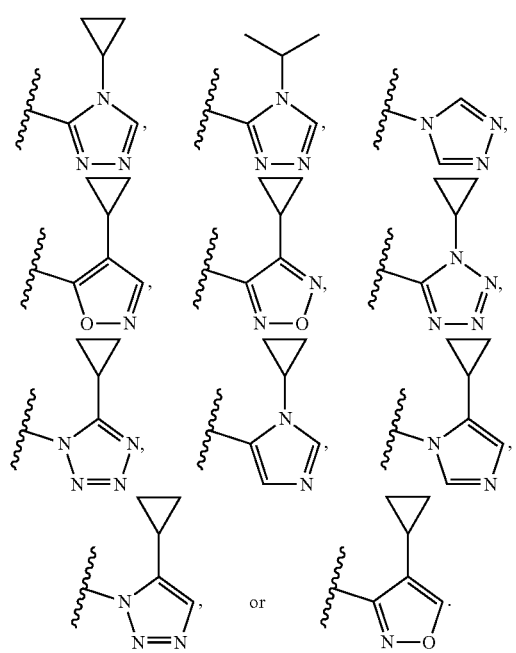,  or

In some embodiments is a compound of Formula (Ic), or a pharmaceutically acceptable salt or solvate thereof, wherein

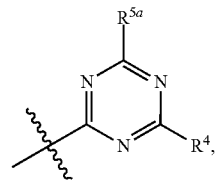

$R^{5a}$ is hydrogen, and $R^4$ is

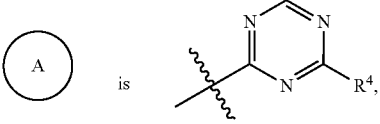

In some embodiments is a compound of Formula (Ic), or a pharmaceutically acceptable salt or solvate thereof, wherein

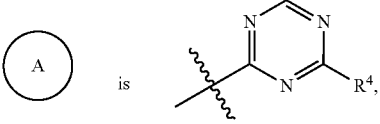

$R^{5a}$ is hydrogen, and $R^4$ is

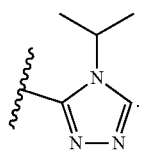 [SMILES: *c1nncn1C(C)C]

In some embodiments is a compound of Formula (Ic), or a pharmaceutically acceptable salt or solvate thereof, wherein

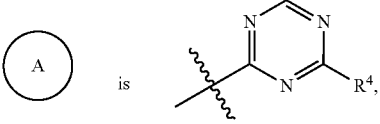

$R^{5a}$ is hydrogen, and $R^4$ is

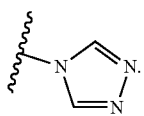

In some embodiments is a compound of Formula (Ic), or a pharmaceutically acceptable salt or solvate thereof, wherein

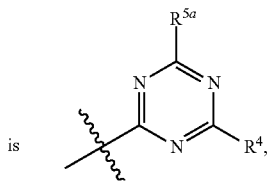

$R^{5a}$ is hydrogen, and $R^4$ is

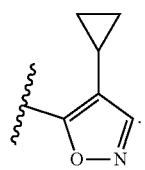

In some embodiments is a compound of Formula (Ic), or a pharmaceutically acceptable salt or solvate thereof, wherein

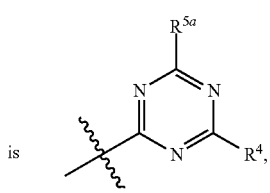

$R^{5a}$ is hydrogen, and $R^4$ is

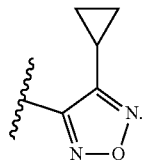 [SMILES: *c1nonc1C1CC1]

In some embodiments is a compound of Formula (Ic), or a pharmaceutically acceptable salt or solvate thereof, wherein

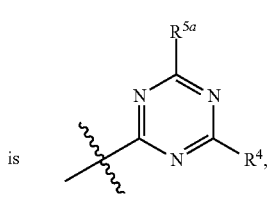

$R^{5a}$ is hydrogen, and $R^4$ is

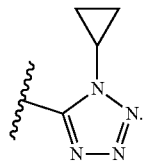 [SMILES: *c1nnnn1C1CC1]

In some embodiments is a compound of Formula (Ic), or a pharmaceutically acceptable salt or solvate thereof, wherein

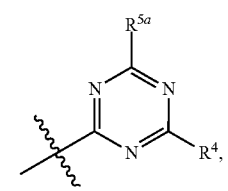

$R^{5a}$ is hydrogen, and $R^4$ is

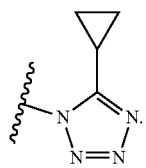 [SMILES: *n1nnnc1C1CC1]

In some embodiments is a compound of Formula (Ic), or a pharmaceutically acceptable salt or solvate thereof, wherein

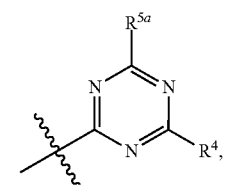

$R^{5a}$ is hydrogen, and $R^4$ is

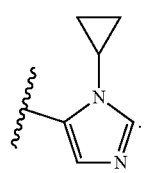 [SMILES: *c1cncn1C1CC1]

In some embodiments is a compound of Formula (Ic), or a pharmaceutically acceptable salt or solvate thereof, wherein

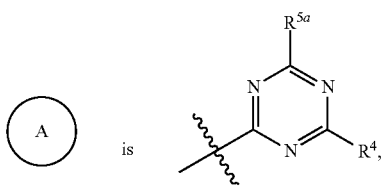 is 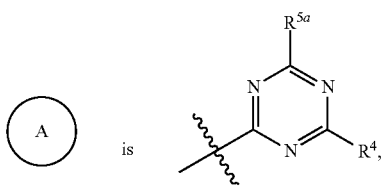

$R^{5a}$ is hydrogen, and $R^4$ is

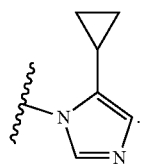

In some embodiments is a compound of Formula (Ic), or a pharmaceutically acceptable salt or solvate thereof, wherein

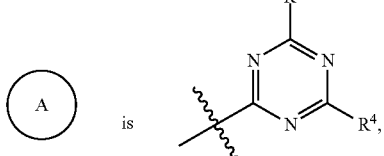 is 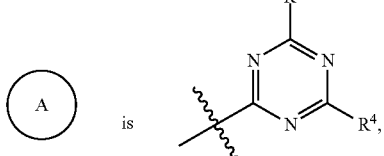

$R^{5a}$ is hydrogen, and $R^4$ is

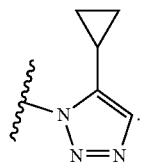

In some embodiments is a compound of Formula (Ic), or a pharmaceutically acceptable salt or solvate thereof, wherein

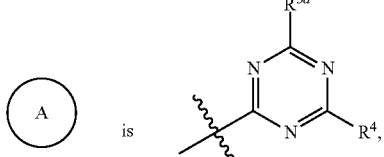 is 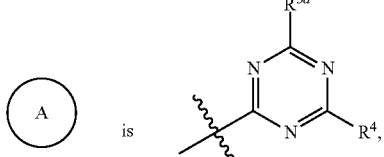

$R^{5a}$ is hydrogen, and $R^4$ is

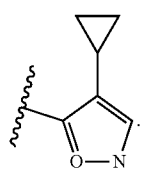

In some embodiments is a compound of Formula (Ic), or a pharmaceutically acceptable salt or solvate thereof, wherein

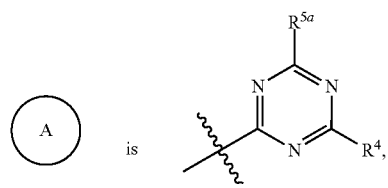 is 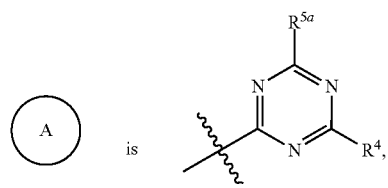

$R^{5a}$ is hydrogen, and $R^4$ is

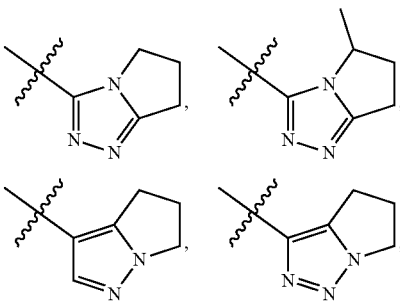

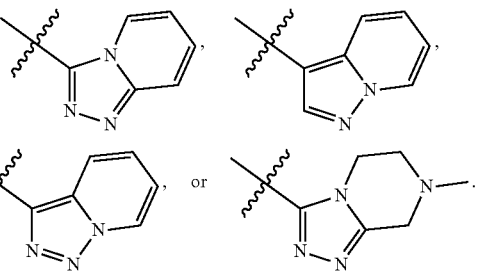

In some embodiments is a compound of Formula (Ic), or a pharmaceutically acceptable salt or solvate thereof, wherein

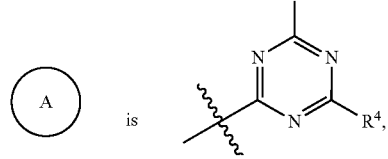 is 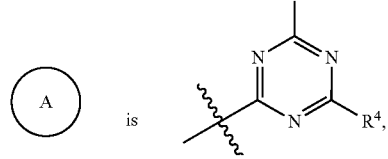

$R^{5a}$ is hydrogen, and $R^4$ is

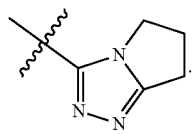 [SMILES: *c1nnc2n1CCC2]

In some embodiments is a compound of Formula (Ic), or a pharmaceutically acceptable salt or solvate thereof, wherein

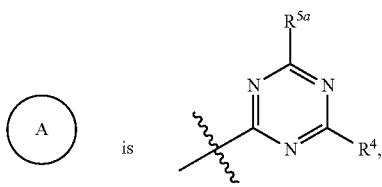

$R^{5a}$ is hydrogen, and $R^4$ is

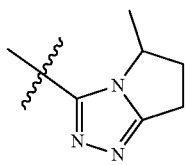

In some embodiments is a compound of Formula (Ic), or a pharmaceutically acceptable salt or solvate thereof, wherein

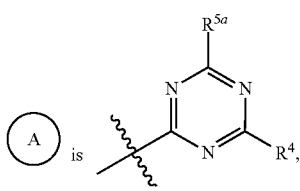

$R^{5a}$ is hydrogen, and $R^4$ is

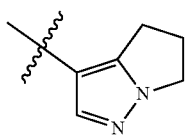

In some embodiments is a compound of Formula (Ic), or a pharmaceutically acceptable salt or solvate thereof, wherein

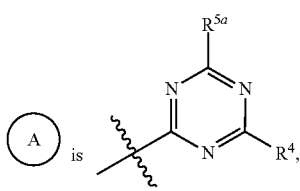

$R^{5a}$ is hydrogen, and $R^4$ is

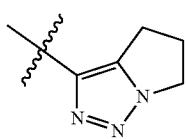

In some embodiments is a compound of Formula (Ic), or a pharmaceutically acceptable salt or solvate thereof, wherein

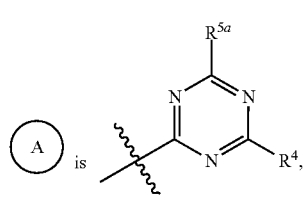

$R^{5a}$ is hydrogen, and $R^4$ is

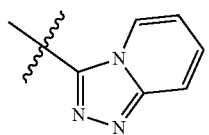

In some embodiments is a compound of Formula (Ic), or a pharmaceutically acceptable salt or solvate thereof, wherein

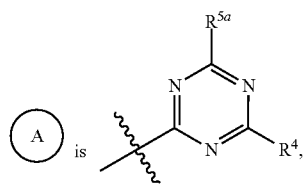

$R^{5a}$ is hydrogen, and $R^4$ is

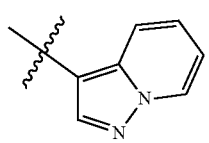

In some embodiments is a compound of Formula (Ic), or a pharmaceutically acceptable salt or solvate thereof, wherein

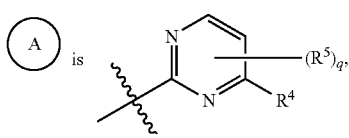

$R^{5a}$ is hydrogen, and $R^4$ is

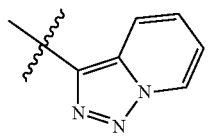

In some embodiments is a compound of Formula (Ic), or a pharmaceutically acceptable salt or solvate thereof, wherein

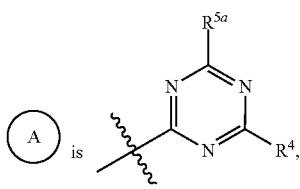

$R^{5a}$ is hydrogen, and $R^4$ is

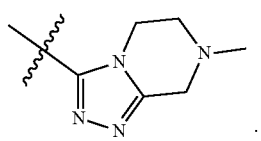 [SMILES: *c1nnc2n1CCN(C)C2]

In another aspect, described herein are pharmaceutical compositions comprising a compound of Formula (I), (Ia), (Ib), or (Ic), or a pharmaceutically acceptable salt or solvate thereof, and at least one pharmaceutically acceptable excipient.

In another aspect, described herein are methods of treating non-alcoholic steatohepatitis in a subject in need thereof, comprising administering to the subject a therapeutically effective amount of a compound of Formula (I), (Ia), (Ib), or (Ic), or a therapeutically effective amount of a pharmaceutically acceptable salt or solvate thereof.

In another aspect, the compound of Formula (I), (Ia), (Ib), or (Ic) is

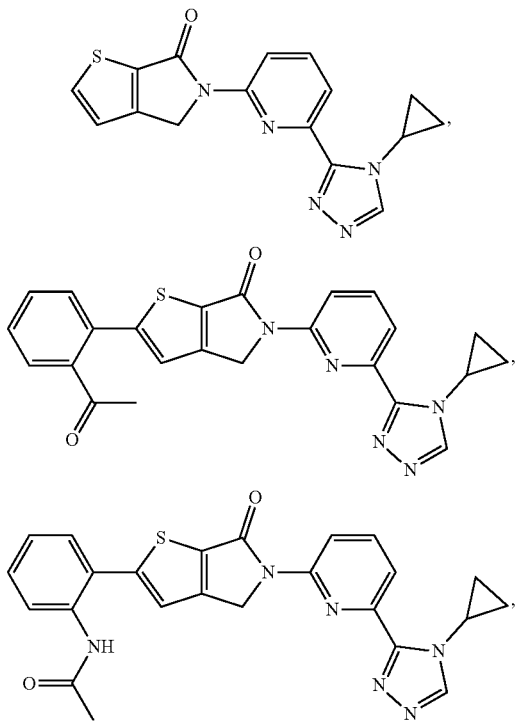

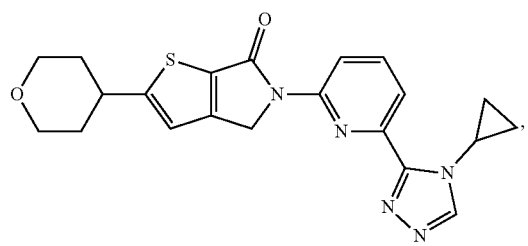

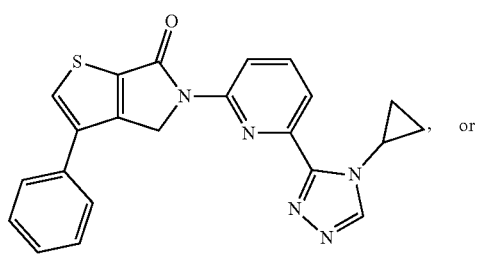

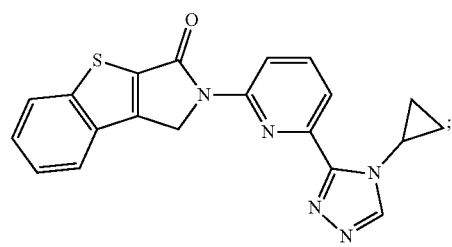

or a pharmaceutically acceptable salt or solvate thereof.

In another aspect, the compound of Formula (I), (Ia), (Ib), or (Ic) is

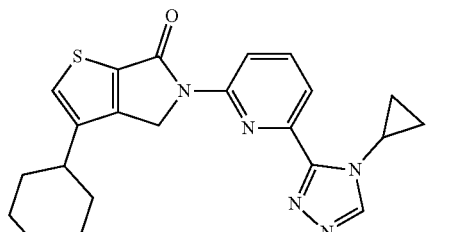

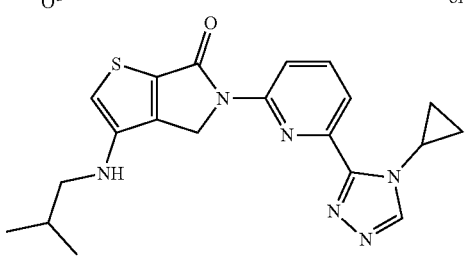

or a pharmaceutically acceptable salt or solvate thereof.

In another aspect, the compound of Formula (I), (Ia), (Ib), or (Ic) is

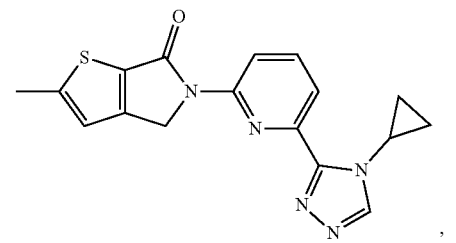

,

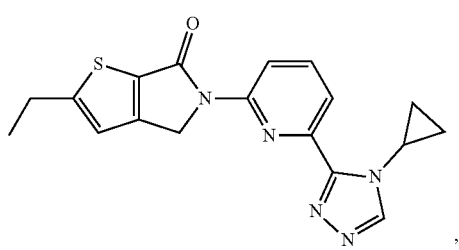

,

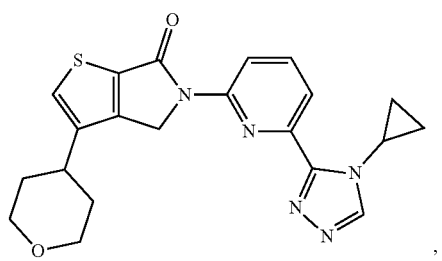

,

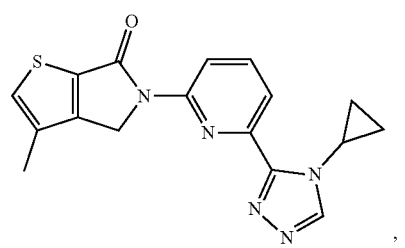

,

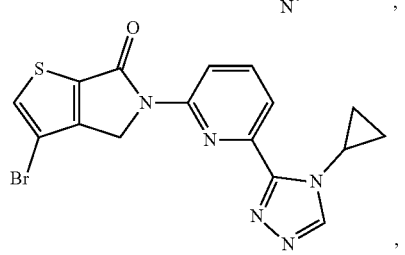

,

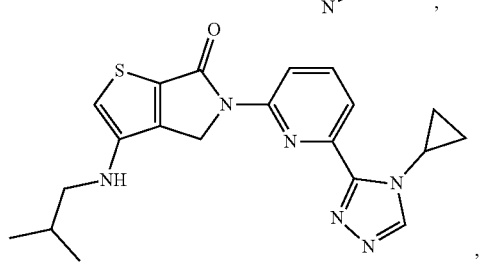

,

-continued

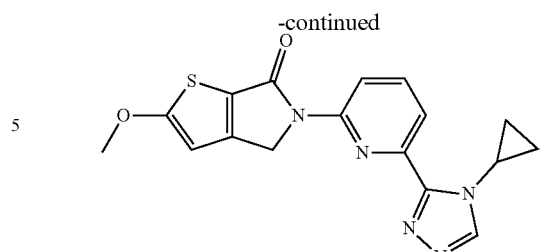

,

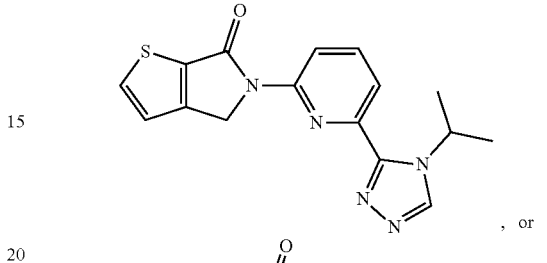

, or

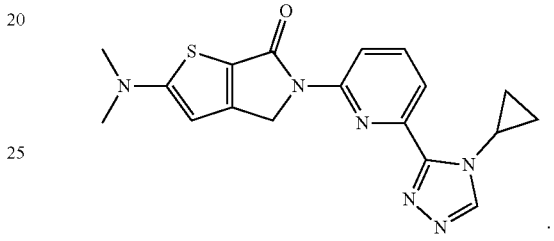

.

Synthesis of Compounds

Compounds described herein are synthesized using standard synthetic techniques or using methods known in the art in combination with methods described herein. In addition, one of ordinary skill in the art of organic synthesis will recognize that the solvents, temperatures and other reaction conditions presented herein may be varied from those described here, and deliver the desired synthetic transformation, or conversion of the specified starting material to the specified product or intermediate.

The starting materials used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in MARCH'S ADVANCED ORGANIC CHEMISTRY, 7th Ed., (Wiley, 2013); Carey and Sundberg, ADVANCED ORGANIC CHEMISTRY 5th Ed., Vols. A and B (Springer, 2007), and Green and Wuts, GREEN'S PROTECTIVE GROUPS IN ORGANIC SYNTHESIS 4th Ed., (Wiley 2007). General methods for the preparation of compounds can be modified by the use of appropriate reagents and conditions for the introduction of the various moieties found in the formulae as provided herein. A detailed description of techniques applicable to the creation of protecting groups and their removal are described in Greene and Wuts, Green's Protective Groups in Organic Synthesis, 4th Ed., John Wiley & Sons, New York, N.Y., 2007, and Kocienski, Protecting Groups, 3rd Ed., Thieme Verlag, New York, N.Y., 2003, which are incorporated herein by reference for such disclosure.

Further Forms of Compounds

In one aspect, compounds described herein possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis-, trans-, syn-, anti-, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

"Pharmaceutically acceptable," as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein with acids. Pharmaceutically acceptable salts are also obtained by reacting a compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a maleic acid salt, a fumaric acid salt, a trifluoroacetic acid salt, a tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^2H$, $^3H$, $^{13}C$, $^{14}C$, $^{15}N$, $^{19}O$, $^{17}O$, $^{31}P$, $^{32}P$, $^{35}S$, $^{18}F$, and $^{36}Cl$, respectively. Compounds described herein, and pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Routes of Administration

Suitable routes of administration include, but are not limited to, oral, intravenous, rectal, aerosol, parenteral, ophthalmic, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (Ia), (Ib), or (Ic), or a pharmaceutically acceptable salt thereof, and at least one pharmaceutically acceptable inactive ingredient. In some embodiments is a pharmaceutical composition comprising a compound of Formula (I), or a pharmaceutically acceptable salt or solvate thereof, and at least one pharmaceutically acceptable excipient. In some embodiments is a pharmaceutical composition comprising a compound of Formula (Ia), or a pharmaceutically acceptable salt or solvate thereof, and at least one pharmaceutically acceptable excipient. In some embodiments is a pharmaceutical composition comprising a compound of Formula (Ib), or a pharmaceutically acceptable salt or solvate thereof, and at least one pharmaceutically acceptable excipient. In some embodiments is a pharmaceutical composition comprising a compound of Formula (Ic), or a pharmaceutically acceptable salt or solvate thereof, and at least one pharmaceutically acceptable excipient.

In some embodiments, the compounds described herein are administered as pharmaceutical compositions in which a compound of Formula (I), (Ia), (Ib), or (Ic), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (Ib), or (Ic), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (Ib), or (Ic), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (Ib), or (Ic), as an active ingredient in free-acid or free-base form, or in a pharmaceutically acceptable salt form. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (Ia), (Ib), or (Ic), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral dosage forms are prepared by mixing a compound of Formula (I), (Ia), (Ib), or (Ic), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), (Ia), (Ib), or (Ic), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (Ia), (Ib), or (Ic), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (Ia), (Ib), or (Ic), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), (Ia), (Ib), or (Ic), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), (Ia), (Ib), or (Ic), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent.

Buccal formulations that include a compound of Formula (I), (Ia), (Ib), or (Ic), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (Ia), (Ib), or (Ic), or a pharmaceutically acceptable salt thereof, are prepared as transdermal dosage forms. In one embodiment, the transdermal formulations described herein include at least three components: (1) a formulation of a compound of Formula (I), (Ia), (Ib), or (Ic), or a pharmaceutically acceptable salt thereof, (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (Ia), (Ib), or (Ic), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Treatment

In some embodiments, described herein is a method of treating non-alcoholic steatohepatitis in a subject in need thereof, comprising administering to the subject a therapeutically effective amount of a compound of Formula (I), (Ia), (Ib), or (Ic), or a therapeutically effective amount of a pharmaceutically acceptable salt or solvate thereof. In some embodiments, described herein is a method of treating non-alcoholic steatohepatitis in a subject in need thereof, comprising administering to the subject a therapeutically effective amount of a compound of Formula (I), or a therapeutically effective amount of a pharmaceutically acceptable salt or solvate thereof. In some embodiments, described herein is a method of treating non-alcoholic steatohepatitis in a subject in need thereof, comprising administering to the subject a therapeutically effective amount of a compound of Formula (Ia), or a therapeutically effective amount of a pharmaceutically acceptable salt or solvate thereof. In some embodiments, described herein is a method of treating non-alcoholic steatohepatitis in a subject in need thereof, comprising administering to the subject a therapeutically effective amount of a compound of Formula (Ib), or a therapeutically effective amount of a pharmaceutically acceptable salt or solvate thereof. In some embodiments, described herein is a method of treating non-alcoholic steatohepatitis in a subject in need thereof, comprising administering to the subject a therapeutically effective amount of a compound of Formula (Ic), or a therapeutically effective amount of a pharmaceutically acceptable salt or solvate thereof.

Combination Treatments

In certain instances, it is appropriate to administer at least one compound of Formula (I), (Ia), (Ib), or (Ic), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (Ia), (Ib), or (Ic), or a pharmaceutically acceptable salt thereof, is co-administered with a second therapeutic agent, wherein the compound of Formula (I), (Ia), (Ib), or (Ic), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (Ia), (Ib), or (Ic), or a pharmaceutically acceptable salt thereof, is initiated prior to, during, or after treatment with a second agent, and continues until any time during treatment with the second agent or after termination of treatment with the second agent. It also includes treatments in which a compound of Formula (I), (Ia), (Ib), or (Ic), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), (Ia), (Ib), or (Ic), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

EXAMPLES

Compounds disclosed herein are made by methods including but not limited to those depicted in the reaction scheme shown below. Procedures are provided herein that, in combination with the knowledge of the synthetic organic chemist of ordinary skill in the art, are in some embodiments, used to prepare the full range of compounds disclosed and claimed herein.

The starting materials and reagents used in preparing these compounds are either available from commercial suppliers such as Bachem Americas (Torrance, Calif.) or Sigma-Aldrich (St. Louis, Mo.), or are prepared by methods known to those skilled in the art following procedures set forth in references such as: Fieser and Fieser's Reagents for Organic Synthesis, Volumes 1-28 (John Wiley and Sons, 2016); Rodd's Chemistry of Carbon Compounds, Volumes I-IV and Supplement ($2^{nd}$ edition, Elsevier Science Publishers, 2008); Organic Reactions, Volumes 1-92 (John Wiley and Sons, 2017); March's Advanced Organic Chemistry, (John Wiley and Sons, $7^{th}$ edition, 2013); and Comprehensive Organic Transformations (Richard C. Larock, John Wiley and Sons, $2^{nd}$ edition, 1999). This scheme is merely illustrative of some methods by which the compounds disclosed herein are in some embodiments synthesized, and various modifications to this scheme can be made and will be suggested to one skilled in the art having referred to this disclosure. The starting materials and the intermediates, and the final products of the reaction may be isolated and purified if desired using conventional techniques. Such materials may be characterized using conventional means, including physical constants and spectral data.

Unless otherwise noted, reagents and solvents are used as received from commercial suppliers. Proton nuclear magnetic resonance spectra are obtained on a Bruker 400 MHz spectrometer. Chemical shifts are reported in ppm (δ) and coupling constants, J values, are reported in hertz (Hz). Mass spectra are obtained on an Agilent G6110A Mass Spectrometer in ESI or APCI mode when appropriate.

Some abbreviations used herein are as follows:
DCM: dichloromethane
DMAP: 4-dimethylaminopyridine
DMF: N,N-dimethylformamide
DMF-DMA: N,N-dimethylformamide dimethyl acetal
EDCJ: 1-ethyl-3-(3-dimethylaminopropyl) carbodiimide
EtOAc: ethyl acetate
EtOH: ethanol
MeOH: methanol
NBS: N-bromosuccinimide
PE: petroleum ether Example 1: Preparation of 5-(6-(4-Cyclopropyl-4H-1,2,4-triazol-3-yl)pyridin-2-yl)-4,5-dihydro-6H-thieno[2,3-c]pyrrol-6-one (Example 1)

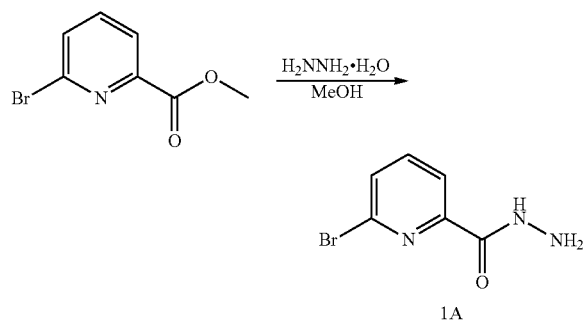

Step 1: Hydrazine hydrate (1.16 mg, 23.1 mmol, 10 eq) was added to a solution of methyl 6-bromopicolinate (500 mg, 2.31 mmol, 1.0 eq) in methanol (15 mL) at room temperature, then the reaction was stirred for 1 hour. The reaction mixture was concentrated under reduced pressure to give the desired hydrazide product 1A which was used without further purification: $^1$H NMR (400 MHz, CDCl$_3$) δ 8.84 (s, 1H), 8.12 (d, J=7.5 Hz, 1H), 7.71 (t, J=7.7 Hz, 1H), 7.62 (d, J=7.9 Hz, 1H), 4.10 (br s, 2H).

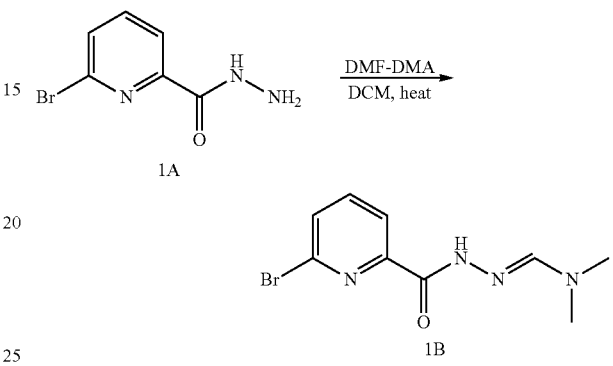

Step 2: A solution of 1A (500 mg, 2.31 mmol, 1.0 eq) and DMF-DMA (1.38 g, 11.6 mmol, 5.0 eq) in DCM (10 mL) was refluxed for 6 hours. After cooling, the reaction mixture was concentrated under reduced pressure to give the desired product 1B which was used in the subsequent step without any further purification.

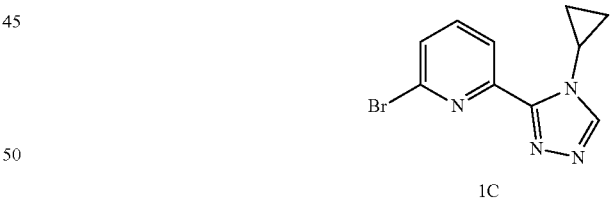

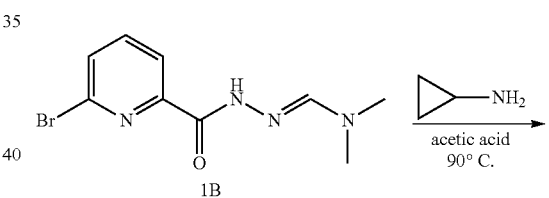

Step 3: Cyclopropylamine (396 mg, 6.93 mmol, 3.0 eq) was added to a stirred solution of 1B (630 mg, 2.31 mmol, 1.0 equiv) in glacial acetic acid (15 mL) at room temperature. After stirring at 90° C. for 3 hours, the reaction mixture was allowed to cool to room temperature. The solvent was removed under reduced pressure and the residue was purified by column chromatography (30%-100% EtOAc in PE) to give 500 mg of 1C. The material was then used directly in the next step. $^1$H NMR (400 MHz, CDCl$_3$) δ 8.29 (s, 1H), 8.24 (d, J=7.7 Hz, 1H), 7.70 (t, J=7.8 Hz, 1H), 7.55 (d, J=7.9 Hz, 1H), 3.91-3.83 (m, 1H), 1.20 (q, J=6.9 Hz, 2H), 0.93 (q, J=6.6 Hz, 2H).

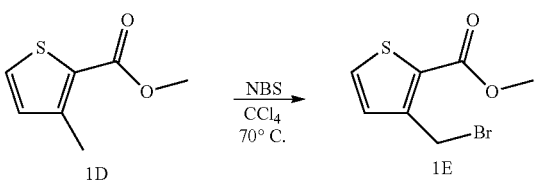

Step 4: A mixture of methyl 3-methylthiophene-2-carboxylate (1D) (5.00 g, 32.0 mmol), 2,2'-azobisisobutyronitrile (526 mg, 3.20 mmol) and N-bromosuccinimide (5.70 g, 32.0 mmol) in CCl$_4$ (300 mL) was heated to 70° C. After 3 hr, the mixture was allowed to cool to room temperature and was filtered. The resulting filter cake was washed with carbon tetrachloride (2×50 mL). The filtrate was diluted with ethyl acetate (300 mL) and washed with water (40 mL), saturated aqueous sodium bicarbonate (40 mL) and saturated brine (40 mL). The organic layer was dried over anhydrous Na$_2$SO$_4$, filtered and concentrated under reduced pressure. The crude product was purified by silica gel chromatography (1%-2% EtOAc in PE) to afford compound 1E (4.0 g, 54%) as a colorless oil. ESI m/z 234.9 [M+H]$^+$.

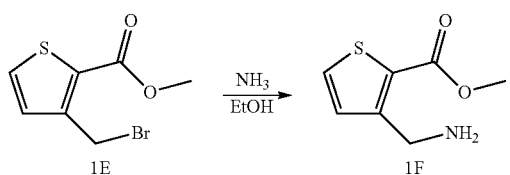

Step 5: A mixture of 1E (4.0 g, 17.1 mmol) in 2N NH$_3$/EtOH (23 mL) was stirred at room temperature overnight. The reaction mixture was concentrated at reduced pressure and the residue was purified by silica gel chromatography (2.5%-10% MeOH in DCM) to give compound 1F (1.2 g, 41%) as a white solid. ESI m/z 172.0 [M+H]$^+$.

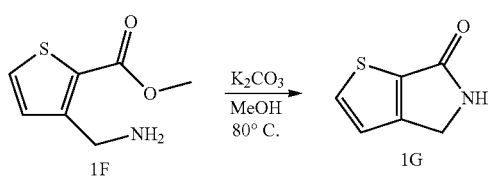

Step 6: A mixture of 1F (500 mg, 2.9 mmol) and anhydrous potassium carbonate (801 mg, 5.8 mmol) in methanol (40 mL) was stirred at 80° C. After 16 hr the reaction mixture was concentrated under reduced pressure. The residue was diluted with water (50 mL) and extracted with ethyl acetate (3×100 mL). The organic layers were combined, dried over anhydrous sodium sulfate and concentrated under reduced pressure. The residue was purified by silica gel chromatography (5%-10% MeOH in DCM) to afford compound 1G (400 mg, 50%) as a white solid. ESI m/z 177.9 [M+K]$^+$.

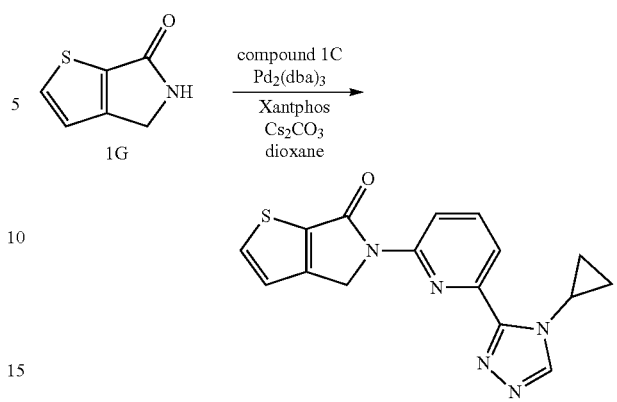

Step 7: A stirred mixture of compound 1G (200 mg, 1.4 mmol), compound 1C (371 mg, 1.4 mmol), Pd$_2$(dba)$_3$ (64 mg, 0.07 mmol), Cs$_2$CO$_3$ (1.4 g, 4.2 mmol) and Xantphos (58 mg, 0.1 mmol) in 1,4-dioxane (30 mL) was heated to 100° C. overnight. The reaction mixture was allowed to cool to room temperature and filtered. The resulting filtrate was concentrated under reduced pressure and the crude material was purified by silica gel chromatography (1.5% MeOH in DCM) to give Example 1 (80 mg, 18%) as a white powder: $^1$H NMR (400 MHz, CDCl$_3$) δ 8.63 (d, J=9.2 Hz, 1H), 8.22 (s, 1H), 7.95-7.86 (m, 2H), 7.76 (d, J=4.8 Hz, 1H), 7.13 (d, J=4.8 Hz, 1H), 5.0 (s, 2H), 3.91 (m, 1H), 1.15-1.09 (m, 2H), 0.97-0.93 (m, 2H); ESI m/z 324.0 [M+H]$^+$.

Example 2: Preparation of 2-(2-Acetylphenyl)-5-(6-(4-cyclopropyl-4H-1,2,4-triazol-3-yl) pyridin-2-yl)-4,5-dihydro-6H-thieno[2,3-c]pyrrol-6-one (Example 2)

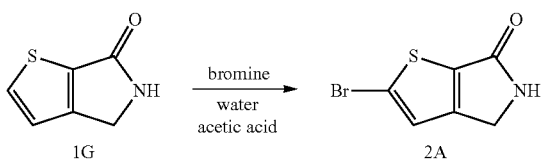 [SMILES: O=C1NCc2ccsc21 ; O=C1NCc2cc(Br)sc21]

Step 1: Bromine (3.4 g, 20 mmol) was added to a solution of 1G (1.5 g, 10 mmol) in acetic acid (20 mL) and water (10 mL) at 0° C. After stirring overnight, the reaction mixture was diluted with water (50 mL) and the mixture was extracted with EtOAc (2×100 mL). The combined organic fractions were washed with 5% aq. Na$_2$SO$_3$ (100 mL), sat. aq. NaHCO$_3$ (100 mL) and brine (100 mL). The reaction mixture was dried over Na$_2$SO$_4$, filtered and concentrated under vacuum. The residue was purified by flash chromatography over silica gel (5% MeOH in DCM) to yield 2A (1.2 g, 51% yield) as a yellow solid: $^1$H NMR (400 MHz, MeOD) δ 7.27 (s, 1H), 4.38 (s, 3H); ESI m/z 218.0, 220.0 [M+H]$^+$.

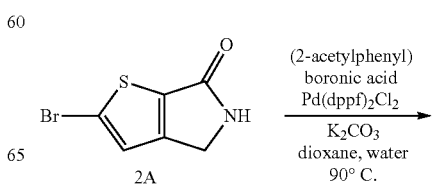

-continued

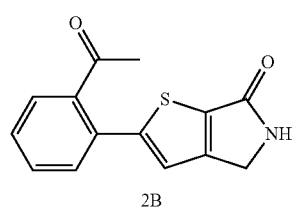

2B

Step 2: A mixture of compound 2A (200 mg, 0.92 mmol), (2-acetylphenyl)boronic acid (226 mg, 1.38 mmol), potassium carbonate (381 mg, 2.76 mmol) and Pd(dppf)$_2$Cl$_2$ (34 mg, 0.046 mmol) in 1,4-dioxane (20 mL) and water (5 mL) was stirred at 90° C. for 10 hours under a nitrogen atmosphere. The mixture was poured into water and extracted with EtOAc (100 mL×3). The combined organic fractions were washed with water and brine, dried over anhydrous Na$_2$SO$_4$ and concentrated under reduced pressure. The residue was purified by chromatography on silica gel (1%-5% MeOH in DCM) to give 2B (200 mg, 84% yield) as a white solid: ESI m/z 258.1 [M+H]$^+$.

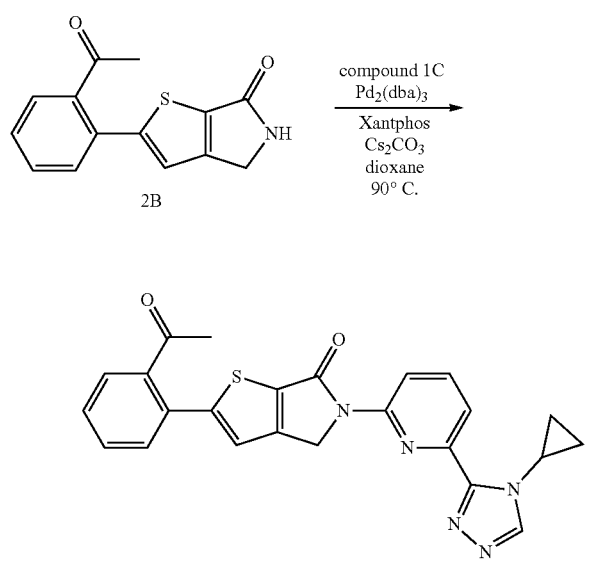

Example 2

Step 3: A mixture of 2B (200 mg, 0.78 mmol), 1C (206 mg, 0.78 mmol), Cs$_2$CO$_3$ (762 mg, 2.34 mmol), Xantphos (32 mg, 0.055 mmol) and Pd$_2$(dba)$_3$ (36 mg, 0.039 mmol) in dioxane (25 mL) was stirred at 90° C. overnight under nitrogen. The mixture was concentrated under reduced pressure and purified by chromatography on silica gel (1%-5% MeOH in DCM) to give Example 2 (80 mg, 23% yield) as a white solid: $^1$H NMR (400 MHz, CDCl$_3$) δ 8.65 (dd, J=8 Hz, 0.8 Hz, 1H), 8.24 (s, 1H), 7.97-7.89 (m, 2H), 7.57-7.49 (m, 4H), 7.03 (s, 1H), 5.02 (s, 2H), 3.96-3.90 (m, 1H), 2.32 (s, 3H), 1.18-1.13 (m, 2H), 0.98-0.94 (m, 2H); ESI m/z 442.0 [M+H]$^+$.

Example 3: Preparation of N-(3-(5-(6-(4-Cyclopropyl-4H-1,2,4-triazol-3-yl)pyridin-2-yl)-6-oxo-5,6-dihydro-4H-thieno[2,3-c]pyrrol-2-yl)phenyl)acetamide (Example 3)

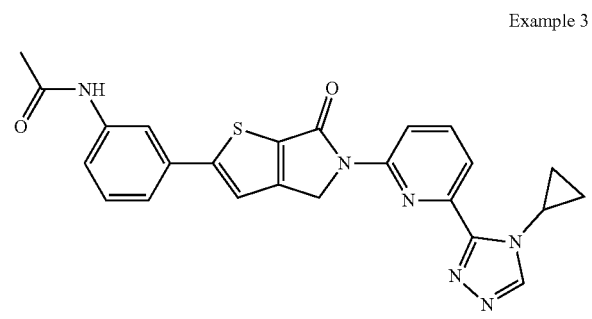 [SMILES: CC(=O)Nc1cccc(-c2cc3c(s2)C(=O)N(c2cccc(-c4nncn4C4CC4)n2)C3)c1]

Example 3

Example 3 was prepared according to the procedure for Example 2 substituting (3-acetamidophenyl)boronic acid in place of (2-acetylphenyl) boronic acid. $^1$H NMR (400 MHz, DMSO-d$_6$) δ 8.72-8.66 (m, 3H), 8.13-8.05 (m, 3H), 7.98 (d, J=8 Hz, 1H), 7.92 (d, J=7.6 Hz, 1H), 7.81 (d, J=7.2 Hz, 1H), 7.66 (d, J=7.6 Hz, 1H), 7.40-7.33 (m, 2H), 5.30 (s, 2H), 4.16-4.10 (m, 1H), 1.17-1.12 (m, 2H), 1.02-0.98 (m, 2H); ESI m/z 434.0 [M+H]$^+$.

Example 4: Preparation of 5-(6-(4-cyclopropyl-4H-1,2,4-triazol-3-yl)pyridin-2-yl)-2-(tetrahydro-2H-pyran-4-yl)-4,5-dihydro-6H-thieno[2,3-c]pyrrol-6-one (Example 4)

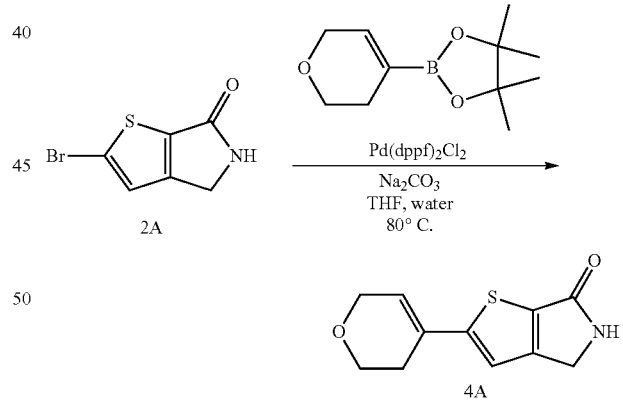

Step 1: A mixture of 2A (600 mg, 2.75 mmol), 2-(3,6-dihydro-2H-pyran-4-yl)-4,4,5,5-tetramethyl-1,3,2-dioxaborolane (867 mg, 4.13 mmol), Pd(dppf)Cl$_2$ (402 mg, 0.55 mmol) and Na$_2$CO$_3$ (875 mg, 8.25 mmol) in THF (15 mL) and water (3 mL) was stirred at 80° C. overnight. The mixture was extracted with EtOAc (100 mL×3). The organic fractions were dried over anhydrous Na$_2$SO$_4$, filtered and concentrated under reduced pressure. The residue was purified by chromatography on silica gel (1%-1.25% MeOH in DCM) to give 4A (212 mg, 34% yield) as a yellow solid: ESI m/z 222.0 [M+H]$^+$.

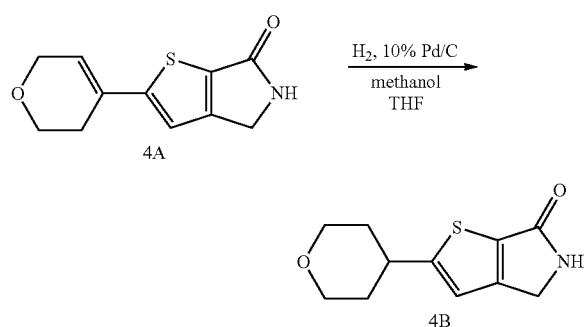

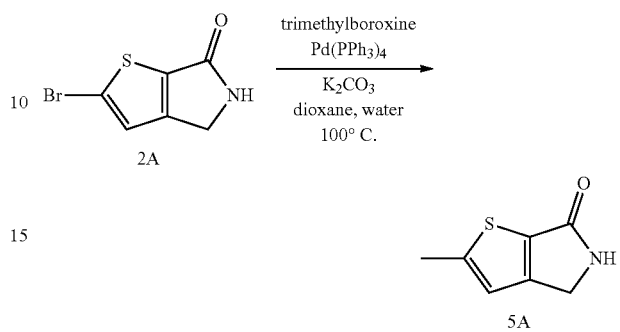

Example 5: Preparation of 5-(6-(4-cyclopropyl-4H-1,2,4-triazol-3-yl)pyridin-2-yl)-2-methyl-4,5-dihydro-6H-thieno[2,3-c]pyrrol-6-one (Example 5)

Step 2: A mixture of 4A (215 mg, 0.97 mmol) and 10% palladium on carbon (100 mg) was stirred in methanol (20 mL) and THF (20 mL) under a hydrogen atmosphere overnight. The reaction mixture was filtered through Celite and the filtrate was concentrated under reduced pressure to give 4B (230 mg, 100% yield) as a yellow solid: $^1$H NMR (400 MHz, CDCl$_3$) δ 6.83 (s, 1H), 6.11 (s, 1H), 4.35 (s, 2H), 4.09 (dd, J=11.2 Hz, 3.2 Hz, 2H), 3.55 (td, J=11.7 Hz, 2.0 Hz, 2H), 3.13 (s, 1H), 2.04-1.94 (m, 2H), 1.88 (td, J=11.8, 3.7 Hz, 2H); ESI m/z 224.1 [M+H]$^+$.

Step 1: A stirred mixture of 2A (500 mg, 2.29 mmol), trimethylboroxine (4.3 g, 34.39 mmol), Pd(PPh$_3$)$_4$ (265 mg, 0.23 mmol), and K$_2$CO$_3$ (1.6 g, 11.45 mmol) in 1,4-dioxane (40 mL) and water (5 mL) was heated to 100° C. for 6 hours under nitrogen. The reaction mixture was allowed to cool to room temperature, poured into water, and extracted with EtOAc (3×80 mL). The combined organic fractions were washed with brine, dried with anhydrous sodium sulfate, filtered and concentrated under reduced pressure. The residue was purified by column chromatography on silica gel (0.5%-30% EtOAc in PE) to give compound 5A (220 mg, 63% yield) as a white solid: ESI m/z 154.0 [M+H]$^+$.

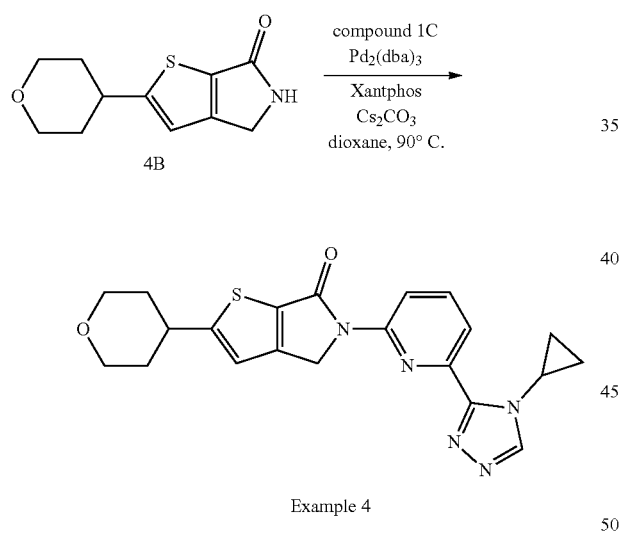

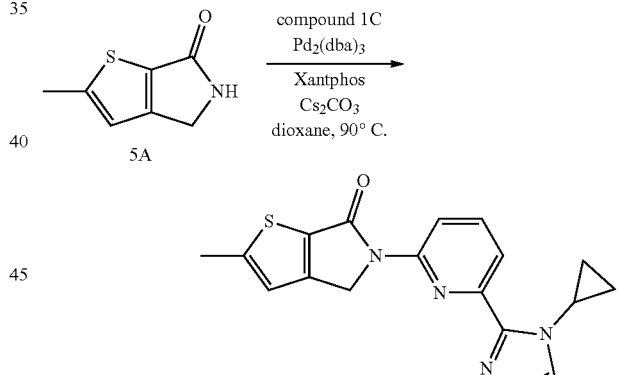

Step 3: A mixture of 4B (200 mg, 0.90 mmol), 1C (239 mg, 0.90 mmol), Cs$_2$CO$_3$ (880 mg, 2.70 mmol), Xantphos (104 mg, 0.18 mmol) and Pd$_2$(dba)$_3$ (82 mg, 0.09 mmol) in dioxane (15 mL) was stirred at 90° C. overnight under nitrogen. The mixture was poured into water and extracted with EtOAc (100 mL×3). The organic fractions were dried over anhydrous Na$_2$SO$_4$, filtered and concentrated under reduced pressure. The residue was purified by chromatography on silica gel (1%-2% MeOH in DCM) to give Example 4 (70 mg, 20% yield) as a yellow oil: $^1$H NMR (400 MHz, CDCl$_3$) δ 8.62 (dd, J=1.2 Hz 1H), 8.22 (s, 1H), 7.94-7.86 (m, 2H), 6.89 (s, 1H), 4.94 (s, 2H), 4.10-4.07 (m, 2H), 3.93-3.87 (m, 1H), 3.54 (t, J=12 Hz, 2H), 3.18-3.10 (m, 1H), 2.03-1.95 (m, 2H), 1.92-1.81 (m, 2H), 1.11 (q, J=6.8 Hz, 2H), 0.97-0.93 (m, 2H); ESI m/z 408.1 [M+H]$^+$.

Step 2: A stirred mixture of 5A (220 mg, 1.44 mmol), compound 1C (381 mg, 1.44 mmol), Pd$_2$(dba)$_3$ (66 mg, 0.072 mmol), Xantphos (58 mg, 58 mmol) and Cs$_2$CO$_3$ (1.41 g, 4.32 mmol) in 1,4-dioxane (40 mL) was heated to 100° C. overnight under nitrogen. The reaction mixture was allowed to cool to room temperature and filtered. The filtrate was concentrated under reduced pressure and the residue was purified by silica column chromatography (0.5%-2.5% MeOH in DCM). The product was further purified by preparative HPLC to give Example 5 (28 mg, 6% yield) as a white solid: $^1$H NMR (400 MHz, CDCl$_3$) δ 8.62-8.60 (m, 1H), 8.22 (s, 1H), 7.91-7.84 (m, 2H), 6.80 (s, 1H), 4.91 (s, 2H), 3.93-3.88 (m, 1H), 2.61 (s, 3H), 1.13-1.08 (m, 2H), 0.96-0.92 (m, 2H); ESI m/z 338.1 [M+H]$^+$.

Example 6: Preparation of 5-(6-(4-cyclopropyl-4H-1,2,4-triazol-3-yl)pyridin-2-yl)-2-ethyl-4,5-dihydro-6H-thieno[2,3-c]pyrrol-6-one (Example 6)

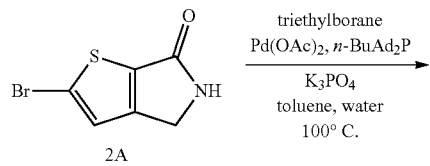

Step 1: A stirred mixture of 2A (600 mg, 2.75 mmol), triethylborane (1M in THF, 8.25 mL, 8.25 mmol), Pd(OAc)$_2$ (273 mg, 0.83 mmol), butyl di-1-adamantylphosphine (179 mg, 0.50 mmol) and K$_3$PO$_4$.3H$_2$O (2.2 g, 8.25 mmol) in 1,4-dioxane (40 mL) and water (4 mL) was heated to 100° C. overnight under nitrogen. The reaction mixture was allowed to cool to room temperature, poured into water and extracted with EtOAc (3×80 mL). The combined organic fractions were washed with brine, dried with anhydrous sodium sulfate, filtered and concentrated under reduced pressure. The residue was purified by column chromatography on silica gel (0.5%-50% EtOAc in PE) to give a mixture (240 mg) containing 6A: ESI m/z 167.8 [M+H]$^+$.

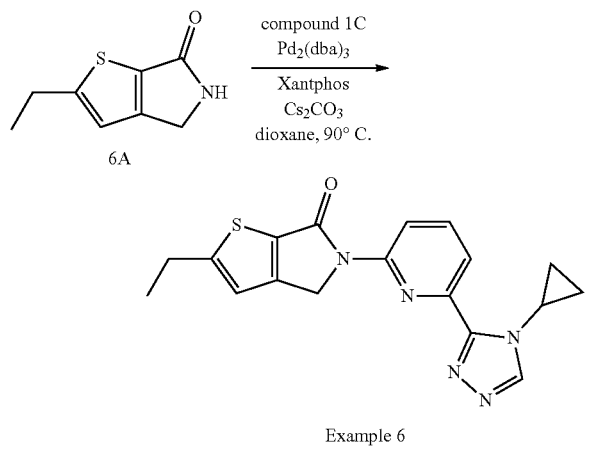

Example 6

Step 2: A mixture of 6A (240 mg, 1.44 mmol), compound 1C (381 mg, 1.44 mmol), Pd$_2$(dba)$_3$ (66 mg, 0.072 mmol), Xantphos (58 mg, 58 mmol) and Cs$_2$CO$_3$ (1.41 g, 4.32 mmol) in 1,4-dioxane (40 mL) was stirred at 100° C. overnight under nitrogen. The reaction mixture was allowed to cool to room temperature and filtered. The filtrate was concentrated under reduced pressure and the residue was purified by silica gel column chromatography (0.5%-2.5% MeOH in DCM). The product was further purified by preparative reverse phase HPLC to afford Example 6 (35 mg, 7% yield) as a white solid: $^1$H NMR (400 MHz, CDCl$_3$) δ 8.62-8.60 (m, 1H), 8.22 (s, 1H), 7.91-7.84 (m, 2H), 6.84 (s, 1H), 4.91 (s, 2H), 3.93-3.88 (m, 1H), 2.68-2.92 (m, 2H), 1.37 (m, 3H), 1.13-1.08 (m, 2H), 0.96-0.92 (m, 2H); ESI m/z 352.1 [M+H]$^+$.

Example 7: Preparation of 5-(6-(4-cyclopropyl-4H-1,2,4-triazol-3-yl)pyridin-2-yl)-3-phenyl-4,5-dihydro-6H-thieno[2,3-c]pyrrol-6-one (Example 7)

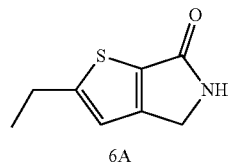
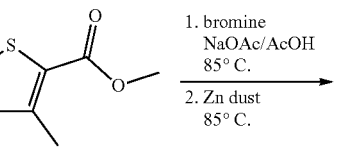

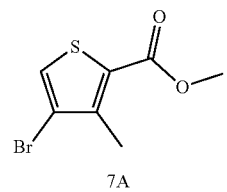

Step 1: A solution of 1D (20 g, 103 mmol) and sodium hydroxide (12.3 g, 307 mmol) in acetic acid (75 mL) was heated to 60° C. Bromine (46.9 g, 294 mmol) was added dropwise in order to keep the reaction temperature below 85° C. After stirring at 85° C. for 6 h, the reaction mixture was allowed to cool to 50° C. Zinc dust (15.4 g, 236 mmol) was added in 3 gram portions to the mixture to keep the reaction temperature below 85° C. After stirring at 85° C. for 1 h, the hot reaction mixture was filtered through a small bed of Celite. The filtrate was diluted with water (300 mL) and the mixture was extracted with hexane (300 mL). The organic fraction was washed with water and concentrated under vacuum to give 7A (27 g, 89% yield) as an off-white solid: $^1$H NMR (400 MHz, CDCl$_3$) δ 7.42 (s, 1H), 3.86 (s, 3H), 2.54 (s, 3H); ESI m/z 234.9, 236.9 [M+H]$^+$.

Step 2: A mixture of 7A (0.5 g, 2.14 mmol), N-bromosuccinimide (0.392 g, 2.2 mmol) and 2,2'-azobis(2-methylpropionitrile) (0.175 g, 1.05 mmol) in ACN (20 mL) was stirred overnight at 90° C. under nitrogen. The mixture was then filtered, evaporated and purified by column chromatography on silica gel (petroleum ether) to give 7B (0.4 g, 60% yield) as a yellow oil: $^1$H NMR (400 MHz, CDCl$_3$) δ 7.48 (s, 1H), 4.90 (s, 2H), 3.93 (s, 3H); ESI m/z 314.7 [M+H]$^+$.

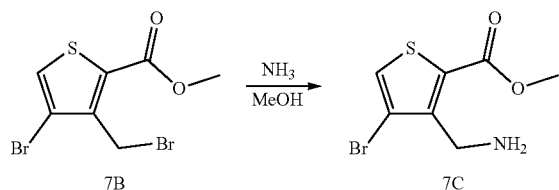

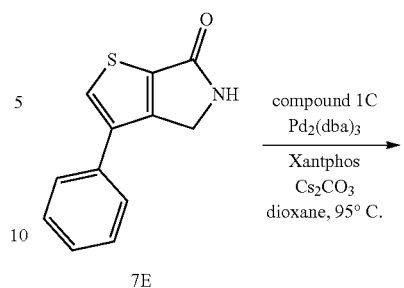

Step 3: A mixture of 7B (18 g, 58.3 mmol) and ammonia in methanol (7.0 M, 230 mL) was stirred at room temperature overnight. The mixture was concentrated under reduced pressure and purified by column chromatography on silica (1%-5% EtOAc in PE) to afford compound 7C (10.7 g, 74% yield) as an off-white solid: ESI m/z 249.9, 251.8 [M+H]$^+$.

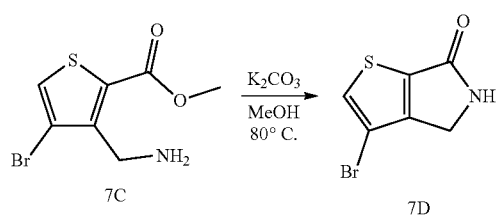

Step 4: A mixture of 7C (10 g, 40.2 mmol) and potassium carbonate (16.7 g, 120.5 mmol) in methanol (120 mL) was heated at 80° C. overnight under nitrogen. The mixture was concentrated under reduced pressure and purified by column chromatography on silica (1%-50% EtOAc in PE) to afford compound 7D (2.8 g, 32% yield) as a yellow solid: $^1$H NMR (400 MHz, CDCl$_3$) δ 7.57 (s, 1H), 6.98 (s, 1H), 4.30 (s, 2H); ESI m/z 217.8, 219.8 [M+H]$^+$.

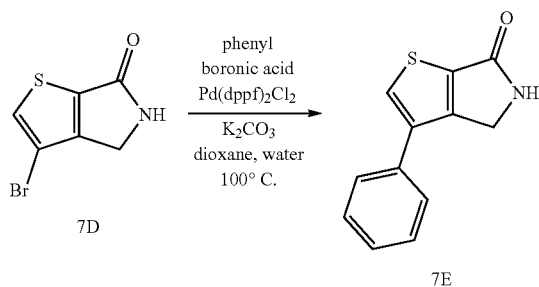 [SMILES: O=C1NCc2c(Br)csc21 ; O=C1NCc2c(-c3ccccc3)csc21]

Step 5: A mixture of 7D (300 mg, 1.38 mmol), phenylboronic acid (252 mg, 2.06 mmol), potassium carbonate (572 mg, 4.14 mmol) and Pd(dppf)$_2$Cl$_2$ (63 mg, 0.069 mmol) in 1,4-dioxane (20 mL) and water (10 mL) was stirred at 100° C. overnight under a nitrogen atmosphere. The mixture was poured into water and extracted with EtOAc (100 mL×3). The organic fraction was washed with water and brine, dried over anhydrous sodium sulfate and concentrated under reduced pressure. The residue was purified by chromatography on silica gel (1%-5% MeOH in DCM) to give compound 7E (197 mg, 66% yield) as a white solid: ESI m/z 216.2 [M+H]$^+$.

Example 7

Step 6: A mixture of 7E (130 mg, 0.60 mmol), compound 1C (160 mg, 0.60 mmol), cesium carbonate (586 mg, 1.80 mmol), Xantphos (24 mg, 0.042 mmol) and Pd(dba)$_3$ (27 mg, 0.037 mmol) in 1,4-dioxane (20 mL) was stirred at 95° C. overnight under nitrogen. The mixture was concentrated under reduced pressure and purified by chromatography on silica gel (1%-5% MeOH in DCM) to give Example 7 (50 mg, 21% yield) as a white solid: $^1$H NMR (400 MHz, CDCl$_3$) δ 8.70 (s, 1H), 8.51 (d, J=8 Hz, 1H), 8.43 (s, 1H), 8.06 (t, J=8 Hz, 1H), 7.88 (d, J=7.2 Hz, 1H), 7.71 (d, J=7.2 Hz, 1H), 7.51-7.38 (m, 3H), 5.41 (s, 2H), 4.21-4.14 (m, 1H), 1.11-1.06 (m, 4H); ESI m/z 400.0 [M+H]$^+$.

Example 8: Preparation of 5-(6-(4-cyclopropyl-4H-1,2,4-triazol-3-yl)pyridin-2-yl)-3-(tetrahydro-2H-pyran-4-yl)-4,5-dihydro-6H-thieno[2,3-c]pyrrol-6-one (Example 8)

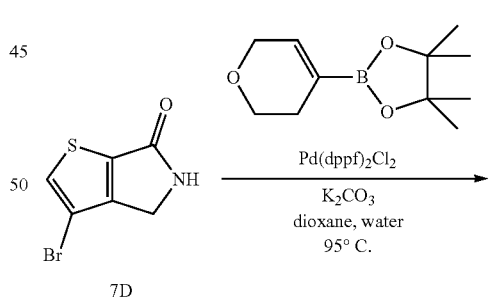

8A

Step 1: A mixture of 7D (600 mg, 2.75 mmol), 2-(3,6-dihydro-2H-pyran-4-yl)-4,4,5,5-tetramethyl-1,3,2-dioxaborolane (867 mg, 4.13 mmol), potassium carbonate (1.14 g, 8.25 mmol) and Pd(dppf)$_2$Cl$_2$ (126 mg, 0.138 mmol) in 1,4-dioxane (40 mL) and water (10 mL) was stirred at 95° C. overnight under nitrogen. The mixture was poured into water and extracted with EtOAc (100 mL×3), the organic fractions were washed with water and brine, dried over Na$_2$SO$_4$ and concentrated under reduced pressure. The residue was purified by chromatography on silica gel (1%-5% MeOH in DCM) to give compound 8A (330 mg, 54% yield) as a white solid: ESI m/z 222.1 [M+H]$^+$.

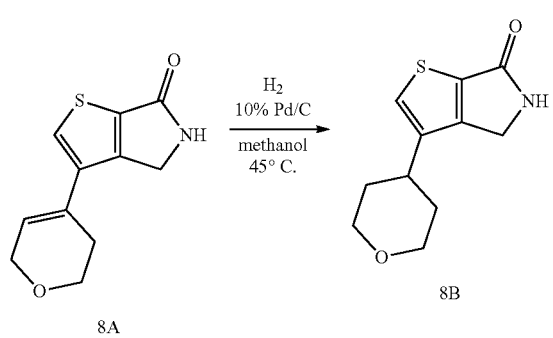 [SMILES: O=C1NCc2c(C3=CCOCC3)csc21 ; O=C1NCc2c(C3CCOCC3)csc21]

Step 2: A mixture of 8A (300 mg, 1.36 mmol) and 10% palladium on carbon (300 mg) in methanol (20 mL) was heated to 45° C. overnight under one atmosphere of hydrogen. The reaction mixture was filtered through Celite and the filtrate was concentrated under vacuum. The residue was purified by silica column chromatography (5% MeOH in DCM) to give compound 8B (80 mg, 59% yield) as a white solid: ESI m/z 224.1 [M+H]$^+$.

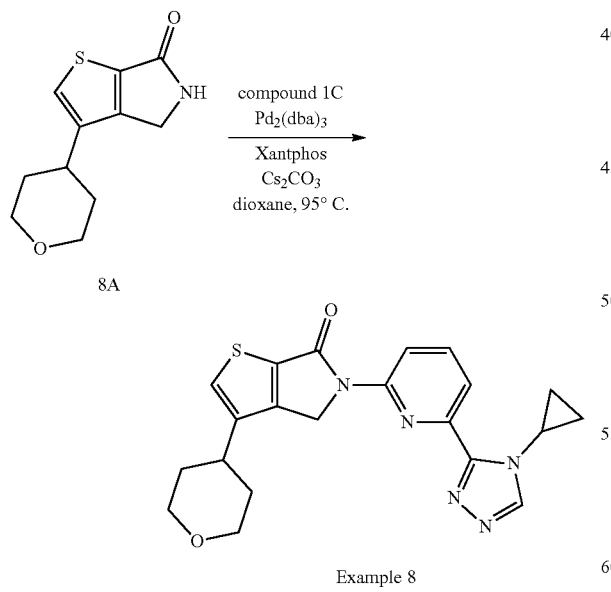

Step 3: A mixture of 8B (170 mg, 0.76 mmol), compound 1C (155 mg, 0.76 mmol), cesium carbonate (743 mg, 2.28 mmol), Xantphos (31 mg, 0.053 mmol) and Pd$_2$(dba)$_3$ (35 mg, 0.038 mmol) in 1,4-dioxane (15 mL) was stirred at 95° C. overnight under nitrogen. The mixture was concentrated under reduced pressure and purified by chromatography on silica gel (1%-5% MeOH in DCM) to give Example 8 (45 mg, 15% yield) as a white solid: $^1$H NMR (400 MHz, CDCl$_3$) δ 8.62 (dd, J=7.2 Hz, 2 Hz, 1H), 8.23 (s, 1H), 7.92-7.87 (m, 2H), 7.40 (s, 1H), 5.00 (s, 2H), 4.08 (dd, J=11.2 Hz, 2.8 Hz, 2H), 3.91-3.85 (m, 1H), 3.56-3.50 (m, 2H), 2.97-2.89 (m, 1H), 1.89-1.77 (m, 4H), 1.13-1.08 (m, 2H), 0.99-0.95 (m, 2H); ESI m/z 408.0 [M+H]$^+$.

Example 9: Preparation of 5-(6-(4-cyclopropyl-4H-1,2,4-triazol-3-yl)pyridin-2-yl)-3-methyl-4,5-dihydro-6H-thieno[2,3-c]pyrrol-6-one (Example 9)

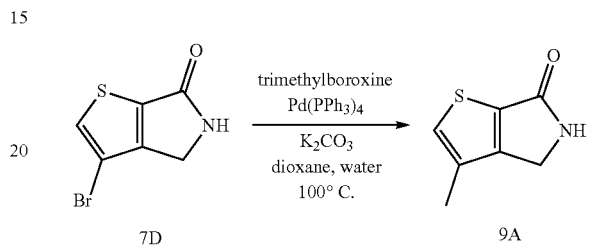

Step 1: A mixture of 7D (350 mg, 1.60 mmol), trimethylboroxine (3.0 g, 24.1 mmol), Pd(PPh$_3$)$_4$ (185 mg, 0.16 mmol) and potassium carbonate (1.1 g, 8.02 mmol) in 1,4-dioxane (30 mL) and water (2 mL) was heated to 100° C. for 6 hours under nitrogen. After cooling to room temperature, the reaction mixture was diluted with water and extracted with EtOAc (3×80 mL). The organic fractions were washed with brine, dried with sodium sulfate and concentrated under reduced pressure. The residue was purified by column chromatography on silica gel (0.5%-1% MeOH in DCM) to give the compound 9A (240 mg, 98% yield) as a yellow solid: $^1$H NMR (400 MHz, DMSO-d$_6$) δ 8.33 (s, 1H), 7.54 (s, 1H), 4.23 (s, 2H), 2.19 (s, 3H); ESI m/z 154.0 [M+H]$^+$.

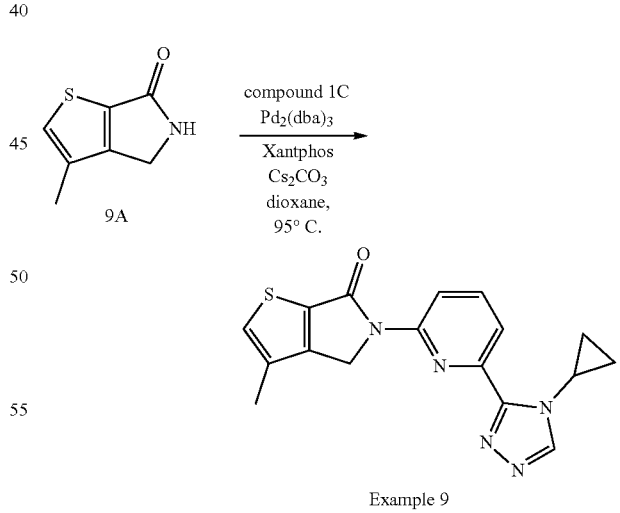

Step 2: A mixture of 9A (240 mg, 1.63 mmol), 1C (432 mg, 1.63 mmol), Pd$_2$(dba)$_3$ (100 mg, 0.11 mmol), Xantphos (91 mg, 0.16 mmol) and cesium carbonate (1.5 g, 4.70 mmol) in 1,4-dioxane (30 mL) was heated to 95° C. overnight under nitrogen. The reaction mixture was allowed to cool to room temperature and filtered. The resulting filtrate was concentrated under reduced pressure and the residue was purified by silica column chromatography (0.5%-1.25% MeOH in DCM) to give the Example 9 (120 mg, 23% yield) as an off-white solid: $^1$H NMR (400 MHz, CDCl$_3$) δ 8.65-8.61 (m, 1H), 8.24 (s, 1H), 7.90-7.88 (m, 2H), 7.35 (d, J=0.8 Hz, 1H), 4.89 (s, 2H), 3.92-3.86 (m, 1H), 2.29 (s, 3H), 1.14-1.09 (m, 2H), 0.97-0.93 (m, 2H); ESI m/z 338.0 [M+H]$^+$.

Example 10: Preparation of 3-bromo-5-(6-(4-cyclopropyl-4H-1,2,4-triazol-3-yl)pyridin-2-yl)-4,5-dihydro-6H-thieno[2,3-c]pyrrol-6-one (Example 10)

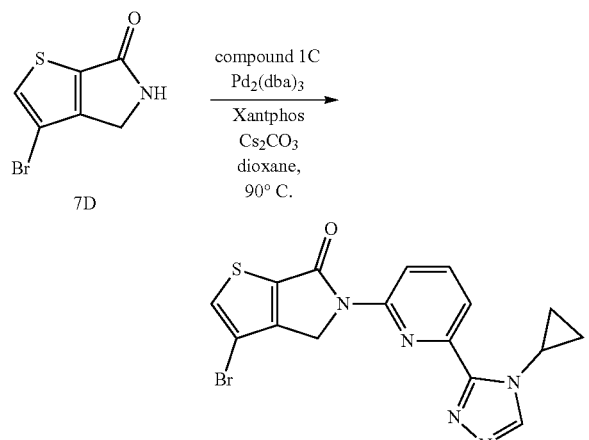

Example 10

A mixture of 7D (500 mg, 2.29 mmol), 1C (608 mg, 2.29 mmol), Pd$_2$(dba)$_3$ (147 mg, 0.16 mmol), Xantphos (132 mg, 0.22 mmol) and cesium carbonate (2.23 g, 6.82 mmol) in 1,4-dioxane (50 mL) was heated to 90° C. overnight under nitrogen. The reaction mixture was allowed to cool to room temperature and filtered. The resulting filtrate was concentrated under reduced pressure and the residue was purified by silica column chromatography (1%-1.25% MeOH in DCM) to give Example 10 (200 mg, 22% yield) as a yellow solid: $^1$H NMR (400 MHz, DMSO-d$_6$) δ 8.69 (s, 1H), 8.47 (d, J=8 Hz, 1H), 8.26 (s, 1H), 8.06 (t, J=8 Hz, 1H), 7.85 (d, J=7.2 Hz, 1H), 5.07 (s, 2H), 4.06-4.02 (m, 1H), 1.10-0.99 (m, 4H); ESI m/z 401.9, 403.9 [M+H]$^+$.

Example 11: Preparation of 5-(6-(4-cyclopropyl-4H-1,2,4-triazol-3-yl)pyridin-2-yl)-3-(isobutylamino)-4,5-dihydro-6H-thieno[2,3-c]pyrrol-6-one (Example 11)

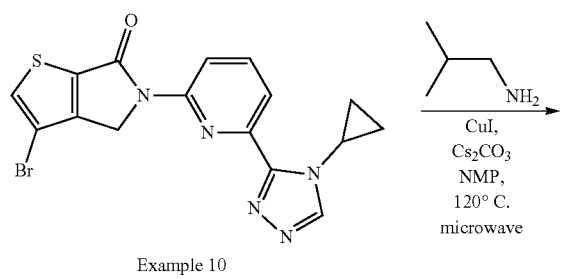

Example 10

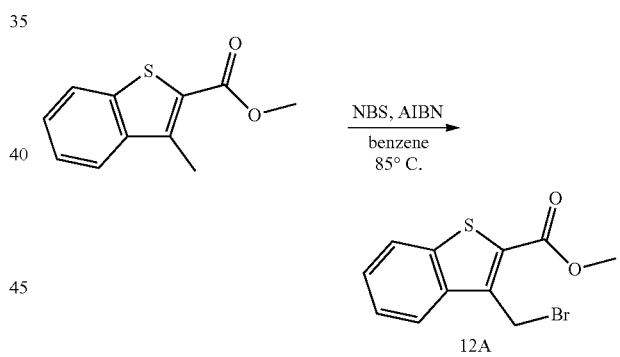

Example 11

A mixture of Example 10 (100 mg, 0.25 mmol), 2-methylpropan-1-amine (72 mg, 1.0 mmol), CuI (48 mg, 0.25 mmol), and cesium carbonate (162 mg, 0.50 mmol) in NMP (6 mL) was heated at 120° C. for 40 in by microwave. The mixture was concentrated under vacuum and purified by column chromatography on silica gel (1%-2% MeOH in DCM) to afford Example 11 (3 mg, 3% yield) as a yellow solid: $^1$H NMR (400 MHz, DMSO-d$_6$) δ 8.74 (s, 1H), 8.50 (d, J=8.4 Hz, 1H), 8.04 (t, J=8 Hz, 1H), 7.78 (d, J=7.2 Hz, 1H), 6.47 (s, 1H), 4.94 (s, 2H), 2.86 (d, J=8.4 Hz, 1H), 1.92-1.86 (m, 1H), 1.08-1.04 (m, 2H), 0.96-0.95 (m, 6H), 0.88-0.84 (m, 2H); ESI m/z 395.0 [M+H]$^+$.

Example 12: Preparation of 2-(6-(4-cyclopropyl-4H-1,2,4-triazol-3-yl)pyridin-2-yl)-1,2-dihydro-3H-benzo[4,5]thieno[2,3-c]pyrrol-3-one (Example 12)

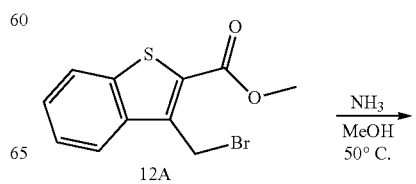

Step 1: A mixture of methyl 3-methylbenzo[b]thiophene-2-carboxylate (2.26 g, 11.1 mmol), N-bromosuccinimide (1.96 g, 11.10 mmol) and 2,2'-azobisisobutyronitrile (903 mg, 5.5 mmol) in benzene (30 mL) was stirred at 85° C. overnight. The mixture was concentrated under reduced pressure and purified by chromatography on silica gel (2%-25% EtOAc in PE) to give compound 12A (1.68 g, 54% yield) as a white solid: ESI m/z 285.4, 287.4 [M+H]$^+$.

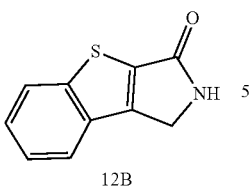

12B

Step 2: Compound 12A (1.6 g, 5.61 mmol) was stirred in a solution of ammonia in methanol (7.0 M, 50 mL) at 50° C. overnight in a sealed tube. The mixture was concentrated under reduced pressure and purified by chromatography on silica gel (2%-50% EtOAc in PE) to give 12B (3 g, 80% yield) as an off-white solid: ESI m/z 190.1 [M+H]⁺.

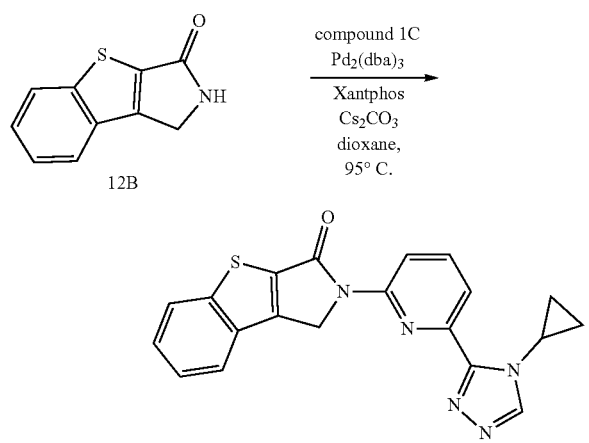

Example 12

Step 3: A mixture of 12B (160 mg, 0.85 mmol), 1C (173 mg, 0.85 mmol), cesium carbonate (831 mg, 2.55 mmol), Xantphos (34 mg, 0.0595 mmol) and Pd$_2$(dba)$_3$ (39 mg, 0.0425 mmol) in 1,4-dioxane (20 mL) was stirred at 95° C. overnight under nitrogen. The mixture was concentrated under reduced pressure and purified by chromatography on silica gel (1%-5% MeOH in DCM) to give Example 12 (50 mg, 16% yield) as a white solid: $^1$H NMR (400 MHz, DMSO-d$_6$) δ 8.73 (s, 1H), 8.53 (dd, J=8.4 Hz, 1H), 8.21-8.15 (m, 2H), 8.07 (t, J=8.4 Hz, 1H), 7.85 (d, J=7.6 Hz, 1H), 7.59-7.57 (m, 2H), 5.37 (s, 2H), 4.16-4.10 (m, 1H), 1.15-1.11 (m, 2H), 1.05-0.95 (m, 2H); ESI m/z 374.0 [M+H]⁺.

Example 13: Preparation of 5-(6-(4-cyclopropyl-4H-1,2,4-triazol-3-yl)pyridin-2-yl)-2-methoxy-4,5-dihydro-6H-thieno[2,3-c]pyrrol-6-one (Example 13)

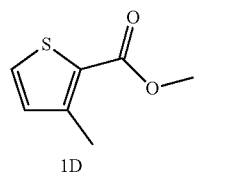

1D

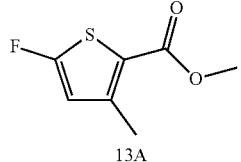

13A

Step 1: n-BuLi (2.5 M in n-hexane, 6.7 mL, 16.7 mmol) was added to a stirred solution of diisopropylamine (1.56 g, 15.37 mmol) in THF (40 mL) at −78° C. The reaction mixture was stirred at 0° C. for 10 minutes and then cooled to −60° C. A solution of 1D (2.0 g, 12.81 mmol) in THF (40 mL) was added dropwise and the reaction was stirred at −60° C. for 30 min. A solution of N-fluorobenzenesulfonimide (5.25, 16.65 mmol) in THF (5 mL) was added and the reaction was stirred at −60° C. for 2 hours. The reaction mixture was quenched with a solution of saturated ammonium chloride and extracted with dichloromethane (2×100 mL). The combined organic fractions were dried over anhydrous sodium sulfate, filtered and concentrated under vacuum to a volume of ~50 mL. The mixture was then purified by flash silica gel column chromatography (1% DCM in PE). The collected fractions were concentrated to a volume of ~50 mL. Since the product was volatile, the solution of 13A was used directly in the next step: $^1$H NMR (400 MHz, CDCl$_3$) δ 6.35 (d, J=1.2 Hz, 1H), 3.83 (s, 3H), 2.49 (s, 3H).

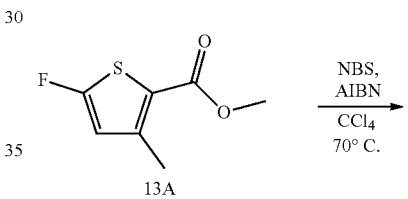

13A

13B

Step 2: A stirred mixture of 13A (estimated 3.44 mmol), 2,2'-azobisisobutyronitrile (113 mg, 0.688 mmol) and N-bromosuccinimide (613 mg, 3.44 mmol) in carbon tetrachloride (20 mL) was heated to 80° C. for 4 hours. Then the reaction mixture was cooled to room temperature and filtered. The filter cake was washed with carbon tetrachloride (2×20 mL). The filtrate was diluted with ethyl acetate (200 mL) and washed with water (40 mL), saturated aqueous sodium bicarbonate (40 mL) and brine (40 mL). The organic fraction was dried over anhydrous sodium sulfate, filtered and concentrated under reduced pressure to afford 13B (1 g) as a crude oil. The product was used without further purification.

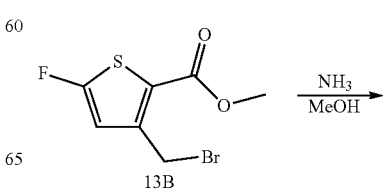

13B

-continued

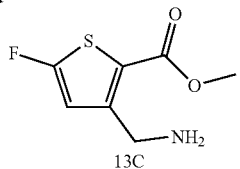

Step 3: 13B (800 mg, 3.16 mmol) was stirred in a solution of ammonia in methanol (7N, 30 mL) at room temperature overnight. The reaction mixture was concentrated at reduced pressure and the residue was purified by silica gel column chromatography (2%-10% MeOH in DCM) to give a mixture containing 13C (330 mg). The mixture was used in the next step. ESI m/z 190.1 [M+H]$^+$.

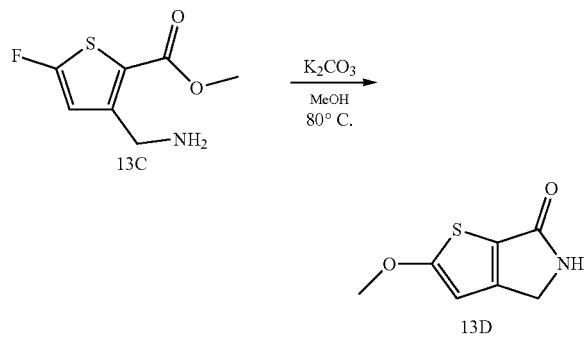

Step 4: A stirred mixture of 13C (300 mg, 1.59 mmol) and potassium carbonate (438 mg, 3.17 mmol) in methanol (30 mL) was stirred for overnight at 80° C. After cooling, the reaction mixture was concentrated under reduced pressure and purified by silica gel column chromatography (2%-5% MeOH in DCM) to afford a mixture containing 13D (110 mg): $^1$H NMR (400 MHz, CDCl$_3$) δ 6.24 (s, 1H), 4.31 (s, 2H), 3.96 (s, 3H); ESI m/z 170.2 [M+H]$^+$.

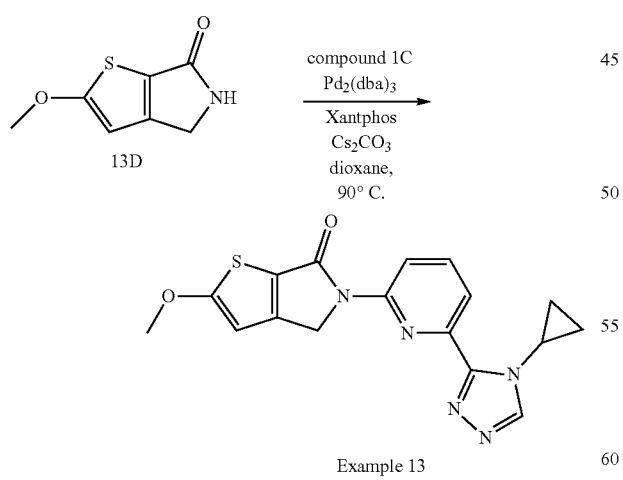

Example 13

Step 5: A stirred mixture of 13D (110 mg, 0.65 mmol), compound 1C (172 mg, 0.65 mmol), Cs$_2$CO$_3$ (741 mg, 2.28 mmol), Xantphos (53 mg, 0.091 mmol) and Pd$_2$(dba)$_3$ (60 mg, 0.065 mmol) in 1,4-dioxane (6 mL) was stirred at 90° C. overnight under nitrogen. The mixture was concentrated under reduced pressure and purified by silica gel column chromatography (1%-5% MeOH in DCM) and preparative reverse phase HPLC to give Example 13 (15 mg, 7%) as a white solid: $^1$H NMR (400 MHz, CDCl$_3$) δ 8.58 (dd, J=8 Hz, 1.2 Hz, 1H), 8.21 (s, 1H), 7.89-7.82 (m, 2H), 6.30 (s, 1H), 4.89 (s, 2H), 3.99 (s, 3H), 3.92-3.86 (m, 1H), 1.13-1.08 (m, 2H), 0.96-0.91 (m, 2H); ESI m/z 354.1 [M+H]$^+$.

Example 14: Preparation of 5-(6-(4-isopropyl-4H-1,2,4-triazol-3-yl)pyridin-2-yl)-4,5-dihydro-6H-thieno[2,3-c]pyrrol-6-one (Example 14)

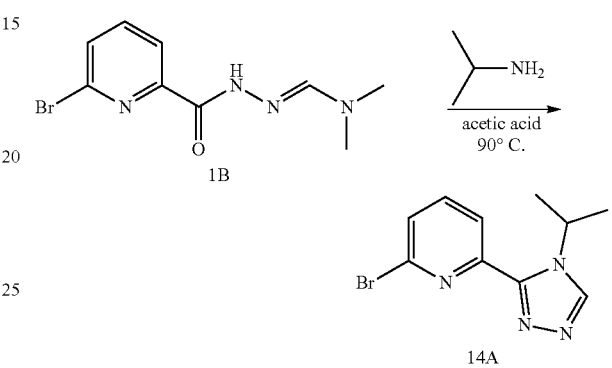

Step 1: A mixture of 1B (2.1 g, 7.75 mmol), propan-2-amine hydrochloride (3.71 g, 38.8 mmol) and DIPEA (5.0 g, 38.8 mmol) in ACN (32 mL) and acetic acid (8 mL) was heated to 90° C. overnight. The mixture was concentrated and purified by column chromatography on silica gel (1%-50% EtOAc in PE) to afford 14A (1.7 g, 82% yield) as a white solid: $^1$H NMR (400 MHz, DMSO-d$_6$) δ 8.92 (s, 1), 8.15 (d, J=8 Hz, 1H), 7.96-7.92 (m, 1H), 7.77 (d, J=8 Hz, 1H), 5.34-5.24 (m, 1H), 1.48 (d, J=6.8 Hz, 6H); ESI m/z 266.9, 268.9 [M+H]$^+$.

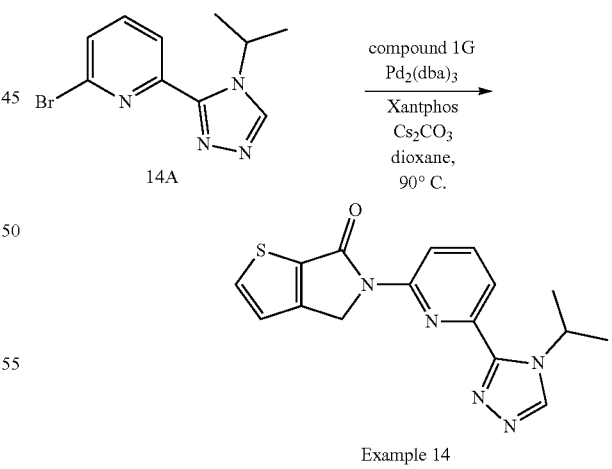

Example 14

Step 2: A stirred mixture of 14A (286 mg, 108 mmol), 1G (150 mg, 1.08 mmol), Cs$_2$CO$_3$ (1.06 g, 3.24 mmol), Xantphos (87 mg, 0.15 mmol) and Pd$_2$(dba)$_3$ (99 mg, 0.108 mmol) in 1,4-dioxane (10 mL) was heated at 90° C. overnight under nitrogen. The mixture was concentrated under reduced pressure and purified by chromatography on silica gel (1%-5% MeOH in DCM) followed by preparative reverse phase HPLC to give the title compound (80 mg, 23% yield) as a white solid: $^1$H NMR (400 MHz, CDCl$_3$) δ 8.62 (d, J=8.4 Hz, 1H), 8.42 (s, 1H), 8.02 (d, J=7.6 Hz, 1H), 7.89 (t, J=8 Hz, 1H), 7.69 (d, J=4.8 Hz, 1H), 7.16 (d, J=4.8 Hz, 1H), 5.63-5.53 (m, 1H), 4.97 (s, 2H), 1.62 (d, J=6.8 Hz, 6H); ESI m/z 326.1 [M+H]$^+$.

Example 15: Preparation of 5-(6-(4-cyclopropyl-4H-1,2,4-triazol-3-yl)pyridin-2-yl)-2-(dimethyl-amino)-4,5-dihydro-6H-thieno[2,3-c]pyrrol-6-one (Example 15)

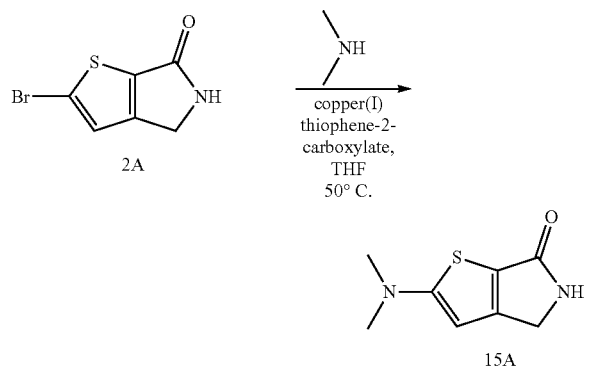

Step 1: A stirred mixture of 2A (500 mg, 2.29 mmol), dimethylamine (2M in THF, 40 mL) and copper(I) thiophene-2-carboxylate (219 mg, 1.15 mmol) was heated to 50° C. for 10 hours under a nitrogen atmosphere. After cooling to room temperature, the reaction mixture was poured into water and extracted with EtOAc (3×80 mL). The combined organic fractions were washed with brine, dried with anhydrous sodium sulfate, and concentrated under reduced pressure. The residue was purified by column chromatography on silica gel (0.5%-50% EtOAc in PE) and then further purified by prep-TLC (silica gel, 5% MeOH in DCM) to give compound 15A (50 mg, 12% yield) as a yellow solid: $^1$H NMR (400 MHz, CDCl$_3$) δ 6.15 (s, 1H), 5.77 (s, 1H), 4.24 (s, 2H), 3.0 (s, 6H); ESI m/z 183.0 [M+H]$^+$.

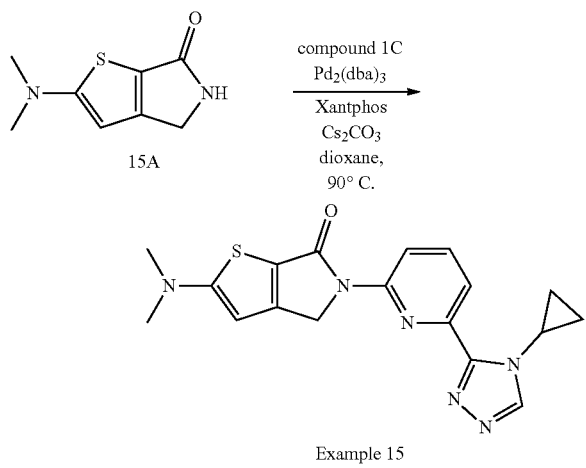

Step 2: A mixture of 15A (50 mg, 0.27 mmol), compound 1C (73 mg, 0.27 mmol), Pd$_2$(dba)$_3$ (25 mg, 0.027 mmol), Xantphos (22 mg, 0.038 mmol) and Cs$_2$CO$_3$ (312 g, 0.96 mmol) in 1,4-dioxane (6 mL) was stirred at 90° C. overnight under nitrogen. The reaction mixture was allowed to cool to room temperature and filtered. The filtrate was concentrated under reduced pressure and the residue was purified by silica gel column chromatography (0.5%-2.5% MeOH in DCM) to afford Example 15 (35 mg, 35% yield) as a yellow solid: $^1$H NMR (400 MHz, DMSO-d$_6$) δ 8.67 (s, 1H), 8.46 (d, J=8.4, 1H), 7.95 (m, 1H), 7.73 (d, J=7.2, 1H), 6.07 (s, 1H), 4.95 (s, 2H), 4.09-4.02 (m, 1H), 3.03 (s, 6H), 1.10-1.05 (m, 2H), 0.96-0.94 (m, 2H); ESI m/z 367.1 [M+H]$^+$.

Example 16: ASK1 Kinase Assay

The ASK1 enzymatic assay was run following Promega ASK1 Kinase Enzyme System (Cat #V3881). The kit provides the protocol, enzymes and all reagents necessary to run an assay.

The compounds, enzyme, substrate and ATP were diluted in provided assay buffer. The final concentration of the enzyme was 50 nM, substrate (Myelin basic protein) 1 μg/mL and ATP 10 μM. The compound and the enzyme were pre-incubated in a 384-well white solid bottom plate (Greiner, Cat #784075) for 10 minutes. After incubation, the substrate and ATP were added and incubated for an additional 60 minutes. After 60 minutes, ADP-Glo™ was added and the plate was incubated for another 40 minutes. After 40 minutes, Kinase Detection Reagent was added and the plate was incubated for 45 minutes. After 45 minutes, the plate was read on a Perkin Elmer EnVision using luminescence read (0.5 seconds/well).

| Example | ASK1 IC$_{50}$ |
| --- | --- |
| 1 | A |
| 2 | A |
| 3 | A |
| 4 | A |
| 5 | A |
| 6 | A |
| 7 | 45% inhibition at 10 μM |
| 8 | B |
| 9 | A |
| 10 | A |
| 11 | B |
| 12 | A |
| 13 | A |
| 14 | A |

A < 1 μM; ≤1 μM < B ≤ 10 μM

Example 17: Clinical Trial of ASK1 Inhibitors in Human NASH

Patient Selection/Management

Patient inclusion criteria are: age 18-75, greater than 60 U/L serum alanine transaminase (ALT), ultrasound-documented fatty liver, biopsy-consistent NASH without cirrhosis, platelet count ≥75,000/mm$^3$, absolute neutrophil count ≥1500/mm$^3$, hemoglobin ≥11.0 g/dL, and creatinine clearance ≥70 mL/min as calculated with the Cockcroft-Gault equation.

Histological criteria used for NASH in biopsy analysis are: steatosis (>5% of hepatocytes containing liver fat), hepatocyte ballooning, and lobular inflammation, regardless of the amount of fibrosis.

Patients are required to have a stable weight (within 4%) before screening, and to maintain their existing diets and physical activity levels over the course of the study.

Patient exclusion criteria are: any other cause of liver disease (e.g., viral hepatitis, autoimmune hepatitis, hemochromatosis, and others), hepatocellular carcinoma (HCC), daily alcohol consumption higher than 30 g in males and 20 g in females, or drug-induced/secondary NASH.

Cohort Design Drug Administration

The study is randomized, double-blind, parallel-group, and placebo-controlled. Patients successfully meeting selection criteria are stratified by comorbid conditions that may exacerbate liver injury (e.g. type-2 diabetes). After stratification, subjects are randomly assigned to one of five parallel treatment groups: placebo or 4 escalating doses of any of the ASK-1 inhibitors of Formula I or II described herein. The inhibitor is administered orally once daily for 4 weeks. On completion of treatment, subjects are followed for 4 weeks.

Measures of Drug Efficacy

Serum ALT and AST (liver function markers) are measured from weekly blood samples collected during the treatment and follow-up periods. Normal levels are defined as 43 U/L ALT and 36 U/L AST for males, and 34 U/L ALT and 34 U/L AST for females.

Cytokeratin-18 fragments (resulting from caspase-3 cleavage and apoptotic activity, liver damage markers) are measured using ELISA from blood samples collected at week 2 and week 4 of the treatment period.

Concentrations of ASK-1 inhibitors are determined in plasma by using a validated bioanalytical assay to assess drug concentration. Steady state analysis of pharmacokinetic parameters (e.g. ($C_{max}$), time of $C_{max}$ ($T_{max}$), half-life ($T_{1/2}$), and area under the plasma concentration versus time curve over the dosing interval ($AUC_{tau}$)) occurs between weeks 2 and 4.

Safety Analysis

Safety monitoring includes clinical laboratory tests, physical examinations, vital signs measurements, 12-lead electrocardiograms, and documentation of adverse events (AEs).

Efficacy Endpoints

Absolute and percent change from baseline in ALT levels, AST levels, and CK-18 fragment levels at week 4 are assessed by an analysis of covariance (ANCOVA) model with adjustment for baseline values.

Plasma concentration-time data for each subject are analyzed using standard noncompartmental methods to compute pharmacokinetic parameters. Exposure/response relationships for ASK-1 inhibitors are determined by fitting $C_{max}$ or $AUC_{tau}$ to time-weighted absolute changes in CK-18 fragment, AST, or ALT levels.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), or a pharmaceutically acceptable salt or solvate thereof:

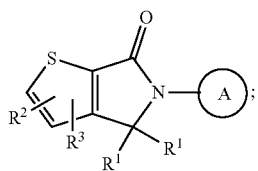

Formula (I)

wherein

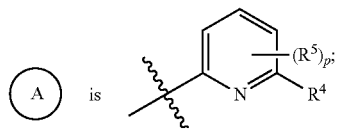

each $R^1$ is independently selected from a group consisting of hydrogen, halogen, and $C_{1-6}$alkyl;

$R^2$ is selected from a group consisting of hydrogen, halogen, —$OR^6$, —$N(R^6)_2$, $C_{1-6}$alkyl, $C_{2-9}$heterocycle, and $C_{6-10}$aryl, wherein $C_{1-6}$alkyl, $C_{2-9}$heterocycle, and $C_{6-10}$aryl, are optionally substituted with one, two, or three substituents selected from the group consisting of —C(=O)$R^{14}$, and —N($R^{13}$)C(=O)$R^{14}$;

$R^3$ is selected from a group consisting of hydrogen, halogen, and $C_{1-6}$alkyl; or $R^2$ and $R^3$ are combined to form a phenyl ring;

$R^4$ is $C_{1-9}$heteroaryl; wherein $C_{1-9}$heteroaryl is optionally substituted with one, two, or three substituents selected from the group consisting of $C_{1-6}$alkyl, and $C_{3-8}$cycloalkyl;

each $R^5$ is independently selected from a group consisting of halogen, —CN, and $C_{1-6}$alkyl;

each $R^6$ is independently selected from the group consisting of hydrogen, and $C_{1-6}$alkyl, $R^{13}$ is independently selected from the group consisting of hydrogen, $C_{1-6}$ alkyl and $C_{3-8}$ cycloalkyl;

Each $R^{14}$ is independently selected from the group consisting of $C_{1-6}$ alkyl and $C_{3-8}$ cycloalkyl;

p is 0, 1, 2, or 3.

2. The compound of claim 1, or a pharmaceutically acceptable salt or solvate thereof, wherein $R^2$ is selected from a group consisting of hydrogen, halogen, and $C_{1-6}$alkyl.

3. The compound of claim 1, or a pharmaceutically acceptable salt or solvate thereof, wherein $R^2$ is hydrogen.

4. The compound of claim 1, or a pharmaceutically acceptable salt or solvate thereof, wherein $R^2$ is selected from a group consisting of $C_{2-9}$heterocycle, and $C_{6-10}$aryl; wherein $C_{2-9}$heterocycle, and $C_{6-10}$aryl, are optionally substituted with one, two, or three substituents selected from the group consisting of —C(=O)$R^{14}$, and —N($R^{13}$)C(=O)$R^{14}$.

5. The compound of claim 1, or a pharmaceutically acceptable salt or solvate thereof, wherein $R^2$ is phenyl optionally substituted with one or two substituents selected from the group consisting of —C(=O)$R^{14}$, and —N($R^{13}$)C(=O)$R^{14}$.

6. The compound of claim 1, or a pharmaceutically acceptable salt or solvate thereof, wherein $R^3$ is hydrogen or $C_{1-6}$alkyl.

7. The compound of claim 1, or a pharmaceutically acceptable salt or solvate thereof, wherein $R^2$ and $R^3$ are combined to form a phenyl ring.

8. The compound of claim 1, or a pharmaceutically acceptable salt or solvate thereof, wherein $R^4$ triazole; wherein triazole is optionally substituted with one or two substituents selected from the group consisting of $C_{1-6}$alkyl, and $C_{3-8}$cycloalkyl.

9. The compound of claim 8, a pharmaceutically acceptable salt or solvate thereof, wherein R⁴ is
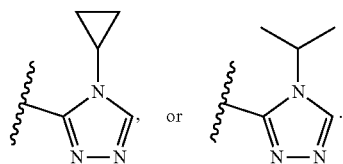 or 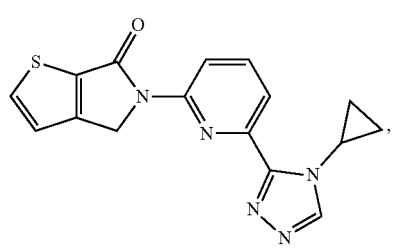.
10. The compound of claim 1, or a pharmaceutically acceptable salt or solvate thereof, having the structure:
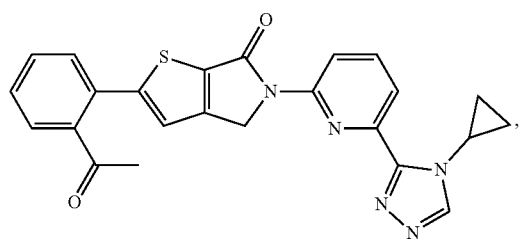,
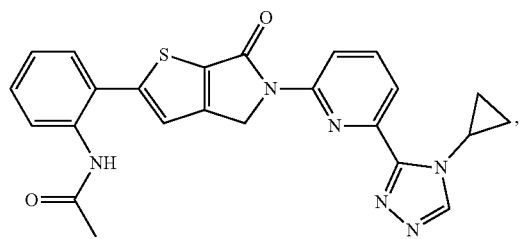,
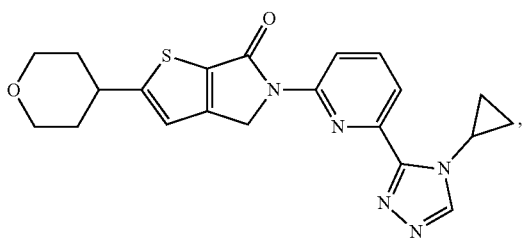,
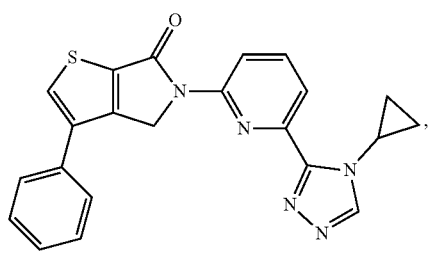,
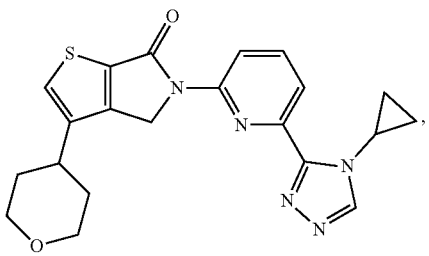,
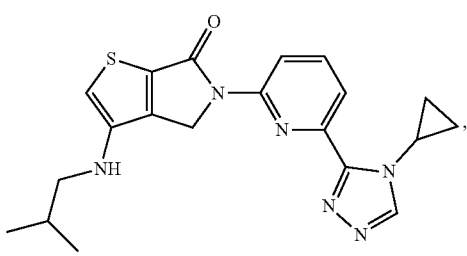,
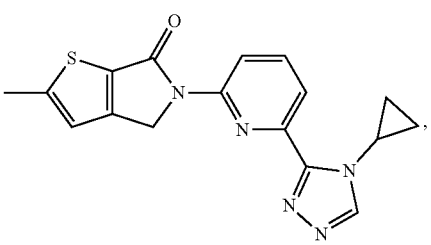,
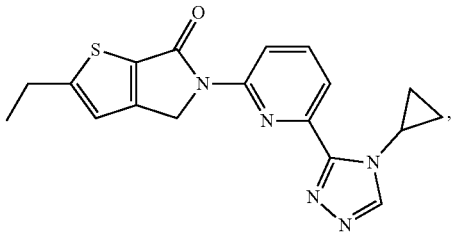,
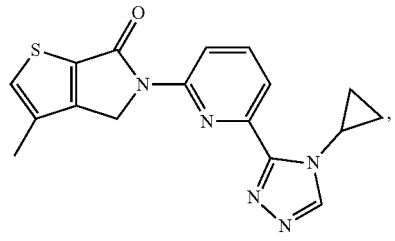,
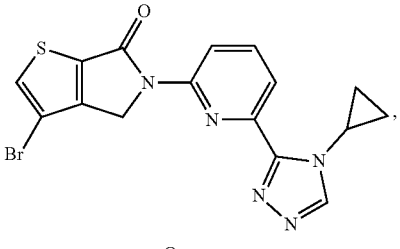,
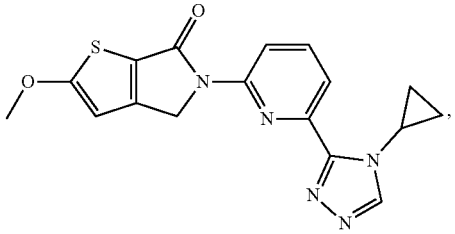,

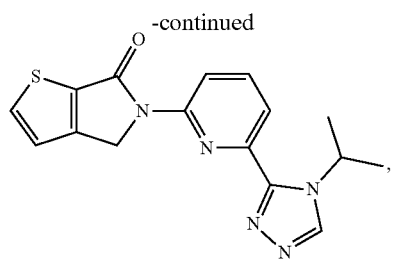

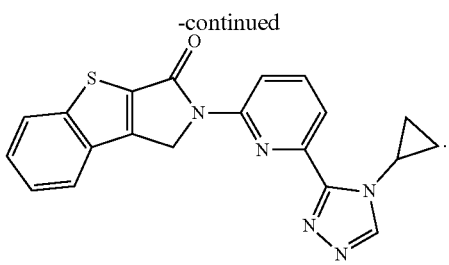

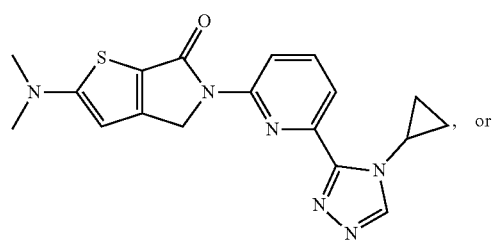

11. A pharmaceutical composition comprising a compound of claim 1, or a pharmaceutically acceptable salt or solvate thereof, and at least one pharmaceutically acceptable excipient.

12. A method of treating non-alcoholic steatohepatitis in a subject in need thereof, comprising administering to the subject a therapeutically effective amount of a compound of claim 1, or a pharmaceutically acceptable salt or solvate thereof.

* * * * *